US008183280B2

(12) United States Patent
Evans et al.

(10) Patent No.: US 8,183,280 B2
(45) Date of Patent: May 22, 2012

(54) FAP INHIBITORS

(75) Inventors: David Michael Evans, Southampton (GB); John Horton, Southampton (GB); Julie Elizabeth Trim, Southampton (GB)

(73) Assignee: Vantia Limited, Chilworth (GB)

(*) Notice: Subject to any disclaimer, the term of this patent is extended or adjusted under 35 U.S.C. 154(b) by 306 days.

(21) Appl. No.: 11/991,286

(22) PCT Filed: Aug. 31, 2006

(86) PCT No.: PCT/IB2006/003512
§ 371 (c)(1),
(2), (4) Date: Sep. 15, 2009

(87) PCT Pub. No.: WO2007/085895
PCT Pub. Date: Aug. 2, 2007

(65) Prior Publication Data
US 2010/0081701 A1 Apr. 1, 2010

Related U.S. Application Data

(60) Provisional application No. 60/713,324, filed on Sep. 2, 2005.

(30) Foreign Application Priority Data

Sep. 2, 2005 (EP) .................... 05108049

(51) Int. Cl.
A61K 31/40 (2006.01)
C07D 207/16 (2006.01)
(52) U.S. Cl. ........................ 514/423; 548/540
(58) Field of Classification Search .................. 514/423; 548/540
See application file for complete search history.

(56) References Cited

U.S. PATENT DOCUMENTS

| 4,826,870 | A | 5/1989 | Higuchi et al. |
| 4,873,342 | A | 10/1989 | Tanaka et al. |
| 5,028,604 | A | 7/1991 | Torizuka |
| 5,286,732 | A | 2/1994 | Vincent |
| 5,462,928 | A | 10/1995 | Bachovchin et al. |
| 5,494,919 | A | 2/1996 | Morriello et al. |
| 5,536,737 | A | 7/1996 | Kobayashi et al. |
| 5,547,978 | A | 8/1996 | Christensen et al. |
| 5,574,017 | A | 11/1996 | Gutheil |
| 6,017,929 | A | 1/2000 | Tanaka |
| 6,911,467 | B2 * | 6/2005 | Evans ............ 514/423 |
| 2003/0096857 | A1 | 5/2003 | Evans |
| 2003/0225102 | A1 | 12/2003 | Sankaranarayanan |
| 2004/0214762 | A1 | 10/2004 | Demuth et al. |

FOREIGN PATENT DOCUMENTS

| EP | 0201741 | B1 | 11/1986 |
| EP | 201741 | B1 * | 11/1986 |
| EP | 0280956 | B1 | 9/1988 |
| EP | 0 419 683 | A1 | 4/1991 |
| EP | 0 536 399 | A1 | 4/1993 |
| EP | 1 134 213 | A | 9/2001 |
| EP | 1245568 | B1 | 10/2002 |
| EP | 1 522 540 | A | 4/2005 |
| JP | 63-033361 | A | 2/1988 |
| JP | 7-126229 | A | 5/1995 |
| WO | WO-95/03277 | A1 | 2/1995 |
| WO | WO-95/13069 | A1 | 5/1995 |
| WO | WO-96/20725 | A2 | 7/1996 |
| WO | WO-00/10549 | A | 3/2000 |
| WO | WO-00/55125 | A2 | 9/2000 |
| WO | WO-00/55126 | A2 | 9/2000 |
| WO | WO-01/34594 | A1 | 5/2001 |
| WO | WO-01/55105 | A1 | 8/2001 |
| WO | WO-01/81337 | A1 | 11/2001 |
| WO | WO-02/30891 | A1 | 4/2002 |
| WO | WO-02/070511 | A1 | 9/2002 |
| WO | WO-03/000250 | A1 | 1/2003 |
| WO | WO-03/002595 | A3 | 1/2003 |
| WO | WO-03/004468 | A1 | 1/2003 |
| WO | WO-03/092605 | A2 | 11/2003 |
| WO | WO-2004/004658 | A2 | 1/2004 |
| WO | WO 2007005991 | A1 * | 1/2007 |

OTHER PUBLICATIONS

Jarho et al. J. Med. Chem. 2005, 48, 4772-4782.*
Fukushima et al. Bioorg. Med. Chem. 2004, 6053-6061.*
Patani et al. Chem. Rev. 1996, 96, 3147-3176.*
Kohl et al.; "The role of Dipeptidylpeptidase IV Positive T Cells in Wound Healing and Angiogenesis"; Agents and Actions, Birkhaeuser Verlag, Basel, Ch, vol. 32, No. ½, Jan. 1991, pp. 125-127, XP002944505, ISSN: 065-4299.
Tanaka et al.; "New Potent Prolyl Endopeptidase Inhibitors: Synthesis and Structure-Activity Relationships of Indan and Tetralin Derivatives and Their Analogues"; J. Med. Chem, 1994, 37, 2071-2078.
Wallén et al.; New Prolyl Oligopeptidase Inhibitors Developed from Dicarboxylic Acid Bis(L-prolyl-pyrrolidine) Amides; J. Med. Chem.; 2003, 46, 4543-4551.
Willand et al.; "Solid and solution phase syntheses of the 2-cyanopyrrolidide DPP-IV inhibitor NVP-DPP728"; Tetrahedron 58 (2002); 5741-5746.
Vendeville; "Comparison of the Inhibition of Human and Trypanosoma cruzi Prolyl Endopeptidases"; Bioorganic & Medicinal Chemistry 10 (2002) 1719-1729.

(Continued)

Primary Examiner — Joseph Kosack
Assistant Examiner — Matthew Coughlin
(74) Attorney, Agent, or Firm — Woodcock Washburn LLP

(57) ABSTRACT

The present invention concerns compounds, according to general formula (I), which find utility preferably for the treatment of cancer.

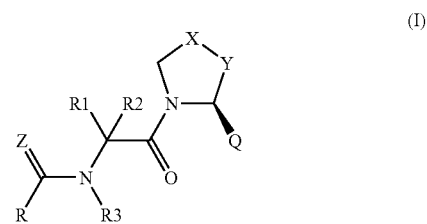

4 Claims, No Drawings

OTHER PUBLICATIONS

Database Beilstein; Beilstein Institute for Organic Chemistry, Frankfurt-Main, DE; Citation No. 5585605 BRN 4756745 1991, XP002465867 abstract.

Database Beilstein; Beilstein Institute for Organic Chemistry, Frankfurt-Main, DE; Citation No. 5854968 BRN 6657836 1993, XP002465868 abstract.

Karoly, K., et al.; "Prolyl endopeptidase inhibitors<1>: N-acyl derivatives of L-thioproline-pyrrolidine" Bioorganic & Medicinal Chemistry Letters, Oxford, GB, vol. 7, No. 13, Jul. 8, 1997, pp. 1701-1704, XP004136283, ISSN: 0960-894X; table 2; compounds 1, 2, 7.

Vendeville, S. et al; "Automated parallel synthesis of a tetrahydroisoquinolin-based library: potential prolyl endopeptidase inhibitors" Bioorganic & Medicinal Chemistry Letters, Oxford, GB, vol. 9, No. 3, Feb. 8, 1999, pp. 437-442, XP004157243, ISSN: 0960-894X; table 1; compounds 1B, 1C.

Wallen, et al.; "Conformationally rigid N-acyl-5-alkyl-1-prolyl-pyrrolidines as prolyl oligopeptidase inhibitors" Bioorganic & Medicinal Chemistry, Elsevier Science Ltd., GB, vol. 11, No. 17, Aug. 15, 2003, pp. 3611-3619, XP002286663; ISSN: 0968-0896; table 1; compound 3.

Hermecz, I., et al.; "Prolyl edopeptidase inhibators"; Farmaco (Società Chemica Italiana: 1989) Mar. 2000, vol. 55, No. 3, Mar. 2000, pp. 188-190, XP002465847; ISSN: 0014-827X; compounds 1,2.

Portevin, B., et al.; "New Prolyl Endopeptidase Inhibitors: In Vitro and In Vivo Activities of Azabicycloú2.2.2Octane, Azabicylcoú2.2.1Heptane, and Perhydroindole Derivatives" Journal of Medicinal Chemistry, American Chemical Society, Washington, US, vol. 39, No. 12, Jun. 7, 1996, pp. 2379-2391, XP002036250; ISSN: 0022-2623; table 2; compounds 3, 4, 6.

Barlow, J., et al.; "Structure/activity studies related to 2-(3,4-dichlorophenyl)-N-methyl N-[2-(1- pyroolidinyl)-1-substituted-ethyl] acetamides: a novel series of potent and selective opioid agonists" Journal of Medicinal Chemistry, American Chemical Society, Washington, US, vol. 34, No. 11, Nov. 1991; pp. 3149-3158, XP002249917, ISSN: 0022-2623; table 1; compound 6.

Opacic, et al.; "The novel L- and D-amino acid derivatives of hydroxyurea and hydantoins: synthesis, X-ray crystal structure study, and cytostatic and antiviral activity evaluation" Journal of Medicinal Chemistry; Jan. 27, 2005, vol. 48, No. 2, pp. 475-482, XP002465848, ISSN: 0022-2623, p. 476; table 1.

Database Beilstein; Beilstein Institute for Organic Chemistry, Frankfurt-Main, DE, BRN 6345302, 1993, XP002465869 abstract.

Database Beilstein; Beilstein Institute for Organic Chemistry, Frankfurt-Main, DE, BRN 339514, 1959, XP002465870 abstract.

Freifelder, M., et al.; "Isomeric Hydroxyacetanilides by Reductive Acylation of Nitrophenols" Journal of Organic Chemistry, American Chemical Society, Easton, US, vol. 27, No. 3, Mar. 1962, pp. 1092-1093, XP002993727, ISSN: 0022-3263; table I.

Database Beilstein, Beilstein Institute for Organic Chemistry, Frankfurt-Main, DE; BRN 4734423, 1998, XP002465871 abstract.

Garcia, J., et al.; "Nitrosation of Peptide Bonds Cleavage of Nitrosated Peptides by Pyrrolidine and Alpha Amino Esters" Tetrahedron, vol. 40, No. 16, 1984, pp. 3121-3128, XP002465849, ISSN: 0040-4020, table I; compound 3.

Database Beilstein, Beilstein Institute for Organic Chemistry, Frankfurt-Main, DE, BRN 5340411, 1992, XP002465872 abstract.

Rossiter, B., et al.; "Enantioselective conjugate addition to cyclic enones with scalemic lithium organo(amido)cuprates, Part IV, Relationship between ligand structure and enantioselectivity" Tetrahedron, 1993, United Kingdom, vol. 49, No. 5, 1993, pp. 965-986, XP002465850, ISSN: 0040-4020, table 1; compounds 12A, 19A.

Mazurkiewicz, R., et al.; "An efficient synthesis of N, N-disubstituted 5-aminooxazoles", Synthesis, 1992, Germany, No. 10, 1992, pp. 941-943, XP002465851, ISSN: 0039-7881, compounds IC, 1D, 1G, 1H.

Database Beilstein, Beilstein Institute for Organic Chemistry, Frankfurt-Main, DE, BRN 7885658, 1998, XP002465873 abstract.

Database Beilstein, Beilstein Institute for Organic Chemistry, Frankfurt-Main, DE, BRN 6335157, 1993, XP002465874 abstract.

Amedjkouh, M., et al.; "Synthesis of chiral diamines using novel 2-trichloromethyloxaxolidin- 4-one precursors derived from 5-oxoproline and proline" Tetrahedron: Asymmetry, Elsevier Science Publishers, Amsterdam, NL, vol. 13, No. 20, Oct. 18, 2002, pp. 2229-2234, XP004390583, ISSN: 0957-4166, compounds 9A, 9B.

Coutts, S., et al.; "Structure-Activity Relationships of Boronic Acid Inhibitors of Dipeptidyl Peptidase IV"; I., Variation of the P2 Position of XAA-Boropro Dipeptides Journal of Medicinal Chemistry, American Chemical Society; Washington, US, vol. 39, No. 10, 1996, pp. 2087-2094, XP002074031; ISSN: 0022-2632; p. 2088, right-hand column; table 1; compounds 1A, 1B, 1Q, 1P.

McIntyre, J., et al.; "Talabostat. Oncolytic, Hematopoietic agent, dipeptidyl-peptidase IV (CD26) inhibitor, fibroblast activation protein inhibitor" Drug of the Future, vol. 29, No. 9, Sep. 2004, pp. 882-886, XP002465852, ISSN: 0377-8282 the whole document.

Toide, K., et al.; "A Novel Prolyl Endopeptidase Inhibitor, JTP-4819, For the Treatment of Alzheimer's Disease: Review of Preclinical Pharmacology" CNS Drug Reviews, Branford, CT, US, vol. 2, No. 3, 1996, pp. 343-362, XP009012974, ISSN: 1080-563X; pp. 358-359; figure 1.

Database Beilstein; Beilstein Institute for Organic Chemistry; Frankfurt-Main, DE; BRN 8444882, 1996, XP002465875, abstract.

Tsutsumi, S., et al.; "Synthesis and structure-activity relationships of peptidyl alpha-keto heterocycles as novel inhibitors of prolyl endopeptidases" Journal of Medicinal Chemistry, American Chemical Society, Washington, US, vol. 37, No. 21, 1994, pp. 3492-3502, XP002265524; ISSN: 0022-2623 tables 1, 2.

Bastos, I., M.D., et al.; "Molecular, Functional and Structural Properties of the Prolyl Oligopeptidase of Trypanosoma cruzi (POP Tc80), which is required for parasite entry into mammalian cells" The Biochemical Journal, May 15, 2005, vol. 388, No. Pt. 1, pp. 39-38, XP002465866; ISSN: 1470-8728; table 2.

Joyeau, et al.; "Synthesis and activity of pyrrolidinyl- and thiazolidinyl-dipeptide derivatives as inhibitors of the Tc80 prolyl oligopeptidase from *Trypanosoma* cruzi"; Eur. J. Med. Chem., 2000, 35, 257-266.

Bachovchin, et al; "Inhibition of IgA1 Proteinases from Neisseria *gonorrhoeae* and *Hemophilus* influenzae by Peptide Prolyl Boronic Acids"; J. Biol. Chem., 1990, 265, 3738-3743.

Wallén et al.; 4-Phenylbutanoyl-2(S)-acylpyrrolidines and 4-Phenylbutanoyl-L-prolyl(S)-acylpyrrolidines as Prolyl Oligopeptidase Inhibitors; Bio. Med. Chem., 2002, 10, 2199-2206.

Tsutsumi; et al.; "α-Ketothiazole Inhibitors of Prolyl Endopeptidase"; Bio. Med. Chem. Lett., (1994), vol. 4, No. 6; pp. 831-834.

Wallén, et al.; "Dicarboxylic Acid bis(L-Prolyl-pyrrolidine) Amides as Prolyl Oligopeptidase Inhibitors"; J. Med. Chem., 2002, 45, pp. 4581-4584.

Saito, et al.; "Synthesis and Inhibitory Activity of Acyl-Peptidyl-Pyrrolidine Derivatives Toward Post-Proline Cleaving Enzyme; A Study of Subsite Specificity"; J. Enzyme Inhib., 1991, 5, 51-75.

Thornberry et al., "Discovery of JANUVIA™ (Sitagliptin), a Selective Dipeptidyl Peptidase IV Inhibitor for the Treatment of Type2 Diabetes" Current Topics in Medicinal Chemistry, 2007, 7(6), 557-568.

Xu et al., "Discovery of potent, selective, and orally bioavailable pyridine-based dipeptidyl peptidase-4 inhibitors" Bioorganic & Medicinal Chemistry Letters, Mar. 1, 2006, 16(5), 1346-1349.

Monsimer et al., "N-Substituted Vanillamides", The Journal of Organic Chemistry, Mar. 1962, 27(3), 1093-1094.

* cited by examiner

FAP INHIBITORS

FIELD OF THE INVENTION

The present invention relates to compounds, which act as FAP inhibitors, pharmaceutical products comprising the compounds, and methods of treatment using the compounds.

BACKGROUND

The enzyme fibroblast activation protein alpha (FAPα), herein abbreviated FAP, is a serine protease that possesses dipeptidyl-peptidase activity specific for N-terminal Xaa-Pro sequences. In addition to the dipeptidyl peptidase activity FAP also possesses collagenolytic activity capable of degrading gelatin and type I collagen. FAP is a type II transmembrane serine protease which is expressed as a homodimer. The 95-kDa protein exhibits 48% amino acid identity with DPIV and displays structural similarity to other members of the dipeptidyl peptidase family including DP8 and DP9. Unlike DPIV, FAP has also been reported to possess endopeptidase activity (Aertgeerts, J. Biol. Chem., 2005, 280, 19441). FAP overexpression has been shown to potentiate tumour growth (Cheng, Mol. Cancer. Ther., 2005, 4, 351), and this potentiation is dependent upon its enzymatic activity. Natural substrates for FAP have not yet been identified. FAP is not expressed by normal mature somatic tissues and benign epithelial tumours but is expressed on stromal fibroblasts in more than 90% of carcinomas including breast, colon, ovarian, bladder and pancreas (Garin-Chesa et al., Proc. Natl. Acad. Sci., 1990, 87: 7235) as determined by immunohistochemistry, making this a very specific target for potential anti-tumour agents. Expression of FAP has also been correlated with invasive potential of melanoma cells (Aoyama et al., Proc. Natl. Acad. Sci., 1990, 87: 8296) and its presence has been associated with metastasis of colorectal tumours (Iwasa et al., Cancer Letts., 2003, 199: 91). Its presence has been shown to increase tumour formation in animal models (Cheng et al., Cancer Res., 2002, 62: 4767).

The catalytic action of FAP expressed in stromal fibroblasts in carcinomas has been utilised in the conversion of prodrugs of cytotoxic or cytostatic drugs to active drugs as a potential treatment for cancer (EP 1333033).

In addition to its activity in tumour tissue FAP is also expressed in organs undergoing non-malignant remodelling, for example liver fibrosis (Levy et al., Hepatol., 1999, 29: 1768). In patients with fibrosis as a result of alcohol abuse or viral challenge, the cells responsible for the excessive scarring and constriction of the liver express large quantities of FAP. There is evidence to suggest that FAP plays an important role in the formation of the fibrotic scar.

Normal tissue is normally FAP negative, however, it is found transiently in healing wounds (Ramirez-Montagut et al., Oncogene, 2004, 23, 5435) and it is possible FAP plays a role in tissue remodelling and repair. Other potential indications for FAP inhibitors include blood cell disorders such as anemia and chemotherapy-induced neutopenia (Rosenblum et al., Curr. Opin. Chem. Biol., 2003, 7, 496).

The only FAP inhibitor reported to date is ValboroPro (PT-100, Talobostat) which has been reported to show potent anti-tumour activity in mice, slowing growth of syngeneic tumours and causing regression and rejection of tumours after oral administration (Adams et al., Cancer Res., 2004, 64: 5471). This compound is currently undergoing clinical trials as a treatment for cancer (McIntyre, Drugs of the Future, 2004, 29, 882). However, this compound, which is a non-specific inhibitor of dipeptidyl peptidases, has been shown to be a potent inhibitor of DPIV (Coutts et. al., J. Med. Chem., 1996, 39, 2087). It has been demonstrated (Cheng, Mol. Cancer Ther., 2005, 4, 351) that FAP-driven tumour growth can be attenuated using ValboroPro; this effect is unlikely to be due to DPIV inhibition suggesting that FAP plays an important role in the promotion of tumour growth. Valboro-Pro has also been shown to stimulate the growth of hematopoietic progenitorcells and to accelerate neutrophil and erythrocyte regeneration, this regeneration was observed in DPIV knock-out mice (Jones, Blood, 2003, 102, 150).

Inhibitors of DPIV are at present in clinical trials for treatment of type II diabetes. Of the many reported inhibitors of DPIV one class of compound reported are the aminoacyl pyrrolidine nitriles (Evans, IDrugs, 2002, 5, 577). However, these fall into two distinct classes; those with an unsubstituted amino group at the N-terminus (WO 9515309, WO 0181337, WO 0181304), and the N-allylglycine derivatives (WO 0196295). No data has been reported for the activity of these compounds as FAP inhibitors. There are no reports of DPIV inhibitors with an N-acyl or N-carbamoyl N-terminus.

Whilst inhibitors of prolyl ologopeptidases (which have endopeptidase activity) are known, they appear not to have been reported as showing any activity against cancer in clinical testing.

According to an aspect, the present invention aims at providing active, selective FAP inhibitors, preferably without DPIV inhibition. Preferably, the compounds are easy to synthesize. More preferably, they are orally available.

DISCLOSURE OF THE INVENTION

According to an aspect, the present invention relates to the compounds of claim 1.

The term "alkyl" includes saturated hydrocarbon residues including:
linear groups up to 10 atoms ($C_1$-$C_{10}$). Examples of such alkyl groups include, but are not limited, to $C_1$-methyl, $C_2$-ethyl, $O_3$-propyl and $C_4$-n-butyl;
branched groups of between 3 and 10 atoms ($C_3$-$C_{10}$). Examples of such alkyl groups include, but are not limited to, $C_3$-iso-propyl, $O_4$-sec-butyl, $C_4$ iso-butyl, $C_4$-tert-butyl and $C_5$-neo-pentyl;
cyclic groups of between 3 and 8 atoms ($C_3$-$C_8$). Examples of such groups include, but are not limited to, $C_3$-cyclopropyl, $C_4$-cyclobutyl, $C_5$-cyclopentyl and $C_6$-cyclohexyl;
combinations of linear, branched and cyclic groups. Examples of such groups include, but are not limited to,

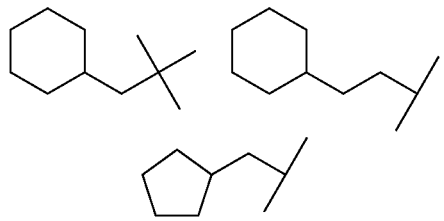

The term "alkenyl" includes monounsaturated hydrocarbon residues including:
linear groups of between 2 and 6 atoms ($C_2$-$C_6$). Examples of such alkenyl groups include, but are not limited to, $C_2$-vinyl, $C_3$-1-propenyl, $C_3$-allyl and $C_4$-2-butenyl;
branched groups of between 3 and 8 atoms ($C_3$-$C_8$). Examples of such alkenyl groups include, but are not limited to, $C_4$-2-methyl-2-propenyl and $C_6$-2,3-dimethyl-2-butenyl;

cyclic groups of between 3 and 8 atoms ($C_3$-$C_8$). Examples of such groups include, but are not limited to, $C_5$-3-cyclopentenyl and $C_6$-1-cyclohexenyl.

The term "aryl" includes optionally substituted phenyl and optionally substituted naphthyl. Examples of such aryl groups include, but are not limited to, phenyl, 2-tolyl, 3-chlorophenyl, 4-chlorophenyl, 3-fluorophenyl, 2-methoxyphenyl, 3-methoxyphenyl, 4-methoxyphenyl, 2,5-difluorophenyl, 1-naphthyl and 2-naphthyl.

The term "heteroaryl" includes optionally substituted heterocycles. Such heteroaryl groups include, but are not limited to, pyridyl, 2-chloropyridyl, 4-methylpyridyl, thienyl, 3-chlorothienyl, 2,3-dimethylthiophenyl, furyl and 2-methylfuryl.

Further aspects of the invention are provided according to the claims.

According to an aspect the compounds of the invention are inhibitors of FAP. According to an aspect the compounds of the invention are useful for the treatment of cancer and/or liver cirrhosis. According to an aspect of the present invention it is envisionaged that at least one FAP inhibitor may be co-administered with at least one known cancer agent. Such anti-cancer agents include the compounds mentioned in claim 12 of WO2004045593.

According to an aspect, the present invention relates to the particularly preferred compounds of claim 25. The particularly preferred compounds are inhibitors of FAP of high activity.

According to an aspect, the invention is further related to pharmaceutical compositions incorporating a compound according to the invention used as a FAP inhibitor; these compositions are particularly useful for medical indications such as the treatment of cancer and liver cirrhosis.

According to an aspect, the invention concerns the use of a compound of the invention for the manufacture of a medicament for the treatment of a condition selected among cancer, liver cirrhosis, malignant and benign tumours, ectopic tissue growth, wound healing, organ fibrosis, cirrhosis, metastasis, blood cell disorders, anemia, and chemotherapy-induced neutropenia.

The compounds according to the present invention are useful for treatment of several diseases, disorders or conditions. The term "treatment" used herein relates to both treatment in order to cure or alleviate a disease, disorder or a condition, and to treatment in order to prevent the development of a disease, disorder or a condition. The treatment may either be performed in an acute or in a chronic way. The human or animal to be treated, i.e. the patient, may be any human or non-human mammal in need of treatment according to the invention.

The term "therapeutically effective amount" relates to an amount that will lead to the desired therapeutical effect. The therapeutically effective amount will be determined by the attending physician taking into consideration all appropriate factors. Generally a single dose will comprise between 0.1 mg and 1000 mg, preferably between 1 mg and 250 mg, of the active compound according to the invention. The dose may be given on a single occasion or repeatedly. When given repeatedly, it may be given at regular intervals, such as once, twice or three times daily, or on demand, according to the condition being treated.

According to an aspect, the invention concerns a pharmaceutical composition comprising a compound according to the invention as an active agent. Any excipients used will depend on the intended nature of the formulation, which will, in turn, depend on the intended route of administration. Administration may be oral, transmucosal (such as sublingual, buccal, intranasal, vaginal and rectal), transdermal or by injection (such as subcutaneous, intramuscular and intravenous). Oral administration is generally preferred. For oral administration, the formulation may be a tablet, a capsule or a sachet.

The pharmaceutical composition according to an aspect of the present invention may be presented in any form that is known in the art. For example, the formulation may be presented as a tablet, capsule, powder, suppository, cream, solution or suspension, or in a more complex form such as an adhesive patch. The formulation will generally include one or more excipients, such as diluents, bulking agents, binding agents, dispersants, solvents, preservatives, flavouring agents and the like.

The pharmaceutical composition according to the present invention may optionally comprise at least one further additive such as a disintegrating agent, binder, lubricant, flavoring agent, preservative, colorant and a mixture thereof. Representative examples can be found in "*Handbook of Pharmaceutical Excipients*"; Ed. A. H. Kibbe, $3^{rd}$ Ed., American Pharmaceutical Association, USA and Pharmaceutical Press UK, 2000.

The compounds of the present invention can be prepared by methods generally known in the art and illustrated in the following non-limiting examples.

The compounds according to general formula 1 can be prepared using conventional synthetic methods.

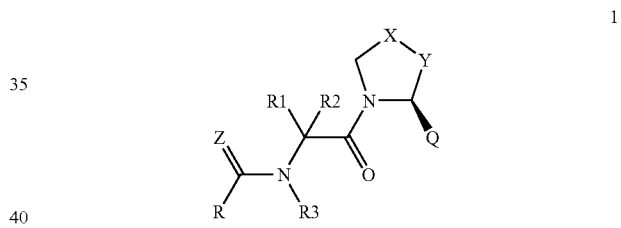

1

In a first step (Scheme 1) a nitrogen containing heterocycle (5) is coupled using standard peptide coupling conditions to an alpha amino acid (6) suitably amino-protected with a standard protecting group such as tert-butyloxycarbonyl (BOC), benzyloxycarbonyl (Z) or 9-fluorenylmethyloxycarbonyl (Fmoc). The use of such groups is well known in the art. Where R1 has a reactive functional group such as an amine or a carboxylic acid, this group will also be protected. The principles of functional group protection are well known in the art and are described in, for example, J. F. W. McOmie, "Protective Groups in Organic Chemistry", Plenum Press, 1973; T. W. Greene and P. G. M. Wuts, "Protective Groups in Organic Synthesis", $3^{rd}$ edition, John Wiley, 1999; and P. J. Kocienski, "Protecting groups", Georg Thieme Verlag, 1994.

Scheme 1

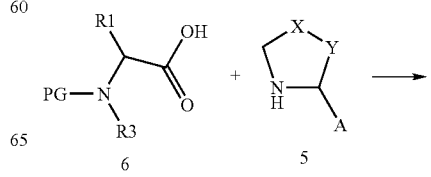

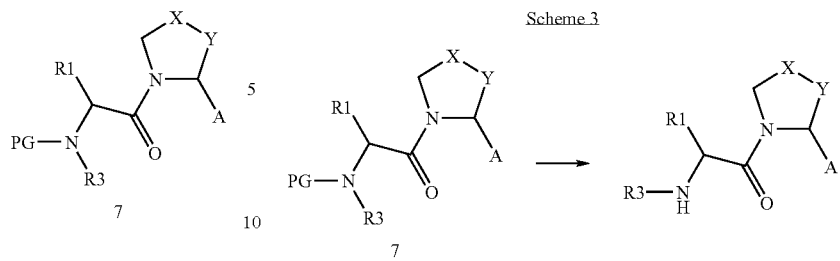

In a second step when the group A of 7 is a carbamoyl group this is dehydrated to the corresponding nitrile using standard dehydrating conditions such as trifluoroacetic anhydride, or phosphorous oxychloride in pyridine or DMF (Scheme 2). Deprotection using standard methods followed by reaction with an acid chloride or isocyanate in the presence of base gives the compounds of the invention. Alternatively such compounds may be prepared from the deprotected compound by coupling the amine with a carboxylic acid using standard coupling conditions or reacting the amine with a further amine in the presence of CDI or phosgene or diphosgene.

Scheme 2

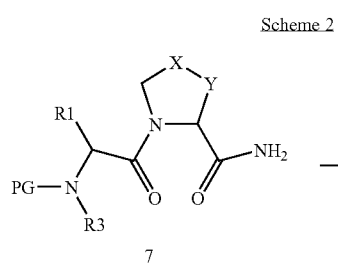

Alternatively in a second step the intermediate 7 can be deprotected using standard methods and reacted with an acid chloride or isocyanate in the presence of base (Scheme 3). Alternatively such compounds may be prepared from the deprotected compound by coupling the amine with a carboxylic acid using standard coupling conditions or reacting the amine with a further amine in the presence of CDI or phosgene or diphosgene.

Scheme 3

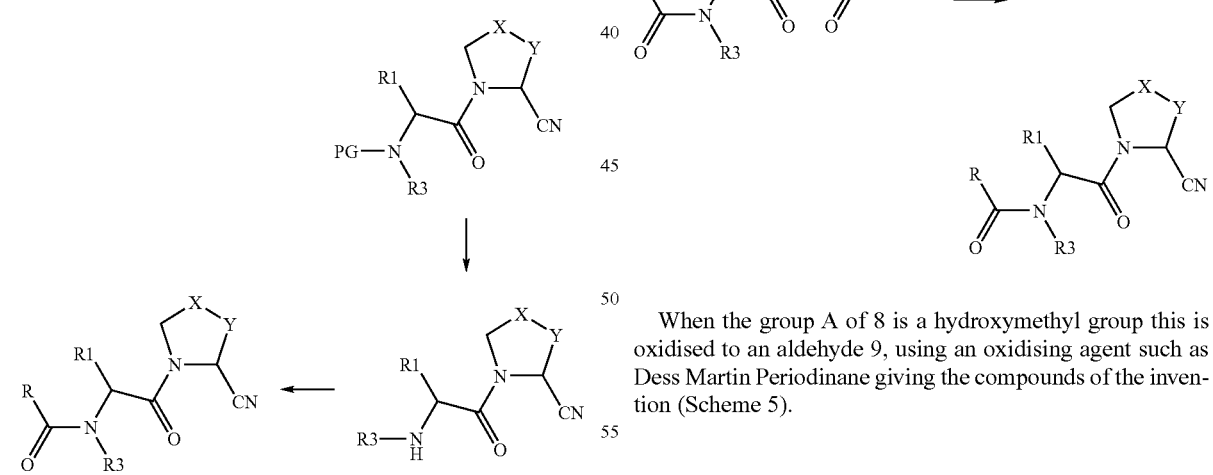

When the group A of 8 is a carbamoyl group this is dehydrated to a nitrile using standard dehydrating conditions such as trifluoroacetic anhydride, or phosphorous oxychloride in pyridine or DMF giving the compounds of the invention (Scheme 4).

Scheme 4

When the group A of 8 is a hydroxymethyl group this is oxidised to an aldehyde 9, using an oxidising agent such as Dess Martin Periodinane giving the compounds of the invention (Scheme 5).

Scheme 5

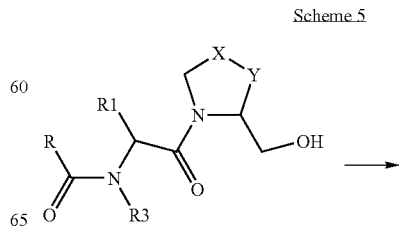

-continued

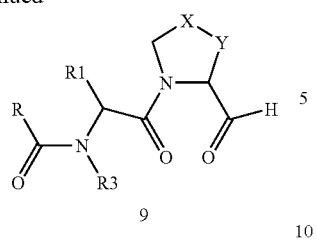

The aldehyde 9 can be further manipulated to give ketones (Scheme 6). This involves reaction of the aldehyde with organometallic reagents such as Grignard reagents or lithiated aromatics and heteroaromatics and the subsequent oxidation of the resulting alcohol using an oxidising agent such as Dess Martin Periodinane giving the compounds of the invention.

Scheme 6

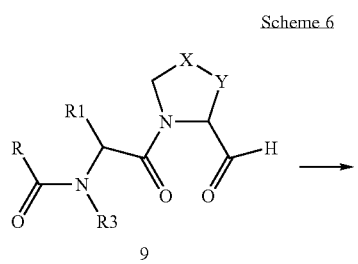

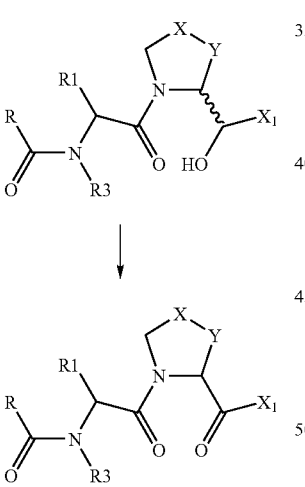

An alternative route to the ketones starts from a nitrogen containing heterocycle-2-carboxaldehyde suitably amino-protected with a standard protecting group such as tert-butyloxycarbonyl (BOC), benzyloxycarbonyl (Z) or 9-fluorenylmethyloxycarbonyl (Fmoc). The use of such groups is well known in the art. In a first step the aldehyde is reacted with organometallic reagents such as Grignard reagents or lithiated aromatics and heteroaromatics (Scheme 7). The protecting group is removed by standard methods giving compound 10.

Scheme 7

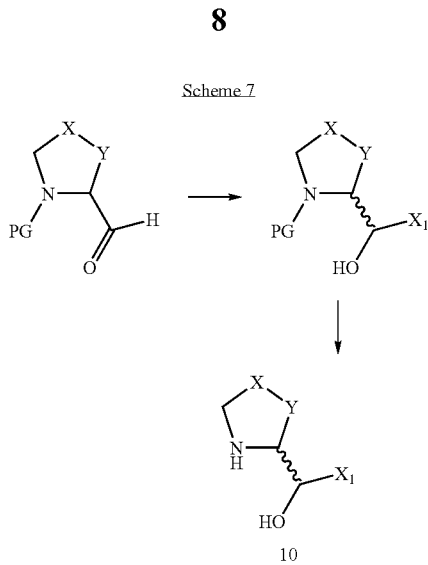

An alpha amino acid suitably carboxyl-protected with a standard protecting group is reacted with an acid chloride or isocyanate in the presence of base (Scheme 8). Alternatively such compounds may be prepared from the deprotected compound by coupling the amine with a carboxylic acid using standard coupling conditions or reacting the amine with a further amine in the presence of CDI or phosgene or diphosgene. The carboxylic acid is protected as an ester such as methyl, benzyl or tert-butyl. The use of such groups is well known in the art. Where R1 has a reactive functional group such as an amine or a carboxylic acid, this group will also be protected. After deprotection using standard methodology the resulting acid is coupled with the amine 10 using standard coupling methodology. Subsequent oxidation of the resulting alcohol using an oxidising agent such as Dess Martin Periodinane gives the compounds of the invention.

Scheme 8

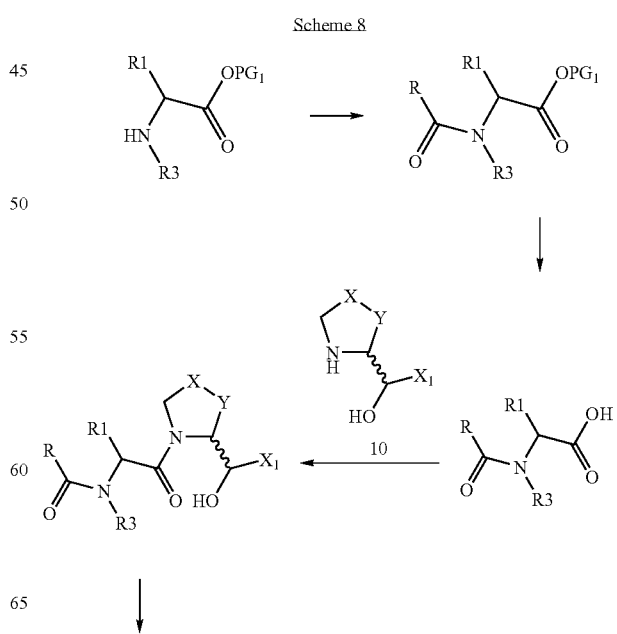

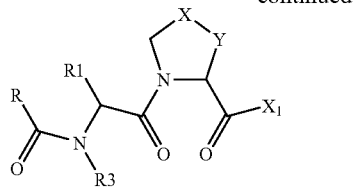

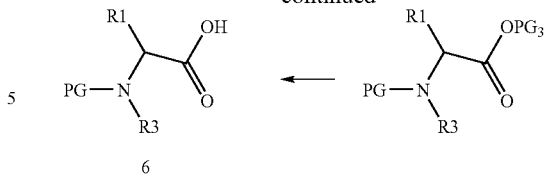

When the A group of 8 is a boronic acid this is protected as an ester by protecting groups described in the literature such as pinanediol esters. This protecting group is removed by methods described in the literature such as sodium metaperiodate/ammonium acetate or phenylboronic acid giving the compounds of the invention (Scheme 9).

Scheme 9

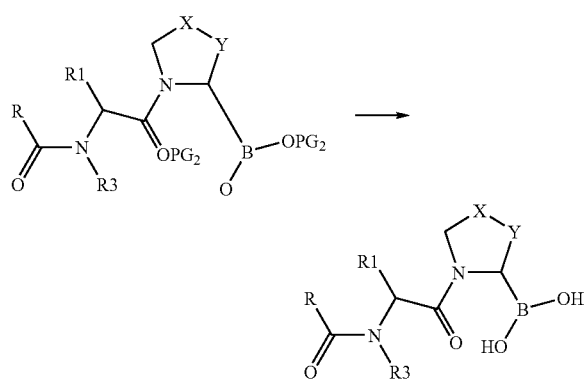

When the R3 group of the alpha amino acid 6 is not hydrogen the required amino acid is prepared from the carboxyl protected amino acid by reductive amination of the free amino group with an aldehyde and either sodium cyanoborohydride or sodium triacetoxyborohydride or similar reagent (Scheme 10) This is followed by protection of the amino function and deprotection of the carboxyl function using standard methods to give the required amino acids. The carboxylic acid is protected as an ester such as methyl, benzyl or tert-butyl. The amine is protected with a standard protecting group such as tert-butyloxycarbonyl (BOC), benzyloxycarbonyl (Z) or 9-fluorenylmethyloxycarbonyl (Fmoc). The use of such groups is well known in the art. Where R1 has a reactive functional group such as an amine or a carboxylic acid, this group will also be protected Scheme 10

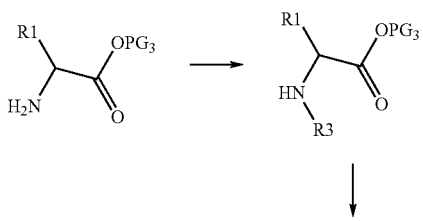

The nitrogen containing heterocycle derivatives are either known compounds or can be prepared by simple modification of published synthetic routes.

The general methods are further illustrated in the following, non-limiting examples. These examples shall not be construed as a limitation of how the invention may be practiced.

Examples of Q being CN are provided in Examples E1-E24, E34-E61 and Tables 1-23. Examples of Q being $B(OH)_2$ are provided in Examples E29-E30. Examples of Q being $C(=O)X^1$ are provided in Examples E31-E33 and E62-E66. Examples of Q being H are provided in Examples E25-E28 and Tables 24-25.

All citations are incorporated by reference.

The compounds were tested for protease (FAP, DPIV, DP8 and DP9) inhibitory activity using a fluorogenic assay utilising dipeptide-AFC substrates. For example, DPIV inhibitory activity was measured using H-Ala-Pro-AFC as a substrate using a method described in WO 9515309. The particularly preferred compounds were competitive inhibitors with $IC_{50}$ of <1 μM for FAP and $IC_{50}$>1 μM for DPIV, DP8 and DP9.

The following abbreviations have been used:
Bu Butyl
Ch Cyclohexyl
DMF N,N-Dimethylformamide
Fmoc 9-Fluorenylmethyloxycarbonyl
h Hours
Hex Hexyl
HBTU 2-(1H-Benzotriazole-1-yl)-1,1,3,3-tetramethyluronium hexafluorophosphate
iBu Iso-Butyl
iPr Iso-Propyl
min Minutes
MS Mass spectrum
Nuclear magnetic resonance spectrum—NMR
NMR spectra were recorded at a frequency of 270 MHz unless otherwise indicated
Oic Octahydroindole-2-carboxyl
Pet. Petroleum ether fraction boiling at 60 ether 80° C.
Pic Pipecolinyl
Pr Propyl
PyBOP® Benzotriazole-1-yl-oxy-tris-pyrrolidino-phosphonium hexafluorophosphate
PyBroP® Bromo-tris-pyrrolidino-phosphonium hexafluorophosphate
THF Tetrahydrofuran
Tic 1,2,3,4-Tetrahydroisoquinoline-3-carboxyl

EXAMPLE E1

(2S)-1-((2'S)-2'-(2-Methoxybenzoylamino)-3'-methylpentanoyl)pyrrolidine-2-carbonitrile A. (2S)-1-((2'S)-2'-(tert-Butyloxycarbonylamino)-3'-methylpentanoyl)pyrrolidine-2-carboxamide $N^\alpha$-(tert-Butyloxycarbonyl)-L-isoleucine (4.2 g, 18.2 mmol) was dissolved in $CH_2Cl_2$/DMF (9:1, 100 ml). The solution was cooled to 0° C., L-prolinamide (2.5 g, 21.7 mmol), 1-hydroxybenzotriazole hydrate (4.9 g, 36.2 mmol) and water soluble carbodiimide (4.4 g, 22.0 mmol) were added and after 15 min the pH adjusted to pH9 with triethylamine. After 18 h at 0° C. to room temperature the solvent was removed in vacuo and the residue was taken up in ethyl acetate (200 ml). The solution was washed with 0.3M $KHSO_4$, sat. $NaHCO_3$, water and brine, dried ($Na_2SO_4$) and evaporated in vacuo. The residue was purified by flash chromatography (eluant: 2% methanol, 98% chloroform) to give a colourless oil identified as the title compound (4.8 g, 14.58 mmol, 80%).

B. (2S)-1-((2'S)-2'-(tert-Butyloxycarbonylamino)-3'-methylpentanoyl)pyrrolidine-2-carbonitrile (2S)-1-((2S)-2-(tert-Butyloxycarbonylamino)-3-methylpentanoyl)pyrrolidine-2-carboxamide (4.8 g, 14.58 mmol) was dissolved in dry THF (100 ml). The solution was cooled to 0° C., triethylamine (2.8 g, 28 mmol) was added followed by the slow addition of trifluoroacetic anhydride (6.8 g, 32.4 mmol). The pH was adjusted to pH9 with triethylamine. After 30 min the reaction mixture was diluted with ethyl acetate (100 ml). The solution was washed with 0.3M $KHSO_4$, sat. $NaHCO_3$, water and brine, dried ($Na_2SO_4$) and evaporated in vacuo. The residue was purified by flash chromatography (eluant: 60% Pet. ether, 40% ethyl acetate) to give a colourless oil identified as the title compound (3.4 g, 11.0 mmol, 75%).

C. (2S)-1-((2'S)-2'-(2-Methoxybenzoylamino)-3'-methylpentanoyl)pyrrolidine-2-carbonitrile (2S)-1-((2S)-2-(tert-Butyloxycarbonylamino)-3-methylpentanoyl)pyrrolidine-2-carbonitrile (1.51 g, 4.88 mmol) was treated with trifluoroacetic acid (50 ml). After 1 h at room temperature the solvent was removed in vacuo and the residue dissolved in $CH_2Cl_2$ (100 ml). The solution was cooled to 0° C., triethylamine (980 mg, 9.8 mmol) was added followed by 2-anisoyl chloride (920 mg, 5.4 mmol). After 18 h at 0° C. to room temperature the solvent was removed in vacuo and the residue dissolved in ethyl acetate (200 ml). This solution was washed with 0.3M $KHSO_4$, sat. $NaHCO_3$, water and brine, dried ($Na_2SO_4$) and evaporated in vacuo. The residue was purified by flash chromatography (eluant: 60% Pet. ether, 40% ethyl acetate) to give a colourless oil identified as the title compound (1.53 g, 4.46 mmol, 91%).

EXAMPLE E2

(2S)-1-((2'S)-2'-(Ethylcarbamoylamino)-3'-methylpentanoyl)pyrrolidine-2-carbonitrile (2S)-1-((2S)-2-(tert-Butyloxycarbonylamino)-3-methylpentanoyl)pyrrolidine-2-carbonitrile (3.28 g, 10.2 mmol) was treated with trifluoroacetic acid (50 ml). After 1 h at room temperature the solvent was removed in vacuo and the residue dissolved in $CH_2Cl_2$ (100 ml). The solution was cooled to 0° C., triethylamine (2.5 g, 25 mmol) was added followed by ethylisocyanate (810 mg, 11.4 mmol). After 18 h at 0° C. to room temperature the solvent was removed in vacuo and the residue dissolved in ethyl acetate (200 ml). This solution was washed with 0.3M $KHSO_4$, sat. $NaHCO_3$, water and brine, dried ($Na_2SO_4$) and evaporated in vacuo. The residue was recrystallised from Pet. ether and ethyl acetate to give a white solid identified as the title compound (2.58 g, 9.21 mmol, 87%).

EXAMPLE E3

(2S)-1-((2'S)-2'-(3-Methoxybenzoylamino)-3'-methylpentanoyl)pyrrolidine-2-carbonitrile (2S)-1-((2S)-2-Amino-3-methylpentanoyl)pyrrolidine-2-carbonitrile hydrochloride (50 mg, 0.2 mmol) was dissolved in $CH_2Cl_2$ (100 ml). The solution was cooled to 0° C., triethylamine (50 mg, 0.5 mmol) was added followed by 3-anisoyl chloride (38 mg, 0.22 mmol). After 18 h at 0° C. to room temperature the solvent was removed in vacuo and the residue dissolved in ethyl acetate (200 ml). This solution was washed with 0.3M $KHSO_4$, sat. $NaHCO_3$, water and brine, dried ($Na_2SO_4$) and evaporated in vacuo. The residue was purified by flash chromatography (eluant: 60% Pet. ether, 40% ethyl acetate) to give a colourless oil identified as the title compound (59 mg, 0.17 mmol, 86%).

EXAMPLE E4

(2S)-1-((2'S)-2'-(4-Methoxybenzoylamino)-3'-methylpentanoyl)pyrrolidine-2-carbonitrile (2S)-1-((2S)-2-Amino-3-methylpentanoyl)pyrrolidine-2-carbonitrile hydrochloride (50 mg, 0.2 mmol) was dissolved in $CH_2Cl_2$ (100 ml). The solution was cooled to 0° C., triethylamine (50 mg, 0.5 mmol) was added followed by 4-anisoyl chloride (38 mg, 0.22 mmol). After 18 h at 0° C. to room temperature the solvent was removed in vacuo and the residue dissolved in ethyl acetate (200 ml). This solution was washed with 0.3M $KHSO_4$, sat. $NaHCO_3$, water and brine, dried ($Na_2SO_4$) and evaporated in vacuo. The residue was purified by flash chromatography (eluant: 60% Pet. ether, 40% ethyl acetate) to give a colourless oil identified as the title compound (46 mg, 0.13 mmol, 67%).

EXAMPLE E5

(2S)-1-((2'S)-2'-(Pivaloylamino)-3'-methylpentanoyl)pyrrolidine-2-carbonitrile (2S)-1-((2S)-2-Amino-3-methylpentanoyl)pyrrolidine-2-carbonitrile hydrochloride (50 mg, 0.2 mmol) was dissolved in $CH_2Cl_2$ (100 ml). The solution was cooled to 0° C., triethylamine (50 mg, 0.5 mmol) was added followed by pivaloyl chloride (24 mg, 0.20 mmol). After 18 h at 0° C. to room temperature the solvent was removed in vacuo and the residue dissolved in ethyl acetate (200 ml). This solution was washed with 0.3M $KHSO_4$, sat. $NaHCO_3$, water and brine, dried ($Na_2SO_4$) and evaporated in vacuo. The residue was purified by flash chromatography (eluant: 60% Pet. ether, 40% ethyl acetate) to give a colourless oil identified as the title compound (37 mg, 0.13 mmol, 63%).

EXAMPLE E6

(2S)-1-((2'S)-1'-(3-Methoxybenzoyl)pyrrolidine-2'-carbonyl)pyrrolidine-2-carbonitrile A. (2S)-1-((2'S)-1'-(tert-Butyloxycarbonylamino)pyrrolidine-2'-carbonyl)pyrrolidine-2-carboxamide $N^\alpha$-(tert-Butyloxycarbonyl)-L-proline (5.0 g, 23.26 mmol) was dissolved in $CH_2Cl_2$/DMF (9:1, 100 ml). The solution was cooled to 0° C., L-prolinamide (2.9 g, 25.2 mmol) 1-hydroxybenzotriazole hydrate (6.3 g, 46.7 mmol) and water soluble carbodiimide (5.6 g, 28.0 mmol) were added and after 15 min the pH adjusted to pH9 with triethylamine. After 18 h at 0° C. to room temperature the solvent was removed in vacuo and the residue was taken up in ethyl acetate (200 ml). This solution was washed with 0.3M KHSO$_4$, sat. NaHCO$_3$, water and brine, dried (Na$_2$SO$_4$) and evaporated in vacuo. The residue was purified by flash chromatography (eluant: 9% methanol, 91% chloroform) to give a colourless oil identified as the title compound (5.36 g, 17.2 mmol, 74%).

B. (2S)-1-((2'S)-1'-(tert-Butyloxycarbonylamino) pyrrolidine-2'-carbonyl)pyrrolidine-2-carbonitrile (2S)-1-((2S)-1-(tert-Butyloxycarbonylamino) pyrrolidine-2-carbonyl)pyrrolidine-2-carboxamide (5.26 g, 16.4 mmol) was dissolved in dry THF (100 ml). The solution was cooled to 0° C., triethylamine (3.3 g, 33 mmol) was added followed by the slow addition of trifluoroacetic anhydride (7.8 g, 37.1 mmol). The pH was adjusted to pH9 with triethylamine. After 30 min the reaction mixture was diluted with ethyl acetate (100 ml), washed with water and brine, dried (Na$_2$SO$_4$) and evaporated in vacuo. The residue was purified by flash chromatography (eluant: 4% methanol, 96% chloroform) to give a colourless oil identified as the title compound (3.9 g, 13.3 mmol, 79%).

C. (2S)-1-((2'S)-1'-(3-Methoxybenzoyl)pyrrolidine-2-carbonyl)pyrrolidine-2'-carbonitrile (2S)-1-((2S)-1-(tert-Butyloxycarbonylamino)pyrrolidine-2-carbonyl)pyrrolidine-2-carbonitrile (3.8 g, 12.9 mmol) was treated with trifluoroacetic acid (50 ml). After 1 h at room temperature the solvent was removed in vacuo and the residue dissolved in CH$_2$Cl$_2$ (100 ml). The solution was cooled to 0° C., triethylamine (2.7, 27 mmol) was added followed by 3-anisoyl chloride (2.51 g, 14.7 mmol). After 18 h at 0° C. to room temperature the solvent was removed in vacuo and the residue dissolved in ethyl acetate (200 ml). This solution was washed with 0.3M KHSO$_4$, sat. NaHCO$_3$, water and brine, dried (Na$_2$SO$_4$) and evaporated in vacuo. The residue was purified by flash chromatography (eluant: 3% methanol, 97% chloroform) to give an orange oil identified as the title compound (3.6 g, 11.6 mmol, 85%).

EXAMPLE E7

(2S)-1-((2'S)-1'-(Isopropylcarbamoyl)pyrrolidine-2-carbonyl)pyrrolidine-2-carbonitrile (2S)-1-((2S)-1-(tert-Butyloxycarbonylamino)pyrrolidine-2-carbonyl)pyrrolidine-2-carbonitrile (1.43 g, 4.88 mmol) was treated with trifluoroacetic acid (50 ml). After 1 h at room temperature the solvent was removed in vacuo and the residue dissolved in CH$_2$Cl$_2$ (100 ml). The solution was cooled to 0° C., triethylamine (980 mg, 9.8 mmol) was added followed by isopropylisocyanate (515 mg, 6.65 mmol). After 18 h at 0° C. to room temperature the solvent was removed in vacuo and the residue dissolved in ethyl acetate (200 ml). This solution was washed with 0.3M KHSO$_4$, sat. NaHCO$_3$, water and brine, dried (Na$_2$SO$_4$) and evaporated in vacuo. The residue was purified by flash chromatography (eluant: 4% methanol, 96% chloroform) to give a colourless oil identified as the title compound (1.29 g, 4.65 mmol, 95%).

EXAMPLE E8

(2S)-1-((2'S)-2'-(2-Methoxybenzoylamino)-3',3'-dimethylbutanoyl)pyrrolidine-2-carbonitrile (2S)-1-((2S)-2-Amino-3,3-dimethylbutanoyl)pyrrolidine-2-carbonitrile hydrochloride (150 mg, 0.61 mmol; prepared according to Jenkins et al., WO 9515309) was dissolved in CH$_2$Cl$_2$ (40 ml). The solution was cooled to 0° C., triethylamine (120 mg, 1.2 mmol) was added followed by 2-anisoyl chloride (120 mg, 0.7 mmol). After 18 h at 0° C. to room temperature the solvent was removed in vacuo and the residue dissolved in ethyl acetate (200 ml). This solution was washed with 0.3M KHSO$_4$, sat. NaHCO$_3$, water and brine, dried (Na$_2$SO$_4$) and evaporated in vacuo. The residue was purified by flash chromatography (eluant: 60% Pet. ether, 40% ethyl acetate) to give a white solid identified as the title compound (172 mg, 0.5 mmol, 82%).

EXAMPLE E9

(2S)-1-((2'S)-1'-(3-Chlorobenzoyl)pyrrolidine-2'-carbonyl)pyrrolidine-2-carbonitrile A. Synthesis of Fmoc-Pro-Sieber Resin Fmoc-Sieber resin (1 g, 0.6 mmol/g substitution) was swollen with CH$_2$Cl$_2$ for 10 min. The resin was further washed with DMF three times. The Fmoc-group was removed with 20% piperidine in DMF for 30 min. Further repeated washings were done with DMF (3×2 min), CH$_2$Cl$_2$ (3×2 min), and DMF (1×1 min). Then Fmoc-L-proline (1.5 mmol, 2.5 equivalents with respect to resin loading), PyBop® (1.5 mmol) and diisopropylethylamine (3.0 mmol) together in DMF (10 ml) were added to the resin. The resin was shaken at room temperature for 60 min. A small sample of resin was subjected to Kaiser test for the completion of reaction. The resin was filtered and washed with DMF (3×2 min), CH$_2$Cl$_2$ (2×2 min), MeOH (2×2 min), CH$_2$Cl$_2$ (2×2 min) and MeOH (3×2 min).

B. Synthesis of Fmoc-Pro-Pro-Sieber Resin

Resin from step A was swollen with CH$_2$Cl$_2$ (1×10 min) then further washed with DMF three times. The Fmoc group was removed with 20% piperidine in DMF for 30 min. Further resin washings were done with DMF (3×2 min), CH$_2$Cl$_2$ (3×2 min) and DMF (1×1 min). Then Fmoc-L-Proline (1.5 mmol, 2.5 equivalents with respect to initial resin loading), PyBop® (1.5 mmol) and diisopropylethylamine (3 mmol) together in DMF (10 ml) were added to the resin. The resin was shaken at room temperature for 60 min. A small sample of resin was submitted for isatin test for completion of reaction. The resin was filtered and washed with DMF (3×2 min), CH$_2$Cl$_2$ (2×2 min), MeOH (2×2 min), CH$_2$Cl$_2$ (2×2 min) and MeOH (3×2 min).

C. Synthesis of 3-chlororobenzoyl-Pro-Pro-Sieber Resin

Resin from step B was swollen with CH$_2$Cl$_2$ (1×10 min). The resin was further washed with DMF three times. The Fmoc group was removed with 20% piperidine in DMF for 30 min. Further resin washings were done with DMF (3×2 min) and CH$_2$Cl$_2$ (3×2 min). Then 3-chlorobenzoyl chloride (1.5 mmol, 2.5 equivalents with respect to original resin loading) and diisopropylethylamine (3 mmol) were added in CH$_2$Cl$_2$ (10 ml) were added to the resin. The resin was shaken at room temperature for 18 h. A small sample was subjected to isatin test for completion of reaction. The resin was filtered and washed with CH$_2$Cl$_2$ (3×2 min), MeOH (2×2 min), CH$_2$Cl$_2$ (2×2 min), and MeOH (2×2 min).

D. (2S)-1-((2'S)-1'-(3-Chlorobenzoyl)pyrrolidine-2'-carbonyl)pyrrolidine-2-carbonitrile Resin from step C was swollen with CH$_2$Cl$_2$ (12 ml). Then trifluoroacetic anhydride (3 mmol, 5 equivalents with respect to initial resin) and pyridine (6 mmol) were added to the resin. The resin shaken at room temperature for 18 h. Resin filtered, washed CH$_2$Cl$_2$. The solvent was removed in vacuo and the residue dissolved in ethyl acetate (70 ml). This solution was washed with 0.3M KHSO$_4$, water, 1M NaHCO$_3$, water and brine, dried (Na$_2$SO$_4$) and evaporated in vacuo, the residue was lyophilised from acetonitrile/water to yield an orange oil identified as the title compound (150 mg, 0.45 mmol).

EXAMPLE E10

(2S)-1-((2'S)-2'-(3-Methoxybenzoylamino)-4'-methylpentanoyl)pyrrolidine-2-carbonitrile

A. Synthesis of Boc-Leu-Pro-Sieber Resin 2 g of resin synthesised as described for step A of Example E9 was swollen with CH$_2$Cl$_2$ (1×10 min) then further washed with DMF three times. The Fmoc group was removed with 20% piperidine in DMF for 30 min. Further resin washings were done with DMF (3×2 min), CH$_2$Cl$_2$ (3×2 min) and DMF (1×1 min). Then Boc-L-leucine (3 mmol, 2.5 equivalents with respect to initial resin loading), PyBop® (3 mmol) and diisopropylethylamine (6 mmol) together in DMF (20 ml) were added to the resin. The resin was shaken at room temperature for 60 min. A small sample of resin was submitted for isatin test for completion of reaction. The resin was filtered and washed with DMF (3×2 min), CH$_2$Cl$_2$ (2×2 min), MeOH (2×2 min), CH$_2$Cl$_2$ (2×2 min) and MeOH (3×2 min).

B. (2S)-1-((2'S)-2'-(tert-Butyloxycarbonylamino)-4'-methylpentanoyl)pyrrolidine-2-carbonitrile Resin from step C was swollen with CH$_2$Cl$_2$ (6 ml). Then trifluoroacetic anhydride (6 mmol, 5 equivalents with respect to initial resin) and 12 mmol of pyridine were added to the resin. Resin shaken at room temperature for 18 h. Resin filtered, washed CH$_2$Cl$_2$. The solvent was removed in vacuo and the residue dissolved in ethyl acetate (70 ml). This solution was washed with 0.3M KHSO$_4$, water, 1M NaHCO$_3$, water and brine, dried (Na$_2$SO$_4$) and evaporated in vacuo, the residue was lyophilised from acetonitrile/water to yield an orange oil identified as the title compound (220 mg, 0.72 mmol, 60%).

C. (2S)-1-((2'S)-2'-(3-Methoxybenzoylamino)-4'-methylpentanoyl)pyrrolidine-2-carbonitrile (2S)-1-((2S)-2-(tert-Butyloxycarbonylamino)-4-methylpentanoyl)pyrrolidine-2-carbonitrile (50 mg, 0.16 mmol) was treated with trifluoroacetic acid (5 ml). After 1 h at room temperature the solvent was removed in vacuo and the residue dissolved in CH$_2$Cl$_2$ (5 ml). The solution was cooled to 0° C., triethylamine (32 mg, 0.32 mmol) was added followed by 3-anisoyl chloride (30 mg, 0.176 mmol). After 18 h at 0° C. to room temperature the solvent was removed in vacuo and the residue dissolved in ethyl acetate (70 ml). This solution washed with 0.3M KHSO$_4$, sat. NaHCO$_3$, water and brine, dried (Na$_2$SO$_4$) and evaporated in vacuo. The residue was purified by flash chromatography (eluant: 60% Pet. ether, 40% ethyl acetate) to give a colourless oil identified as the title compound (35 mg, 0.10 mmol, 64%).

EXAMPLE E11

(2S)-1-((2'S)-2'-(2''-Phenylethylthiocarbamoylamino)-3'-methylpentanoyl)pyrrolidine-2-carbonitrile (2S)-1-((2S)-2-(2-Amino)-3-methylpentanoyl)pyrrolidine-2-carbonitrile hydrochloride (75 mg, 0.3 mmol) was dissolved in CH$_2$Cl$_2$ (20 ml). To this solution was added triethylamine (100 mg, 1.0 mmol) followed by 2-phenylethylisothiocyanate (50 mg, 0.31 mmol). After 18 h at room temperature the solvent was removed in vacuo and the residue dissolved in ethyl acetate (70 ml). This solution was washed with 0.3M KHSO$_4$, sat. NaHCO$_3$, water and brine, dried (Na$_2$SO$_4$) and evaporated in vacuo. The residue was purified by flash chromatography (eluant: 20% Pet. ether, 80% ethyl acetate) to give a white solid identified as the title compound (86 mg, 0.23 mmol, 76%).

EXAMPLE E12

(2S)-1-((2'S)-1'-(Propylthiocarbamoyl)pyrrolidine-2'-carbonyl)pyrrolidine-2-carbonitrile (2S)-1-((2S)-1-(2-tert-Butyloxycarbonylamino)pyrrolidine-2-carbonyl)pyrrolidine-2-carbonitrile (160 mg, 0.55 mmol) was treated with trifluoroacetic acid (50 ml). After 1 h at room temperature the solvent was removed in vacuo and the residue dissolved in CH$_2$Cl$_2$ (20 ml). Triethylamine (150 mg, 1.5 mmol) was added followed by n-propylisothiocyanate (55 mg, 0.5 mmol). After 18 h at room temperature the solvent was removed in vacuo and the residue dissolved in ethyl acetate (70 ml). This solution was washed with 0.3M KHSO$_4$, sat. NaHCO$_3$, water and brine, dried (Na$_2$SO$_4$) and evaporated in vacuo. The residue was purified by flash chromatography (eluant: 20% Pet. ether, 80% ethyl acetate) to give a white solid identified as the title compound (55 mg, 0.19 mmol, 34%).

EXAMPLE E13

(2S)-1-(2'-(N-(2-Methoxybenzoyl)-N-(2-methylpropyl)amino)acetyl)pyrrolidine-2-carbonitrile

A. N$^\alpha$-(2-Methylpropyl)glycine methyl ester

Glycine methylester hydrochloride (2.0 g, 16.0 mmol) was dissolved in MeOH/AcOH (9:1, 25 ml). Triethylamine (1.8 g, 18.0 mmol) was added followed by 2-butanone (1.3 g, 18.0 mmol). After 2 h at room temperature sodium triacetoxyborohydride (3.81 g, 18.0 mmol) was added. After 18 h at room temperature the solvent was removed in vacuo and the residue was taken up in chloroform (200 ml). This solution was washed with sat. NaHCO$_3$, water and brine, dried (Na$_2$SO$_4$) and evaporated in vacuo to give a colourless oil identified as the title compound (646 mg, 4.46 mmol, 28%).

B. N$^\alpha$-(tert-Butyloxycarbonyl)-N$^\alpha$-(2-methylpropyl) glycine methyl ester N)-(2-Methylpropyl)glycine methyl ester (646 mg, 4.45 mmol) was dissolved in CH$_2$Cl$_2$ (25 ml). Triethylamine (560 mg, 5.6 mmol) was added followed by di-tertbutyl dicarbonate (1.07 g, 4.90 mmol). After 18 h at room temperature N,N-dimethylethylenediamine (1 ml) was added, the solvent was removed in vacuo and the residue was taken up in chloroform (100 ml). This solution was washed with 0.3M KHSO$_4$, sat. NaHCO$_3$, water and brine, dried (Na$_2$SO$_4$) and evaporated in vacuo to give an amber oil identified as the title compound (960 mg, 3.92 mmol, 88%).

C. N$^\alpha$-(tert-Butyloxycarbonyl)-N$^\alpha$-(2-methylpropyl) glycine

N$^\alpha$-(tert-Butyloxycarbonyl)-N$^\alpha$-(2-methylpropyl) glycine methyl ester (960 mg, 3.91 mmol) was dissolved in THF/H$_2$O (9:1, 25 ml). Lithium hydroxide monohydrate (492 mg, 11.7 mmol) was added. After 18 h at room temperature the reaction mixture was diluted with ethyl acetate (100 ml). This solution was washed with 1M HCl, water and brine, dried (Na$_2$SO$_4$) and evaporated in vacuo to give a colourless oil identified as the title compound (360 mg, 1.56 mmol, 40%).

D. (2S)-1-(2'-(N-tert-Butyloxycarbonyl-N-(2-methylpropyl)amino)acetyl)pyrrolidine-2-carboxamide N$^\alpha$-(tert-Butyloxycarbonyl)-N$^\alpha$-(2-methylpropyl) glycine (360 mg, 1.56 mmol) was dissolved in CH$_2$Cl$_2$/DMF (9:1, 20 ml). The solution was cooled to 0° C., L-prolinamide hydrochloride (282 mg, 1.87 mmol), 1-hydroxybenzotriazole hydrate (295 mg, 2.18 mmol) and water soluble carbodiimide (358 mg, 1.87 mmol) were added and after 15 min the pH adjusted to pH9 with triethylamine. After 18 h at 0° C. to room temperature the solvent was removed in vacuo and the residue was taken up in ethyl acetate (100 ml). This solution was washed with 0.3M KHSO$_4$, sat. NaHCO$_3$, water and brine, dried (Na$_2$SO$_4$) and evaporated in vacuo. The residue was purified by flash chromatography (eluant: 4% methanol, 94% chloroform, 2% triethylamine) to give a colourless oil identified as the title compound (330 mg, 1.01 mmol, 65%).

E. (2S)-1-(2'-(N-tert-Butyloxycarbonyl-N-(2-methylpropyl)amino)acetyl)pyrrolidine-2-carbonitrile (2S)-1-(2-(N-tert-Butyloxycarbonyl-N-(2-methylpropyl) amino)acetyl)pyrrolidine-2-carboxamide (330 mg, 1.01 mmol) was dissolved in dry THF (20 ml). The solution was cooled to 0° C., triethylamine (210 mg, 2.1 mmol) was added followed by the slow addition of trifluoroacetic anhydride (460 g, 2.2 mmol). The pH was adjusted to pH9 with triethylamine. After 30 min the reaction mixture was diluted with ethyl acetate (100 ml), washed with water and brine, dried (Na$_2$SO$_4$) and evaporated in vacuo. The residue was purified by flash chromatography (eluant: 3% methanol, 97% chloroform) to give an orange oil identified as the title compound (156 mg, 0.50 mmol, 50%).

F. (2S)-1-(2'-(N-(2-Methoxybenzoyl)-N-(2-methylpropyl)amino)acetyl)pyrrolidine-2-carbonitrile (2S)-1-(2-(N-tert-Butyloxycarbonyl-N-(2-methylpropyl) amino)acetyl)pyrrolidine-2-carbonitrile (25 mg, 0.081 mmol) was treated with trifluoroacetic acid (50 ml). After 1 h at room temperature the solvent was removed in vacuo and the residue dissolved in CH$_2$Cl$_2$ (100 ml). The solution was cooled to 0° C., triethylamine (30 mg, 0.3 mmol) was added followed by 2-anisoyl chloride (15 mg, 0.088 mmol). After 18 h at 0° C. to room temperature the solvent was removed in vacuo and the residue dissolved in ethyl acetate (200 ml). This solution was washed with 0.3M KHSO$_4$, sat. NaHCO$_3$, water and brine, dried (Na$_2$SO$_4$) and evaporated in vacuo. The residue was purified by flash chromatography (eluant: 2% methanol, 98% chloroform) to give a colourless oil identified as the title compound (18 mg, 0.052 mmol, 66%).

EXAMPLE E14

(2S)-1-((2'S)-2'-(2-Methoxybenzoylamino)-5'-amino-pentanoyl)pyrrolidine-2-carbonitrile (2S)-1-((2S)-2-(2-Methoxybenzoylamino)-5-(9-fluorenylmethyloxycarbonyl carbonylamino) pentanoyl)pyrrolidine-2-carbonitrile (200 mg, 0.35 mmol) prepared by the method described for Example E10 was dissolved in acetonitrile (10 ml), diethylamine (10 ml) was added. After 90 min at room temperature the solvent was removed in vacuo. The residue was purified by flash chromatography (eluant: 1% triethylamine, 5% methanol, 94% chloroform) to give a colourless oil identified as the title compound (99 mg, 0.28 mmol, 80%).

EXAMPLE E15

(2S)-1-((2'S)-2'-(2-Methoxybenzoylamino)-6'-amino-hexanoyl)pyrrolidine-2-carbonitrile (2S)-1-((2S)-2-(2-Methoxybenzoylamino)-6-(9-fluorenylmethyloxycarbonyl carbonylamino) hexanoyl)pyrrolidine-2-carbonitrile (176 mg, 0.3 mmol) prepared by the method described for Example E10 was dissolved in acetonitrile (10 ml), diethylamine (10 ml) was added. After 90 min at room temperature the solvent was removed in vacuo. The residue was purified by flash chromatography (eluant: 1% triethylamine, 5% methanol, 94% chloroform) to give a colourless oil identified as the title compound (78 mg, 0.22 mmol, 73%).

EXAMPLE E16

(4R)-1-((2'S)-2'-(3-Methoxybenzoylamino)-3'-methylpentanoyl)thiazolidine-4-carbonitrile A. (4R)-3-(tert-Butyloxycarbonyl)thiazolidine-4-carboxamide (4R)-3-(tert-Butyloxycarbonyl)thiazolidine-4-carboxylic acid (12.5 g, 54.1 mmol) was dissolved in CH$_2$Cl$_2$/DMF (9:1, 150 ml). To this solution at 0° C. was added 1-hydroxybenzotriazole hydrate (14.6 g, 108 mmol) and water-soluble carbodiimide (13.0 g, 65 mmol). After 1 h at 0° C. ammonia (35%, 50 ml) was added. After 18 h at 0° C. to room temperature the solvent was removed in vacuo and the residue was taken up in ethyl acetate (500 ml). This solution was washed with 0.3M KHSO$_4$, sat. NaHCO$_3$, water and brine, dried (Na$_2$SO$_4$) and evaporated in vacuo. The residue was purified by flash chromatography (eluant: 2% methanol, 98% chloroform) to give a colourless oil identified as the title compound (8.9 g, 38.4 mmol, 71%).

B. (4R)-Thiazolidine-4-carboxamide hydrochloride (4R)-3-(tert-Butyloxycarbonyl)thiazolidine-4-carboxamide (8.6 g, 37.1 mmol) was dissolved in 4M HCl/dioxan (50 ml). After 1 h at room temperature the solvent was evaporated in vacuo to give a white solid identified as the title compound (6.2 g, 36.8 mmol, 99%).

C. (4R)-1-((2'S)-2'-(2-tert-Butyloxycarbonylamino)-3'-methylpentanoyl)-thiazolidine-4-carboxamide N$^\alpha$-(tert-Butyloxycarbonyl)-L-isoleucine (1.37 g, 5.9 mmol) was dissolved in CH$_2$Cl$_2$/DMF (9:1, 100 ml). The solution was cooled to 0° C., (4R)-thiazolidine-4-carboxamide hydrochloride (1 g, 5.9 mmol), 1-hydroxybenzotriazole hydrate (920 mg, 6.8 mmol) and water soluble carbodiimide (1.4 g, 7.0 mmol) were added and after 15 min the pH adjusted to pH9 with triethylamine. After 18 h at 0° C. to room temperature the solvent was removed in vacuo and the residue was taken up in ethyl acetate (200 ml). This solution was washed with 0.3M KHSO$_4$, sat. NaHCO$_3$, water and brine, dried (Na$_2$SO$_4$) and evaporated in vacuo. The residue was purified by flash chromatography (eluant: 4% methanol, 96% chloroform) to give a colourless oil identified as the title compound (1.65 g, 4.8 mmol, 82%).

D. (4R)-1-((2'S)-2'-(2-tert-Butyloxycarbonylamino)-3'-methylpentanoyl)thiazolidine-4-carbonitrile ((4R)-1-((2S)-2-(2-tert-Butyloxycarbonylamino)-3-methylpentanoyl)thiazolidine-4-carboxamide (1.3 g, 3.76 mmol) was dissolved in dry THF (100 ml). The solution was cooled to 0° C., triethylamine (750 mg, 7.5 mmol) was added followed by the slow addition of trifluoroacetic anhydride (1.7 g, 8.1 mmol). The pH was adjusted to pH9 with triethylamine. After 30 min the reaction mixture was diluted with ethyl acetate (100 ml), washed with water and brine, dried (Na$_2$SO$_4$) and evaporated in vacuo. The residue was purified by flash chromatography (eluant: 80% Pet. ether, 20% ethyl acetate) to give a yellow oil identified as the title compound (321 mg, 0.98 mmol, 26%).

E. (4R)-1-((2'S)-2'-(3-Methoxybenzoylamino)-3'-methylpentanoyl)thiazolidine-4-carbonitrile (4R)-1-((2S)-2-(2-tert-Butyloxycarbonylamino)-3-methylpentanoyl)thiazolidine-4-carbonitrile (50 mg, 0.15 mmol) was treated with trifluoroacetic acid (50 ml). After 1 h at room temperature the solvent was removed in vacuo and the residue dissolved in CH$_2$Cl$_2$ (100 ml). The solution was cooled to 0° C., triethylamine (40 mg, 0.4 mmol) was added followed by 3-anisoyl chloride (26 mg, 0.15 mmol). After 18 h at 0° C. to room temperature the solvent was removed in vacuo and the residue dissolved in ethyl acetate (200 ml). This solution was washed with 0.3M KHSO$_4$, sat. NaHCO$_3$, water and brine, dried (Na$_2$SO$_4$) and evaporated in vacuo. The residue was purified by flash chromatography (eluant: 60% Pet. ether, 40% ethyl acetate) to give a colourless oil identified as the title compound (20 mg, 0.055 mmol, 37%).

EXAMPLE E17

(2S)-1-((2'S)-2'-(2-Methoxybenzoylamino)-3'-methylbutanoyl)-4,4-difluoropyrrolidine-2-carbonitrile

A. Methyl-(2S)—N-(tert-butyloxycarbonyl)pyrrolid-4-one-2-carboxylate

N-(tert-Butyloxycarbonyl)-L-4-trans-hydroxyproline methyl ester (2.5 g, 10.2 mmol) was dissolved in CH$_2$Cl$_2$ (70 ml). Dess-Martin periodinane (5.0 g, 12.1 mmol) was added. After 3 h at room temperature the solvent was removed in vacuo and the residue was taken up in ethyl acetate (300 ml). This solution was washed with sat. NaHCO$_3$, water and brine, dried (Na$_2$SO$_4$) and evaporated in vacuo. The residue was purified by flash chromatography (eluant: 10% ethyl acetate, 90% Pet. ether ° C.) to give a colourless oil identified as the title compound (2.4 g, 9.7 mmol, 95%).

B. Methyl (2S)—N-(tert-butyloxycarbonyl)-4,4-difluoropyrrolidine-2-carboxylate Methyl (2S)—N-(tert-butyloxycarbonyl)pyrrolidin-4-one-2-carboxylate (2.3 g, 9.3 mmol) was dissolved in CH$_2$Cl$_2$ (70 ml). (Diethylamino)sulphur trifluoride (4.5 g, 27.9 mmol) was added to this solution at 0° C. After 18 hs at 0° C. to room temperature the reaction mixture was carefully poured into sat. NaHCO$_3$ (100 ml) and stirred for 15 min and extracted with CH$_2$Cl$_2$. The organic extract was washed with water and brine, dried (Na$_2$SO$_4$) and evaporated in vacuo. The residue was purified by flash chromatography (eluant: 10% ethyl acetate, 90% Pet. ether ° C.) to give a colourless oil identified as the title compound (2.4 g, 8.9 mmol, 96%).

C. (2S)—N-(tert-Butyloxycarbonyl)-4,4-difluoropyrrolidine-2-carboxylic acid Methyl (2S)—N-(tert-butyloxycarbonyl)-4,4-difluoropyrrolidine-2-carboxylate (2.2 g, 8.3 mmol) was dissolved in THF (100 ml). Aqueous lithium hydroxide (1M, 10.6 ml, 10.6 mmol) was added. After 3 h at room temperature the reaction mixture was diluted with ethyl acetate (150 ml), washed with 1M HCl, water, and brine, dried (Na$_2$SO$_4$) and evaporated in vacuo. The residue was purified by flash chromatography (eluant: 95% chloroform, 4% methanol, 1% acetic acid) to give an orange oil identified as the title compound (2.1 g, 8.3 mmol 100%).

D. (2S)—N-(tert-Butyloxycarbonyl)-4,4-difluoropyrrolidine-2-carboxamide (2S)—N-(tert-Butyloxycarbonyl)-4,4-difluoropyrrolidine-2-carboxylic acid (1.0 g, 4.0 mmol) was dissolved in CH$_2$Cl$_2$/DMF (9:1, 50 ml). To this solution at 0° C. was added 1-hydroxybenzotriazole hydrate (1.1 g, 8.1 mmol) and water soluble carbodiimide (960 mg, 4.8 mmol). After 1 h at 0° C. ammonia (35%, 5 ml) was added. After 18 h at 0° C. to room temperature the solvent was removed in vacuo and the residue was taken up in ethyl acetate (200 ml). This solution was washed with 0.3M KHSO$_4$, sat. NaHCO$_3$, water and brine, dried (Na$_2$SO$_4$) and evaporated in vacuo. The residue was purified by flash chromatography (eluant: 85% ethyl acetate, 15% Pet. ether ° C.) to give a colourless oil identified as the title compound (945 mg, 3.8 mmol, 95%).

E. (2S)-1-((2'S)-2'-(2-tert-Butyloxycarbonylamino)-3'-methylbutanoyl)-4,4-difluoropyrrolidine-2-carboxamide (2S)—N-(tert-Butyloxycarbonyl)-4,4-difluoropyrrolidine-2-carboxamide (530 mg, 2.12 mmol) was dissolved in 4M HCl/dioxan (30 ml) after 1 h at room temperature the solvent was removed in vacuo and the residue dissolved in CH$_2$Cl$_2$/DMF (9:1, 20 ml). To this solution at 0° C. was added e-(tert-butyloxycarbonyl)-L-valine (461 mg, 2.12 mmol), 1-hydroxybenzotriazole hydrate (401 mg, 2.97 mmol) and water-soluble carbodiimide (487 mg, 2.54 mmol). After 15 min at 0° C. the pH was adjusted to pH 8 with N,N-disopropylethylamine. After 18 h at 0° C. to room temperature the reaction mixture was diluted with CHCl$_3$ (70 ml). This solution was washed with 0.3M KHSO$_4$, sat. NaHCO$_3$, water and brine, dried (Na$_2$SO$_4$) and evaporated in vacuo. The residue was purified by flash chromatography (Eluant: 97% chloroform, 2% methanol, 1% triethylamine) to give a white solid identified as the title compound (430 mg, 1.23 mmol, 58%).

F. (2S)-1-((2'S)-2'-(2-tert-Butyloxycarbonylamino)-3'-methylbutanoyl)-4,4-difluoropyrrolidine-2-carbonitrile (2S)-1-((2S)-2-(2-tert-Butyloxycarbonylamino)-3-methylbutanoyl)-4,4-difluoropyrrolidine-2-carboxamide (430 mg, 1.23 mmol) was dissolved in dry THF (100 ml). The solution was cooled to 0° C., triethylamine (246 mg, 2.46 mmol) was added followed by the slow addition of trifluoroacetic anhydride (520 mg, 2.46 mmol). The pH was adjusted to pH9 with triethylamine. After 30 min the reaction mixture was diluted with ethyl acetate (100 ml), washed with water and brine, dried ($Na_2SO_4$) and evaporated in vacuo. The residue was purified by flash chromatography (eluant: 80% Pet. ether, 20% ethyl acetate) to give an orange oil identified as the title compound (323 mg, 0.98 mmol, 79%).

G. (2S)-1-((2'S)-2'-(2-Methoxybenzoylamino)-3'-methylbutanoyl)-4,4-difluoropyrrolidine-2-carbonitrile (2S)-1-((2S)-2-(2-tert-Butyloxycarbonylamino)-3-methylbutanoyl)-4,4-difluoropyrrolidine-2-carbonitrile (31 mg, 0.09 mmol) was treated with trifluoroacetic acid (10 ml). After 1 h at room temperature the solvent was removed in vacuo and the residue dissolved in $CH_2Cl_2$ (20 ml). The solution was cooled to 0° C., triethylamine (30 mg, 0.3 mmol) was added followed by 2-anisoyl chloride (18 mg, 0.11 mmol). After 18 h at 0° C. to room temperature the solvent was removed in vacuo and the residue dissolved in ethyl acetate (200 ml). This solution was washed with 0.3M $KHSO_4$, sat. $NaHCO_3$, water and brine, dried ($Na_2SO_4$) and evaporated in vacuo. The residue was purified by flash chromatography (eluant: 80% Pet. ether, 20% ethyl acetate) to give a colourless oil identified as the title compound (14 mg, 0.04 mmol, 43%).

EXAMPLE E18

(2S)-1-((2'S)-2'-(Ethylcarbamoylamino)-3'-methylbutanoyl)-4,4-difluoropyrrolidine-2-carbonitrile (2S)-1-((2S)-2-(2-tert-Butyloxycarbonylamino)-3-methylbutanoyl)-4,4-difluoropyrrolidine-2-carbonitrile (30 mg, 0.091 mmol) was treated with trifluoroacetic acid (10 ml). After 1 h at room temperature the solvent was removed in vacuo and the residue dissolved in $CH_2Cl_2$ (100 ml). The solution was cooled to 0° C., triethylamine (30 mg, 0.3 mmol) was added followed by ethylisocyanate (8 mg, 0.1 mmol). After 18 h at 0° C. to room temperature the solvent was removed in vacuo and the residue dissolved in ethyl acetate (200 ml). The solution was washed with 0.3M $KHSO_4$, sat. $NaHCO_3$, water and brine, dried ($Na_2SO_4$) and evaporated in vacuo. The residue was purified by flash chromatography (eluant: 1% methanol, 99% chloroform) to give a colourless oil identified as the title compound (18 mg, 0.060 mmol, 66%).

EXAMPLE E19

(2S)-1-((2'S)-1'-(Ethylcarbamoyl)pyrrolidine-2'-carbonyl)-4,4-difluoropyrrolidine-2-carbonitrile

A. (2S)-1-((2'S)-1'-(2-tert-Butyloxycarbonylamino)pyrrolidine-2'-carbonyl)-4,4-difluoropyrrolidine-2-carboxamide (2S)—N-(tert-Butyloxycarbonyl)-4,4-difluoropyrrolidine-2-carboxamide (1.16 g, 4.65 mmol) was dissolved in 4M HCl/dioxan (30 ml) after 1 h at room temperature the solvent was removed in vacuo and the residue dissolved in $CH_2Cl_2$/DMF (9:1, 20 ml). To this solution at 0° C. was added $N^{\alpha}$-(tert-butyloxycarbonyl)-L-proline (1.0 g, 4.65 mmol), 1-hydroxybenzotriazole hydrate (880 mg, 6.65 mmol) and water soluble carbodiimide (1.07 g, 5.35 mmol). After 15 min at 0° C. the pH was adjusted to pH 9 with triethylamine. After 18 h at 0° C. to room temperature the reaction mixture was diluted with chloroform (70 ml). This solution was washed with 0.3M $KHSO_4$, sat. $NaHCO_3$, water and brine, dried ($Na_2SO_4$) and evaporated in vacuo. The residue was purified by flash chromatography (Eluant: 97% chloroform, 2% methanol, 1% triethylamine) to give a white solid identified as the title compound (698 mg, 2.01 mmol, 43%).

B. (2S)-1-((2'S)-1'-(2-tert-Butyloxycarbonylamino)pyrrolidine-2'-carbonyl)-4,4-difluoropyrrolidine-2-carbonitrile (2S)-1-((2S)-1-(2-tert-Butyloxycarbonylamino)pyrrolidine-2-carbonyl)-4,4-difluoropyrrolidine-2-carboxamide (698 mg, 2.01 mmol) was dissolved in dry THF (50 ml). The solution was cooled to 0° C., triethylamine (200 mg, 2.0 mmol) was added followed by the slow addition of trifluoroacetic anhydride (844 mg, 4.02 mmol). The pH was adjusted to pH9 with triethylamine. After 30 min the reaction mixture was diluted with ethyl acetate (100 ml), washed with water and brine, dried ($Na_2SO_4$) and evaporated in vacuo. The residue was purified by flash chromatography (eluant: 80% Pet. ether, 20% ethyl acetate) to give an off-white identified as the title compound (232 mg, 0.708 mmol, 35%).

C. (2S)-1-((2'S)-1'-(Ethylcarbamoyl)pyrrolidine-2'-carbonyl)-4,4-difluoropyrrolidine-2-carbonitrile (2S)-1-((2S)-1-(2-tert-Butyloxycarbonylamino)pyrrolidine-2-carbonyl)-4,4-difluoropyrrolidine-2-carbonitrile (30 mg, 0.09 mmol) was treated with trifluoroacetic acid (50 ml). After 1 h at room temperature the solvent was removed in vacuo and the residue dissolved in $CH_2Cl_2$ (100 ml). The solution was cooled to 0° C., triethylamine (30 mg, 0.3 mmol) was added followed by ethylisocyanate (0.8 mg, 0.01 mmol). After 18 h at 0° C. to room temperature the solvent was removed in vacuo and the residue dissolved in ethyl acetate (200 ml). This solution was washed with 0.3M $KHSO_4$, sat. $NaHCO_3$, water and brine, dried ($Na_2SO_4$) and evaporated in vacuo. The residue was purified by flash chromatography (eluant: 60% Pet. ether, 40% ethyl acetate) to give a colourless oil identified as the title compound (25 mg, 0.083 mmol, 92%).

EXAMPLE E20

(2S)-1-((2'S)-2'-(2-Methoxybenzoylamino)-3'-methylpentanoyl)-3,4-dehydropyrrolidine-2-carbonitrile

A. (2S)—N-(tert-Butyloxycarbonyl)-3,4-dehydrpyrrolidine-2-carboxamide (2S)—N-(tert-Butyloxycarbonyl)-3,4-dehydropyrrolidine-2-carboxylic acid (2.0 g, 9.38 mmol) was dissolved in CH₂Cl₂/DMF (9:1, 50 ml). To this solution at 0° C. was added 1-hydroxybenzotriazole hydrate (1.77 g, 13.1 mmol) and water soluble carbodiimide (2.16 g, 11.26 mmol). After 1 h at 0° C. ammonia (35%, 7 ml) was added. After 18 h at 0° C. to room temperature the reaction mixture was diluted with chloroform (150 ml). This solution was washed with 0.3M KHSO₄, sat. NaHCO₃, water and brine, dried (Na₂SO₄) and evaporated in vacuo. The residue was purified by flash chromatography (eluant: 2% methanol, 98% chloroform) to give a white solid identified as the title compound (1.58 g, 7.4 mmol, 79%).

B. (2S)-3,4-Dehydropyrrolidine-2-carboxamide hydrochloride (2S)—N-(tert-Butyloxycarbonyl)-3,4-dehydropyrrolidine-2-carboxamide (1.58 g, 7.44 mmol) was dissolved in 4M HCl/dioxan (50 ml). After 1 h at room temperature the solvent was evaporated in vacuo to give a white solid identified as the title compound (830 mg, 5.58 mmol, 75%).

C. (2S)-1-((2'S)-2'-(2-tert-Butyloxycarbonylamino)-3'-methylpentanoyl)-3,4-dehydropyrrolidine-2-carboxamide $N^{\alpha}$-(tert-Butyloxycarbonyl)-L-isoleucine (645 mg, 2.79 mmol) was dissolved in CH₂Cl₂/DMF (9:1, 100 ml). The solution was cooled to 0° C., (2S)-3,4-dehydropyrrolidine-2-carboxamide hydrochloride (415 mg, 2.79 mmol), 1-hydroxybenzotriazole hydrate (528 mg, 3.91 mmol) and water soluble carbodiimide (642 mg, 3.35 mmol) were added and after 15 min the pH adjusted to pH9 with triethylamine. After 18 h at 0° C. to room temperature the reaction mixture was diluted with chloroform (100 ml). This solution was washed with 0.3M KHSO₄, sat. NaHCO₃, water and brine, dried (Na₂SO₄) and evaporated in vacuo. The residue was purified by flash chromatography (eluant: 4% methanol, 96% chloroform) to give an amber solid identified as the title compound (648 mg, 1.98 mmol, 71%).

D. (2S)-1-((2'S)-2'-(2-tert-Butyloxycarbonylamino)-3'-methylpentanoyl)-3,4-dehydropyrrolidine-2-carbonitrile (2S)-1-((2S)-2-(2-tert-Butyloxycarbonylamino)-3-methylpentanoyl)-3,4-dehydropyrrolidine-2-carboxamide (648 mg, 1.99 mmol) was dissolved in dry THF (100 ml). The solution was cooled to 0° C., triethylamine (398 mg, 3.98 mmol) was added followed by the slow addition of trifluoroacetic anhydride (836 mg, 3.98 mmol). The pH was adjusted to pH9 with triethylamine. After 30 min the reaction mixture was diluted with ethyl acetate (100 ml), washed with water and brine, dried (Na₂SO₄) and evaporated in vacuo. The residue was purified by flash chromatography (eluant: 100% ethyl acetate) to give a pale yellow solid identified as the title compound (408 mg, 1.33 mmol, 67%).

E. (2S)-1-((2'S)-2'-(2-Methoxybenzoylamino)-3'-methylpentanoyl)-3,4-dehydropyrrolidine-2-carbonitrile (2S)-1-((2S)-2-(2-tert-Butyloxycarbonylamino)-3-methylpentanoyl)-3,4-dehydropyrrolidine-2-carbonitrile (15 mg, 0.05 mmol) was treated with trifluoroacetic acid (50 ml). After 1 h at room temperature the solvent was removed in vacuo and the residue dissolved in CH₂Cl₂ (100 ml). The solution was cooled to 0° C., diisopropylethylamine (15 mg, 0.15 mmol) was added followed by 2-anisoyl chloride (9 mg, 0.059 mmol). After 18 h at 0° C. to room temperature the solvent was removed in vacuo and the residue dissolved in ethyl acetate (200 ml). This solution was washed with 0.3M KHSO₄, sat. NaHCO₃, water and brine, dried (Na₂SO₄) and evaporated in vacuo. The residue was purified by flash chromatography (eluant: 60% Pet. ether, 40% ethyl acetate) to give a colourless oil identified as the title compound (12 mg, 0.035 mmol, 71%).

EXAMPLE E21

(2S)-1-((2'S)-2'-(2-Methoxybenzoylamino)-3'-methylpentanoyl)piperidine-2-carbonitrile

A. (2S)—N-(tert-Butyloxycarbonyl)piperidine-2-carboxamide (2S)—N-(tert-Butyloxycarbonyl)pipecolinic acid (3.0 g, 13.0 mmol) was dissolved in CH₂Cl₂/DMF (9:1, 150 ml). To this solution at 0° C. was added 1-hydroxybenzotriazole hydrate (2.0 g, 14.8 mmol) and water soluble carbodiimide (2.74 g, 13.7 mmol). After 1 h at 0° C. ammonia (35%, 25 ml) was added. After 18 h at 0° C. to room temperature the solvent was removed in vacuo and the residue was taken up in ethyl acetate (500 ml). This solution was washed with 0.3M KHSO₄, sat. NaHCO₃, water and brine, dried (Na₂SO₄) and evaporated in vacuo. The residue was purified by flash chromatography (eluant: 4% methanol, 96% chloroform) to give a white solid identified as the title compound (1.7 g, 7.4 mmol, 57%).

B. (2S)-Piperidine-2-carboxamide hydrochloride (2S)—N-(tert-Butyloxycarbonyl)piperidine-2-carboxamide (1.7 g, 7.4 mmol) was dissolved in 4M HCl/dioxan (50 ml). After 1 h at room temperature the solvent was evaporated in vacuo to give a white solid identified as the title compound (1.1 g, 6.7 mmol, 89%).

C. (2S)-1-((2'S)-2'-(2-tert-Butyloxycarbonylamino)-3'-methylpentanoyl)piperidine-2-carboxamide $N^{\alpha}$-(tert-Butyloxycarbonyl)-L-isoleucine (772 mg, 3.3 mmol) was dissolved in CH₂Cl₂ (50 ml). The solution was cooled to 0° C., (2S)-piperidine-2-carboxamide hydrochloride (550 mg, 3.3 mmol) and PyBop® (1.74 g, 3.5 mmol) were added and the pH adjusted to pH9 with triethylamine. After 18 h at 0° C. to room temperature the solvent was removed in vacuo and the residue was taken up in ethyl acetate (200 ml). This solution was washed with 0.3M KHSO₄, sat. NaHCO₃, water and brine, dried (Na₂SO₄) and evaporated in vacuo. The residue was purified by flash chromatography (eluant: 2% methanol, 98% chloroform) to give a yellow oil identified as the title compound (654 mg, 1.9 mmol, 58%).

D. (2S)-1-((2'S)-2'-(2-tert-Butyloxycarbonylamino)-3'-methylpentanoyl)piperidine-2-carbonitrile (2S)-1-((2S)-2-(2-tert-Butyloxycarbonylamino)-3-methylpentanoyl)piperidine-2-carboxamide (654 mg, 1.9 mmol) was dissolved in dry THF (50 ml). The solution was cooled to 0° C., triethylamine (400 g, 4.0 mmol) was added followed by the slow addition of trifluoroacetic anhydride (880 mg, 4.2 mmol). The pH was adjusted to pH9 with triethylamine. After 30 min the reaction mixture was diluted with ethyl acetate (100 ml), washed with water and brine, dried (Na$_2$SO$_4$) and evaporated in vacuo. The residue was purified by flash chromatography (eluant: 60% Pet. ether, 40% ethyl acetate) to give a colourless oil identified as the title compound (300 g, 0.93 mmol, 49%).

E. (2S)-1-((2'S)-2'-(2-Methoxybenzoylamino)-3'-methylpentanoyl)piperidine-2-carbonitrile (2S)-1-((2S)-2-(2-tert-Butyloxycarbonylamino)-3-methylpentanoyl)piperidine-2-carbonitrile (50 mg, 0.15 mmol) was treated with trifluoroacetic acid (50 ml). After 1 h at room temperature the solvent was removed in vacuo and the residue dissolved in CH$_2$Cl$_2$ (100 ml). The solution was cooled to 0° C., triethylamine (43 mg, 0.43 mmol) was added followed by 2-anisoyl chloride (30 mg, 0.18 mmol). After 18 h at 0° C. to room temperature the solvent was removed in vacuo and the residue dissolved in ethyl acetate (200 ml). This solution was washed with 0.3M KHSO$_4$, sat. NaHCO$_3$, water and brine, dried (Na$_2$SO$_4$) and evaporated in vacuo. The residue was purified by flash chromatography (eluant: 60% Pet. ether, 40% ethyl acetate) to give a colourless oil identified as the title compound (20 mg, 0.056 mmol, 38%).

EXAMPLE E22

(2S)-1-((2'S)-2'-(2-Methoxybenzoylamino)-3'-methylpentanoyl)azetidine-2-carbonitrile A. (2S)—N-(tert-Butyloxycarbonyl)azetidine-2-carboxamide (2S)—N-(tert-Butyloxycarbonyl)-L-azetidine-2-carboxylic acid (3.87 g 19.23 mmol) was dissolved in CH$_2$Cl$_2$/DMF (9:1, 150 ml). To this solution at 0° C. was added 1-hydroxybenzotriazole hydrate (3.64 g, 26.92 mmol) and water-soluble carbodiimide (4.42 g, 23.08 mmol). After 1 h at 0° C. ammonia (35%, 15 ml) was added. After 18 h at 0° C. to room temperature the solvent was removed in vacuo and the residue was taken up in ethyl acetate (500 ml). This solution was washed with 0.3M KHSO$_4$, sat. NaHCO$_3$, water and brine, dried (Na$_2$SO$_4$) and evaporated in vacuo. The residue was purified by flash chromatography (eluant: 2% methanol, 98% chloroform) to give a colourless oil identified as the title compound (1.14 g, 5.77 mmol, 30%).

B. (2S)-Azetidine-2-carboxamide hydrochloride (2S)—N-(tert-Butyloxycarbonyl)azetidine-2-carboxamide (1.14 g, 5.69 mmol) was dissolved in 4M HCl/dioxan (50 ml). After 1 h at room temperature the solvent was evaporated in vacuo to give a white solid identified as the title compound (775 mg, 5.63 mmol, 99%).

C. (2S)-1-((2'S)-2'-(2-tert-Butyloxycarbonylamino)-3'-methylpentanoyl)azetidine-2-carboxamide N$^\alpha$-(tert-Butyloxycarbonyl)-L-isoleucine (657 mg, 2.84 mmol) was dissolved in CH$_2$Cl$_2$/DMF (9:1, 100 ml). The solution was cooled to 0° C., (2S)-azetidine-2-carboxamide hydrochloride (388 mg, 2.84 mmol), 1-hydroxybenzotriazole hydrate (538 mg, 3.98 mmol) and water soluble carbodiimide (654 mg, 3.41 mmol) were added and after 15 min the pH adjusted to pH9 with triethylamine. After 18 h at 0° C. to room temperature the reaction mixture was diluted with chloroform (200 ml). This solution was washed with 0.3M KHSO$_4$, sat. NaHCO$_3$, water and brine, dried (Na$_2$SO$_4$) and evaporated in vacuo. The residue was purified by flash chromatography (eluant: 4% methanol, 96% chloroform) to give an orange oil identified as the title compound (620 mg, 1.99 mmol, 70%).

D. (2S)-1-((2'S)-2'-(2-tert-Butyloxycarbonylamino)-3'-methylpentanoyl)azetidine-2-carbonitrile (2S)-1-((2S)-2-(2-tert-Butyloxycarbonylamino)-3-methylpentanoyl)azetidine-2-carboxamide (620 mg, 1.98 mmol) was dissolved in dry THF (100 ml). The solution was cooled to 0° C., triethylamine (390 mg, 3.9 mmol) was added followed by the slow addition of trifluoroacetic anhydride (832 mg, 3.96 mmol). The pH was adjusted to pH9 with triethylamine. After 30 min the reaction mixture was diluted with ethyl acetate (100 ml), washed with water and brine, dried (Na$_2$SO$_4$) and evaporated in vacuo. The residue was purified by flash chromatography (eluant: 3% methanol, 97% chloroform) to give a colourless oil identified as the title compound (354 mg, 1.2 mmol, 61%).

E. (2S)-1-((2'S)-2'-(2-Methoxybenzoylamino)-3'-methylpentanoyl)azetidine-2-carbonitrile (2S)-1-((2S)-2-(2-tert-Butyloxycarbonylamino)-3-methylpentanoyl)azetidine-2-carbonitrile (50 mg, 0.168 mmol) was treated with trifluoroacetic acid (10 ml). After 1 h at room temperature the solvent was removed in vacuo and the residue dissolved in CH$_2$Cl$_2$ (100 ml). The solution was cooled to 0° C., diisopropylethylamine (50 mg, 0.50 mmol) was added followed by 2-anisoyl chloride (28 mg, 0.185 mmol). After 18 h at 0° C. to room temperature the solvent was removed in vacuo and the residue dissolved in ethyl acetate (200 ml). This solution was washed with 0.3M KHSO$_4$, sat. NaHCO$_3$, water and brine, dried (Na$_2$SO$_4$) and evaporated in vacuo. The residue was purified by flash chromatography (eluant: 50% Pet. ether, 50% ethyl acetate) to give a colourless oil identified as the title compound (10 mg, 0.03 mmol, 18%).

EXAMPLE E23

(4R)-1-((2'S)-2'-(3-Methoxybenzoylamino)-3'-methylpentanoyl)thiazolidine-4-carbonitrile-S-oxide (4R)-1-((2S)-2-(3-Methoxybenzoylamino)-3-methylpentanoyl)thiazolidine-4-carbonitrile (70 mg, 0.2 mmol) was dissolved in CH$_2$Cl$_2$ (20 ml). The solution was cooled to 0° C., 3-chloroperoxybenzoic acid (33 mg, 0.19 mmol) was added. After 30 mins at 0° C. the solvent was evaporated in vacuo. The residue was purified by flash chromatography (eluant: 20% Pet. ether, 80% ethyl acetate) to give an orange oil identified as the title compound (14 mg, 0.037 mmol, 19%).

EXAMPLE E24

(4R)-1-((2'S)-2'-(3-Methoxybenzoylamino)-3'-methylpentanoyl)thiazolidine-4-carbonitrile-S,S-dioxide (4R)-1-((2S)-2-(3-Methoxybenzoylamino)-3-methylpentanoyl)thiazolidine-4-carbonitrile (70 mg, 0.2 mmol) was dissolved in CH$_2$Cl$_2$ (20 ml). The solution was cooled to 0° C., 3-chloroperoxybenzoic acid (170 mg, 1.0 mmol) was added. After 18 h at room temperature the reaction mixture was diluted with chloroform (70 ml). This solution was washed with sat. NaHCO$_3$, water and brine, dried (Na$_2$SO$_4$) and evaporated in vacuo. The residue was purified by flash

EXAMPLE E25

1-((2'S)-2'-(2-Methoxybenzoylamino)-3'-methylpentanoyl)pyrrolidine

A. (2S)-2-(2-Methoxybenzoylamino)-3-methylpentanoic acid tertbutyl ester

L-Isoleucine tertbutyl ester hydrochloride (500 mg, 2.23 mmol) was dissolved in $CH_2Cl_2$ (10 ml). Triethylamine (600 g, 6.0 mmol) and 2-anisoyl chloride (456 mg, 2.68 mmol) were added. After 18 h at room temperature the solvent was removed in vacuo and the residue was taken up in ethyl acetate (100 ml). This solution was washed with 0.3M $KHSO_4$, sat. $NaHCO_3$, water and brine, dried ($Na_2SO_4$) and evaporated in vacuo. The residue was purified by flash chromatography (eluant: 60% Pet. ether, 40% ethyl acetate) to give a colourless oil identified as the title compound (341 mg, 1.06 mmol, 48%).

B. (2S)-2-(2-Methoxybenzoylamino)-3-methylpentanoic acid (2S)-2-(2-Methoxybenzoylamino)-3-methylpentanoic acid tertbutyl ester (341 mg, 1.06 mmol) was dissolved in trifluoroacetic acid/$CH_2Cl_2$ (1:1, 10 ml). After 2 h at room temperature the solvent was removed in vacuo and the residue was purified by flash chromatography (eluant: 1% acetic acid, 2% methanol, 97% chloroform) to give a colourless oil identified as the title compound (242 mg, 0.91 mmol, 86%).

C. 1-((2'S)-2'-(2-Methoxybenzoylamino)-3'-methylpentanoyl)pyrrolidine (2S)-2-(2-Methoxybenzoylamino)-3-methylpentanoic acid (25 mg, 0.94 mmol) was dissolved in $CH_2Cl_2$/DMF (9:1, 10 ml). The solution was cooled to 0° C., pyrrolidine (8 mg, 0.113 mmol), 1-hydroxybenzotriazole hydrate (18 mg, 0.132 mmol) and water soluble carbodiimide (22 mg, 0.132=1) were added and after 15 min the pH adjusted to pH9 with triethylamine. After 18 h at 0° C. to room temperature the solvent was removed in vacuo and the residue was taken up in ethyl acetate (70 ml). This solution was washed with 0.3M $KHSO_4$, sat. $NaHCO_3$, water and brine, dried ($Na_2SO_4$) and evaporated in vacuo. The residue was purified by flash chromatography (eluant: 20% Pet. ether, 80% ethyl acetate) to give an amber oil identified as the title compound (10 mg, 0.031 mmol, 33%).

EXAMPLE E26

1-((2'S)-2'-(2-Methoxybenzoylamino)-3'-methylpentanoyl)-3,3-difluoropyrrolidide (2S)-2-(2-Methoxybenzoylamino)-3-methylpentanoic acid (25 mg, 0.94 mmol) was dissolved in $CH_2Cl_2$/DMF (9:1, 10 ml). The solution was cooled to 0° C., 3,3-difluoropyrrolidine hydrochloride (16 mg, 0.113 mmol), 1-hydroxybenzotriazole hydrate (18 mg, 0.132 mmol) and water soluble carbodiimide (22 mg, 0.132 mmol) were added and after 15 min the pH adjusted to pH9 with triethylamine. After 18 h at 0° C. to room temperature the solvent was removed in vacuo and the residue was taken up in ethyl acetate (70 ml). This solution was washed with 0.3M $KHSO_4$, sat. $NaHCO_3$, water and brine, dried ($Na_2SO_4$) and evaporated in vacuo. The residue was purified by flash chromatography (eluant: 50% Pet. ether, 50% ethyl acetate) to give an amber oil identified as the title compound (10 mg, 0.028 mmol, 30%).

EXAMPLE E27

1-(2'S)-1'-(3-Methoxybenzoyl)pyrrolidine-2'-carbonyl)-3-thiazolidine

A. (2S)-1-(3-Methoxybenzoylamino)pyrrolidine-2-carboxylic acid benzyl ester L-Proline benzyl ester hydrochloride (500 mg, 2.073 mmol) was dissolved in $CH_2Cl_2$ (10 ml). Triethylamine (600 mg, 6.0 mmol) and 3-anisoyl chloride (422 mg, 2.48 mmol) were added. After 18 h at room temperature the solvent was removed in vacuo and the residue was taken up in ethyl acetate (100 ml). This solution was washed with 0.3M $KHSO_4$, sat. $NaHCO_3$, water and brine, dried ($Na_2SO_4$) and evaporated in vacuo. The residue was purified by flash chromatography (eluant: 3% methanol, 97% chloroform) to give a colourless oil identified as the title compound (654 mg, 1.93 mmol, 93%).

B. (2S)-1-(3-Methoxybenzoylamino)pyrrolidine-2-carboxylic acid (2S)-1-(3-Methoxybenzoylamino)pyrrolidine-2-carboxylic acid benzyl ester (654 mg, 1.93 mmol) was dissolved in THF/$H_2O$ (9:1, 10 ml). Lithium hydroxide monohydrate (243 mg, 5.79 mmol) was added. After 18 h at room temperature the reaction mixture was diluted with ethyl acetate (50 ml). This solution was washed with 1M $KHSO_4$, water and brine, dried ($Na_2SO_4$) and evaporated in vacuo to give a colourless oil identified as the title compound (470 mg, 1.89 mmol, 98%).

C. 1-((2'S)-1'-(3-Methoxybenzoyl)pyrrolidine-2'-carbonyl)-3-thiazolidide (2S)-1-(3-Methoxybenzoylamino)pyrrolidine-2-carboxylic acid (61 mg, 0.245 mmol) was dissolved in $CH_2Cl_2$/DMF (9:1, 10 ml). To this solution was added thiazolidine (8 mg, 0.113 mmol), PyBrop® (126 mg, 0.271 mmol) and diisopropylethylamine (73.5 mg, 0.735 mmol). After 18 h at room temperature the solvent was removed in vacuo and the residue was taken up in ethyl acetate (70 ml). This solution was washed with 0.3M $KHSO_4$, sat. $NaHCO_3$, water and brine, dried ($Na_2SO_4$) and evaporated in vacuo. The residue was purified by flash chromatography (eluant: 3% methanol, 97% chloroform) to give an amber oil identified as the title compound (27 mg, 0.084 mmol, 34%).

EXAMPLE E28

1-((2'S)-1'-(Isopropylcarbamoyl)pyrrolidine-2'-carbonyl)pyrrolidine

A. (2S)-1-(Isopropylcarbamoyl)pyrrolidine-2-carboxylic acid benzyl ester

L-Proline benzyl ester hydrochloride (500 mg, 2.073 mmol) was dissolved in $CH_2Cl_2$ (10 ml). Triethylamine (600 mg, 6.0 mmol) and isopropylisocyanate (210 mg, 2.48 mmol) were added. After 18 h at room temperature the solvent was removed in vacuo and the residue was taken up in ethyl acetate (100 ml). This solution was washed with 0.3M KHSO$_4$, sat. NaHCO$_3$, water and brine, dried (Na$_2$SO$_4$) and evaporated in vacuo. The residue was purified by flash chromatography (eluant: 3% methanol, 97% chloroform) to give a colourless oil identified as the title compound (528 mg, 1.82 mmol, 88%).

B. (2S)-1-(Isopropylcarbamoyl)pyrrolidine-2-carboxylic acid (2S)-1-(Isopropylcarbamoyl)pyrrolidine-2-carboxylic acid benzyl ester (528 mg, 1.82 mmol) was dissolved in THF/H$_2$O (9:1, 10 ml). Lithium hydroxide monohydrate (229 mg, 5.46 mmol) was added. After 18 h at room temperature the reaction mixture was diluted with ethyl acetate (50 ml). This solution was washed with 1M KHSO$_4$, water and brine, dried (Na$_2$SO$_4$) and evaporated in vacuo to give a colourless oil identified as the title compound (148 mg, 0.74 mmol, 41%).

C. 1-((2'S)-1'-(Isopropylcarbamoyl)pyrrolidine-2'-carbonyl)pyrrolidine 1-((2S)-1-(Isopropylcarbamoyl)pyrrolidine-2-carboxylic acid (25 mg, 0.125 mmol) was dissolved in CH$_2$Cl$_2$ (10 ml). To this solution was added pyrrolidine (7 mg, 0.138 mmol), HBTU (52 mg, 0.138 mmol) and diisopropylethylamine (32.3 mg, 0.323 mmol). After 18 h at 0° C. to room temperature the solvent was removed in vacuo and the residue was taken up in ethyl acetate (70 ml). The solution was washed with 0.3M KHSO$_4$, sat. NaHCO$_3$, water and brine, dried (Na$_2$SO$_4$) and evaporated in vacuo. The residue was purified by flash chromatography (eluant: 1% triethylamine, 2% methanol, 97% chloroform) to give an amber oil identified as the title compound (11 mg, 0.043 mmol, 35%).

EXAMPLE E29

(2R)-1-((2'S)-2'-(2-Methoxybenzoylamino)-3'-methylbutanoyl)pyrrolidine-2-boronic acid

A. (2R)-1-((2'S)-2'-(2-Methoxybenzoylamino)-3'-methylbutanoyl)pyrrolidine-2-boronate-(1S,2S,3R,5S)-pinanediol ester (2R)-1-((2S)-2-(1,1-Dimethylethoxycarbonylamino)-3-methylbutanoyl)pyrrolidine-2-boronate-(1S,2S,3R,5S)-pinanediol ester (synthesised as described in WO 0310127) (70 mg, 0.16 mmol) was dissolved in 4M HCl/dioxin (30 ml). After 1 h at room temperature the solvent was removed in vacuo and the residue dissolved in CH$_2$Cl$_2$ (25 ml). The solution was cooled to 0° C., triethylamine (36 mg, 0.36 mmol) was added followed by 2-anisoyl chloride (30 mg, 0.18 mmol). After 18 h at 0° C. to room temperature the solvent was removed in vacuo and the residue dissolved in ethyl acetate (70 ml). This solution was washed with 0.3M KHSO$_4$, sat. NaHCO$_3$, water and brine, dried (Na$_2$SO$_4$) and evaporated in vacuo. The residue was purified by flash chromatography (eluant: 60% Pet. ether, 40% ethyl acetate) to give a colourless oil identified as the title compound (65 mg, 0.13 mmol, 83%).

B. (2R)-1-((2'S)-2'-(2-Methoxybenzoylamino)-3'-methylbutanoyl)pyrrolidine-2-boronic acid (2R)-1-((2S)-2-(2-Methoxybenzoylamino)-3-methylbutanoyl)pyrrolidine-2-boronate-(1S,2S,3R,5S)-pinanediol ester (70 mg, 0.16 mmol) was dissolved in acetone (10 ml). Sodium iodide (106 mg, 0.71 mmol) and 0.1M ammonium acetate (5 ml) were added. After 18 h at room temperature the acetone was removed in vacuo and 2M sodium hydroxide (10 ml) was added to the residue which was washed with CH$_2$Cl$_2$. The aqueous layer was acidified to pH 7 with 1M HCl and extracted with chloroform (3×50 ml). The combined organic extracts were washed with water and brine, dried (Na$_2$SO$_4$) and evaporated in vacuo to give a colourless oil identified as the title compound (28 mg, 0.08 mmol, 66%).

EXAMPLE E30

(2R)-1-((2'S)-2'-(Ethylcarbamoylamino)-3'-methylbutanoyl)pyrrolidine-2-boronic acid

A. (2R)-1-((2'S)-2'-(Ethylcarbamoylamino)-3'-methylbutanoyl)pyrrolidine-2-boronate-(1S,2S,3R,5S)-pinanediol ester (2R)-1-((2S)-2-(1,1-Dimethylethoxycarbonylamino)-3-methylbutanoyl)pyrrolidine-2-boronate-(1S,2S,3R,5S)-pinanediol ester (synthesised as described in WO 0310127) (70 mg, 0.16 mmol) was dissolved in 4M HCl/dioxin (30 ml). After 1 h at room temperature the solvent was removed in vacuo and the residue dissolved in CH$_2$Cl$_2$ (25 ml). The solution was cooled to 0° C., triethylamine (36 mg, 0.36 mmol) was added followed by ethylisocyanate (15 mg, 0.21 mmol). After 18 h at 0° C. to room temperature the solvent was removed in vacuo and the residue dissolved in ethyl acetate (70 ml). This solution was washed with 0.3M KHSO$_4$, sat. NaHCO$_3$, water and brine, dried (Na$_2$SO$_4$) and evaporated in vacuo. The residue was purified by flash chromatography (eluant: 10% Pet. ether, 90% ethyl acetate) to give a colourless oil identified as the title compound (48 mg, 0.11 mmol, 73%).

B. (2R)-1-((2'S)-2'-(Ethylcarbamoylamino)-3'-methylbutanoyl)pyrrolidine-2-boronic acid (2R)-1-((2S)-2-(Ethylcarbamoylamino)-3-methylbutanoyl)pyrrolidine-2-boronate-(1S,2S,3R,5S)-pinanediol ester (43 mg, 0.10 mmol) was dissolved in acetone (10 ml). Sodium iodide (87 mg, 0.40 mmol) and 0.1M ammonium acetate (5 ml) were added. After 18 h at room temperature the acetone was removed in vacuo and 2M sodium hydroxide (10 ml) was added to the residue which was washed with CH$_2$Cl$_2$. The aqueous layer was acidified to pH 7 with 1M HCl and extracted with chloroform (3×50 ml). The combined organic extracts were washed with water and brine, dried (Na$_2$SO$_4$) and evaporated in vacuo to give a colourless oil identified as the title compound (9 mg, 0.032 mmol, 20%).

EXAMPLE E31

(2S)-2-Formyl-1-((2'S)-2'-(2-methoxybenzoylamino)-3'-methylpentanoyl)pyrrolidide

A. (2S)-1-((2'S)-2'-(tert-Butyloxycarbonylamino)-3'-methylpentanoyl)-2-hydroxymethylpyrrolidine N$^\alpha$-(tert-Butyloxycarbonyl)-L-isoleucine (5.0 g, 21.6 mmol) was dissolved in CH$_2$Cl$_2$/DMF (9:1, 100 ml). The solution was cooled to 0° C., (S)-(+)-2-pyrrolidinemethanol (2.5 g, 24.7 mmol), 1-hydroxybenzotriazole hydrate (5.9 g, 43.7 mmol) and water soluble carbodiimide (5.2 g, 26.0 mmol) were added and after 15 min the pH adjusted to pH9 with triethylamine. After 18 h at 0° C. to room temperature the solvent was removed in vacuo and the residue was taken up in ethyl acetate (300 ml). This solution was washed with 0.3M $KHSO_4$, sat. $NaHCO_3$, water and brine, dried ($Na_2SO_4$) and evaporated in vacuo. The residue was purified by flash chromatography (eluant: 30% Pet. ether, 70% ethyl acetate) to give a colourless oil identified as the title compound (6.8 g, 21.6 mmol, 100%).

B. (2S)-2-Hydroxymethyl-1-((2'S)-2'-(2-methoxybenzoylamino)-3'-methylpentanoyl)pyrrolidide (2S)-1-((2S)-2-(tert-Butyloxycarbonylamino)-3-methylpentanoyl)-2-hydroxymethylpyrrolidine (2.0 g, 6.36 mmol) was treated with 4M HCl/dioxan (50 ml). After 1 h at room temperature the solvent was removed in vacuo and the residue dissolved in $CH_2Cl_2$ (100 ml). The solution was cooled to 0° C., triethylamine (1.4 g, 14 mmol) was added followed by 2-anisoyl chloride (1.2 g, 7.04 mmol). After 18 h at 0° C. to room temperature the solvent was removed in vacuo and the residue dissolved in ethyl acetate (200 ml). This solution was washed with 0.3M $KHSO_4$, sat. $NaHCO_3$, water and brine, dried ($Na_2SO_4$) and evaporated in vacuo. The residue was purified by flash chromatography (eluant: 10% Pet. ether, 90% ethyl acetate) to give a colourless oil identified as the title compound (1.53 g, 4.46 mmol, 91%).

C. (2S)-2-Formyl-1-((2'S)-2'-(2-methoxybenzoylamino)-3'-methylpentanoyl)pyrrolidide (2S)-2-Hydroxymethyl-1-((2S)-2-(2-methoxybenzoylamino)-3-methylpentanoyl)pyrrolidide (1.3 g, 3.73 mmol) was dissolved in $CH_2Cl_2$ (100 ml). Dess Martin Periodinane (2.0 g, 4.8 mmol) was added. After 3 h at room temperature the solvent was removed in vacuo and the residue dissolved in ethyl acetate (200 ml), washed with sat. $NaHCO_3$, water and brine, dried ($Na_2SO_4$) and evaporated in vacuo. The residue was purified by flash chromatography (eluant: 30% Pet. ether, 70% ethyl acetate) to give a colourless oil identified as the title compound (1.05 g, 3.0 mmol, 80%).

EXAMPLE E32

(2S)-2-Acetyl-1-((2'S)-2'-(2-methoxybenzoylamino)-3'-methylpentanoyl)pyrrolidide A. (2S)-2-(1-(1R,S)-Hydroxyethyl)-1-((2'S)-2'-(2-methoxybenzoylamino)-3'-methylpentanoyl)pyrrolidide (2S)-2-Formyl-1-((2S)-2-(2-methoxybenzoylamino)-3-methylpentanoyl)pyrrolidide (100 mg, 0.28 mmol) was dissolved in dry THF (30 ml). Methyl magnesium bromide (1.4M solution in THF/toluene, 4:1, 0.3 ml, 0.42 mmol) was added to this solution at 0° C. After 4 h at 0° C. to room temperature 0.3M $KHSO_4$ (20 ml) was added and the reaction mixture extracted with ethyl acetate. The organic extract was washed with water and brine, dried ($Na_2SO_4$) and evaporated in vacuo. The residue was purified by flash chromatography (eluant: 40% Pet. ether, 60% ethyl acetate) to give a colourless oil identified as the title compound (36 mg, 0.099 mmol, 35%).

B. (2S)-2-Acetyl-1-((2'S)-2'-(2-methoxybenzoylamino)-3'-methylpentanoyl)pyrrolidide (2S)-2-(1-(1R,S)-Hydroxyethyl)-1-((2S)-2-(2-methoxybenzoylamino)-3-methylpentanoyl)pyrrolidide (32 mg, 0.088 mmol) was dissolved in $CH_2Cl_2$ (100 ml). Dess Martin Periodinane (42 mg, 0.099 mmol) was added. After 3 h at room temperature the solvent was removed in vacuo and the residue dissolved in ethyl acetate (70 ml). This solution was washed with sat. $NaHCO_3$, water and brine, dried ($Na_2SO_4$) and evaporated in vacuo. The residue was purified by flash chromatography (eluant: 20% Pet. ether, 80% ethyl acetate) to give a colourless oil identified as the title compound (12 mg, 0.033 mmol, 38%).

EXAMPLE E33

(2S)-2-Propionyl-1-((2'S)-2'-(2-methoxybenzoylamino)-3'-methylpentanoyl)pyrrolidide A. (2S)-2-(1-(1R,S)-Hydroxypropyl)-1-((2'S)-2'-(2-methoxybenzoylamino)-3'-methylpentanoyl)pyrrolidide (2S)-2-Formyl-1-((2S)-2-(2-methoxybenzoylamino)-3-methylpentanoyl)pyrrolidide (150 mg, 0.28 mmol) was dissolved in dry THF (30 ml). Ethyl magnesium bromide (1M solution in THF, 0.56 ml, 0.56 mmol) was added to this solution at 0° C. After 18 h at 0° C. to room temperature 0.3M $KHSO_4$, (20 ml) was added and the reaction mixture extracted with ethyl acetate. The organic extract was washed with water and brine, dried ($Na_2SO_4$) and evaporated in vacuo. The residue was purified by flash chromatography (eluant: 30% Pet. ether, 70% ethyl acetate) to give a colourless oil identified as the title compound (62 mg, 0.16 mmol, 38%).

B. (2S)-2-Propionyl-1-((2'S)-2'-(2-methoxybenzoylamino)-3'-methylpentanoyl)pyrrolidide (2S)-2-(1-(1R,S)-Hydroxypropyl)-1-((2S)-2-(2-methoxybenzoylamino)-3-methylpentanoyl)pyrrolidide (52 mg, 0.138 mmol) was dissolved in $CH_2Cl_2$ (100 ml). Dess Martin Periodinane (70 mg, 0.17 mmol) was added. After 3 h at room temperature the solvent was removed in vacuo and the residue dissolved in ethyl acetate (70 ml). This solution was washed with sat. $NaHCO_3$, water and brine, dried ($Na_2SO_4$) and evaporated in vacuo. The residue was purified by flash chromatography (eluant: 20% Pet. ether, 80% ethyl acetate) to give a colourless oil identified as the title compound (24 mg, 0.064 mmol, 47%).

EXAMPLES E34-E66

Examples E34-E61 were synthesised according to methods described for Examples E1, E2 and E10, while Examples E62-E66 were synthesised according to methods described in Example E31.

| Example No | Name |
|---|---|
| E34 | (2S)-1-(2-(1-Napthoylamino)acetyl)pyrrolidine-2-carbonitrile |
| E35 | (2S)-1-((2S)-2-(4-Methylbenzoyl)octahydroindole-2-carbonyl)pyrrolidine-2-carbonitrile |
| E36 | (2S)-1-((2S)-2-(4-Methoxybenzoylamino)-2-cyclohexylacetyl)pyrrolidine-2-carbonitrile |
| E37 | (2S)-1-((2S)-1-Benzoylpiperidine-2-carbonyl)pyrrolidine-2-carbonitrile |

| Example No | Name |
|---|---|
| E38 | (2S)-1-((2S)-2-(3-Methoxybenzoylamino)-3-methylbutanoyl)pyrrolidine-2-carbonitrile |
| E39 | (2S)-1-((2S)-2-(Pivaloylamino)-3-phenylpropanoyl)pyrrolidine-2-carbonitrile |
| E40 | (2S)-1-((2S)-2-(N-Cyclohexanoyl-N-methylamino)-3-phenylpropanoyl) pyrrolidine-2-carbonitrile |
| E41 | (2S)-1-((2S)-2-(2-Methoxybenzoylamino)-3-(methyloxycarbonyl)propanoyl) pyrrolidine-2-carbonitrile |
| E42 | (2S)-1-((2S)-2-(4-Chlorobenzoylamino)-4-(benzyloxycarbonyl)butanoyl) pyrrolidine-2-carbonitrile |
| E43 | (2S)-1-((2S)-2-(4-Methoxybenzoylamino)-5-(benzyloxycarbonylamino) pentanoyl)pyrrolidine-2-carbonitrile |
| E44 | (2S)-1-((2S)-2-(3-Methoxybenzoylamino)-6-(benzyloxycarbonylamino) hexanoyl)pyrrolidine-2-carbonitrile |
| E45 | (2S)-1-((2S)-2-(Benzoylamino)-3-benzyloxypropanoyl)pyrrolidine-2-carbonitrile |
| E46 | (2S)-1-((2S)-2-(Cyclohexanoylamino)-2-phenylacetyl)pyrrolidine-2-carbonitrile |
| E47 | (2S)-1-((2S)-2-(2-Methoxybenzoylamino)-4-(benzyloxycarbonylamino) butanoyl)pyrrolidine-2-carbonitrile |
| E48 | (2S)-1-((2S)-2-(2-Methoxybenzoylamino)-3-(benzyloxycarbonylamino) propanoyl)pyrrolidine-2-carbonitrile |
| E49 | (2S)-1-((2S)-2-(N-Cyclohexanoyl-N-methylamino)-propanoyl)pyrrolidine-2-carbonitrile |
| E50 | (2S)-1-((2S)-2-(2-Methoxybenzoylamino)-5-N-(acetylamino)-3,3-dimethyl-4-thiopentanoyl)pyrrolidine-2-carbonitrile |
| E51 | (2S)-1-((2S)-2-(N-(2-Methoxybenzoyl)-N-methylamino)-3-methylpentanoyl)pyrrolidine-2-carbonitrile |
| E52 | (2S)-1-(2-(N-Benzyl-N-(2-methoxybenzoyl)amino)acetyl)pyrrolidine-2-carbonitrile |
| E53 | (2S)-1-(2-(2-Methoxybenzoylamino)-2-methylpropanoyl)pyrrolidine-2-carbonitrile |
| E54 | (2S)-1-((2S)-2-(Ethylcarbamoylamino)-3-methylbutanoyl)pyrrolidine-2-carbonitrile |
| E55 | (2S)-1-((2S)-2-(Isopropylcarbamoylamino)propanoyl)pyrrolidine-2-carbonitrile |
| E56 | (2S)-1-((2S)-2-(Ethylcarbamoyl)octahydroindole-2-carbonyl)pyrrolidine-2-carbonitrile |
| E57 | (2S)-1-((2S)-2-(N-Ethylcarbamoyl-N-methylamino)-4-methylpentanoyl) pyrrolidine-2-carbonitrile |
| E58 | (2S)-1-((2S)-2-(Benzylcarbamoylamino)-3,3-dimethylbutanoyl)pyrrolidine-2-carbonitrile |
| E59 | (2S)-1-((2S)-2-(Isopropylcarbamoylamino)-3-phenylpropanoyl)pyrrolidine-2-carbonitrile |
| E60 | (2S)-1-((2S)-2-(Cyclohexylcarbamoylamino)-4-methylpentanoyl)pyrrolidine-2-carbonitrile |
| E61 | (2S)-1-((2S)-2-(Ethylcarbamoylamino)-3-methylpentanoyl)-3,4-dehydropyrrolidine-2-carbonitrile |
| E62 | (2S)-2-Formyl-1-((2S)-2-(2-methoxybenzoylamino)-3-methylbutanoyl)pyrrolidine |
| E63 | (2S)-2-Formyl-1-((2S)-1-(3-methoxybenzoyl)pyrrolidine-2-carbonyl)pyrrolidine |
| E64 | (2S)-2-Formyl-1-((2S)-1-(ethylcarbamoyl)octahydroindole-2-carbonyl)pyrrolidine |
| E65 | (2S)-2-Formyl-1-((2S)-2-(2-methoxybenzoyl)octahydroindole-2-carbonyl)pyrrolidine |
| E66 | (2S)-2-Formyl-1-((2S)-2-(2-methoxybenzoylamino)-3-phenylpropanoyl)pyrrolidine |

| Example No. | Structure | Mol Wt | MS: [M + H]+ |
|---|---|---|---|
| E1 | 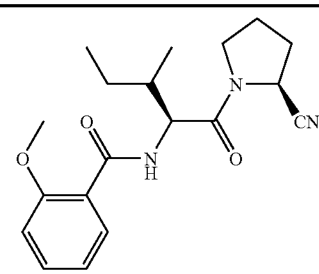 | 342.43 | 344.2 |
| E2 | 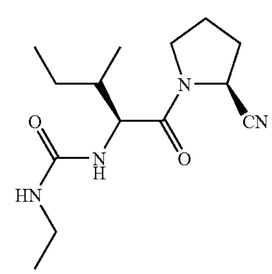 | 280.37 | 281.2 |

-continued

| Example No. | Structure | Mol Wt | MS: [M + H]+ |
|---|---|---|---|
| E3 | 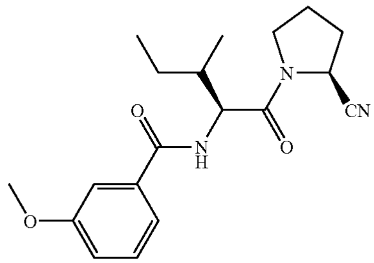 | 343.43 | 344.2 |
| E4 | 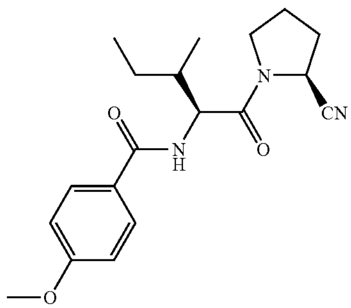 | 343.43 | 344.2 |
| E5 | 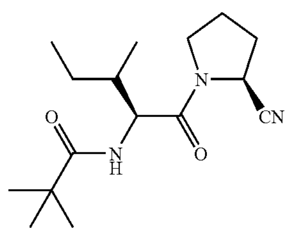 | 293.41 | 294.1 |
| E6 | 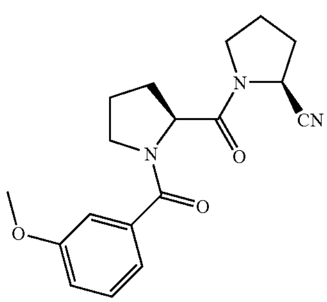 | 327.39 | 328.1 |
| E7 | 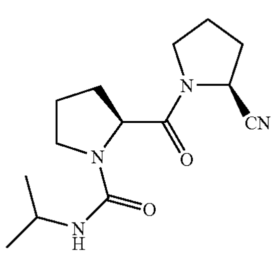 | 278.36 | 279.2 |

-continued

| Example No. | Structure | Mol Wt | MS: [M + H]+ |
|---|---|---|---|
| E8 | 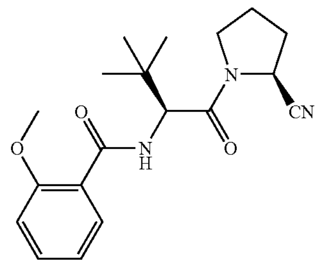 | 343.43 | 344.2 |
| E9 | 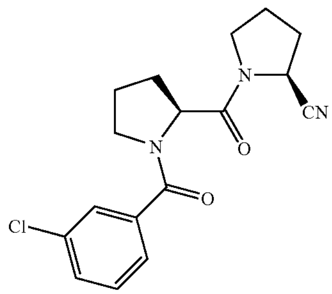 | 331.80 | 332.1 |
| E10 | 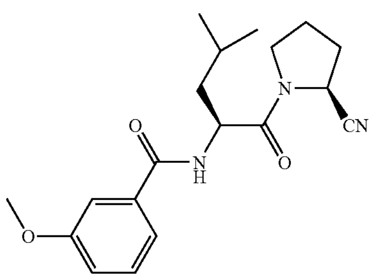 | 343.43 | 344.2 |
| E11 | 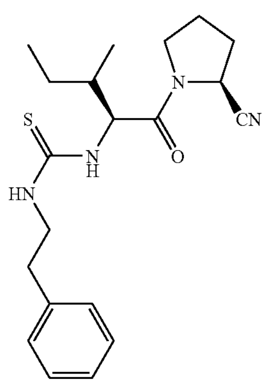 | 372.54 | 373.1 |
| E12 | 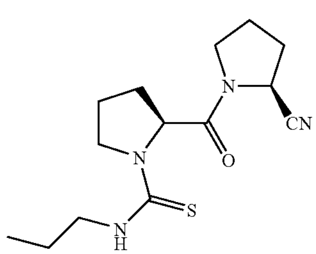 | 294.42 | 295.1 |

-continued

| Example No. | Structure | Mol Wt | MS: [M + H]+ |
|---|---|---|---|
| E13 | 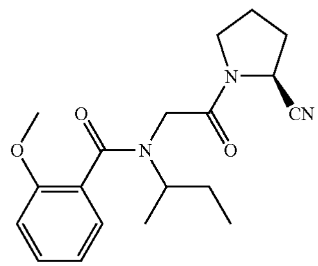 | 343.43 | 344.2 |
| E14 | 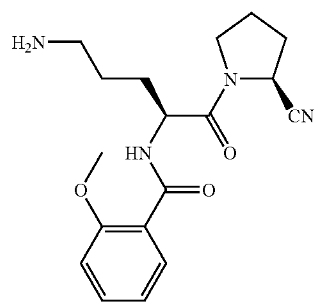 | 344.42 | 344.42 |
| E15 | 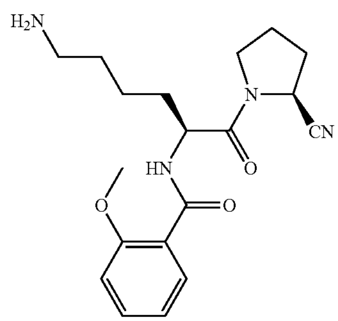 | 358.44 | 359.2 |
| E16 | 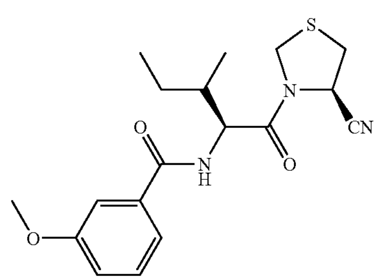 | 361.47 | 362.1 |
| E17 | 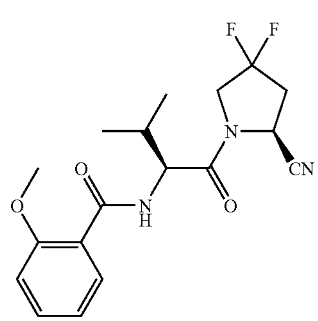 | 365.38 | 366.2 |

-continued

| Example No. | Structure | Mol Wt | MS: [M + H]+ |
|---|---|---|---|
| E18 | 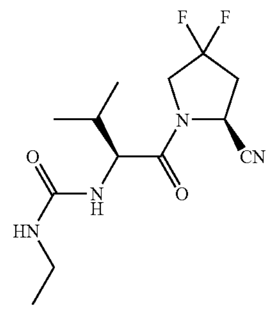 | 302.33 | 303.1 |
| E19 | 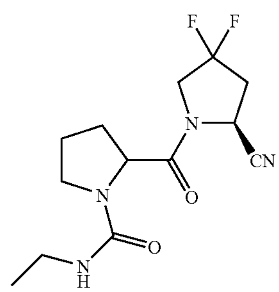 | 300.31 | 301.1 |
| E20 | 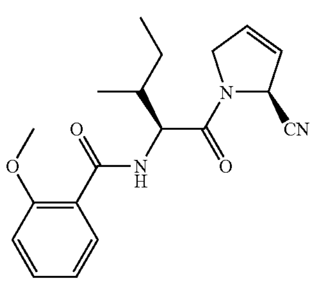 | 341.41 | 342.2 |
| E21 | 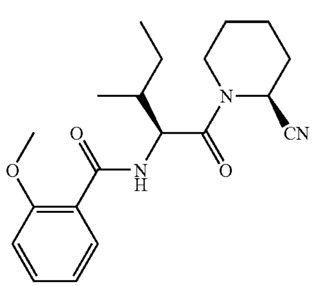 | 357.46 | 358.2 |
| E22 | 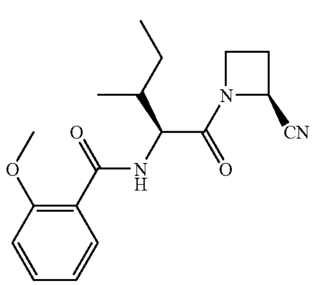 | 329.40 | 330.2 |

-continued

| Example No. | Structure | Mol Wt | MS: [M + H]+ |
|---|---|---|---|
| E23 | 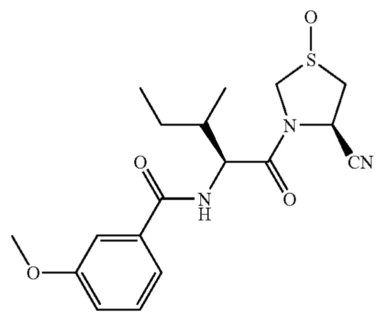 | 377.48 | 378.2 |
| E24 | 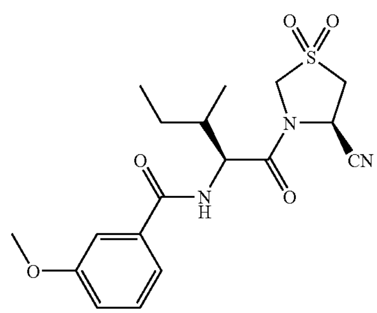 | 393.47 | 394.1 |
| E25 | 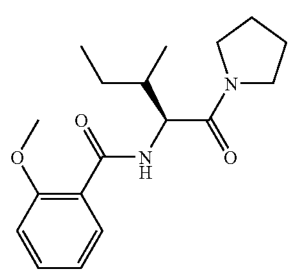 | 318.42 | 319.1 |
| E26 | 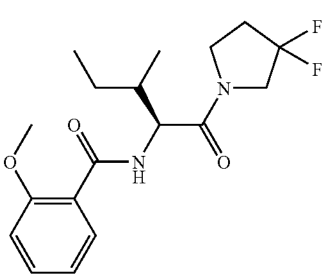 | 354.40 | 355.2 |
| E27 | 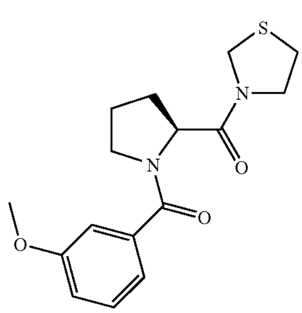 | 320.41 | 321.1 |

-continued

| Example No. | Structure | Mol Wt | MS: [M + H]+ |
|---|---|---|---|
| E28 | 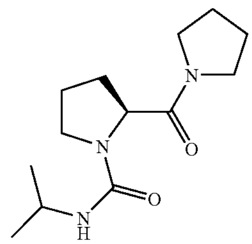 | 253.35 | 254.2 |
| E29 | 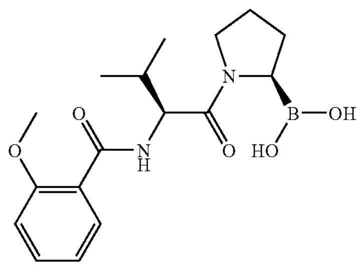 | 348.21 | 349.2 |
| E30 | 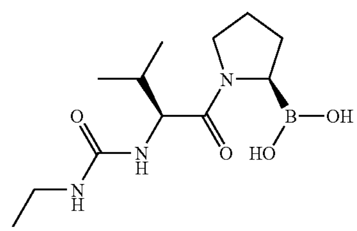 | 285.15 | 286.4 |
| E31 | 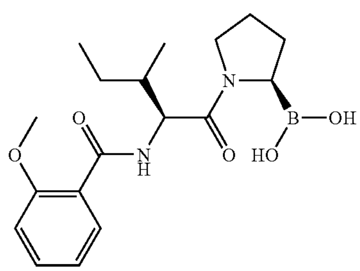 | 346.43 | 347.2 |
| E32 | 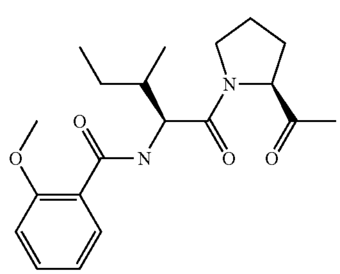 | 360.46 | 361.2 |
| E33 | 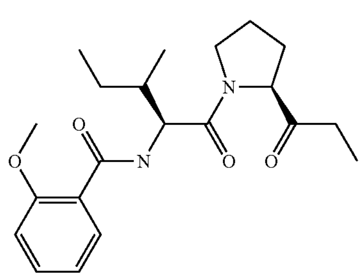 | 374.48 | 397.2 (M +Na) |

| Example No. | Structure | Mol Wt | MS: [M + H]+ |
|---|---|---|---|
| E34 | 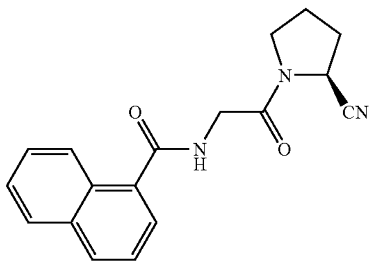 | 307.36 | 308.1 |
| E35 | 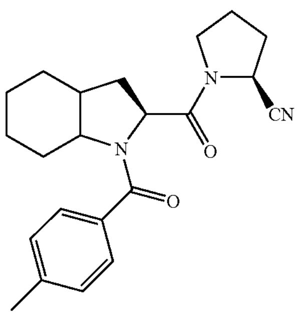 | 365.48 | 366.2 |
| E36 | 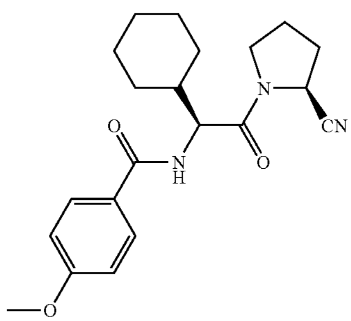 | 369.47 | 370.2 |
| E37 | 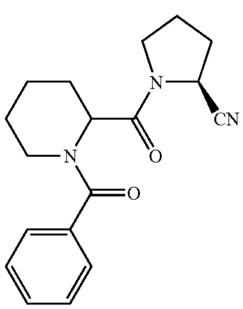 | 311.39 | 312.2 |
| E38 | 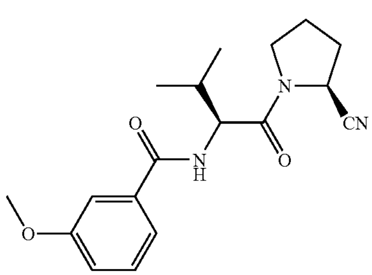 | 329.40 | 330.1 |

-continued
| Example No. | Structure | Mol Wt | MS: [M + H]+ |
|---|---|---|---|
| E39 | 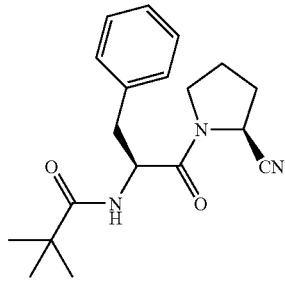 | 327.43 | 328.2 |
| E40 | 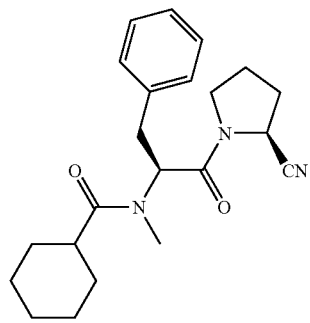 | 367.50 | 368.1 |
| E41 | 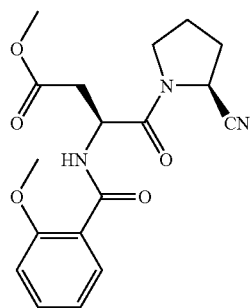 | 359.39 | 360.1 |
| E42 | 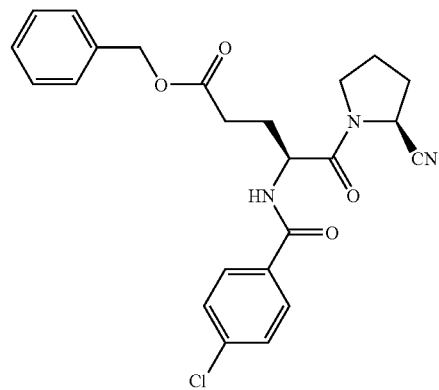 | 453.93 | 454.1, 455.3 |

-continued
| Example No. | Structure | Mol Wt | MS: [M + H]+ |
|---|---|---|---|
| E43 | 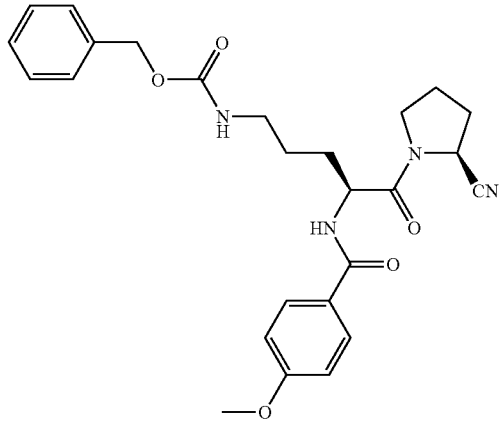 | 478.55 | 479.2 |
| E44 | 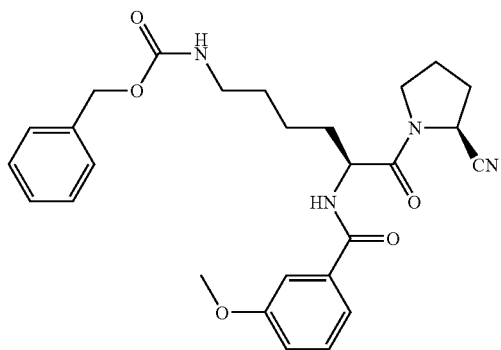 | 492.58 | 493.2 |
| E45 | 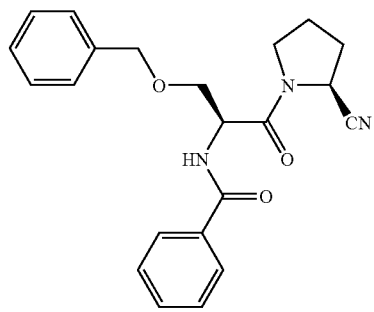 | 377.45 | 378.1 |
| E46 | 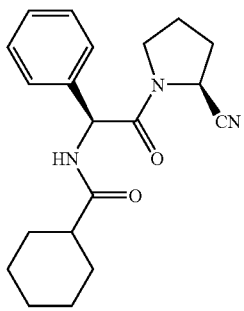 | 339.44 | 340.3 |

-continued
| Example No. | Structure | Mol Wt | MS: [M + H]+ |
|---|---|---|---|
| E47 | 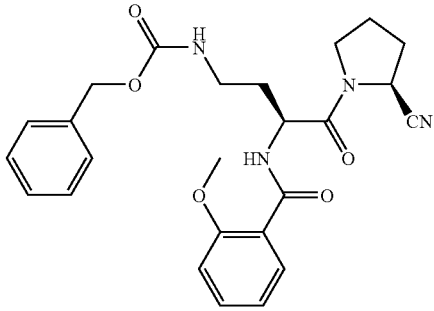 | 464.53 | 465.2 |
| E48 | 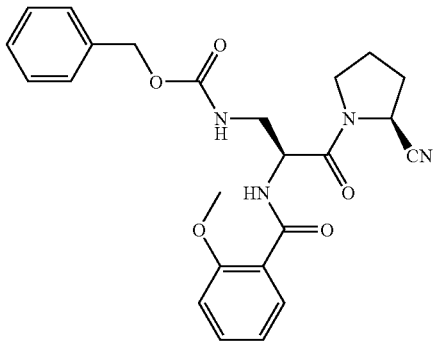 | 450.50 | 451.3 |
| E49 | 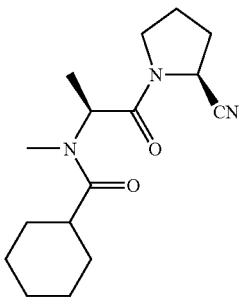 | 291.40 | 292.2 |
| E50 | 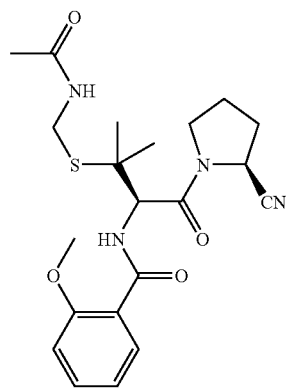 | 432.55 | 433.1 |

| Example No. | Structure | Mol Wt | MS: [M + H]+ |
|---|---|---|---|
| E51 | 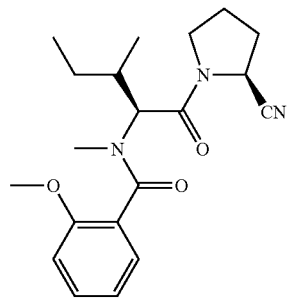 | 357.46 | 358.15 |
| E52 | 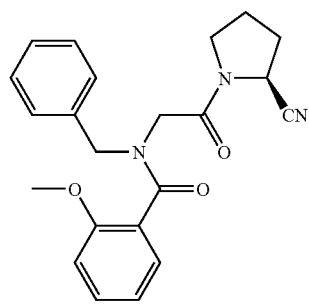 | 377.45 | 378.2 |
| E53 | 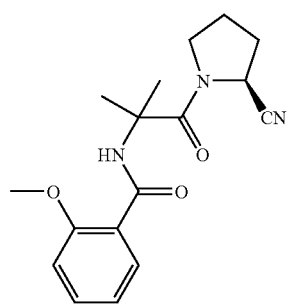 | 315.38 | 316.2 |
| E54 | 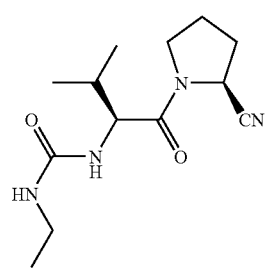 | 266.35 | 267.2 |
| E55 | 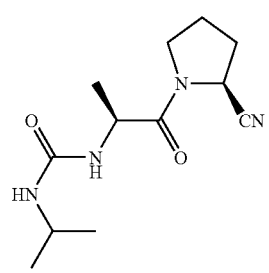 | 252.32 | 253.1 |

-continued

| Example No. | Structure | Mol Wt | MS: [M + H]+ |
|---|---|---|---|
| E56 | 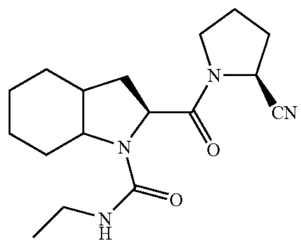 | 319.42 | 319.6 |
| E57 | 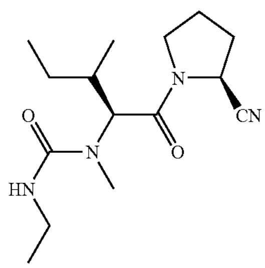 | 294.40 | 295.2 |
| E58 | 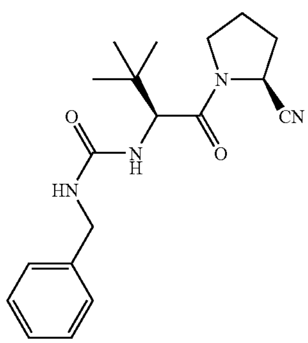 | 342.44 | 343.3 |
| E59 | 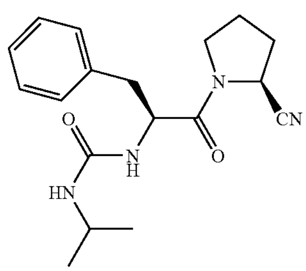 | 328.42 | 329.2 |
| E60 | 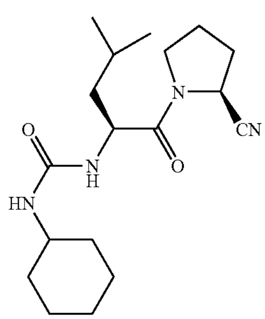 | 331.47 | 335.2 |

-continued

| Example No. | Structure | Mol Wt | MS: [M + H]+ |
|---|---|---|---|
| E61 | 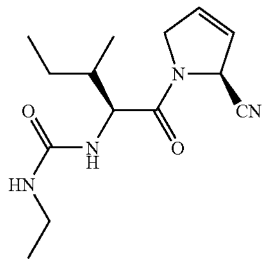 | 278.36 | 279.1 |
| E62 | 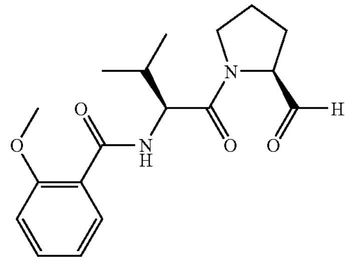 | 334.40 | 333.2 |
| E63 | 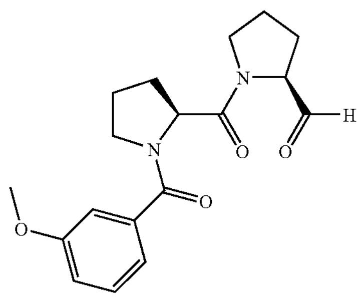 | 330.39 | 331.3 |
| E64 | 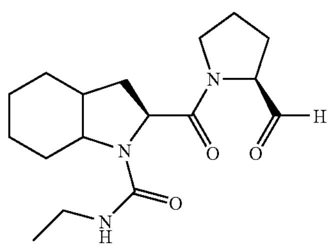 | 321.42 | 322.3 |
| E65 | 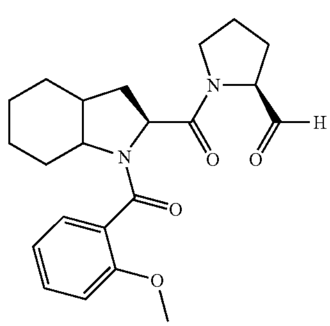 | 384.48 | 385.2 |

| Example No. | Structure | Mol Wt | MS: [M + H]+ |
|---|---|---|---|
| E66 | 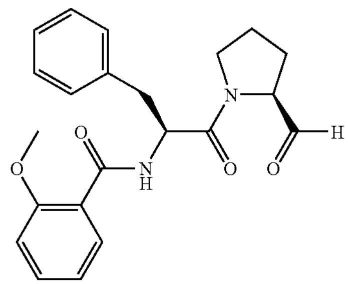 | 380.45 | 381.3 |

The 1H NMR data for Examples E1-E66 are as follows

| Example No | $^1$H NMR: δ(ppm) |
|---|---|
| E1 | (CDCl$_3$): δ 0.982 (3H, t, J = 7.4 Hz), 1.02 (3H, d, J = 6.4 Hz), 1.19-1.26 (2H, m), 1.93-1.95 (2H, m), 2.12-2.25 (4H, m), 3.72-3.76 (1H, m), 3.97 (3H, s), 4.76-4.80 (2H, m), 6.94-7.02 (2H, m), 7.39-7.46 (1H, m), 8.08-8.12 (1H, m), 8.45 (1H, d, J = 7.4 Hz) |
| E2 | (CDCl$_3$): δ 0.86-0.96 (6H, m), 1.07-1.19 (5H, m), 1.59-1.74 (2H, m), 2.05-2.27 (4H, m), 3.10-3.22 (3H, m), 3.68-3.74 (1H, m), 3.91-4.00 (1H, m), 4.41 (1H, d, J = 8.9 Hz), 4.65-4.69 (1H, m) |
| E3 | (CDCl$_3$): δ 0.88-1.02 (7H, m), 1.1-1.3 (1H, m), 1.63-1.70 (1H, m), 1.9-2.1 (2H, m), 2.2-2.4 (3H, m), 3.79 (3H, s), 3.9-4.1 (1H, m), 4.67-4.96 (2H, m), 6.99-7.11 (2H, m), 7.26-7.27 (3H, m) |
| E4 | (CDCl$_3$): δ 0.88-0.94 (3H, m), 1.04-1.06 (2H, m), 1.1-1.3 (1H, m), 1.55-1.70 (1H, m), 1.90-2.05 (1H, m), 2.1-2.3 (3H, m), 3.7-3.8 (1H, m), 3.82 (3H, s), 3.9-4.0 (1H, m), 4.7-4.76 (2H, m), 6.70 (1H, d, J = 8.6 Hz), 6.90 (2H, d, J = 8 Hz), 7.71 (2H, d, J = 8 Hz) |
| E5 | (CDCl$_3$): δ 0.87-0.90 (7H, m), 1.2 (9H, s), 1.51-1.60 (1H, s), 1.8-1.83 (1H, m), 2.1-2.22 (4H, m), 3.66-3.67 (1H, m), 3.82-3.84 (1H, m), 4.5-4.53 (1H, m), 4.71-4.74 (1H, m), 6.19-6.22 (1H, m) |
| E6 | (CDCl$_3$): δ 2.03-2.29 (10H, m), 3.51-3.58 (1H, m), 3.65-3.70 (1H, m), 3.79 (3H, s), 4.68-4.73 (1H, m), 4.82-4.86 (1H, m), 6.91-6.96 (1H, m), 7.04-7.11 (1H, m), 7.24-7.30 (2H, m) |
| E7 | (CDCl$_3$): δ 1.11 (6H, d, J = 6.4 Hz), 2.03-2.26 (9H, m), 3.25-3.30 (1H, m), 3.42-3.49 (1H, m), 3.58-3.67 (1H, m), 3.78-3.89 (2H, m), 4.53-4.56 (1H, m), 4.78-4.82 (1H, m) |
| E8 | (CDCl$_3$): δ 1.108 (9H, s), 2.02-2.21 (5H, m), 3.78-3.79 (1H, m), 3.99 (3H, s), 4.77 (2H, d, J = 8.9 Hz), 6.95-7.07 (2H, m), 8.116 (1H, d, J = 7.9 Hz), 8.65 (1H, d, J = 8.7 Hz) |
| E9 | (CDCl$_3$): δ 1.80-2.50 (7H, m), 3.40-3.60 (1H, m), 3.60-3.80 (2H, m), 3.90-4.10 (1H, m), 4.70-4.80 (1H, m), 4.80-4.95 (1H, m), 7.20-7.70 (5H, m) |
| E10 | (CDCl$_3$): δ 0.90-1.10 (6H, m), 1.50-1.80 (3H, m), 2.10-2.40 (4H, m), 3.60-3.75 (1H, m), 3.75-3.90 (4H, m), 4.70-4.80 (1H, m), 4.85-5.00 (1H, m), 6.85-6.95 (1H, m), 7.25-7.40 (3H, m) |
| E11 | (CDCl$_3$): δ 0.89-0.97 (6H, m), 1.1-1.29 (1H, m), 1.63-1.85 (2H, m), 2.1-2.12 (4H, m), 2.83-2.88 (2H, m), 3.60-3.63 (3H, m), 3.8-3.9 (2H, m), 4.3-4.4 (1H, m), 4.83-4.89 (1H, m), 6.68-6.90 (1H, m), 7.16-7.26 (5H, m), 7.9-7.7 (1H, m) |
| E12 | (CDCl$_3$): δ 0.91 (3H, t, J = 7 Hz), 1.58 (2H, t, J = 7 Hz), 1.9-2.21 (7H, m), 2.36-2.40 (1H, m), 3.42-3.62 (5H, m), 4.04-4.07 (1H, m), 4.81-4.83 (1H, m), 5.06-5.09 (1H, m), 5.50-5.52 (1H, m) |
| E13 | (CDCl$_3$): δ 0.65-0.90 (3H, m), 0.90-1.55 (4H, m), 1.85-2.45 (3H, m), 3.40-4.00 (8H, m), 4.75-5.00 (1H, m), 6.80-7.10 (2H, m), 7.15-7.40 (2H, m) |
| E14 | (CDCl$_3$): δ 1.50-2.00 (3H, m) 2.05-2.50 (7H, m), 2.70-2.90 (2H, m), 3.85-3.90 (2H, m), 3.99 (3H, s), 4.70-4.80 (1H, m), 4.90-5.10 (1H, m), 6.90-7.20 (2H, m), 7.40-7.50 (1H, m), 8.05-8.15 (1H, m), 8.62 (1H, d, J = 7.91 Hz) |
| E15 | (CDCl$_3$): δ 1.40-1.70 (4H, m), 1.70-2.10 (5H, m), 2.10-2.40 (3H, m), 2.65-2.80 (2H, m), 3.65-3.95 (2H, m), 4.00 (3H, s), 4.75-4.85 (1H, m), 4.90-5.10 (1H, m), 6.90-7.10 (2H, m), 7.30-7.40 (1H, m), 8.05-8.15 (1H, m), 8.60 (1H, d, J = 7.91 Hz) |
| E16 | (CDCl$_3$): δ 0.9-0.92 (3H, m), 1.02-1.05 (3H, m), 1.15-1.35 (1H, m), 1.6-1.8 (1H, m), 1.9-2.1 (1H, m), 3.24 (2H, s), 3.81 (3H, s), 4.68-4.73 (2H, m), 5.11 (1H, d, J = 8 Hz), 5.25 (1H, s), 6.83-6.86 (1H, m), 7.01-7.1 (1H, m), 7.27-7.30 (3H, m) |
| E17 | (CDCl$_3$): δ 1.07 (6H, d, J = 6.68 Hz), 2.05-2.30 (1H, m), 2.64-2.82 (2H, m), 3.99 (3H, s), 4.00-4.18 (1H, m), 4.38-4.58 (2H, m), 5.01 (1H, t, J = 6.44 Hz), 6.82-7.00 (2H, m), 7.46 (1H, t, J = 7.67 Hz), 8.10 (1H, d, J = 6.68 Hz), 8.44 (1H, d, J = 7.67 Hz) |
| E18 | (CDCl$_3$): δ 0.99 (6H, d, J = 6.43), 1.13 (3H, t, J = 7.42 Hz), 1.85-2.05 (1H, m), 2.65-2.85 (2H, m), 3.05-3.30 (3H, m), 3.95-4.10 (1H, m), 4.16 (1H, t, J = 8.41 Hz), 4.30-4.50 (1H, m), 4.80-5.00 (2H, m), 5.46 (1H, d, J = 8.41 Hz) |
| E19 | (CDCl$_3$): δ 1.11 (3H, t), 1.90-2.20 (2H, m), 2.20-2.40 (1H, m), 2.60-2.80 (2H, m), 3.10-3.35 (4H, m), 3.40-3.55 (1H, m), 3.88-4.05 (2H, m), 4.20-4.50 (3H, m), 4.95-5.10 (1H, br, t) |
| E20 | (CDCl$_3$): δ 0.93 (3H, t, J = 7.42 Hz), 1.05 (2H, d, J = 6.68 Hz), 1.12-1.40 (1H, m), 1.60-1.80 (1H, m), 1.90-2.10 (1H, m), 3.98 (3H, s), 4.40-4.55 (1H, m), 4.72 (1H, t, J = 8.41 Hz), 4.82-4.96 (1H, m), 5.35-5.45 (1H, m), 5.80-5.90 (1H, m), 6.05-6.18 (1H, m), 6.90-7.10 (2H, m), 7.44 (1H, t, J = 7.05 Hz), 8.11 (1H, d, J = 6.43, J = 6.43 Hz), 8.45 (1H, d, J = 8.16 Hz) |
| E21 | (CDCl$_3$): δ 0.87-0.92 (8H, m), 1.2-1.3 (1H, m), 1.4-2.0 (6H, m), 3.28-3.39 (1H, m), 3.99 (3H, s), 4.1-4.16 (1H, m), 5.09-5.15 (1H, m), 5.75-5.86 (1H, m), 6.95 (1H, d, J = 8 Hz), 7.1 (1H, m), 7.44 (1H, m), 8.12 (1H, m), 8.44-8.50 (1H, m) |

-continued

| Example No | ¹H NMR: δ(ppm) |
|---|---|
| E22 | (CDCl₃): δ 0.85-1.05 (6H, m), 1.02-1.40 (1H, m), 1.55-1.75 (1H, m), 1.80-2.00 (1H, m), 2.55-2.80 (1H, m), 3.00-3.15 (1H, m), 3.97 (3H, s), 4.28-4.55 (3H, m), 4.80-4.95 (1H, m), 6.90-7.10 (2H, m), 7.44 (1H, t, J = 7.67 Hz), 8.12 (1H, d, J = 7.67 Hz), 8.40 (1H, d, J = 7.42 Hz) |
| E23 | (CDCl₃): δ 0.89-1.02 (7H, m), 1.2-1.3 (1H, m), 1.61-1.63 (1H, m), 2.01-2.07 (1H, m), 3.12-3.18 (1H, m), 3.56-3.58 (1H, m), 3.80 (3H, s), 4.26-4.31 (1H, m), 4.78-4.82 (1H, m), 5.64-5.73 (2H, m), 6.99-7.00 (2H, m), 7.24-7.28 (4H, m) |
| E24 | (CDCl₃): δ 0.89-1.02 (7H, m), 1.2-1.3 (1H, m), 1.61-1.63 (1H, m), 2.01-2.07 (1H, m), 3.58-3.60 (2H, m), 3.81 (3H, s), 4.74-4.61 (2H, m), 5.64-5.58 (2H, m), 6.91-7.00 (1H, m), 7.10-7.20 (1H, m), 7.24-7.28 (4H, m) |
| E25 | (CDCl₃): δ 0.80-1.05 (6H, m), 1.05-2.05 (6H, m), 3.00-3.15 (1H, m), 3.35-3.60 (3H, m), 3.68-3.90 (1H, m), 3.98 (3H, s), 4.80-4.95 (1H, m), 6.90-7.10 (2H, m), 7.35-7.45 (1H, t), 8.10-8.20 (1H, d), 8.45-8.65 (1H, m) |
| E28 | (CDCl₃): δ 1.05-1.25 (6H, d), 1.70-2.40 (9H, m), 3.20-4.20 (7H, m), 4.55-4.70 (1H, m) |
| E29 | (CDCl₃): δ 0.84-0.92 (8H, m), 1.91-2.05 (5H, m), 2.96-2.99 (1H, m), 3.46-3.52 (1H, m), 3.81-3.92 (1H, m), 3.96 (3H, s), 4.75-4.82 (1H, m), 6.93-7.06 (2H, m), 7.39-7.42 (1H, m), 8.10-8.14 (1H, m), 8.34-8.38 (1H, m) |
| E30 | (CDCl₃): δ 0.83-1.27 (9H, m), 1.99-2.16 (5H, m), 3.10-3.20 (1H, m), 3.42-3.47 (1H, m), 3.50-3.65 (2H, m), 4.10 (1H, d), 5.28 (1H, s) |
| E31 | (CDCl₃): δ 0.81-0.92 (3H, m), 1.02-1.05 (3H, m), 1.10-1.30 (1H, m), 1.55-1.75 (1H, m), 1.86-2.20 (6H, m), 3.65-3.68 (1H, m), 3.92 (3H, s), 4.47-4.50 (1H, m), 4.85-4.88 (1H, m), 6.91-7.03 (2H, m), 7.30-7.45 (1H, m), 8.09-8.11 (1H, d), 8.43-8.46 (1H, d), 9.51 (1H, s) |
| E32 | (CDCl₃): δ 0.86-0.91 (6H, m), 1.05-1.09 (3H, m), 1.21-1.26 (1H, m), 1.55-1.65 (1H, m), 1.85-1.93 (2H, m), 2.21 (3H, s), 3.67-3.71 (1H, m), 3.96 (3H, s), 4.08-4.11 (1H, m), 4.57-4.63 (1H, m), 4.85-4.91 (1H, m), 6.95 (1H, d, J = 8.4 Hz), 7.01-7.06 (1H, m), 8.13 (1H, d, J = 7.2 Hz), 8.46 (1H, d) |
| E33 | (CDCl₃): δ 0.92-1.00 (6H, m), 1.06-1.09 (3H, m), 1.18-1.23 (2H, m), 1.62-2.13 (6H, m), 2.52-2.59 (2H, m), 3.68-3.72 (1H, m), 3.95 (3H, s), 4.58-4.63 (1H, m), 4.84-4.90 (1H, m), 6.93-6.96 (1H, m), 7.01-7.06 (1H, m), 7.39-7.44 (1H, m), 8.14 (1H, d, J = 6.7 Hz) 8.40-8.44 (1H, m) |
| E34 | (CDCl₃): 2.10-2.40 (4H, m), 3.45-3.80 (2H, m), 4.20-4.50 (2H, m), 4.80-4.90 (1H, m), 6.90-7.10 (1H, m), 7.40-7.70 (4H, m), 7.80-8.00 (2H, m), 8.45 (1H, d, J = 7.42 Hz) |
| E35 | (CDCl₃): 0.80-1.10 (1H, m), 1.20-1.80 (6H, m), 1.80-2.50 (10H, m), 3.50-3.70 (2H, m), 4.00-4.15 (1H, m), 4.65-4.75 (1H, m), 4.80-4.95 (1H, m), 7.10-7.40 (5H, m) |
| E36 | (CDCl₃): 1.00-1.40 (5H, m), 1.50-1.90 (7H, m), 2.10-2.40 (3H, m), 3.60-4.00 (5H, m), 4.70-4.80 (2H, m), 6.57 (1H, d, J = 8.40 Hz), 6.90 (2H, d, J = 8.64 Hz), 7.73 (2H, d, J = 8.64 Hz) |
| E37 | (CDCl₃): 1.35-1.90 (5H, m), 1.95-2.40 (5H, m), 3.50-3.90 (4H, m), 4.75-4.85 (1H, m), 5.30-5.45 (1H, m), 7.30-8.20 (5H, m) |
| E38 | (CDCl₃): 0.90-1.10 (6H, m), 1.40-1.60 (1H, m), 2.10-2.40 (4H, m), 3.70-4.00 (5H, m), 4.70-4.85 (2H, m), 6.70-6.85 (1H, m), 6.95-7.10 (1H, m), 7.20-7.40 (3H, m) |
| E39 | (CDCl₃): 1.11 (9H, s), 1.70-2.15 (4H, m), 2.55-2.65 (1H, m), 2.95-3.05 (2H, m), 3.30-3.45 (1H, m), 4.60-4.80 (2H, m), 6.35-6.45 (1H, m), 7.20-7.40 (5H, m) |
| E40 | (CDCl₃): 1.00-2.50 (12H, m), 2.85-3.10 (1H, m), 3.14 (3H, s), 3.40-3.60 (2H, m), 4.55-4.70 (1H, m), 5.35-5.50 (1H, m), 7.10-7.50 (5H, m) |
| E41 | (CDCl₃): 1.10-1.30 (1H, m) 2.00-2.40 (4H, m), 2.75-2.95 (2H, m), 3.72 (3H, s), 3.80-3.95 (1H, m), 3.98 (3H, s), 4.70-4.80 (1H, m), 5.25-5.40 (1H, m), 6.97 (1H, d, J = 8.42 Hz), 7.05 (1H, t, J = 7.67 Hz), 7.46 (1H, t, J = 7.67 Hz), 8.14 (1H, d, J = 7.91 Hz), 8.83 (1H, d, J = 8.15 Hz) |
| E42 | (CDCl₃): 1.80-2.30 (4H, m) 2.45-2.90 (2H, m), 3.10-3.30 (1H, m), 3.60-4.10 (3H, m), 4.70-5.20 (4H, m), 7.20-7.50 (7H, m), 7.60-7.80 (3H, m) |
| E43 | (CDCl₃): 1.20-1.40 (1H, m), 1.50-1.90 (4H, m), 2.00-2.40 (4H, m), 3.20-3.30 (1H, m), 3.60-3.90 (5H, m), 4.75-4.85 (1H, m), 4.85-4.95 (1H, m), 5.07 (2H, s), 6.88 (2H, d, J = 8.66 Hz), 7.00-7.10 (2H, m), 7.20-7.50 (5H, m), 7.74 (2H, d, J = 8.66 Hz) |
| E44 | (CDCl₃): 1.40-1.70 (5H, m), 1.70-2.00 (1H, m), 2.10-2.40 (4H, m) 3.10-3.40 (2H, m) 3.60-3.90 (5H, m), 4.70-4.90 (5H, m), 5.00-5.20 (2H, m), 6.90-7.10 (2H, m), 7.20-7.50 (8H, m) |
| E45 | (CDCl₃): 1.90-2.40 (4H, m), 3.50-3.90 (4H, m), 4.40-4.80 (4H, m), 5.05-5.30 (1H, m), 6.95-7.15 (2H, m), 7.20-7.60 (7H, m), 7.70-7.90 (2H, m) |
| E46 | (CDCl₃): 1.00-1.50 (6H, m) 1.60-2.40 (9H, m), 2.95-3.20 (1H, m), 3.65-3.85 (1H, m), 4.67 (1H, d, J = 6.67 Hz), 5.67 (1H, d, J = 7.15 Hz) 6.90-7.10 (1H, m), 7.20-7.60 (5H, m) |
| E47 | (CDCl₃): 1.33 (1H, t J = 7 Hz), 1.70-1.71 (1H, m), 1.95-2.30 (4H, m), 2.96-3.11 (1H, m), 3.46-3.51 (3H, m), 3.98 (3H, m), 4.72-4.73 (1H, m), 4.9-5.13 (3H, m), 6.03-6.07 (1H, m), 6.9-7.1 (2H, m), 7.3-7.5 (6H, m), 8.08-8.1 (1H, m), 8.86-8.89 (1H, m) |
| E48 | (CDCl₃): 2.11-2.24 (4H, m), 3.57-3.6 (1H, m), 3.65-3.83 (2H, m), 3.92 (3H, m), 4.73-4.74 (1H, m), 5.07-5.11 (3H, m), 5.49 (1H, m), 6.9-7.1 (2H, m), 7.25-7.32 (7H, m), 8.11-8.14 (1H, m), 8.81-8.4 (1H, m) |
| E49 | (CDCl₃): 1.10-1.50 (10H, m), 1.60-2.00 (4H, m), 2.00-2.40 (4H, m), 2.85-3.05 (3H, m), 3.50-3.80 (5H, m) |
| E50 | (CDCl₃): 1.50 (6H, d, J = 7.67 Hz), 1.94 (3H, s), 2.10-2.40 (4H, m), 3.70-4.20 (7H, m), 4.65-4.80 (2H, m), 4.94 (1H, d, J = 8.15 Hz), 6.90-7.20 (3H, m), 7.20-7.60 (3H, m), 8.05-8.25 (1H, m) |
| E51 | (CDCl₃): 0.80-1.05 (8H, m), 1.05-1.30 (1H, m), 2.00-2.40 (6H, m), 2.70-3.00 (1H, m), 3.60-3.90 (5H, m), 4.65-4.80 (1H, m), 5.10-5.30 (1H, m), 6.80-7.05 (2H, m), 7.10-7.40 (2H, m) |
| E52 | (CD₃OD): 1.80-2.45 (6H, m), 3.79 (2H, s), 3.89 (3H, s), 4.78 (1H, br, t), 4.87 (2H, s), 6.95-7.25 (2H, m), 7.25-7.60 (7H, m) |
| E54 | (CDCl₃): 0.70-1.20 (10H, m), 1.80-2.00 (1H, m), 2.05-2.35 (5H, m), 3.05-3.30 (2H, m), 3.60-3.80 (1H, m), 3.85-4.00 (1H, m), 4.30-4.50 (1H, m), 4.60-4.75 (1H, m) |
| E55 | (CDCl₃): 1.00-1.20 (9H, m), 1.20-1.40 (3H, m), 2.10-2.40 (3H, m), 3.70-3.90 (2H, m), 4.60-4.80 (2H, m), 5.59 (1H, d, J = 8.81 Hz |
| E56 | (CDCl₃): 1.00-1.20 (6H, m), 1.20-1.55 (1H, m), 1.55-2.50 (10H, m), 3.10-3.35 (3H, m), 3.35-3.65 (2H, m), 3.85-4.00 (1H, m), 4.05-4.20 (1H, m), 4.60-4.80 (1H, m), 5.80-5.90 (1H, m |
| E57 | (CDCl₃): 0.80-0.95 (6H, m), 0.95-1.20 (5H, m), 1.95-2.30 (5H, m), 2.89 (3H, s), 3.15-3.40 (2H, m), 3.65-3.80 (2H, m), 3.90-4.10 (1H, m), 4.35-4.55 (1H, m), 4.60-4.70 (1H, m), 4.85 (1H, d, J = 11.12 Hz) |
| E58 | (CDCl₃): 0.99 (9H, s), 1.80-2.15 (3H, m), 3.60-3.72 (1H, m), 3.72-3.86 (1H, m), 4.05-4.19 (1H, m), 4.22-4.60 (4H, m), 5.68-5.85 (2H, m), 7.15-7.35 (5H, m). |
| E59 | (CDCl₃): 0.90-1.50 (6H, m), 1.50-2.10 (4H, m), 2.50-2.70 (1H, m), 2.90-3.20 (3H, m), 3.40-3.55 (1H, m), 3.75-3.90 (1H, m), 4.60-4.80 (2H, m), 5.60-5.80 (1H, m), 7.15-7.40 (5H, m) |

-continued
| Example No | ¹H NMR: δ(ppm) |
|---|---|
| E60 | (CDCl₃): 0.80-2.00 (19H, m), 2.05-2.40 (4H, m), 3.35-3.50 (1H, m), 3.55-3.70 (1H, m), 3.80-3.95 (1H, m), 4.50-4.80 (3H, m), 5.48 (1H, d, J = 8.67 Hz) |
| E61 | (CDCl₃): 0.90 (3H, t, J = 7.42 Hz), 0.97 (3H, d, J = 6.68 Hz), 1.10 (3H, t, J = 7.30 Hz), 1.58-1.88 (2H, m), 3.05-3.35 (2H, m), 4.30-4.52 (2H, m), 4.80-5.00 (1H, m), 5.10-5.25 (1H, m), 5.30-5.40 (1H, m), 5.75-5.90 (1H, m), 5.90-6.05 (1H, m), 6.05-6.20 (1H, m) |
| E63 | (CDCl₃) 1.64-2.40 (8H, m), 3.45-3.90 (7H, m), 4.60-4.70 (1H, m), 4.80-4.90 (1H, m), 6.85-7.00 (1H, m), 7.00-7.18 (2H, m), 7.20-7.35 (1H, m), 9.54 (1H, s) |
| E64 | (CDCl₃) 0.80-1.50 (6H, m), 1.60-2.20 (13H, m), 3.10-3.30 (2H, m), 3.40-3.60 (2H, m), 3.80-4.20 (1H, m), 4.50-4.70 (2H, m), 9.53 (1H, s) |
| E65 | (CDCl₃) 1.00-1.70 (8H, m), 1.80-2.40 (6H, m), 3.20-3.50 (3H, m), 3.72 (3H, s), 3.80-4.00 (1H, m), 4.20-4.60 (1H, m), 4.60-4.80 (1H, m), 6.70-6.85 (2H, m), 6.90-7.20 (1H, m), 7.50-7.90 (1H, m), 9.43 (1H, s) |
EXAMPLES
TABLE 1
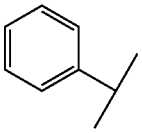
| Example No. | R | X | Mol Wt | [M + H]+ |
|---|---|---|---|---|
| 1 | CH₃ | CH₂ | 251.33 | 252.39 |
| 2 | | S | 269.367 | 270.37 |
| 3 | | CH₂CH₂ | 265.357 | 266.37 |
| 4 | | CF₂ | 287.31 | 288.47 |
| 5 | 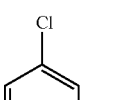 | CH₂ | 313.401 | 314.39 |
| 6 | | S | 331.438 | 332.18 |
| 7 | | CH₂CH₂ | 327.428 | 328.35 |
| 8 | | CF₂ | 349.381 | 350.44 |
| 9 | 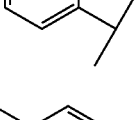 | CH₂ | 347.846 | 348.32 |
| 10 | | S | 365.883 | 366.17 |
| 11 | | CH₂CH₂ | 361.873 | 362.29 |
| 12 | | CF₂ | 383.826 | 384.42 |
| 13 | 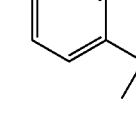 | CH₂ | 347.846 | 348.39 |
| 14 | | S | 365.883 | 366.1 |
| 15 | | CH₂CH₂ | 361.873 | 362.28 |
| 16 | | CF₂ | 383.826 | 384.45 |
| 17 | 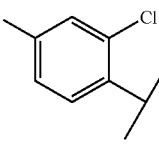 | CH₂ | 347.846 | 348.37 |
| 18 | | S | 365.883 | 366.11 |
| 19 | | CH₂CH₂ | 361.873 | 362.32 |
| 20 | | CF₂ | 383.826 | 384.46 |
| 21 |  | CH₂ | 382.291 | 382.35 |
| 22 | | S | 400.328 | 400.09 |
| 23 | | CH₂CH₂ | 396.318 | 396.23 |
| 24 | | CF₂ | 418.271 | 418.36 |

TABLE 1-continued
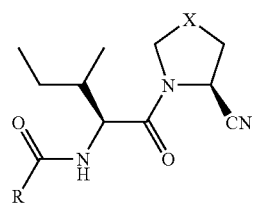
| Example No. | R | X | Mol Wt | [M + H]+ |
|---|---|---|---|---|
| 25 | 3,4-diCl-phenyl | CH₂ | 382.291 | 382.36 |
| 26 | | S | 400.328 | 400.1 |
| 27 | | CH₂CH₂ | 396.318 | 396.26 |
| 28 | | CF₂ | 418.271 | 418.29 |
| 29 | 3,5-diCl-phenyl | CH₂ | 382.291 | 382.33 |
| 30 | | S | 400.328 | 400.16 |
| 31 | | CH₂CH₂ | 396.318 | 396.27 |
| 32 | 3-F-phenyl | CH₂ | 331.391 | 332.34 |
| 33 | | S | 349.428 | 350.16 |
| 34 | | CH₂CH₂ | 345.418 | 346.29 |
| 35 | | CF₂ | 367.371 | 368.45 |
| 36 | 4-F-phenyl | CH₂ | 331.391 | 332.35 |
| 37 | | S | 349.428 | 350.15 |
| 38 | | CH₂CH₂ | 345.418 | 346.35 |
| 39 | | CF₂ | 367.371 | 368.44 |
| 40 | 4-MeO-phenyl | S | 361.464 | 362.17 |
| 41 | | CH₂CH₂ | 357.454 | 358.3 |
| 42 | | CF₂ | 379.407 | 380.48 |
| 43 | 3-MeO-phenyl | CH₂CH₂ | 357.454 | 358.38 |
| 44 | | CF₂ | 379.407 | 380.51 |
| 45 | benzo[1,3]dioxol-5-yl | CF₂ | 393.39 | 394.54 |
| 46 | 2-methylphenyl | CH₂ | 327.428 | 328.4 |
| 47 | | S | 345.465 | 346.16 |
| 48 | | CH₂CH₂ | 341.455 | 342.37 |
| 49 | | CF₂ | 363.408 | 364.41 |

TABLE 1-continued
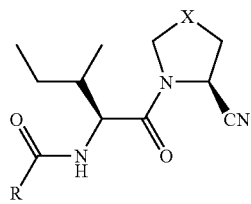
| Example No. | R | X | Mol Wt | [M + H]+ |
|---|---|---|---|---|
| 50 | 3-isopropylphenyl | CH₂ | 327.428 | 328.43 |
| 51 | | S | 345.465 | 346.17 |
| 52 | | CH₂CH₂ | 341.455 | 342.33 |
| 53 | | CF₂ | 363.408 | 364.44 |
| 54 | 4-isopropylphenyl | CH₂ | 327.428 | 328.42 |
| 55 | | S | 345.465 | 346.21 |
| 56 | | CH₂CH₂ | 341.455 | 342.33 |
| 57 | | CF₂ | 363.408 | 364.46 |
| 58 | 3-CF₃-phenyl | CH₂ | 381.398 | 382.38 |
| 59 | | S | 399.435 | 400.15 |
| 60 | | CH₂CH₂ | 395.425 | 396.33 |
| 61 | | CF₂ | 417.378 | 418.4 |
| 62 | 3-NO₂-phenyl | CH₂ | 358.398 | 359.38 |
| 63 | | S | 376.435 | 377.22 |
| 64 | | CF₂ | 394.378 | 395.61 |
| 65 | 1-naphthyl | CH₂ | 363.461 | 364.42 |
| 66 | | S | 381.498 | 382.24 |
| 67 | | CH₂CH₂ | 377.488 | 378.37 |
| 68 | | CF₂ | 399.441 | 400.49 |
| 69 | 2-naphthyl | CH₂ | 363.461 | 364.41 |
| 70 | | S | 381.498 | 382.19 |
| 71 | | CH₂CH₂ | 377.488 | 378.36 |
| 72 | | CF₂ | 399.441 | 400.46 |
| 73 | 4-tert-butylphenyl | CH₂ | 369.509 | 370.48 |
| 74 | | S | 387.546 | 388.24 |
| 75 | | CH₂CH₂ | 383.536 | 384.39 |
| 76 | | CF₂ | 405.489 | 406.47 |

TABLE 1-continued
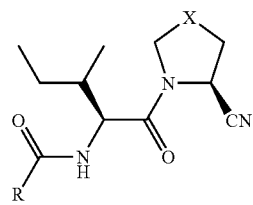
| Example No. | R | X | Mol Wt | [M + H]+ |
|---|---|---|---|---|
| 77 | 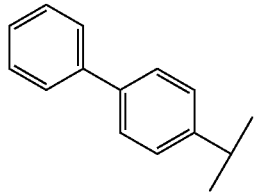 | CH₂ | 389.499 | 391.45 |
| 78 | 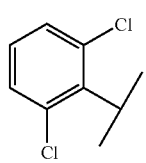 | CH₂ | 331.391 | 332.39 |
| 79 | | S | 349.428 | 350.18 |
| 80 | | CH₂CH₂ | 345.418 | 346.38 |
| 81 | | CF₂ | 367.371 | 368.45 |
| 82 | 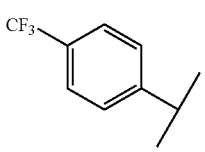 | CH₂ | 382.291 | 382.31 |
| 83 | | S | 400.328 | 400.1 |
| 84 | | CH₂CH₂ | 396.318 | 396.25 |
| 85 | | CF₂ | 418.271 | 418.32 |
| 86 | 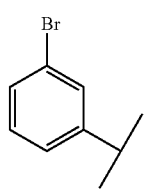 | CH₂ | 381.398 | 382.4 |
| 87 | | S | 399.435 | 400.06 |
| 88 | | CH₂CH₂ | 395.425 | 396.32 |
| 89 | 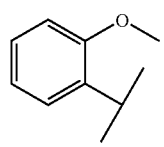 | CH₂ | 392.302 | 392.34 |
| 90 | | S | 410.339 | 410.05 |
| 91 | | CF₂ | 428.282 | 428.28 |
| 92 | | S | 361.464 | 362.16 |
| 93 | 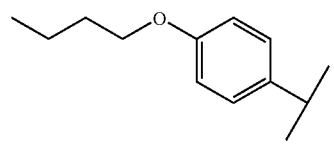 | CH₂ | 385.508 | 386.47 |
| 94 | | S | 403.545 | 404.24 |
| 95 | | CH₂CH₂ | 399.535 | 400.43 |
| 96 | | CF₂ | 421.488 | 422.46 |
| 97 | 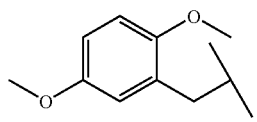 | CH₂ | 387.48 | 388.47 |
| 98 | | S | 405.417 | 406.2 |
| 99 | | CH₂CH₂ | 401.507 | 402.37 |
| 100 | | CF₂ | 423.46 | 424.41 |

TABLE 1-continued

| Example No. | R | X | Mol Wt | [M + H]+ |
|---|---|---|---|---|
| 101 | (pentyl-phenyl) | CH₂ | 397.563 | 398.47 |
| 102 | | S | 415.6 | 416.25 |
| 103 | | CH₂CH₂ | 411.59 | 412.41 |
| 104 | | CF₂ | 433.543 | 434.45 |
| 105 | (benzyl) | CH₂ | 327.428 | 328.41 |
| 106 | | S | 345.465 | 346.19 |
| 107 | | CH₂CH₂ | 341.455 | 342.35 |
| 108 | | CF₂ | 363.408 | 364.52 |
| 109 | (phenethyl) | CH₂ | 341.455 | 342.43 |
| 110 | | CH₂CH₂ | 355.482 | 356.35 |
| 111 | | CF₂ | 377.435 | 378.58 |
| 112 | (benzothiophene) | CH₂ | 369.487 | 370.38 |
| 113 | | CF₂ | 405.467 | 406.37 |
| 114 | (thiophene) | CH₂ | 319.427 | 320.33 |
| 115 | | S | 337.464 | 338.15 |
| 116 | | CH₂CH₂ | 333.454 | 334.3 |
| 117 | | CF₂ | 355.407 | 356.33 |
| 118 | (furan) | CH₂ | 303.262 | 304.32 |
| 119 | | S | 321.399 | 322.14 |
| 120 | | CH₂CH₂ | 317.389 | 318.35 |
| 121 | | CF₂ | 339.342 | 340.39 |
| 122 | (2-chloropyridine) | CH₂ | 348.834 | 349.34 |
| 123 | | S | 366.871 | 367.28 |
| 124 | | CH₂CH₂ | 362.861 | 363.33 |
| 125 | (benzyloxy) | CH₂ | 357.454 | 358.42 |
| 126 | | S | 375.491 | 376.24 |
| 127 | | CH₂CH₂ | 371.481 | 372.35 |
| 128 | | CF₂ | 393.434 | 394.43 |
| 129 | (cyclohexyl) | CH₂ | 319.449 | 320.43 |
| 130 | | S | 337.486 | 338.2 |
| 131 | | CH₂CH₂ | 333.476 | 334.34 |
| 132 | | CF₂ | 355.429 | 356.5 |

TABLE 1-continued
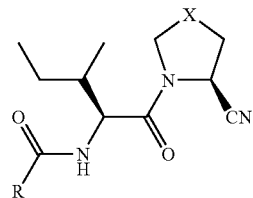
| Example No. | R | X | Mol Wt | [M + H]+ |
| --- | --- | --- | --- | --- |
| 133 | cyclopentyl-CH2- | CH2 | 305.422 | 306.46 |
| 134 | | S | 323.459 | 324.15 |
| 135 | | CF2 | 341.402 | 342.46 |
| 136 | cyclobutyl-CH2- | CH2 | 291.395 | 292.4 |
| 137 | | S | 309.432 | 310.19 |
| 138 | | CH2CH2 | 305.422 | 306.35 |
| 139 | | CF2 | 327.375 | 328.42 |
| 140 | cyclopropyl-CH2- | CH2 | 277.368 | 278.38 |
| 141 | | S | 295.405 | 296.15 |
| 142 | | CF2 | 313.348 | 314.45 |
| 143 | cyclopentyl-CH2CH2- | CH2 | 319.449 | 320.44 |
| 144 | | S | 337.486 | 338.2 |
| 145 | | CH2CH2 | 333.476 | 334.39 |
| 146 | | CF2 | 355.429 | 356.47 |
| 147 | t-Bu-CH2- | S | 344.448 | 311.91 |
| 148 | | CF2 | 329.391 | 330.46 |
| 149 | t-Bu-CH2CH2- | CH2 | 307.438 | 308.46 |
| 150 | | S | 325.475 | 326.21 |
| 151 | | CH2CH2 | 321.465 | 322.4 |
| 152 | | CF2 | 343.418 | 344.48 |
| 153 | n-hexyl- | CH2 | 307.438 | 308.41 |
| 154 | | CF2 | 343.418 | 344.49 |
| 155 | | CH2 | 335.492 | 336.46 |
| 156 | | S | 353.529 | 354.26 |
| 157 | | CH2CH2 | 349.519 | 350.39 |
| 158 | | CF2 | 371.472 | 372.61 |
| 159 | MeO2C-(CH2)3- | CH2 | 323.393 | 324.4 |
| 160 | | S | 341.43 | 342.17 |
| 161 | MeO2C-(CH2)6- | CH2 | 379.501 | 380.48 |
| 162 | | S | 397.538 | 398.24 |
| 163 | | CF2 | 415.481 | 416.48 |

TABLE 1-continued

[Structure: N-acyl amino acid derivative with thiazolidine/pyrrolidine ring bearing CN group, where X is a ring atom and R is substituent on the acyl group]

| Example No. | R | X | Mol Wt | [M + H]+ |
|---|---|---|---|---|
| 164 | phenylcyclopropyl | CH₂ | 353.466 | 354.42 |
| 165 | | S | 371.503 | 372.22 |
| 166 | | CH₂CH₂ | 367.493 | 368.37 |
| 167 | | CF₂ | 389.446 | 390.51 |
| 168 | 2-(trifluoromethoxy)phenyl | CH₂ | 397.397 | 398.39 |
| 169 | | S | 415.434 | 416.21 |
| 170 | | CH₂CH₂ | 411.424 | 412.33 |
| 171 | | CF₂ | 433.377 | 434.44 |
| 172 | 2,6-difluorophenyl | CH₂ | 349.381 | 350.36 |
| 173 | | S | 367.418 | 368.1 |
| 174 | | CH₂CH₂ | 363.408 | 364.31 |
| 175 | | CF₂ | 385.361 | 386.47 |
| 173 | 4-(dimethylamino)phenyl | CH₂ | 356.47 | 357.45 |
| 177 | | S | 374.507 | 375.21 |
| 178 | | CF₂ | 392.45 | 393.52 |
| 179 | pyridin-3-yl | CH₂ | 314.389 | 315.38 |
| 180 | | S | 332.426 | 333.17 |
| 181 | | CH₂CH₂ | 328.416 | 329.32 |
| 182 | | CF₂ | 350.369 | 351.42 |
| 183 | pyridin-4-yl | S | 332.426 | 333.17 |
| 184 | | CH₂CH₂ | 328.416 | 329.32 |
| 185 | | CF₂ | 350.369 | 351.44 |
| 186 | adamantyl | CH₂ | 371.525 | 372.46 |
| 187 | | S | 389.562 | 390.25 |
| 188 | | CH₂CH₂ | 385.552 | 386.44 |
| 189 | | CF₂ | 407.505 | 408.49 |
| 190 | 2,4,5-trifluorophenyl | CH₂S | 367.371 | 368.35 |
| 191 | | | 385.408 | 386.01 |
| 192 | thiophen-2-yl | CH₂ | 333.454 | 334.38 |
| 193 | | S | 351.491 | 352.14 |
| 194 | | CH₂CH₂ | 347.481 | 348.31 |
| 195 | | CF₂ | 369.434 | 370.44 |

TABLE 1-continued
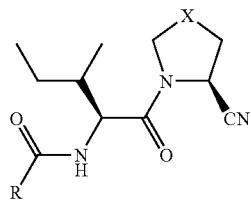
| Example No. | R | X | Mol Wt | [M + H]+ |
|---|---|---|---|---|
| 196 | (phenoxyethyl) | CH₂ | 343.427 | 344.41 |
| 197 | | S | 361.464 | 362.14 |
| 198 | | CH₂CH₂ | 357.454 | 358.33 |
| 199 | | CF₂ | 379.407 | 380.48 |
| 200 | (3,4-difluorophenyl) | CH₂ | 349.381 | 350.4 |
| 201 | | S | 367.418 | 368.12 |
| 202 | | CH₂CH₂ | 363.408 | 364.34 |
| 203 | (1-phenyl-2-methylbutyl) | CH₂ | 355.482 | 356.4 |
| 204 | | S | 373.519 | 374.18 |
| 205 | | CH₂CH₂ | 369.509 | 370.39 |
| 206 | | CF₂ | 391.462 | 392.49 |
| 207 | (3-thienyl) | CH₂ | 319.427 | 320.31 |
| 208 | | S | 337.464 | 338.1 |
| 209 | | CH₂CH₂ | 333.454 | 334.28 |
| 210 | | CF₂ | 355.407 | 356.36 |
| 211 | (2,3-difluorophenyl) | CH₂ | 349.381 | 350.4 |
| 212 | | S | 367.418 | 368.2 |
| 213 | (3-tert-butylbenzothiophene) | CF₂ | 405.467 | 406.38 |
| 214 | (3,5-difluorophenyl) | CH₂ | 349.381 | 350.38 |
| 215 | | S | 367.418 | 368.09 |

TABLE 2
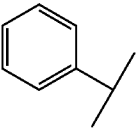
| Example No. | R | X' | Mol Wt | [M + H]+ |
|---|---|---|---|---|
| 216 | CH₃ | CH₂ | 237.303 | 238.36 |
| 217 | 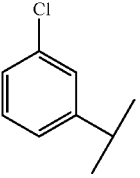 | CH₂ | 299.374 | 300.36 |
| 218 | | —CH=CH— | 311.385 | 312.12 |
| 219 | 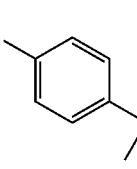 | CH₂ | 333.819 | 334.33 |
| 220 | | —CH=CH— | 345.83 | 346.16 |
| 21 | 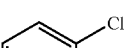 | CH₂ | 333.819 | 334.35 |
| 222 | | —CH=CH— | 345.83 | 346.11 |
| 223 | 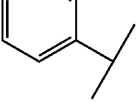 | CH₂ | 333.819 | 334.38 |
| 224 | | —CH=CH— | 345.83 | 346.12 |
| 225 | 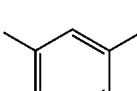 | CH₂ | 368.264 | 368.38 |
| 226 | | —CH=CH— | 380.275 | 380.09 |
| 227 |  | CH₂ | 368.264 | 368.3 |
| 228 | | —CH=CH— | 380.275 | 380.11 |
| 229 |  | CH₂ | 368.264 | 368.36 |
| 230 | | —CH=CH— | 380.275 | 380.08 |

TABLE 2-continued
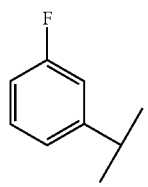
| Example No. | R | X' | Mol Wt | [M + H]+ |
|---|---|---|---|---|
| 231 | 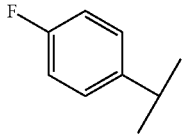 | CH₂ | 317.364 | 318.38 |
| 232 | | —CH=CH— | 329.375 | 330.17 |
| 233 | 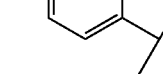 | CH₂ | 317.364 | 318.4 |
| 234 | | —CH=CH— | 329.375 | 330.15 |
| 235 | 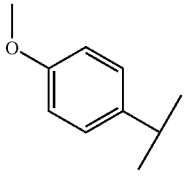 | CH₂ | 329.4 | 330.39 |
| 236 | | —CH=CH— | 341.411 | 342.16 |
| 237 | 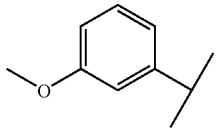 | CH₂ | 329.4 | 330.42 |
| 238 | | —CH=CH— | 341.411 | 342.16 |
| 239 | 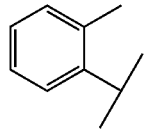 | CH₂ | 313.401 | 314.41 |
| 240 | | —CH=CH— | 325.412 | 326.2 |
| 241 | 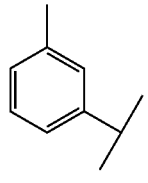 | CH₂ | 313.401 | 314.38 |
| 242 | | —CH=CH— | 325.412 | 326.21 |
| 243 | 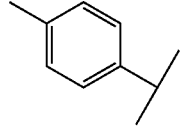 | CH₂ | 313.401 | 314.43 |
| 244 | | —CH=CH— | 325.412 | 326.26 |
| 245 | 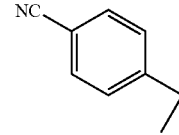 | CH₂ | 324.384 | 325.34 |
| 246 | | —CH=CH— | 336.395 | 337.23 |

TABLE 2-continued

| Example No. | R | X' | Mol Wt | [M + H]+ |
|---|---|---|---|---|
| 247 | 3-(CF₃)-phenyl | CH₂ | 367.382 | 368.39 |
| 248 | 3-(CF₃)-phenyl | —CH=CH— | 379.382 | 380.17 |
| 249 | 3-NO₂-phenyl | CH₂ | 344.371 | 345.43 |
| 250 | 3-NO₂-phenyl | —CH=CH— | 356.382 | 357.13 |
| 251 | 3-CN-phenyl | —CH=CH— | 336.395 | 336.09 |
| 252 | 1-naphthyl | CH₂ | 349.434 | 350.44 |
| 253 | 1-naphthyl | —CH=CH— | 361.445 | 362.17 |
| 254 | 2-naphthyl | CH₂ | 349.434 | 350.43 |
| 255 | 2-naphthyl | —CH=CH— | 361.445 | 362.18 |
| 256 | 4-tert-butyl-phenyl | CH₂ | 355.482 | 356.43 |
| 257 | 4-tert-butyl-phenyl | —CH=CH— | 367.493 | 368.23 |
| 258 | 4-biphenyl | —CH=CH— | 387.483 | 389.19 |

TABLE 2-continued
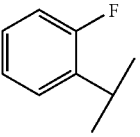
| Example No. | R | X' | Mol Wt | [M + H]+ |
|---|---|---|---|---|
| 259 | 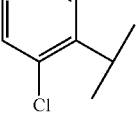 | CH₂ | 317.364 | 318.37 |
| 260 | | —CH=CH— | 329.375 | 330.2 |
| 261 | 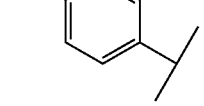 | CH₂ | 368.264 | 368.34 |
| 262 | | —CH=CH— | 380.275 | 380.07 |
| 263 | 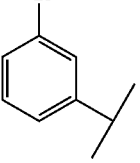 | CH₂ | 367.371 | 368.41 |
| 264 | | —CH=CH— | 379.382 | 380.19 |
| 265 | 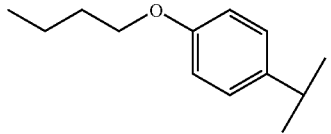 | CH₂ | 378.275 | 378.35 |
| 266 | | —CH=CH— | 390.286 | 390.07 |
| 267 | 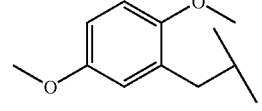 | CH₂ | 371.481 | 372.46 |
| 268 | | —CH=CH— | 383.492 | 384.25 |
| 269 | 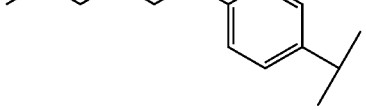 | CH₂ | 373.453 | 374.44 |
| 270 | | —CH=CH— | 385.464 | 386.21 |
| 271 | 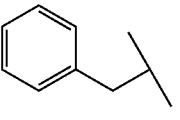 | CH₂ | 383.536 | 384.51 |
| 272 | | —CH=CH— | 395.547 | 396.26 |
| 273 | 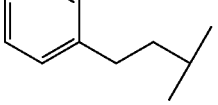 | CH₂ | 313.401 | 314.45 |
| 274 | | —CH=CH— | 325.412 | 326.22 |
| 275 |  | CH₂ | 327.428 | 328.45 |
| 276 | | —CH=CH— | 339.439 | 340.19 |

TABLE 2-continued

| Example No. | R | X' | Mol Wt | [M + H]+ |
|---|---|---|---|---|
| 277 | thiophene | CH₂ | 305.4 | 306.34 |
| 278 | | —CH=CH— | 317.411 | 318.04 |
| 279 | furan | CH₂ | 289.335 | 290.39 |
| 280 | | —CH=CH— | 301.346 | 302.12 |
| 281 | 2-chloropyridine | CH₂ | 334.807 | 335.5 |
| 282 | | —CH=CH— | 346.818 | 347.19 |
| 283 | benzyloxy | CH₂ | 343.427 | 344.43 |
| 284 | | —CH=CH— | 355.438 | 356.21 |
| 285 | cyclohexyl | CH₂ | 305.422 | 306.44 |
| 286 | | —CH=CH— | 317.433 | 318.2 |
| 287 | cyclopentyl | CH₂ | 291.395 | 22.42 |
| 288 | | —CH=CH— | 303.406 | 304.13 |
| 289 | cyclobutyl | CH₂ | 277.368 | 278.43 |
| 290 | | —CH=CH— | 289.379 | 290.12 |
| 291 | cyclopropyl | CH₂ | 263.341 | 364.46 |
| 292 | | —CH=CH— | 275.352 | 276.08 |
| 293 | cyclopentylmethyl | CH₂ | 305.422 | 306.41 |
| 294 | | —CH=CH— | 317.433 | 318.25 |
| 295 | tert-butyl | CH₂ | 279.384 | 280.48 |
| 296 | | —CH=CH— | 291.395 | 292.16 |

TABLE 2-continued

| Example No. | R | X' | Mol Wt | [M + H]+ |
|---|---|---|---|---|
| 297 | (neopentyl-like branched alkyl) | CH$_2$ | 293.411 | 294.45 |
| 298 | | —CH=CH— | 305.422 | 306.19 |
| 299 | (n-hexyl branched) | CH$_2$ | 293.411 | 294.42 |
| 300 | | —CH=CH— | 305.422 | 306.18 |
| 301 | (2-ethylhexyl branched) | CH$_2$ | 321.465 | 322.49 |
| 302 | | —CH=CH— | 333.476 | 334.25 |
| 303 | (methyl ester alkyl) | CH$_2$ | 309.366 | 310.38 |
| 304 | | —CH=CH— | 321.377 | 322.17 |
| 305 | (methyl ester long alkyl) | CH$_2$ | 365.474 | 366.46 |
| 306 | | —CH=CH— | 377.485 | 378.24 |
| 307 | (phenylcyclopropyl) | CH$_2$ | 339.439 | 340.43 |
| 308 | | —CH=CH— | 351.45 | 352.2 |
| 309 | (2-OCF$_3$-phenyl) | CH$_2$ | 383.37 | 384.42 |
| 310 | | —CH=CH— | 395.381 | 396.15 |
| 311 | (2,6-difluorophenyl) | CH$_2$ | 335.354 | 336.37 |
| 312 | | —CH=CH— | 347.365 | 348.11 |
| 313 | (4-dimethylaminophenyl) | CH$_2$ | 342.443 | 343.44 |
| 314 | | —CH=CH— | 354.454 | 355.2 |

TABLE 2-continued

| Example No. | R | X' | Mol Wt | [M + H]+ |
|---|---|---|---|---|
| 315 | (3-pyridyl) | CH₂ | 300.362 | 301.38 |
| 316 | (1-adamantyl) | CH₂ | 357.498 | 358.46 |
| 317 | (1-adamantyl) | —CH=CH— | 369.509 | 370.27 |
| 318 | (2,4,5-trifluorophenyl) | CH₂ | 353.344 | 354.39 |
| 319 | (2,4,5-trifluorophenyl) | —CH=CH— | 365.355 | 366.13 |
| 320 | (2-thienyl) | CH₂ | 319.427 | 320.37 |
| 321 | (2-thienyl) | —CH=CH— | 331.438 | 332.15 |
| 322 | (phenoxymethyl) | CH₂ | 329.4 | 330.47 |
| 323 | (phenoxymethyl) | —CH=CH— | 341.411 | 342.19 |
| 324 | (3,4-difluorophenyl) | CH₂ | 335.354 | 336.46 |
| 325 | (3,4-difluorophenyl) | —CH=CH— | 347.365 | 348.17 |
| 326 | (1-phenylpropyl) | CH₂ | 341.455 | 342.44 |
| 327 | (1-phenylpropyl) | —CH=CH— | 353.466 | 354.21 |
| 328 | (3-thienyl) | CH₂ | 305.4 | 306.34 |
| 329 | (3-thienyl) | —CH=CH— | 317.411 | 318.14 |
| 330 | (2,3-difluorophenyl) | CH₂ | 335.354 | 336.37 |
| 331 | (2,3-difluorophenyl) | —CH=CH— | 347.365 | 348.12 |

TABLE 2-continued
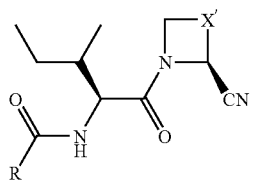
| Example No. | R | X' | Mol Wt | [M + H]+ |
|---|---|---|---|---|
| 332 | (3,5-difluorophenyl, isopropyl) | CH₂ | 335.354 | 336.43 |
| 333 | | —CH=CH— | 347.365 | 348.16 |
TABLE 3
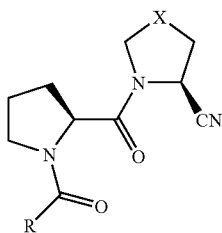
| Example No. | R | X | Mol Wt | [M + H]+ |
|---|---|---|---|---|
| 334 | CH₃ | CH₂CH₂ | 249.314 | 250.24 |
| 335 | | CF₂ | 271.267 | 271.41 |
| 336 | (phenyl, isopropyl) | CH₂ | 297.358 | 298.37 |
| 337 | | CH₂CH₂ | 311.385 | 312.25 |
| 338 | | CF₂ | 333.338 | 334.4 |
| 339 | (3-chlorophenyl, isopropyl) | CH₂CH₂ | 345.83 | 346.22 |
| 340 | | CF₂ | 367.783 | 368.36 |
| 341 | (4-chlorophenyl, isopropyl) | CH₂ | 331.803 | 332.33 |
| 342 | | CH₂CH₂ | 345.83 | 346.21 |
| 343 | | CF₂ | 367.783 | 368.35 |
| 344 | (2-chlorophenyl, isopropyl) | CH₂ | 331.803 | 332.36 |
| 345 | | CH₂CH₂ | 345.83 | 346.22 |
| 346 | | CF₂ | 367.783 | 368.41 |

TABLE 3-continued

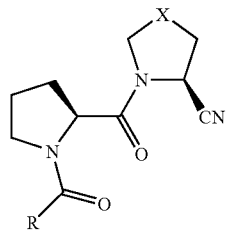

| Example No. | R | X | Mol Wt | [M + H]+ |
|---|---|---|---|---|
| 347 | 2,4-dichlorophenyl | CH₂ | 366.248 | 366.3 |
| 348 | 2,4-dichlorophenyl | CH₂CH₂ | 380.275 | 380.2 |
| 349 | 3,4-dichlorophenyl | CH₂ | 366.248 | 366.31 |
| 350 | 3,4-dichlorophenyl | CH₂CH₂ | 380.275 | 380.17 |
| 351 | 3,4-dichlorophenyl | CF₂ | 402.228 | 402.42 |
| 352 | 3,5-dichlorophenyl | CH₂ | 366.248 | 366.29 |
| 353 | 3-fluorophenyl | CH₂ | 315.348 | 316.36 |
| 354 | 3-fluorophenyl | CH₂CH₂ | 329.375 | 330.21 |
| 355 | 3-fluorophenyl | CF₂ | 351.328 | 352.39 |
| 356 | 4-fluorophenyl | CH₂ | 315.348 | 316.39 |
| 357 | 4-fluorophenyl | CH₂CH₂ | 329.375 | 330.25 |
| 358 | 4-fluorophenyl | CF₂ | 351.328 | 352.34 |
| 359 | 4-methoxyphenyl | CH₂ | 327.384 | 328.39 |
| 360 | 4-methoxyphenyl | CH₂CH₂ | 341.411 | 342.23 |
| 361 | 4-methoxyphenyl | CF₂ | 363.364 | 364.39 |
| 362 | 3-methoxyphenyl | CH₂CH₂ | 341.411 | 342.26 |
| 363 | 3-methoxyphenyl | CF₂ | 363.364 | 364.4 |

TABLE 3-continued

| Example No. | R | X | Mol Wt | [M + H]+ |
|---|---|---|---|---|
| 364 | 2-methylphenyl | CH$_2$ | 311.385 | 312.38 |
| 365 | | CH$_2$CH$_2$ | 325.412 | 326.29 |
| 366 | | CF$_2$ | 347.365 | 348.38 |
| 367 | 3-methylphenyl | CH$_2$ | 311.385 | 312.39 |
| 368 | | CH$_2$CH$_2$ | 325.412 | 326.26 |
| 369 | | CF$_2$ | 347.365 | 348.38 |
| 370 | 4-methylphenyl | CH$_2$ | 311.385 | 312.38 |
| 371 | | CH$_2$CH$_2$ | 325.412 | 326.26 |
| 372 | | CF$_2$ | 347.365 | 348.41 |
| 373 | 3-CF$_3$-phenyl | CH$_2$ | 365.355 | 366.38 |
| 374 | | CH$_2$CH$_2$ | 379.382 | 380.27 |
| 375 | 3-NO$_2$-phenyl | CH$_2$ | 342.355 | 343.36 |
| 376 | | CH$_2$CH$_2$ | 356.382 | 357.26 |
| 377 | 1-naphthyl | CH$_2$CF$_2$ | 347.418 | 348.4 |
| 378 | | | 383.398 | 384.38 |
| 379 | 2-naphthyl | CH$_2$ | 347.418 | 348.39 |
| 380 | | CH$_2$CH$_2$ | 361.445 | 362.29 |
| 381 | | CF$_2$ | 383.398 | 384.42 |

TABLE 3-continued
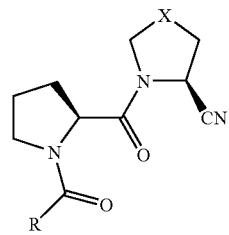
| Example No. | R | X | Mol Wt | [M + H]+ |
| --- | --- | --- | --- | --- |
| 382 | | CH₂ | 353.466 | 354.43 |
| 383 | | CH₂CH₂ | 367.493 | 368.33 |
| 384 | | CF₂ | 389.446 | 390.46 |
| 385 | | CH₂ | 315.348 | 316.34 |
| 386 | | CH₂CH₂ | 329.375 | 330.26 |
| 387 | | CF₂ | 351.328 | 352.41 |
| 388 | | CH₂ | 366.248 | 366.3 |
| 389 | | CH₂CH₂ | 380.275 | 380.2 |
| 390 | | CF₂ | 402.228 | 402.29 |
| 391 | | CH₂ | 365.355 | 366.36 |
| 392 | | CH₂CH₂ | 379.382 | 380.24 |
| 393 | | CF₂ | 401.335 | 402.37 |
| 394 | | CH₂ | 376.259 | 376.29 |
| 395 | | CH₂CH₂ | 390.286 | 390.16 |
| 396 | | CF₂ | 412.239 | 412.2 |
| 397 | | CH₂ | 327.384 | 328.38 |
| 398 | | CF₂ | 363.364 | 364.41 |
| 399 | | CH₂ | 369.465 | 370.44 |
| 400 | | CH₂CH₂ | 383.492 | 384.32 |
| 401 | | CF₂ | 405.445 | 406.44 |
| 402 | | CH₂ | 371.437 | 372.41 |
| 403 | | CH₂CH₂ | 385.464 | 387.32 |
| 404 | | CF₂ | 407.417 | 408.41 |

TABLE 3-continued

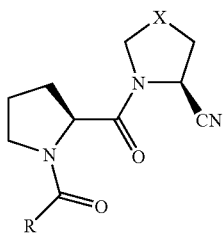

| Example No. | R | X | Mol Wt | [M + H]+ |
|---|---|---|---|---|
| 405 | hexyl-phenyl-CH | CH₂ | 381.52 | 382.5 |
| 406 | hexyl-phenyl-CH | CH₂CH₂ | 395.547 | 396.34 |
| 407 | hexyl-phenyl-CH | CF₂ | 417.5 | 418.45 |
| 408 | phenyl-CH | CH₂ | 311.385 | 312.4 |
| 409 | phenyl-CH | CH₂CH₂ | 325.412 | 326.27 |
| 410 | phenyl-CH | CF₂ | 347.365 | 348.42 |
| 411 | phenyl-CH₂-CH | CH₂ | 325.412 | 326.41 |
| 412 | phenyl-CH₂-CH | CH₂CH₂ | 339.439 | 340.28 |
| 413 | phenyl-CH₂-CH | CF₂ | 361.392 | 362.4 |
| 414 | benzothiophene-CH | CH₂ | 353.444 | 354.38 |
| 415 | thiophene-CH | CH₂ | 303.384 | 304.34 |
| 416 | thiophene-CH | CH₂CH₂ | 317.411 | 318.19 |
| 417 | thiophene-CH | CF₂ | 339.364 | 340.36 |
| 418 | furan-CH | CH₂ | 287.319 | 288.38 |
| 419 | furan-CH | CH₂CH₂ | 301.346 | 302.2 |
| 420 | furan-CH | CF₂ | 323.299 | 324.34 |
| 421 | 2-Cl-pyridine-CH | CF₂ | 368.771 | 369.35 |
| 422 | PhCH₂OCH₂-CH | CH₂ | 341.411 | 342.41 |
| 423 | PhCH₂OCH₂-CH | CH₂CH₂ | 355.438 | 356.29 |
| 424 | PhCH₂OCH₂-CH | CF₂ | 377.391 | 378.41 |
| 425 | cyclohexyl-CH | CH₂ | 303.406 | 304.4 |
| 426 | cyclohexyl-CH | CF₂ | 339.386 | 340.4 |

TABLE 3-continued
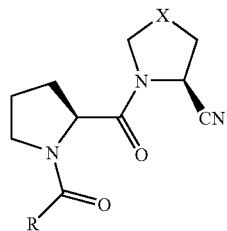
| Example No. | R | X | Mol Wt | [M + H]+ |
|---|---|---|---|---|
| 427 | cyclopentylmethyl | CH₂ | 289.379 | 290.4 |
| 428 | | CH₂CH₂ | 303.406 | 304.27 |
| 429 | | CF₂ | 325.359 | 326.45 |
| 430 | cyclobutylmethyl | CH₂ | 275.352 | 276.41 |
| 431 | | CH₂CH₂ | 289.379 | 290.27 |
| 432 | | CF₂ | 311.332 | 312.39 |
| 433 | cyclopropylmethyl | CH₂ | 261.325 | 262.39 |
| 434 | | CH₂CH₂ | 275.352 | 276.25 |
| 435 | | CF₂ | 297.305 | 298.38 |
| 436 | cyclopentylethyl | CH₂ | 303.406 | 304.43 |
| 437 | | CH₂CH₂ | 317.433 | 318.27 |
| 438 | | CF₂ | 339.386 | 340.45 |
| 439 | tert-butylmethyl | CH₂ | 277.368 | 278.45 |
| 440 | | CH₂CH₂ | 291.395 | 292.25 |
| 441 | | CF₂ | 313.348 | 314.4 |
| 442 | neopentylmethyl | CH₂ | 291.395 | 292.43 |
| 443 | | CF₂ | 327.375 | 328.42 |
| 444 | heptyl | CH₂ | 291.395 | 292.43 |
| 445 | | CF₂ | 327.375 | 328.44 |
| 446 | 2-ethylhexyl | CH₂ | 319.449 | 320.47 |
| 447 | | CF₂ | 355.429 | 356.47 |
| 448 | methyl ester C3 | CH₂ | 307.35 | 308.35 |
| 449 | methyl ester C7 | CH₂ | 363.458 | 364.44 |
| 450 | | CF₂ | 399.438 | 400.46 |

TABLE 3-continued
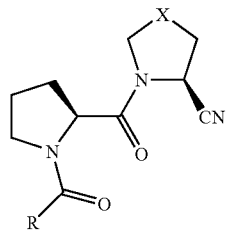
| Example No. | R | X | Mol Wt | [M + H]+ |
|---|---|---|---|---|
| 451 | 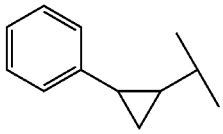 | CH₂ | 337.423 | 338.41 |
| 452 | | CH₂CH₂ | 351.45 | 352.24 |
| 453 | | CF₂ | 373.403 | 374.43 |
| 454 | 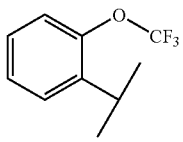 | CH₂ | 381.354 | 382.39 |
| 455 | | CH₂CH₂ | 395.381 | 396.23 |
| 456 | | CF₂ | 417.334 | 418.31 |
| 457 | 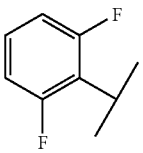 | CH₂ | 333.338 | 334.37 |
| 458 | | CH₂CH₂ | 347.365 | 348.23 |
| 459 | | CF₂ | 369.318 | 370.36 |
| 460 | 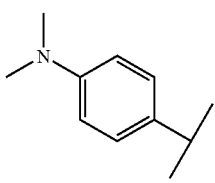 | CH₂ | 340.427 | 341.43 |
| 461 | | CF₂ | 376.407 | 376.43 |
| 462 |  | CF₂ | 334.326 | 335.38 |
| 463 | 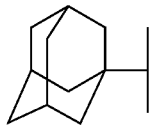 | CH₂ | 355.482 | 356.44 |
| 464 | | CH₂CH₂ | 369.509 | 370.34 |
| 465 | | CF₂ | 391.462 | 392.49 |
| 466 | 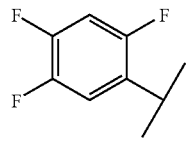 | CH₂ | 351.328 | 352.36 |
| 467 | | CH₂CH₂ | 365.355 | 366.21 |
| 468 | 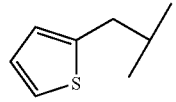 | CH₂ | 317.411 | 318.33 |
| 469 | | CH₂CH₂ | 331.438 | 332.2 |
| 470 | | CF₂ | 353.391 | 354.36 |

TABLE 3-continued
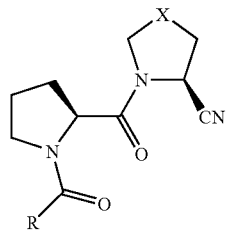
| Example No. | R | X | Mol Wt | [M + H]+ |
|---|---|---|---|---|
| 471 | phenoxyethyl | $CH_2$ | 327.384 | 328.38 |
| 472 | | $CH_2CH_2$ | 341.411 | 342.27 |
| 473 | | $CF_2$ | 363.364 | 364.4 |
| 474 | 3,4-difluorophenyl-ethyl | $CH_2$ | 333.338 | 334.39 |
| 475 | | $CH_2CH_2$ | 347.365 | 348.24 |
| 476 | 1-phenylpropyl(methyl) | $CH_2$ | 339.439 | 340.42 |
| 477 | | $CH_2CH_2$ | 353.466 | 354.31 |
| 478 | | $CF_2$ | 375.419 | 376.45 |
| 479 | thiophen-3-yl-ethyl | $CH_2$ | 303.384 | 304.33 |
| 480 | | $CH_2CH_2$ | 317.411 | 318.2 |
| 481 | | $CF_2$ | 339.364 | 340.35 |
| 482 | 2,3-difluorophenyl-ethyl | $CH_2$ | 333.338 | 334.37 |
| 483 | | $CH_2CH_2$ | 347.365 | 348.22 |
| 484 | benzothiophene-t-butyl | $CF_2$ | 389.424 | 390.34 |
| 485 | 3,5-difluorophenyl-ethyl | $CH_2$ | 333.338 | 334.41 |

TABLE 4
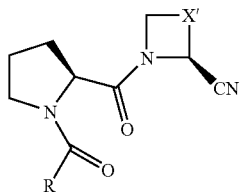
| Example No | R | X' | Mol Wt | [M + H]+ |
|---|---|---|---|---|
| 486 | CH₃ | CH₂ | 221.26 | 222.2 |
| 487 |  | —CH=CH— | 233.271 | 234.07 |
| 488 | phenyl | CH₂ | 283.331 | 284.04 |
| 489 |  | —CH=CH— | 295.342 | 296.11 |
| 490 | 3-Cl-phenyl | CH₂ | 317.776 | 318.12 |
| 491 |  | —CH=CH— | 329.787 | 330.11 |
| 492 | 4-Cl-phenyl | CH₂ | 317.776 | 318.07 |
| 493 |  | —CH=CH— | 329.787 | 330.11 |
| 494 | 2-Cl-phenyl | CH₂ | 317.776 | 318.11 |
| 495 |  | —CH=CH— | 329.787 | 330.13 |
| 496 | 2,4-diCl-phenyl | CH₂ | 352.221 | 352.04 |
| 497 |  | —CH=CH— | 364.232 | 364.08 |
| 498 | 3,4-diCl-phenyl | CH₂ | 352.221 | 352.09 |
| 499 |  | —CH=CH— | 364.232 | 364.05 |
| 500 | 3,5-diCl-phenyl | CH₂ | 352.221 | 352.07 |
| 501 |  | —CH=CH— | 364.232 | 364.07 |

TABLE 4-continued
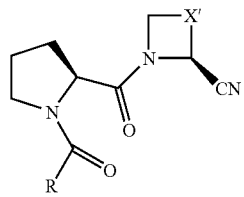
| Example No | R | X' | Mol Wt | [M + H]+ |
|---|---|---|---|---|
| 502 | 3-F-C6H4-CH2- | CH2 | 301.321 | 302.09 |
| 503 | 3-F-C6H4-CH2- | —CH=CH— | 313.332 | 314.13 |
| 504 | 4-F-C6H4-CH2- | CH2 | 301.321 | 302.09 |
| 505 | 4-F-C6H4-CH2- | —CH=CH— | 313.332 | 314.12 |
| 506 | 4-MeO-C6H4-CH2- | CH2 | 313.357 | 314.16 |
| 507 | 4-MeO-C6H4-CH2- | —CH=CH— | 325.368 | 326.16 |
| 508 | 3-MeO-C6H4-CH2- | CH2 | 313.357 | 314.12 |
| 509 | 3-MeO-C6H4-CH2- | —CH=CH— | 325.368 | 326.15 |
| 510 | benzo[1,3]dioxol-5-yl-CH2- | CH2 | 327.34 | 328.08 |
| 511 | benzo[1,3]dioxol-5-yl-CH2- | —CH=CH— | 339.351 | 339.51 |
| 512 | 2-Me-C6H4-CH2- | —CH=CH— | 309.369 | 310.14 |
| 513 | 3-Me-C6H4-CH2- | CH2 | 297.358 | 298.12 |
| 514 | 3-Me-C6H4-CH2- | —CH=CH— | 309.369 | 310.13 |
| 515 | 4-Me-C6H4-CH2- | CH2 | 297.358 | 298.1 |
| 516 | 4-Me-C6H4-CH2- | —CH=CH— | 309.369 | 310.13 |

TABLE 4-continued
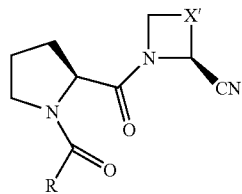
| Example No | R | X' | Mol Wt | [M + H]+ |
|---|---|---|---|---|
| 517 | NC-C6H4- | —CH=CH— | 320.352 | 321.09 |
| 518 | 3-CF3-C6H4- | CH2 | 351.328 | 352.1 |
| 519 | 3-CF3-C6H4- | —CH=CH— | 363.339 | 364.12 |
| 520 | 3-NO2-C6H4- | CH2 | 328.328 | 329.09 |
| 521 | 3-CN-C6H4- | CH2 | 308.341 | 309.17 |
| 522 | 1-naphthyl | CH2 | 333.391 | 334.18 |
| 523 | 1-naphthyl | —CH=CH— | 345.402 | 346.15 |
| 524 | 2-naphthyl | CH2 | 333.391 | 334.13 |
| 525 | 2-naphthyl | —CH=CH— | 345.402 | 346.14 |
| 526 | 4-tBu-C6H4- | CH2 | 339.439 | 340.2 |
| 527 | 4-tBu-C6H4- | —CH=CH— | 351.45 | 352.2 |

TABLE 4-continued

| Example No | R | X' | Mol Wt | [M + H]+ |
|---|---|---|---|---|
| 528 | biphenyl | —CH=CH— | 371.44 | 371.17 |
| 529 | 2-fluorophenyl | CH₂ | 301.321 | 302.13 |
| 530 | 2-fluorophenyl | —CH=CH— | 313.332 | 314.13 |
| 531 | 2,6-dichlorophenyl | CH₂ | 352.221 | 352.04 |
| 532 | 2,6-dichlorophenyl | —CH=CH— | 364.232 | 364.04 |
| 533 | 4-(trifluoromethyl)phenyl | CH₂ | 351.328 | 352.11 |
| 534 | 4-(trifluoromethyl)phenyl | —CH=CH— | 363.339 | 364.15 |
| 535 | 3-bromophenyl | CH₂ | 362.232 | 362.06 |
| 536 | 3-bromophenyl | —CH=CH— | 374.243 | 374.05 |
| 537 | 2-methoxyphenyl | CH₂ | 313.357 | 314.15 |
| 538 | 2-methoxyphenyl | —CH=CH— | 325.368 | 326.15 |
| 539 | 4-butoxyphenyl | CH₂ | 355.438 | 356.17 |
| 540 | 4-butoxyphenyl | —CH=CH— | 367.449 | 368.19 |
| 541 | 4-nitrophenyl | —CH=CH— | 340.339 | 341.2 |

TABLE 4-continued
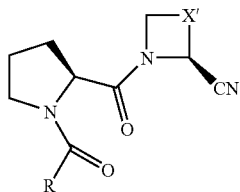
| Example No | R | X' | Mol Wt | [M + H]+ |
|---|---|---|---|---|
| 542 | 2,5-dimethoxy-phenyl-CH(CH3)- | CH2 | 357.41 | 358.18 |
| 543 | | —CH=CH— | 369.421 | 370.19 |
| 544 | 4-pentyl-phenyl-CH(CH3)- | CH2 | 367.493 | 368.24 |
| 545 | | —CH=CH— | 379.504 | 380.26 |
| 546 | phenyl-C(CH3)2-CH2- | CH2 | 297.358 | 298.13 |
| 547 | | —CH=CH— | 309.369 | 310.16 |
| 548 | phenyl-CH2CH2-CH(CH3)- | CH2 | 311.385 | 312.17 |
| 549 | | —CH=CH— | 323.396 | 324.13 |
| 550 | benzothiophen-2-yl-CH(CH3)- | CH2 | 339.417 | 340.01 |
| 551 | | —CH=CH— | 351.428 | 351.98 |
| 552 | thien-2-yl-CH(CH3)- | CH2 | 289.357 | 290.07 |
| 553 | | —CH=CH— | 301.368 | 302.09 |
| 554 | furan-2-yl-CH(CH3)- | CH2 | 273.292 | 274.13 |
| 555 | | —CH=CH— | 285.303 | 286.1 |
| 556 | phenyl-CH2-O-CH2-C(CH3)2- | CH2 | 327.384 | 328.21 |
| 557 | | —CH=CH— | 339.395 | 340.18 |
| 558 | cyclohexyl-CH(CH3)- | CH2 | 289.379 | 290.14 |
| 559 | | —CH=CH— | 301.39 | 302.16 |

TABLE 4-continued
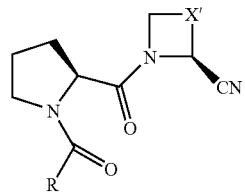
| Example No | R | X' | Mol Wt | [M + H]+ |
|---|---|---|---|---|
| 560 |  | CH₂ | 275.352 | 276.12 |
| 561 | cyclopentyl-CH(CH₃)- | —CH=CH— | 287.363 | 288.18 |
| 562 |  | CH₂ | 261.325 | 262.19 |
| 563 | cyclobutyl-CH(CH₃)- | —CH=CH— | 273.336 | 274.09 |
| 564 |  | CH₂ | 247.298 | 248.09 |
| 565 | cyclopropyl-CH(CH₃)- | —CH=CH— | 259.309 | 260.07 |
| 566 |  | CH₂ | 289.379 | 290.16 |
| 567 | cyclopentyl-CH₂-CH(CH₃)- | —CH=CH— | 301.39 | 302.13 |
| 568 |  | CH₂ | 263.341 | 264.17 |
| 569 | t-Bu-CH(CH₃)- | —CH=CH— | 275.352 | 276.18 |
| 570 |  | CH₂ | 277.368 | 278.12 |
| 571 |  | —CH=CH— | 289.379 | 290.13 |
| 572 |  | CH₂ | 277.368 | 278.13 |
| 573 | n-hexyl-CH(CH₃)- | —CH=CH— | 289.379 | 290.17 |
| 574 |  | —CH=CH— | 317.433 | 318.21 |
| 575 |  | CH₂ | 293.323 | 294.06 |
| 576 | MeO₂C-(CH₂)₃-CH(CH₃)- | —CH=CH— | 305.334 | 306.12 |
| 577 |  | CH₂ | 349.431 | 350.24 |
| 578 | MeO₂C-(CH₂)₇-CH(CH₃)- | —CH=CH— | 361.442 | 362.21 |
| 579 |  | CH₂ | 323.396 | 324.17 |
| 580 | Ph-cyclopropyl-CH(CH₃)- | —CH=CH— | 335.407 | 336.18 |

TABLE 4-continued
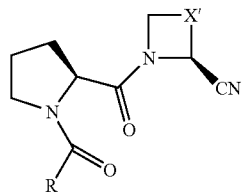
| Example No | R | X' | Mol Wt | [M + H]+ |
|---|---|---|---|---|
| 581 | 2-(OCF3)benzyl | CH2 | 367.327 | 368.11 |
| 582 | | —CH=CH— | 379.338 | 380.15 |
| 583 | 2,6-difluorobenzyl | CH2 | 319.311 | 320.1 |
| 584 | | —CH=CH— | 331.322 | 332.13 |
| 585 | 4-(dimethylamino)benzyl | CH2 | 326.4 | 327.16 |
| 586 | | —CH=CH— | 338.411 | 339.19 |
| 587 | 1-adamantylmethyl | CH2 | 341.455 | 342.21 |
| 588 | | —CH=CH— | 353.466 | 354.22 |
| 589 | 2,4,5-trifluorobenzyl | CH2 | 337.301 | 338.14 |
| 590 | | —CH=CH— | 349.312 | 350.12 |
| 591 | 2-thienylmethyl | CH2 | 303.384 | 304.04 |
| 592 | | —CH=CH— | 315.395 | 316.1 |
| 593 | phenoxy-neopentyl | CH2 | 313.357 | 314.16 |
| 594 | | —CH=CH— | 325.368 | 326.17 |
| 595 | 3,4-difluorobenzyl | CH2 | 319.311 | 320.14 |

TABLE 4-continued
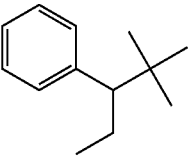
| Example No | R | X' | Mol Wt | [M + H]+ |
|---|---|---|---|---|
| 596 | 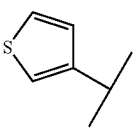 | CH$_2$ | 325.412 | 326.19 |
| 597 | | —CH=CH— | 337.423 | 338.2 |
| 598 | 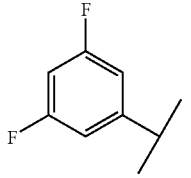 | CH$_2$ | 289.357 | 290.08 |
| 599 | | —CH=CH— | 301.368 | 302.05 |
| 600 | 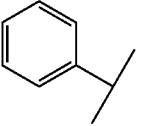 | —CH=CH— | 331.322 | 332.17 |
| 601 | 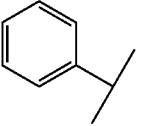 | CH$_2$ | 319.311 | 320.12 |
| 602 | | —CH=CH— | 331.322 | 332.17 |
TABLE 5
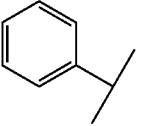
| Example No | R | R1 | Mol Wt | {M + H}+ |
|---|---|---|---|---|
| 603 | CH$_3$ | Me | 209.249 | 209.16 |
| 604 | | tBu | 251.33 | 252.5 |
| 605 | | iBu | 251.33 | 252.4 |
| 606 | | nBu | 251.33 | 250.95 |
| 607 | | Ph | 271.32 | 271.43 |
| 608 | | Ch | 277.368 | 278.4 |
| 609 | 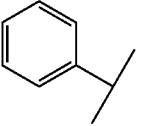 | Me | 271.32 | 272.24 |
| 610 | | tBu | 313.401 | 314.45 |
| 611 | | iBu | 313.401 | 313.89 |
| 612 | | nBu | 313.401 | 314.18 |
| 613 | | Ph | 333.391 | 334.36 |
| 614 | | Ch | 339.439 | 340.35 |

TABLE 5-continued
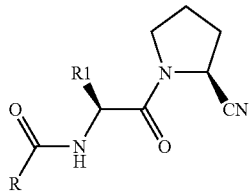
| Example No | R | R1 | Mol Wt | {M + H}+ |
|---|---|---|---|---|
| 615 | 3-Cl-Ph | Me | 305.765 | 306.12 |
| 616 | | tBu | 347.846 | 348.41 |
| 617 | | iBu | 347.846 | 348.16 |
| 618 | | nBu | 347.846 | 348.15 |
| 619 | | Ph | 367.836 | 368.38 |
| 620 | | Ch | 373.884 | 374.34 |
| 621 | 4-Cl-Ph | Me | 305.765 | 306.1 |
| 622 | | iPr | 333.819 | 334.06 |
| 623 | | tBu | 347.846 | 348.4 |
| 624 | | iBu | 347.846 | 348.15 |
| 625 | | nBu | 347.846 | 348.15 |
| 626 | | Ph | 367.836 | 368.35 |
| 627 | | Ch | 373.884 | 374.34 |
| 628 | 2-Cl-Ph | Me | 305.765 | 306.18 |
| 629 | | iPr | 333.819 | 332.89 |
| 630 | | tBu | 347.846 | 348.45 |
| 631 | | iBu | 347.846 | 348.16 |
| 632 | | nBu | 347.846 | 348.13 |
| 633 | | Ph | 367.836 | 368.37 |
| 634 | | Ch | 373.884 | 374.33 |
| 635 | 2,4-diCl-Ph | Me | 340.21 | 340.06 |
| 636 | | tBu | 382.291 | 382.44 |
| 637 | | iBu | 382.291 | 382.13 |
| 638 | | nBu | 382.291 | 382.06 |
| 639 | | Ph | 402.281 | 402.36 |
| 640 | | Ch | 408.329 | 408.28 |
| 641 | 3,4-diCl-Ph | Me | 340.21 | 340.09 |
| 642 | | iPr | 368.264 | 369.12 |
| 643 | | tBu | 382.291 | 382.43 |
| 644 | | nBu | 382.291 | 382.1 |
| 645 | | Ph | 402.281 | 402.34 |
| 646 | | Ch | 408.329 | 408.33 |
| 647 | 3,5-diCl-Ph | Me | 340.21 | 340.1 |
| 648 | | iPr | 368.264 | 367.92 |
| 649 | | tBu | 382.291 | 382.44 |
| 650 | | iBu | 382.291 | 382.13 |
| 651 | | nBu | 382.291 | 382.13 |
| 652 | | Ph | 402.281 | 402.3 |
| 653 | | Ch | 408.329 | 408.3 |
| 654 | 3-F-Ph | Me | 289.31 | 290.07 |
| 655 | | tBu | 331.391 | 332.45 |
| 656 | | iBu | 331.391 | 332.21 |
| 657 | | nBu | 331.391 | 332.19 |
| 658 | | Ph | 351.381 | 352.38 |
| 659 | | Ch | 357.429 | 358.33 |

TABLE 5-continued
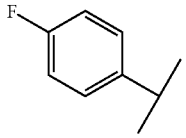
| Example No | R | R1 | Mol Wt | {M + H}+ |
|---|---|---|---|---|
| 660 | 4-F-phenyl | Me | 289.31 | 290.07 |
| 661 | | tBu | 331.391 | 332.44 |
| 662 | | iBu | 331.391 | 332.22 |
| 663 | | nBu | 331.391 | 332.15 |
| 664 | | Ph | 351.381 | 352.4 |
| 665 | | Ch | 357.429 | 358.34 |
| 666 | 4-MeO-phenyl | Me | 301.346 | 302.14 |
| 667 | | tBu | 343.427 | 344.5 |
| 668 | | iBu | 343.427 | 344.21 |
| 669 | | nBu | 343.427 | 344.23 |
| 670 | | Ph | 363.417 | 365.44 |
| 671 | 3-MeO-phenyl | Me | 301.346 | 302.11 |
| 672 | | tBu | 343.427 | 344.51 |
| 673 | | nBu | 343.427 | 344.19 |
| 674 | | Ph | 363.417 | 364.4 |
| 675 | | Ch | 369.465 | 370.4 |
| 676 | benzo[1,3]dioxol-5-yl | Me | 315.329 | 316 |
| 677 | | nBu | 357.41 | 359.15 |
| 678 | | Ph | 377.4 | 379.52 |
| 679 | 2-Me-phenyl | Me | 285.347 | 286.14 |
| 680 | | iPr | 313.401 | 314.2 |
| 681 | | tBu | 327.428 | 328.51 |
| 682 | | iBu | 327.428 | 328.22 |
| 683 | | nBu | 327.428 | 328.2 |
| 684 | | Ph | 347.418 | 348.43 |
| 685 | | Ch | 353.466 | 354.37 |
| 686 | 3-Me-phenyl | Me | 285.347 | 286.14 |
| 687 | | iPr | 313.401 | 314.34 |
| 688 | | tBu | 327.428 | 328.48 |
| 689 | | iBu | 327.428 | 328.17 |
| 690 | | nBu | 327.428 | 328.22 |
| 691 | | Ph | 347.418 | 348.4 |
| 692 | | Ch | 353.466 | 354.38 |
| 693 | 4-Me-phenyl | Me | 285.347 | 286.06 |
| 694 | | tBu | 327.428 | 328.51 |
| 695 | | iBu | 327.428 | 328.19 |
| 696 | | nBu | 327.428 | 328.16 |
| 697 | | Ph | 347.418 | 348.43 |
| 698 | | Ch | 353.466 | 354.38 |
| 699 | 4-CN-phenyl | Me | 296.33 | 297.08 |
| 700 | | iBu | 338.411 | 339.18 |
| 701 | | nBu | 338.411 | 339.2 |
| 702 | | Ph | 358.401 | 359.37 |
| 703 | | Ch | 364.449 | 365.36 |

TABLE 5-continued
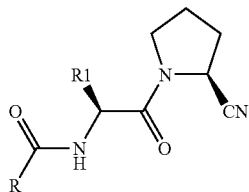
| Example No | R | R1 | Mol Wt | {M + H}+ |
|---|---|---|---|---|
| 704 | CF₃ (3-position phenyl) | Me | 339.317 | 340.13 |
| 705 | | iPr | 367.371 | 368.01 |
| 706 | | tBu | 381.398 | 382.48 |
| 707 | | nBu | 381.398 | 382.18 |
| 708 | | Ph | 401.388 | 402.39 |
| 709 | | Ch | 407.436 | 408.31 |
| 710 | NO₂ (3-position phenyl) | tBu | 358.398 | 359.46 |
| 711 | | iBu | 358.398 | 359.23 |
| 712 | | Ph | 378.388 | 379.41 |
| 713 | | Ch | 384.436 | 385.38 |
| 714 | 1-naphthyl | Me | 321.38 | 322.21 |
| 715 | | iPr | 349.434 | 350.39 |
| 716 | | tBu | 363.461 | 364.48 |
| 717 | | iBu | 363.461 | 364.22 |
| 718 | | nBu | 363.461 | 364.17 |
| 719 | | Ph | 383.451 | 384.44 |
| 720 | | Ch | 389.499 | 390.43 |
| 721 | 2-naphthyl | Me | 321.38 | 322.14 |
| 722 | | iPr | 349.434 | 350.1 |
| 723 | | tBu | 363.461 | 364.49 |
| 724 | | iBu | 363.461 | 364.22 |
| 725 | | nBu | 363.461 | 364.21 |
| 726 | | Ch | 389.499 | 390.41 |
| 727 | 4-tBu-phenyl | Me | 327.428 | 328.2 |
| 728 | | iPr | 355.482 | 355.78 |
| 729 | | tBu | 369.509 | 370.56 |
| 730 | | nBu | 369.509 | 370.26 |
| 731 | | Ph | 389.499 | 390.51 |
| 732 | | Ch | 395.547 | 396.46 |
| 733 | biphenyl | Me | 347.418 | 349.52 |
| 734 | | nBu | 389.499 | 391.27 |
| 735 | | Ph | 409.489 | 411.29 |
| 736 | 2-F-phenyl | Me | 289.31 | 290.12 |
| 737 | | tBu | 331.391 | 332.49 |
| 738 | | iBu | 331.391 | 332.24 |
| 739 | | nBu | 331.391 | 332.18 |
| 740 | | Ph | 351.381 | 352.39 |
| 741 | | Ch | 357.429 | 358.32 |

TABLE 5-continued
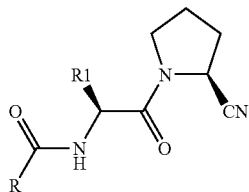
| Example No | R | R1 | Mol Wt | {M + H}+ |
|---|---|---|---|---|
| 742 | 2,6-dichlorophenyl | Me | 340.21 | 340.05 |
| 743 | | iPr | 368.264 | 368.24 |
| 744 | | tBu | 382.291 | 382.45 |
| 745 | | iBu | 382.291 | 382.13 |
| 746 | | nBu | 382.291 | 382.12 |
| 747 | | Ph | 402.281 | 402.34 |
| 748 | | Ch | 408.329 | 408.28 |
| 749 | 4-CF3-phenyl | Me | 339.317 | 340.13 |
| 750 | | tBu | 381.398 | 382.51 |
| 751 | | Bu | 381.398 | 382.19 |
| 752 | | Ph | 401.388 | 402.38 |
| 753 | | Ch | 407.436 | 408.34 |
| 754 | 3-Br-phenyl | Me | 350.221 | 350 |
| 755 | | tBu | 392.302 | 392.44 |
| 756 | | iBu | 392.302 | 392.12 |
| 757 | | nBu | 392.302 | 392.09 |
| 758 | | Ph | 412.292 | 412.29 |
| 759 | | Ch | 418.34 | 418.24 |
| 760 | 2-methoxyphenyl | Me | 301.346 | 302.12 |
| 761 | | iBu | 343.427 | 344.22 |
| 762 | | nBu | 343.427 | 344.18 |
| 763 | | Ph | 363.417 | 364.42 |
| 764 | | Ch | 369.465 | 370.39 |
| 765 | 4-butoxyphenyl | Me | 343.427 | 344.19 |
| 766 | | iPr | 371.481 | 372.1 |
| 767 | | tBu | 385.508 | 386.57 |
| 768 | | nBu | 385.508 | 386.25 |
| 769 | | Ph | 405.498 | 406.48 |
| 770 | | Ch | 411.546 | 412.43 |
| 771 | 4-NO2-phenyl | Me | 316.317 | 317.09 |
| 772 | | iBu | 358.398 | 359.21 |
| 773 | | nBu | 358.398 | 359.19 |
| 774 | 2,5-dimethoxyphenyl | Me | 345.399 | 346.16 |
| 775 | | tBu | 387.48 | 388.57 |
| 776 | | iBu | 387.48 | 388.24 |
| 777 | | nBu | 387.48 | 388.24 |
| 778 | | Ph | 407.47 | 408.43 |
| 779 | | Ch | 413.518 | 414.38 |
| 780 | 4-pentylphenyl | Me | 355.482 | 356.22 |
| 781 | | iPr | 383.536 | 383.17 |
| 782 | | tBu | 397.563 | 398.55 |
| 783 | | nBu | 397.563 | 398.27 |
| 784 | | Ph | 417.553 | 418.45 |
| 785 | | Ch | 423.601 | 424.43 |

TABLE 5-continued
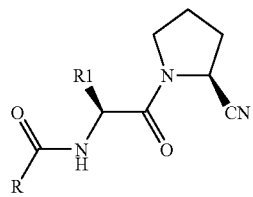
| Example No | R | R1 | Mol Wt | {M + H}+ |
|---|---|---|---|---|
| 786 | | Me | 285.347 | 286.14 |
| 787 | | iPr | 313.401 | 314.06 |
| 788 | | tBu | 327.428 | 328.48 |
| 789 | | iBu | 327.428 | 328.25 |
| 790 | | nBu | 327.428 | 328.15 |
| 791 | | Ph | 347.418 | 348.43 |
| 792 | | Ch | 353.466 | 354.37 |
| 793 | | Me | 299.374 | 300.24 |
| 794 | | tBu | 341.455 | 342.51 |
| 795 | | iBu | 341.455 | 342.25 |
| 796 | | nBu | 341.455 | 342.2 |
| 797 | | Ph | 361.445 | 362.44 |
| 798 | | Ch | 367.493 | 368.43 |
| 799 | | Me | 327.406 | 328.14 |
| 800 | | iPr | 355.46 | 356.36 |
| 801 | | tBu | 369.487 | 370.45 |
| 802 | | Me | 277.346 | 277.98 |
| 803 | | tBu | 319.427 | 320.42 |
| 804 | | iBu | 319.427 | 320.16 |
| 805 | | nBu | 319.427 | 320.21 |
| 806 | | Ph | 339.417 | 340.38 |
| 807 | | Ch | 345.465 | 346.3 |
| 808 | | Me | 261.281 | 262.1 |
| 809 | | tBu | 303.362 | 304.44 |
| 810 | | iBu | 303.362 | 304.19 |
| 811 | | nBu | 303.362 | 304.14 |
| 812 | | Ph | 323.352 | 324.36 |
| 813 | | Ch | 329.4 | 330.37 |
| 814 | | Me | 306.753 | 307 |
| 815 | | tBu | 348.834 | 349.45 |
| 816 | | iBu | 348.834 | 349.17 |
| 817 | | nBu | 348.834 | 349.13 |
| 818 | | Ph | 368.824 | 369.37 |
| 819 | | Ch | 374.872 | 375.33 |
| 820 | | Me | 315.373 | 316.14 |
| 821 | | tBu | 357.454 | 358.49 |
| 822 | | iBu | 357.454 | 358.22 |
| 823 | | nBu | 357.454 | 358.19 |
| 824 | | Ph | 377.444 | 378.45 |
| 825 | | Ch | 383.492 | 384.43 |
| 826 | | Me | 277.368 | 278.23 |
| 827 | | iPr | 305.422 | 306.29 |
| 828 | | tBu | 319.449 | 320.53 |
| 829 | | iBu | 319.449 | 320.27 |
| 830 | | nBu | 319.449 | 320.24 |
| 831 | | Ch | 345.487 | 346.43 |
| 832 | | Me | 263.341 | 264.07 |
| 833 | | iPr | 291.395 | 292.47 |
| 834 | | tBu | 305.422 | 306.5 |
| 835 | | iBu | 305.422 | 306.2 |
| 836 | | nBu | 305.422 | 306.17 |
| 837 | | Ph | 325.412 | 326.44 |
| 838 | | Ch | 331.46 | 332.41 |

TABLE 5-continued
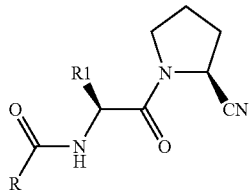
| Example No | R | R1 | Mol Wt | {M + H}+ |
|---|---|---|---|---|
| 839 | | Me | 249.314 | 250.16 |
| 840 | | iPr | 277.368 | 278.43 |
| 841 | | tBu | 291.395 | 292.52 |
| 842 | | iBu | 291.395 | 292.19 |
| 843 | | nBu | 291.395 | 292.15 |
| 844 | | Ph | 311.385 | 312.39 |
| 845 | | Ch | 317.433 | 318.42 |
| 846 | | Me | 235.287 | 235.95 |
| 847 | | iPr | 263.341 | 264.19 |
| 848 | | tBu | 277.368 | 278.48 |
| 849 | | iBu | 277.368 | 278.29 |
| 850 | | nBu | 277.368 | 278.17 |
| 851 | | Ph | 297.358 | 298.39 |
| 852 | | Ch | 303.406 | 304.36 |
| 853 | | Me | 277.368 | 278.13 |
| 854 | | iPr | 305.422 | 307.66 |
| 855 | | tBu | 319.449 | 320.53 |
| 856 | | iBu | 319.449 | 320.25 |
| 857 | | nBu | 319.449 | 320.26 |
| 858 | | Ph | 339.439 | 340.44 |
| 859 | | Ch | 345.487 | 346.4 |
| 860 | | Me | 251.33 | 251.82 |
| 861 | | iPr | 279.384 | 280.53 |
| 862 | | tBu | 293.411 | 294.61 |
| 863 | | iBu | 293.411 | 294.04 |
| 864 | | nBu | 293.411 | 294.21 |
| 865 | | Ph | 313.401 | 314.39 |
| 866 | | Ch | 319.449 | 320.39 |
| 867 | | Me | 265.357 | 266.16 |
| 868 | | iPr | 293.411 | 293.92 |
| 869 | | tBu | 307.438 | 308.5 |
| 870 | | iBu | 307.438 | 308.24 |
| 871 | | nBu | 307.438 | 308.26 |
| 872 | | Ph | 327.428 | 328.46 |
| 873 | | Ch | 333.476 | 334.42 |
| 874 | | Me | 265.357 | 266.13 |
| 875 | | iPr | 293.411 | 293.68 |
| 876 | | tBu | 307.438 | 308.51 |
| 877 | | iBu | 307.438 | 308.25 |
| 878 | | nBu | 307.438 | 308.21 |
| 879 | | Ph | 327.428 | 328.47 |
| 880 | | Ch | 333.476 | 334.41 |
| 881 | | Me | 293.411 | 294.24 |
| 882 | | iPr | 321.465 | 322.51 |
| 883 | | tBu | 335.492 | 336.54 |
| 884 | | iBu | 335.492 | 335.79 |
| 885 | | nBu | 335.492 | 336.26 |
| 886 | | Ph | 355.482 | 356.49 |
| 887 | | Ch | 361.53 | 362.43 |
| 888 | | Me | 281.312 | 282.04 |
| 889 | | tBu | 323.393 | 324.49 |
| 890 | | iBu | 323.393 | 324.21 |
| 891 | | nBu | 323.393 | 324.23 |
| 892 | | Ch | 349.431 | 350.4 |

TABLE 5-continued
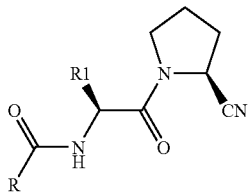
| Example No | R | R1 | Mol Wt | {M + H}+ |
|---|---|---|---|---|
| 893 | | Me | 337.42 | 338.17 |
| 894 | | iPr | 365.474 | 366.21 |
| 895 | | tBu | 379.501 | 380.62 |
| 896 | | iBu | 379.501 | 380.26 |
| 897 | | nBu | 379.501 | 380.27 |
| 898 | | Ph | 399.491 | 400.49 |
| 899 | | Ch | 405.539 | 406.43 |
| 900 | | Me | 311.385 | 312.14 |
| 901 | | iPr | 339.439 | 340.12 |
| 902 | | tBu | 353.466 | 354.52 |
| 903 | | iBu | 353.466 | 354.24 |
| 904 | | nBu | 353.466 | 354.2 |
| 905 | | Ph | 373.456 | 374.45 |
| 906 | | Ch | 379.504 | 380.41 |
| 907 | | Me | 355.316 | 356.09 |
| 908 | | iPr | 383.37 | 384.24 |
| 909 | | tBu | 397.397 | 398.49 |
| 910 | | iBu | 397.397 | 398.2 |
| 911 | | nBu | 397.397 | 398.19 |
| 912 | | Ph | 417.387 | 418.36 |
| 913 | | Ch | 423.435 | 424.32 |
| 914 | | Me | 307.3 | 308.06 |
| 915 | | iPr | 335.354 | 335.12 |
| 916 | | tBu | 349.381 | 350.49 |
| 917 | | iBu | 349.381 | 350.2 |
| 918 | | nBu | 349.381 | 350.12 |
| 919 | | Ph | 369.371 | 370.4 |
| 920 | | Ch | 375.419 | 376.38 |
| 921 | | Me | 314.389 | 315.11 |
| 922 | | iPr | 342.443 | 343.02 |
| 923 | | tBu | 356.47 | 357.49 |
| 924 | | iBu | 356.47 | 357.27 |
| 925 | | nBu | 356.47 | 357.21 |
| 926 | | Ch | 382.508 | 383.42 |
| 927 | | Me | 272.308 | 273.08 |
| 928 | | iPr | 300.362 | 301.02 |
| 929 | | tBu | 314.389 | 315.46 |
| 930 | | iBu | 314.389 | 315.17 |
| 931 | | nBu | 314.389 | 315.2 |
| 932 | | Ph | 334.379 | 335.4 |
| 933 | | Ch | 340.427 | 341.37 |
| 934 | | Me | 272.308 | 273.07 |
| 935 | | iBu | 314.389 | 315.18 |
| 936 | | Ch | 340.427 | 341.36 |
| 937 | | Me | 329.444 | 330.22 |
| 938 | | tBu | 371.525 | 372.57 |
| 939 | | nBu | 371.525 | 372.29 |
| 940 | | Ph | 391.515 | 392.49 |
| 941 | | Ch | 397.563 | 398.44 |

TABLE 5-continued
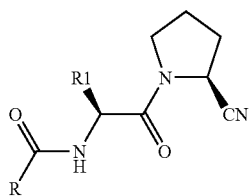
| Example No | R | R1 | Mol Wt | {M + H}+ |
|---|---|---|---|---|
| 942 | 2,4,5-trifluorophenyl-CH(CH3)- | Me | 325.29 | 326.09 |
| 943 | | iPr | 353.344 | 354.29 |
| 944 | | tBu | 367.371 | 368.44 |
| 945 | | iBu | 367.371 | 368.18 |
| 946 | | nBu | 367.371 | 368.15 |
| 947 | | Ph | 387.361 | 388.39 |
| 948 | | Ch | 393.409 | 394.38 |
| 949 | thien-2-yl-CH(CH3)- | Me | 291.373 | 292.13 |
| 950 | | iPr | 319.427 | 320.15 |
| 951 | | tBu | 333.454 | 334.45 |
| 952 | | iBu | 333.454 | 334.2 |
| 953 | | nBu | 333.454 | 334.21 |
| 954 | | Ph | 353.444 | 354.34 |
| 955 | | Ch | 359.492 | 360.35 |
| 956 | phenoxy-CH(CH3)- | Me | 301.346 | 302.11 |
| 957 | | iPr | 329.4 | 330.13 |
| 958 | | tBu | 343.427 | 344.5 |
| 959 | | iBu | 343.427 | 344.22 |
| 960 | | nBu | 343.427 | 344.17 |
| 961 | | Ph | 363.417 | 364.41 |
| 962 | | Ch | 369.465 | 370.42 |
| 963 | 3,4-difluorophenyl-CH(CH3)- | tBu | 349.381 | 350.39 |
| 964 | | iBu | 349.381 | 350.12 |
| 965 | | Ph | 369.371 | 370.41 |
| 966 | | Ch | 375.419 | 376.36 |
| 967 | thien-3-yl-CH(CH3)- | Me | 277.346 | 278.08 |
| 968 | | tBu | 319.427 | 320.35 |
| 969 | | iBu | 319.427 | 320.18 |
| 970 | | nBu | 319.427 | 320.21 |
| 971 | | Ph | 339.417 | 340.34 |
| 972 | | Ch | 345.465 | 346.31 |
| 973 | 2,3-difluorophenyl-CH(CH3)- | Me | 307.3 | 308.05 |
| 974 | | iPr | 335.354 | 336.21 |
| 975 | | tBu | 349.381 | 350.46 |
| 976 | | iBu | 349.381 | 350.2 |
| 977 | | nBu | 349.381 | 350.16 |
| 978 | | Ph | 369.371 | 370.37 |
| 979 | | Ch | 375.419 | 376.37 |
| 980 | 3-tert-butyl-benzothien-yl | iPr | 355.46 | 355.93 |
| 981 | 3,5-difluorophenyl-CH(CH3)- | tBu | 349.381 | 350.4 |
| 982 | | iBu | 349.381 | 350.24 |
| 983 | | Ph | 369.371 | 370.41 |
| 984 | | Ch | 375.419 | 376.43 |

TABLE 6
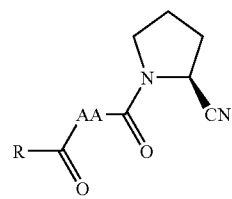
| Example No | R | AA | Mol Wt | [M + H]+ |
|---|---|---|---|---|
| 985 | CH₃ | Oic | 289.379 | 289.39 |
| 986 | phenyl-CH(CH₃)- | Tic | 359.429 | 360.28 |
| 987 | phenyl-CH(CH₃)- | Oic | 351.45 | 352.4 |
| 988 | 3-Cl-phenyl-CH(CH₃)- | Tic | 393.874 | 394.31 |
| 989 | 3-Cl-phenyl-CH(CH₃)- | Pic | 345.83 | 346.18 |
| 990 | 3-Cl-phenyl-CH(CH₃)- | Oic | 385.895 | 386.4 |
| 991 | 4-Cl-phenyl-CH(CH₃)- | Tic | 393.874 | 394.29 |
| 992 | 4-Cl-phenyl-CH(CH₃)- | Oic | 385.895 | 386.39 |
| 993 | 2-Cl-phenyl-CH(CH₃)- | Tic | 393.874 | 394.3 |
| 994 | 2-Cl-phenyl-CH(CH₃)- | Oic | 385.895 | 386.38 |
| 995 | 2,4-diCl-phenyl-CH(CH₃)- | Tic | 428.319 | 428.19 |
| 996 | 2,4-diCl-phenyl-CH(CH₃)- | Oic | 420.34 | 420.32 |
| 997 | 3,4-diCl-phenyl-CH(CH₃)- | Tic | 428.319 | 428.2 |
| 998 | 3,4-diCl-phenyl-CH(CH₃)- | Pic | 380.275 | 380.22 |
| 999 | 3,4-diCl-phenyl-CH(CH₃)- | Oic | 420.34 | 420.31 |
| 1000 | 3,5-diCl-phenyl-CH(CH₃)- | Tic | 428.319 | 428.19 |
| 1001 | 3,5-diCl-phenyl-CH(CH₃)- | Oic | 420.34 | 420.3 |

TABLE 6-continued
| Example No | R | AA | Mol Wt | [M + H]+ |
|---|---|---|---|---|
| 1002 | 3-F-phenyl | Pic | 329.375 | 330.33 |
| 1003 | | Oic | 369.44 | 370.4 |
| 1004 | 4-F-phenyl | Tic | 377.419 | 378.31 |
| 1005 | | Oic | 369.44 | 370.41 |
| 1006 | 4-OMe-phenyl | Tic | 389.455 | 390.32 |
| 1007 | | Pic | 341.411 | 342.27 |
| 1008 | | Oic | 381.476 | 382.43 |
| 1009 | 3-OMe-phenyl | Tic | 389.455 | 390.35 |
| 1010 | | Pic | 341.411 | 342.36 |
| 1011 | | Oic | 381.476 | 382.45 |
| 1012 | 2-Me-phenyl | Tic | 373.456 | 374.34 |
| 1013 | | Pic | 325.412 | 326.38 |
| 1014 | | Oic | 365.477 | 366.41 |
| 1015 | 3-Me-phenyl | Tic | 373.456 | 374.31 |
| 1016 | | Pic | 325.412 | 326.24 |
| 1017 | | Oic | 365.477 | 366.41 |
| 1018 | 4-Me-phenyl | Tic | 373.456 | 374.34 |
| 1019 | | Pic | 325.412 | 326.31 |
| 1020 | 4-CN-phenyl | Tic | 384.439 | 385.29 |
| 1021 | | Oic | 376.46 | 377.4 |

TABLE 6-continued
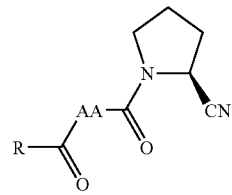
| Example No | R | AA | Mol Wt | [M + H]+ |
|---|---|---|---|---|
| 1022 | 3-CF₃-phenyl | Tic | 427.426 | 428.27 |
| 1023 | | Oic | 419.447 | 420.38 |
| 1024 | 3-NO₂-phenyl | Tic | 404.426 | 405.27 |
| 1025 | | Pic | 356.382 | 357.32 |
| 1026 | | Oic | 396.447 | 397.39 |
| 1027 | 1-naphthyl | Tic | 409.489 | 410.32 |
| 1028 | | Pic | 361.445 | 362.36 |
| 1029 | | Oic | 401.51 | 402.44 |
| 1030 | 2-naphthyl | Tic | 409.489 | 410.26 |
| 1031 | | Pic | 361.445 | 362.34 |
| 1032 | | Oic | 401.51 | 402.43 |
| 1033 | 4-tBu-phenyl | Tic | 415.537 | 416.35 |
| 1034 | | Pic | 367.493 | 368.34 |
| 1035 | | Oic | 407.558 | 408.47 |
| 1036 | 4-biphenyl | Tic | 435.527 | 437.27 |
| 1037 | 2-F-phenyl | Tic | 377.419 | 378.34 |
| 1038 | | Pic | 329.375 | 330.3 |
| 1039 | | Oic | 369.44 | 370.4 |

TABLE 6-continued
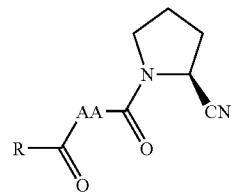
| Example No | R | AA | Mol Wt | [M + H]+ |
|---|---|---|---|---|
| 1040 | 2,6-dichlorobenzyl | Tic | 428.319 | 428.18 |
| 1041 | | Oic | 420.34 | 420.29 |
| 1042 | 4-CF3-benzyl | Tic | 427.426 | 428.27 |
| 1043 | | Oic | 419.447 | 420.38 |
| 1044 | 3-bromobenzyl | Tic | 438.33 | 438.18 |
| 1045 | | Pic | 390.286 | 390.22 |
| 1046 | | Oic | 430.351 | 430.28 |
| 1047 | 2-methoxybenzyl | Tic | 389.455 | 390.34 |
| 1048 | | Pic | 341.411 | 342.37 |
| 1049 | | Oic | 381.476 | 382.43 |
| 1050 | 4-butoxybenzyl | Tic | 431.536 | 432.38 |
| 1051 | | Pic | 383.492 | 384.43 |
| 1052 | | Oic | 423.557 | 424.44 |
| 1053 | 2,5-dimethoxybenzyl | Tic | 433.508 | 434.31 |
| 1054 | | Pic | 385.464 | 386.34 |
| 1055 | | Oic | 425.529 | 426.4 |
| 1056 | 4-pentylbenzyl | Tic | 443.591 | 444.36 |
| 1057 | | Pic | 395.547 | 396.46 |
| 1058 | | Oic | 435.612 | 436.47 |
| 1059 | neopentylbenzyl | Tic | 373.456 | 374.36 |
| 1060 | | Pic | 325.412 | 326.36 |
| 1061 | | Oic | 365.477 | 366.43 |
| 1062 | phenylpropyl | Tic | 387.483 | 388.38 |
| 1063 | | Oic | 379.504 | 380.46 |

TABLE 6-continued
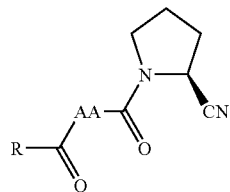
| Example No | R | AA | Mol Wt | [M + H]+ |
|---|---|---|---|---|
| 1064 | thiophene | Tic | 365.455 | 366.27 |
| 1065 | | Oic | 357.476 | 358.36 |
| 1066 | furan | Tic | 349.39 | 350.27 |
| 1067 | | Oic | 341.411 | 342.38 |
| 1068 | 2-Cl-pyridin-3-yl | Tic | 394.862 | 395.29 |
| 1069 | | Pic | 346.818 | 347.24 |
| 1070 | | Oic | 386.883 | 387.39 |
| 1071 | PhCH₂OCH₂C(CH₃)₂- | Tic | 403.482 | 404.33 |
| 1072 | | Pic | 355.438 | 356.35 |
| 1073 | | Oic | 395.503 | 396.45 |
| 1074 | cyclohexyl | Tic | 365.477 | 366.4 |
| 1075 | | Pic | 317.433 | 318.24 |
| 1076 | | Oic | 357.498 | 358.46 |
| 1077 | cyclopentyl | Tic | 351.45 | 352.35 |
| 1078 | | Pic | 303.406 | 304.33 |
| 1079 | | Oic | 343.471 | 344.43 |
| 1080 | cyclobutyl | Tic | 337.423 | 338.32 |
| 1081 | | Pic | 289.379 | 290.29 |
| 1082 | | Oic | 329.444 | 330.41 |
| 1083 | cyclopropyl | Tic | 323.396 | 324.31 |
| 1084 | | Pic | 275.352 | 276.29 |
| 1085 | | Oic | 315.417 | 316.41 |
| 1086 | cyclopentylethyl | Tic | 365.477 | 366.38 |
| 1087 | | Oic | 357.498 | 358.46 |
| 1088 | tBu-CH(CH₃)- | Oic | 331.46 | 332.41 |

TABLE 6-continued
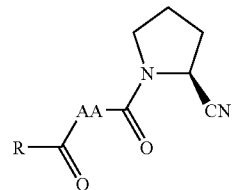
| Example No | R | AA | Mol Wt | [M + H]+ |
|---|---|---|---|---|
| 1089 | | Tic | 353.466 | 354.34 |
| 1090 | | Pic | 305.422 | 306.41 |
| 1091 | | Oic | 345.487 | 346.45 |
| 1092 | | Tic | 353.466 | 354.35 |
| 1093 | | Oic | 345.487 | 346.45 |
| 1094 | | Tic | 381.52 | 382.4 |
| 1095 | | Pic | 333.476 | 334.45 |
| 1096 | | Oic | 373.541 | 374.49 |
| 1097 | | Tic | 369.421 | 370.32 |
| 1098 | | Pic | 321.377 | 322.25 |
| 1099 | | Oic | 361.442 | 362.41 |
| 1100 | | Tic | 425.529 | 426.33 |
| 1101 | | Pic | 377.485 | 378.37 |
| 1102 | | Oic | 417.55 | 418.45 |
| 1103 | | Tic | 399.494 | 400.35 |
| 1104 | | Pic | 351.45 | 352.33 |
| 1105 | | Oic | 391.515 | 392.47 |
| 1106 | | Tic | 443.425 | 444.28 |
| 1107 | | Pic | 395.381 | 396.35 |
| 1108 | | Oic | 435.446 | 436.37 |
| 1109 | | Tic | 395.409 | 396.31 |
| 1110 | | Pic | 347.365 | 348.28 |
| 1111 | | Oic | 387.43 | 388.43 |
| 1112 | | Pic | 354.454 | 354.35 |
| 1113 | | Oic | 394.519 | 395.47 |

TABLE 6-continued
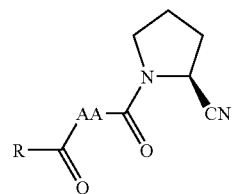
| Example No | R | AA | Mol Wt | [M + H]+ |
|---|---|---|---|---|
| 1114 | (3-pyridyl)ethyl | Tic | 360.417 | 361.3 |
| 1115 | | Pic | 312.373 | 313.26 |
| 1116 | | Oic | 352.438 | 353.38 |
| 1117 | (4-pyridyl)ethyl | Tic | 360.417 | 361.29 |
| 1118 | | Oic | 352.438 | 353.41 |
| 1119 | 1-adamantyl-tBu | Tic | 417.553 | 418.36 |
| 1120 | | Oic | 409.574 | 410.46 |
| 1121 | 2,4,5-trifluorophenylethyl | Tic | 413.399 | 414.2 |
| 1122 | | Oic | 405.42 | 406.37 |
| 1123 | 2-thienylpropyl | Tic | 379.482 | 380.32 |
| 1124 | | Pic | 331.438 | 332.31 |
| 1125 | | Oic | 371.503 | 372.39 |
| 1126 | phenoxyethyl | Tic | 389.455 | 390.34 |
| 1127 | | Pic | 341.411 | 342.36 |
| 1128 | | Oic | 381.476 | 382.45 |
| 1129 | 3,4-difluorophenylethyl | Tic | 395.409 | 396.33 |
| 1130 | | Pic | 347.365 | 348.31 |
| 1131 | | Oic | 387.43 | 388.38 |
| 1132 | phenyl-tBu-ethyl | Tic | 401.51 | 402.38 |
| 1133 | | Pic | 353.466 | 354.33 |
| 1134 | | Oic | 393.531 | 394.47 |
| 1135 | 3-thienylethyl | Tic | 365.455 | 366.3 |
| 1136 | | Pic | 317.411 | 318.27 |
| 1137 | | Oic | 357.476 | 358.35 |

TABLE 6-continued
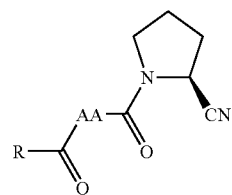
| Example No | R | AA | Mol Wt | [M + H]+ |
|---|---|---|---|---|
| 1138 | | Tic | 395.409 | 396.28 |
| 1139 | 2,3-diF-iPr-Ph | Pic | 347.365 | 348.27 |
| 1140 | | Oic | 387.43 | 388.41 |
| 1141 | | Tic | 395.409 | 396.33 |
| 1142 | 3,5-diF-iPr-Ph | Oic | 387.43 | 388.42 |
TABLE 7
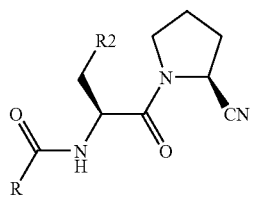
| Example No | R | R2 | Mol Wt | [M + H]+ |
|---|---|---|---|---|
| 1143 | CH₃ | tBu | 265.357 | 266.24 |
| 1144 | | Ph | 285.347 | 286.35 |
| 1145 | | Ch | 291.395 | 292.36 |
| 1146 | | OCH₂Ph | 315.373 | 315.47 |
| 1147 | | CH₂CO₂CH₂Ph | 357.41 | 357.46 |
| 1148 | | tBu | 327.428 | 328.25 |
| 1149 | | Ph | 347.418 | 348.36 |
| 1150 | Ph-iPr | Ch | 353.466 | 354.35 |
| 1151 | | OCH₂Ph | 377.444 | 378.49 |
| 1152 | | CO₂CH₃ | 329.356 | 330.16 |
| 1153 | | CH₂CO₂CH₂Ph | 419.481 | 420.46 |
| 1154 | | tBu | 361.873 | 362.2 |
| 1155 | | Ph | 381.863 | 382.34 |
| 1156 | 3-Cl-iPr-Ph | Ch | 387.911 | 388.33 |
| 1157 | | OCH₂Ph | 411.889 | 412.4 |
| 1158 | | CO₂CH₃ | 363.801 | 364.11 |
| 1159 | | CH₂CO₂CH₂Ph | 453.926 | 454.44 |

TABLE 7-continued

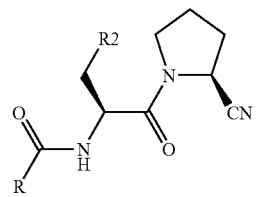

| Example No | R | R2 | Mol Wt | [M + H]+ |
|---|---|---|---|---|
| 1160 | 4-Cl-C6H4 | tBu | 361.873 | 362.19 |
| 1161 | | Ph | 381.863 | 382.31 |
| 1162 | | Ch | 387.911 | 388.35 |
| 1163 | | OCH$_2$Ph | 411.889 | 412.4 |
| 1164 | | CO$_2$CH$_3$ | 363.801 | 364.14 |
| 1165 | | CH$_2$CO$_2$CH$_2$Ph | 453.926 | 454.42 |
| 1166 | 2-Cl-C6H4 | tBu | 361.873 | 362.23 |
| 1167 | | Ph | 381.863 | 382.36 |
| 1168 | | Ch | 387.911 | 388.34 |
| 1169 | | OCH$_2$Ph | 411.889 | 412.4 |
| 1170 | | CO$_2$CH$_3$ | 363.801 | 364.14 |
| 1171 | | CH$_2$CO$_2$CH$_2$Ph | 453.926 | 454.43 |
| 1172 | 2,4-diCl-C6H3 | tBu | 396.318 | 396.16 |
| 1173 | | Ph | 416.308 | 416.29 |
| 1174 | | Ch | 422.356 | 422.24 |
| 1175 | | OCH$_2$Ph | 446.334 | 446.35 |
| 1176 | | CO$_2$CH$_3$ | 398.246 | 398.13 |
| 1177 | | CH$_2$CO$_2$CH$_2$Ph | 488.371 | 488.36 |
| 1178 | 3,4-diCl-C6H3 | tBu | 396.318 | 396.15 |
| 1179 | | Ph | 416.308 | 416.24 |
| 1180 | | Ch | 422.356 | 422.25 |
| 1181 | | OCH$_2$Ph | 446.334 | 446.36 |
| 1182 | | CO$_2$CH$_3$ | 398.246 | 398.07 |
| 1183 | | CH$_2$CO$_2$CH$_2$Ph | 488.371 | 488.32 |
| 1184 | 3,5-diCl-C6H3 | tBu | 396.318 | 396.17 |
| 1185 | | Ph | 416.308 | 416.28 |
| 1186 | | Ch | 422.356 | 422.27 |
| 1187 | | OCH$_2$Ph | 446.334 | 446.37 |
| 1188 | | CO$_2$CH$_3$ | 398.246 | 398.04 |
| 1189 | | CH$_2$CO$_2$CH$_2$Ph | 488.371 | 488.33 |
| 1190 | 3-F-C6H4 | tBu | 345.418 | 346.24 |
| 1191 | | Ph | 365.408 | 366.34 |
| 1192 | | Ch | 371.456 | 372.34 |
| 1193 | | OCH$_2$Ph | 395.434 | 396.47 |
| 1194 | | CO$_2$CH$_3$ | 347.346 | 348.2 |
| 1195 | | CH$_2$CO$_2$CH$_2$Ph | 437.471 | 438.44 |
| 1196 | 4-F-C6H4 | tBu | 345.418 | 346.25 |
| 1197 | | Ph | 365.408 | 366.34 |
| 1198 | | Ch | 371.456 | 372.35 |
| 1199 | | OCH$_2$Ph | 395.434 | 396.46 |
| 1200 | | CO$_2$CH$_3$ | 347.346 | 348.19 |
| 1201 | | CH$_2$CO$_2$CH$_2$Ph | 437.471 | 438.42 |

TABLE 7-continued
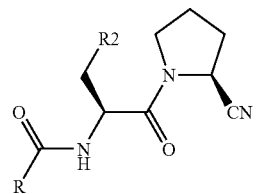
| Example No | R | R2 | Mol Wt | [M + H]+ |
|---|---|---|---|---|
| 1202 | 4-MeO-C6H4- | tBu | 357.454 | 358.25 |
| 1203 | | Ph | 377.444 | 378.4 |
| 1204 | | Ch | 383.492 | 384.39 |
| 1205 | | OCH2Ph | 407.47 | 408.49 |
| 1206 | | CH2CO2CH2Ph | 449.507 | 450.49 |
| 1207 | 3-MeO-C6H4- | tBu | 357.454 | 358.24 |
| 1208 | | Ph | 377.444 | 378.38 |
| 1209 | | Ch | 383.492 | 384.39 |
| 1210 | | OCH2Ph | 407.47 | 408.46 |
| 1211 | | CO2CH3 | 359.382 | 360.16 |
| 1212 | | CH2CO2CH2Ph | 449.507 | 450.48 |
| 1213 | 2-Me-C6H4- | tBu | 341.455 | 342.28 |
| 1214 | | Ph | 361.445 | 362.36 |
| 1215 | | Ch | 367.493 | 368.37 |
| 1216 | | OCH2Ph | 391.471 | 392.51 |
| 1217 | | CO2CH3 | 343.383 | 344.21 |
| 1218 | | CH2CO2CH2Ph | 433.508 | 434.47 |
| 1219 | 3-Me-C6H4- | tBu | 341.455 | 342.26 |
| 1220 | | Ph | 361.445 | 362.36 |
| 1221 | | Ch | 367.493 | 368.35 |
| 1222 | | OCH2Ph | 391.471 | 392.52 |
| 1223 | | CO2CH3 | 343.383 | 344.16 |
| 1224 | | CH2CO2CH2Ph | 433.508 | 434.43 |
| 1225 | 4-Me-C6H4- | tBu | 341.455 | 342.25 |
| 1226 | | Ph | 361.445 | 362.37 |
| 1227 | | Ch | 367.493 | 368.33 |
| 1228 | | OCH2Ph | 391.471 | 392.52 |
| 1229 | | CO2CH3 | 343.383 | 344.19 |
| 1230 | | CH2CO2CH2Ph | 433.508 | 434.45 |
| 1231 | 4-NC-C6H4- | Ph | 372.428 | 373.38 |
| 1232 | | Ch | 378.476 | 379.35 |
| 1233 | | OCH2Ph | 402.454 | 403.46 |
| 1234 | | CO2CH3 | 354.366 | 355.15 |
| 1235 | | CH2CO2CH2Ph | 444.491 | 445.48 |
| 1236 | 3-CF3-C6H4- | tBu | 395.425 | 396.25 |
| 1237 | | Ph | 415.415 | 416.32 |
| 1238 | | Ch | 421.463 | 422.33 |
| 1239 | | OCH2Ph | 445.441 | 446.46 |
| 1240 | | CO2CH3 | 397.353 | 398.19 |
| 1241 | | CH2CO2CH2Ph | 487.478 | 488.43 |
| 1242 | 3-NO2-C6H4- | Ph | 392.415 | 393.36 |
| 1243 | | Ch | 398.463 | 399.34 |
| 1244 | | OCH2Ph | 422.441 | 423.42 |
| 1245 | | CO2CH3 | 374.353 | 375.19 |
| 1246 | | CH2CO2CH2Ph | 464.478 | 465.47 |

TABLE 7-continued

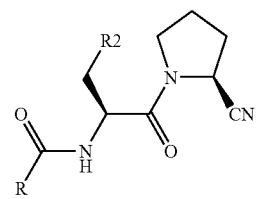

| Example No | R | R2 | Mol Wt | [M + H]+ |
| --- | --- | --- | --- | --- |
| 1247 | naphthalen-1-yl | tBu | 377.488 | 378.26 |
| 1248 | | Ph | 397.478 | 398.4 |
| 1249 | | Ch | 403.526 | 404.38 |
| 1250 | | OCH$_2$Ph | 427.504 | 428.43 |
| 1251 | | CO$_2$CH$_3$ | 379.416 | 380.2 |
| 1252 | | CH$_2$CO$_2$CH$_2$Ph | 469.541 | 470.47 |
| 1253 | naphthalen-2-yl | tBu | 377.488 | 378.26 |
| 1254 | | Ph | 397.478 | 398.39 |
| 1255 | | Ch | 403.526 | 404.37 |
| 1256 | | OCH$_2$Ph | 427.504 | 428.45 |
| 1257 | | CO$_2$CH$_3$ | 379.416 | 380.25 |
| 1258 | | CH$_2$CO$_2$CH$_2$Ph | 469.541 | 470.49 |
| 1259 | 4-tBu-phenyl | tBu | 383.536 | 384.31 |
| 1260 | | Ph | 403.526 | 404.41 |
| 1261 | | Ch | 409.574 | 410.42 |
| 1262 | | OCH$_2$Ph | 433.552 | 434.52 |
| 1263 | | CO$_2$CH$_3$ | 385.464 | 386.19 |
| 1264 | | CH$_2$CO$_2$CH$_2$Ph | 475.589 | 476.52 |
| 1265 | 2-F-phenyl | tBu | 345.418 | 346.24 |
| 1266 | | Ph | 365.408 | 366.34 |
| 1267 | | Ch | 371.456 | 372.35 |
| 1268 | | OCH$_2$Ph | 395.434 | 396.48 |
| 1269 | | CO$_2$CH$_3$ | 347.346 | 348.17 |
| 1270 | | CH$_2$CO$_2$CH$_2$Ph | 437.471 | 438.44 |
| 1271 | 2,6-diCl-phenyl | tBu | 396.318 | 396.16 |
| 1272 | | Ph | 416.308 | 416.26 |
| 1273 | | Ch | 422.356 | 422.26 |
| 1274 | | OCH$_2$Ph | 446.334 | 446.35 |
| 1275 | | CO$_2$CH$_3$ | 398.246 | 398.09 |
| 1276 | | CH$_2$CO$_2$CH$_2$Ph | 488.371 | 488.39 |
| 1277 | 4-CF$_3$-phenyl | tBu | 395.425 | 396.22 |
| 1278 | | Ph | 415.415 | 416.33 |
| 1279 | | Ch | 421.463 | 422.32 |
| 1280 | | OCH$_2$Ph | 445.441 | 446.44 |
| 1281 | | CO$_2$CH$_3$ | 397.353 | 398.18 |
| 1282 | | CH$_2$CO$_2$CH$_2$Ph | 487.478 | 488.44 |
| 1283 | 3-Br-phenyl | tBu | 406.329 | 406.14 |
| 1284 | | Ph | 426.319 | 426.23 |
| 1285 | | OCH$_2$Ph | 456.345 | 456.36 |
| 1286 | | CO$_2$CH$_3$ | 408.257 | 408.1 |
| 1287 | | CH$_2$CO$_2$CH$_2$Ph | 498.382 | 498.38 |
| 1288 | 2-OMe-phenyl | tBu | 357.454 | 358.25 |
| 1289 | | Ph | 377.444 | 378.4 |
| 1290 | | Ch | 383.492 | 384.37 |
| 1291 | | OCH$_2$Ph | 407.47 | 408.46 |
| 1292 | | CO$_2$CH$_3$ | 359.382 | 360.16 |
| 1293 | | CH$_2$CO$_2$CH$_2$Ph | 449.507 | 450.47 |

TABLE 7-continued

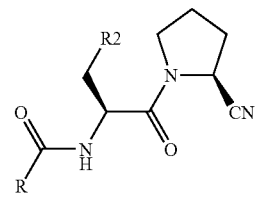

| Example No | R | R2 | Mol Wt | [M + H]+ |
|---|---|---|---|---|
| 1294 | (butoxyphenyl) | tBu | 399.535 | 400.3 |
| 1295 | | Ph | 419.525 | 420.41 |
| 1296 | | Ch | 425.573 | 426.4 |
| 1297 | | OCH₂Ph | 449.551 | 450.52 |
| 1298 | | CO₂CH₃ | 401.463 | 402.28 |
| 1299 | | CH₂CO₂CH₂Ph | 491.588 | 492.51 |
| 1300 | (nitrophenyl) | Ch | 398.463 | 399.32 |
| 1301 | | OCH₂Ph | 422.441 | 423.46 |
| 1302 | | CO₂CH₃ | 374.353 | 375.21 |
| 1303 | (dimethoxyphenyl) | tBu | 401.507 | 402.27 |
| 1304 | | Ph | 421.497 | 422.34 |
| 1305 | | Ch | 427.545 | 428.37 |
| 1306 | | OCH₂Ph | 451.523 | 452.49 |
| 1307 | | CO₂CH₃ | 403.435 | 404.19 |
| 1308 | | CH₂CO₂CH₂Ph | 493.56 | 494.48 |
| 1309 | (pentylphenyl) | tBu | 411.59 | 412.33 |
| 1310 | | Ph | 431.58 | 432.42 |
| 1311 | | Ch | 437.628 | 438.44 |
| 1312 | | OCH₂Ph | 461.606 | 462.55 |
| 1313 | | CO₂CH₃ | 413.518 | 414.25 |
| 1314 | | CH₂CO₂CH₂Ph | 503.643 | 504.56 |
| 1315 | (phenyl) | tBu | 341.455 | 342.27 |
| 1316 | | Ph | 361.445 | 362.37 |
| 1317 | | Ch | 367.493 | 368.36 |
| 1318 | | OCH₂Ph | 391.471 | 392.49 |
| 1319 | | CO₂CH₃ | 343.383 | 344.2 |
| 1320 | | CH₂CO₂CH₂Ph | 433.508 | 434.47 |
| 1321 | (phenyl) | tBu | 355.482 | 356.27 |
| 1322 | | Ph | 375.472 | 376.42 |
| 1323 | | OCH₂Ph | 405.498 | 406.46 |
| 1324 | | CO₂CH₃ | 357.41 | 358.21 |
| 1325 | | CH₂CO₂CH₂Ph | 447.535 | 448.47 |
| 1326 | (benzothiophene) | tBu | 383.514 | 384.23 |
| 1327 | | Ch | 409.552 | 410.26 |
| 1328 | | CO₂CH₃ | 385.442 | 386.17 |
| 1329 | | CH₂CO₂CH₂Ph | 475.567 | 476.46 |
| 1330 | (thiophene) | tBu | 333.454 | 334.22 |
| 1331 | | Ph | 353.444 | 354.29 |
| 1332 | | Ch | 359.492 | 360.31 |
| 1333 | | OCH₂Ph | 383.47 | 384.46 |
| 1334 | | CO₂CH₃ | 335.382 | 336.12 |
| 1335 | | CH₂CO₂CH₂Ph | 425.507 | 426.37 |
| 1336 | (furan) | tBu | 317.389 | 318.25 |
| 1337 | | Ph | 337.379 | 338.32 |
| 1338 | | Ch | 343.427 | 344.32 |
| 1339 | | OCH₂Ph | 367.405 | 368.48 |
| 1340 | | CO₂CH₃ | 319.317 | 320.2 |
| 1341 | | CH₂CO₂CH₂Ph | 409.442 | 410.45 |

TABLE 7-continued

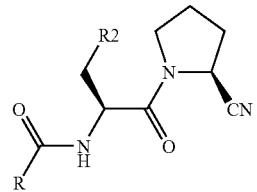

| Example No | R | R2 | Mol Wt | [M + H]+ |
|---|---|---|---|---|
| 1342 | 2-chloropyridin-3-yl ethyl | Ph | 382.851 | 383.32 |
| 1343 | | Ch | 388.899 | 389.33 |
| 1344 | | OCH₂Ph | 412.877 | 413.38 |
| 1345 | | CO₂CH₃ | 364.789 | 365.13 |
| 1346 | | CH₂CO₂CH₂Ph | 454.914 | 455.43 |
| 1347 | benzyloxy-neopentyl | tBu | 371.481 | 372.26 |
| 1348 | | Ph | 391.471 | 392.4 |
| 1349 | | OCH₂Ph | 421.497 | 422.46 |
| 1350 | | CO₂CH₃ | 373.409 | 374.21 |
| 1351 | | CH₂CO₂CH₂Ph | 463.534 | 464.48 |
| 1352 | cyclohexyl | tBu | 333.476 | 334.31 |
| 1353 | | Ph | 353.466 | 354.42 |
| 1354 | | Ch | 359.514 | 360.39 |
| 1355 | | OCH₂Ph | 383.492 | 384.53 |
| 1356 | | CO₂CH₃ | 335.404 | 336.28 |
| 1357 | | CH₂CO₂CH₂Ph | 425.529 | 426.48 |
| 1358 | cyclopentyl | tBu | 319.449 | 320.28 |
| 1359 | | Ph | 339.439 | 340.39 |
| 1360 | | Ch | 345.487 | 346.37 |
| 1361 | | OCH₂Ph | 369.465 | 370.52 |
| 1362 | | CO₂CH₃ | 321.377 | 322.17 |
| 1363 | | CH₂CO₂CH₂Ph | 411.502 | 412.48 |
| 1364 | cyclobutyl | tBu | 305.422 | 306.25 |
| 1365 | | Ph | 325.412 | 326.36 |
| 1366 | | Ch | 331.46 | 332.36 |
| 1367 | | OCH₂Ph | 355.438 | 356.49 |
| 1368 | | CO₂CH₃ | 307.35 | 308.22 |
| 1369 | | CH₂CO₂CH₂Ph | 397.475 | 398.49 |
| 1370 | cyclopropyl | tBu | 291.395 | 292.25 |
| 1371 | | Ph | 311.385 | 312.37 |
| 1372 | | Ch | 317.433 | 318.32 |
| 1373 | | OCH₂Ph | 341.411 | 342.46 |
| 1374 | | CO₂CH₃ | 293.323 | 294.19 |
| 1375 | | CH₂CO₂CH₂Ph | 383.448 | 384.5 |
| 1376 | cyclopentylmethyl | tBu | 333.476 | 334.3 |
| 1377 | | Ph | 353.466 | 354.38 |
| 1378 | | Ch | 359.514 | 360.4 |
| 1379 | | OCH₂Ph | 383.492 | 384.56 |
| 1380 | | CO₂CH₃ | 335.404 | 336.22 |
| 1381 | | CH₂CO₂CH₂Ph | 425.529 | 426.48 |
| 1382 | tert-butyl | tBu | 307.438 | 308.26 |
| 1383 | | Ph | 371.428 | 328.37 |
| 1384 | | Ch | 333.476 | 334.39 |
| 1385 | | OCH₂Ph | 357.454 | 358.48 |
| 1386 | | CO₂CH₃ | 309.366 | 310.58 |
| 1387 | | CH₂CO₂CH₂Ph | 399.491 | 400.54 |
| 1388 | neopentyl | tBu | 321.465 | 322.29 |
| 1389 | | Ph | 341.455 | 342.42 |
| 1390 | | Ch | 347.503 | 348.39 |
| 1391 | | OCH₂Ph | 371.481 | 372.52 |
| 1392 | | CO₂CH₃ | 323.393 | 324.24 |
| 1393 | | CH₂CO₂CH₂Ph | 413.518 | 414.51 |

TABLE 7-continued

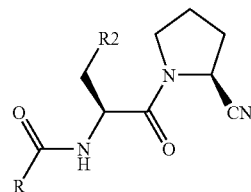

| Example No | R | R2 | Mol Wt | [M + H]+ |
|---|---|---|---|---|
| 1394 | hexyl | tBu | 321.465 | 322.31 |
| 1395 | | Ph | 341.455 | 342.42 |
| 1396 | | OCH₂Ph | 371.481 | 372.51 |
| 1397 | | CO₂CH₃ | 323.393 | 324.28 |
| 1398 | | CH₂CO₂CH₂Ph | 413.518 | 414.49 |
| 1399 | 2-ethylhexyl | tBu | 349.519 | 350.33 |
| 1400 | | Ph | 369.509 | 370.44 |
| 1401 | | Ch | 375.557 | 376.43 |
| 1402 | | OCH₂Ph | 399.535 | 400.55 |
| 1403 | | CO₂CH₃ | 351.447 | 352.3 |
| 1404 | | CH₂CO₂CH₂Ph | 441.572 | 442.55 |
| 1405 | methyl ester butyl | tBu | 337.42 | 338.26 |
| 1406 | | Ph | 357.41 | 358.36 |
| 1407 | | Ch | 363.458 | 364.36 |
| 1408 | | OCH₂Ph | 387.436 | 388.42 |
| 1409 | | CO₂CH₃ | 339.348 | 340.14 |
| 1410 | methyl ester octyl | tBu | 393.528 | 394.32 |
| 1411 | | Ph | 413.518 | 414.4 |
| 1412 | | Ch | 419.566 | 420.4 |
| 1413 | | OCH₂Ph | 443.544 | 444.5 |
| 1414 | | CO₂CH₃ | 395.456 | 396.25 |
| 1415 | | CH₂CO₂CH₂Ph | 485.581 | 486.52 |
| 1416 | 2-(OCF₃)phenyl | tBu | 411.424 | 412.22 |
| 1417 | | Ph | 431.414 | 432.29 |
| 1418 | | Ch | 437.462 | 438.29 |
| 1419 | | OCH₂Ph | 461.44 | 462.46 |
| 1420 | | CO₂CH₃ | 413.352 | 414.14 |
| 1421 | | CH₂CO₂CH₂Ph | 503.477 | 504.44 |
| 1422 | 4-(NMe₂)phenyl | tBu | 370.497 | 371.28 |
| 1423 | | Ph | 390.487 | 391.42 |
| 1424 | | Ch | 396.535 | 397.39 |
| 1425 | | OCH₂Ph | 420.513 | 421.44 |
| 1426 | | CH₂CO₂CH₂Ph | 462.55 | 463.51 |
| 1427 | 3-pyridyl | tBu | 328.416 | 329.27 |
| 1428 | | Ph | 348.406 | 349.37 |
| 1429 | | Ch | 354.454 | 355.32 |
| 1430 | | OCH₂Ph | 378.432 | 379.47 |
| 1431 | | CO₂CH₃ | 330.344 | 331.13 |
| 1432 | | CH₂CO₂CH₂Ph | 420.469 | 421.43 |
| 1433 | 4-pyridyl | Ch | 354.454 | 355.35 |
| 1434 | | OCH₂Ph | 378.432 | 379.53 |
| 1435 | | CO₂CH₃ | 330.344 | 331.14 |
| 1436 | | CH₂CO₂CH₂Ph | 420.469 | 421.46 |

TABLE 7-continued

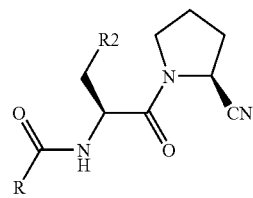

| Example No | R | R2 | Mol Wt | [M + H]+ |
|---|---|---|---|---|
| 1437 | adamantyl | tBu | 385.552 | 386.32 |
| 1438 | | Ph | 405.542 | 406.45 |
| 1439 | | Ch | 411.59 | 412.42 |
| 1440 | | OCH₂Ph | 435.568 | 436.51 |
| 1441 | | CO₂CH₃ | 387.48 | 388.29 |
| 1442 | | CH₂CO₂CH₂Ph | 477.605 | 478.53 |
| 1443 | 2,4,5-trifluorophenyl | tBu | 381.398 | 382.21 |
| 1444 | | Ph | 401.388 | 402.35 |
| 1445 | | Ch | 407.436 | 408.3 |
| 1446 | | OCH₂Ph | 431.414 | 432.37 |
| 1447 | | CO₂CH₃ | 383.326 | 384.16 |
| 1448 | | CH₂CO₂CH₂Ph | 473.451 | 474.46 |
| 1449 | thiophen-2-yl | Ph | 367.471 | 368.34 |
| 1450 | | Ch | 373.519 | 374.35 |
| 1451 | | OCH₂Ph | 397.497 | 398.43 |
| 1452 | | CO₂CH₃ | 349.409 | 350.17 |
| 1453 | | CH₂CO₂CH₂Ph | 439.534 | 440.45 |
| 1454 | phenoxy | tBu | 357.454 | 358.26 |
| 1455 | | Ph | 377.444 | 378.39 |
| 1456 | | OCH₂Ph | 407.47 | 408.48 |
| 1457 | | CO₂CH₃ | 359.382 | 360.21 |
| 1458 | | CH₂CO₂CH₂Ph | 449.507 | 450.49 |
| 1459 | 3,4-difluorophenyl | tBu | 363.408 | 364.22 |
| 1460 | | Ph | 383.398 | 384.34 |
| 1461 | | Ch | 389.446 | 390.34 |
| 1462 | | OCH₂Ph | 413.424 | 414.46 |
| 1463 | | CO₂CH₃ | 365.336 | 366.13 |
| 1464 | | CH₂CO₂CH₂Ph | 455.461 | 456.44 |
| 1465 | phenyl-tBu | tBu | 369.509 | 370.3 |
| 1466 | | Ph | 389.499 | 390.43 |
| 1467 | | Ch | 395.547 | 396.41 |
| 1468 | | OCH₂Ph | 419.525 | 420.48 |
| 1469 | | CO₂CH₃ | 371.437 | 372.23 |
| 1470 | | CH₂CO₂CH₂Ph | 461.562 | 462.52 |
| 1471 | thiophen-3-yl | tBu | 333.454 | 334.22 |
| 1472 | | Ph | 353.444 | 354.3 |
| 1473 | | Ch | 359.492 | 360.32 |
| 1474 | | OCH₂Ph | 383.47 | 384.46 |
| 1475 | | CO₂CH₃ | 335.382 | 336.09 |
| 1476 | | CH₂CO₂CH₂Ph | 425.507 | 426.4 |
| 1477 | 2,3-difluorophenyl | tBu | 363.408 | 364.23 |
| 1478 | | Ph | 383.398 | 384.35 |
| 1479 | | Ch | 389.446 | 390.37 |
| 1480 | | OCH₂Ph | 413.424 | 414.44 |
| 1481 | | CO₂CH₃ | 365.336 | 366.09 |
| 1482 | | CH₂CO₂CH₂Ph | 455.461 | 456.46 |

TABLE 7-continued
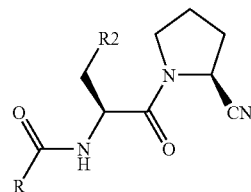
| Example No | R | R2 | Mol Wt | [M + H]+ |
|---|---|---|---|---|
| 1483 | | tBu | 383.514 | 384.22 |
| 1484 | (3-tert-butyl-benzothiophene) | CH$_2$CO$_2$CH$_2$Ph | 475.567 | 476.43 |
| 1485 | | tBu | 363.408 | 364.22 |
| 1486 | (3,5-difluorophenyl) | Ph | 383.398 | 384.3 |
| 1487 | | OCH$_2$Ph | 413.424 | 414.42 |
| 1488 | | CH$_2$CO$_2$CH$_2$Ph | 455.461 | 456.43 |
TABLE 8
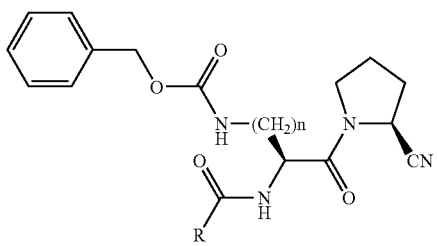
| Example No | R | n | Mol Wt | [M + H]+ |
|---|---|---|---|---|
| 1489 | CH$_3$ | 2 | 372.425 | 373.3 |
| 1490 | CH$_3$ | 1 | 358.398 | 359.2 |
| 1491 | | 2 | 434.496 | 435.27 |
| 1492 | (phenyl) | 1 | 420.469 | 421.2 |
| 1493 | | 3 | 448.523 | 449.45 |
| 1494 | | 4 | 462.55 | 463.42 |
| 1495 | | 2 | 468.941 | 469.22 |
| 1496 | (3-chlorophenyl) | 1 | 454.914 | 455.16 |
| 1497 | | 3 | 482.968 | 483.3 |
| 1498 | | 4 | 496.995 | 497.37 |
| 1499 | | 2 | 468.941 | 469.3 |
| 1500 | (4-chlorophenyl) | 1 | 454.914 | 455.17 |
| 1501 | | 3 | 482.968 | 483.32 |
| 1502 | | 4 | 496.995 | 497.36 |

TABLE 8-continued
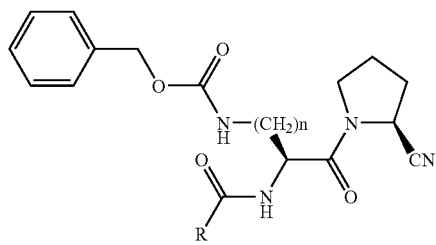
| Example No | R | n | Mol Wt | [M + H]+ |
|---|---|---|---|---|
| 1503 | 2-Cl-C6H4 | 2 | 468.941 | 469.24 |
| 1504 | | 1 | 454.914 | 455.16 |
| 1505 | | 3 | 482.968 | 483.34 |
| 1506 | | 4 | 496.995 | 497.4 |
| 1507 | 2,4-diCl-C6H3 | 2 | 503.386 | 503.24 |
| 1508 | | 1 | 489.359 | 489.1 |
| 1509 | | 3 | 517.413 | 517.32 |
| 1510 | | 4 | 531.44 | 531.36 |
| 1511 | 3,4-diCl-C6H3 | 2 | 503.386 | 503.21 |
| 1512 | | 1 | 489.359 | 489.1 |
| 1513 | | 4 | 531.44 | 531.34 |
| 1514 | 3,5-diCl-C6H3 | 3 | 517.413 | 517.33 |
| 1515 | | 4 | 531.44 | 531.33 |
| 1516 | 3-F-C6H4 | 2 | 452.486 | 453.33 |
| 1517 | | 1 | 438.459 | 439.18 |
| 1518 | | 3 | 466.513 | 467.39 |
| 1519 | | 4 | 480.54 | 481.41 |
| 1520 | 4-F-C6H4 | 2 | 452.486 | 453.33 |
| 1521 | | 1 | 438.459 | 439.2 |
| 1522 | | 3 | 466.513 | 467.35 |
| 1523 | | 4 | 480.54 | 481.38 |
| 1524 | 4-MeO-C6H4 | 2 | 464.522 | 465.34 |
| 1525 | | 1 | 450.495 | 451.21 |
| 1526 | | 4 | 492.576 | 493.43 |

TABLE 8-continued
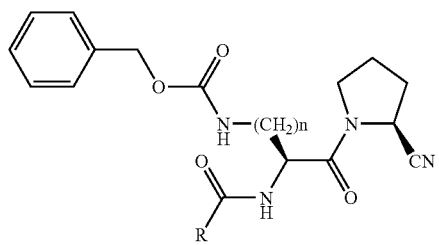
| Example No | R | n | Mol Wt | [M + H]+ |
|---|---|---|---|---|
| 1527 | 3-methoxybenzyl | 2 | 464.522 | 465.35 |
| 1528 | | 1 | 450.495 | 451.21 |
| 1529 | | 3 | 478.549 | 479.37 |
| 1530 | 2-methylbenzyl | 2 | 448.523 | 449.28 |
| 1531 | | 1 | 434.496 | 435.2 |
| 1532 | | 3 | 462.55 | 463.44 |
| 1533 | | 4 | 476.577 | 477.43 |
| 1534 | 3-methylbenzyl | 2 | 448.523 | 449.29 |
| 1535 | | 1 | 434.496 | 435.21 |
| 1536 | | 3 | 462.55 | 463.41 |
| 1537 | | 4 | 476.577 | 477.41 |
| 1538 | 4-methylbenzyl | 2 | 448.523 | 449.27 |
| 1539 | | 1 | 434.496 | 435.22 |
| 1540 | | 3 | 462.55 | 463.38 |
| 1541 | | 4 | 476.577 | 477.43 |
| 1542 | 4-cyanobenzyl | 3 | 473.533 | 474.39 |
| 1543 | | 4 | 487.56 | 488.41 |
| 1544 | 3-trifluoromethylbenzyl | 2 | 502.493 | 503.33 |
| 1545 | | 1 | 488.466 | 489.16 |
| 1546 | | 3 | 516.52 | 517.35 |
| 1547 | | 4 | 530.547 | 531.41 |
| 1548 | 3-nitrobenzyl | 2 | 479.493 | 480.31 |
| 1549 | | 1 | 465.466 | 466.19 |
| 1550 | | 3 | 493.52 | 494.35 |
| 1551 | | 4 | 507.547 | 508.4 |

TABLE 8-continued
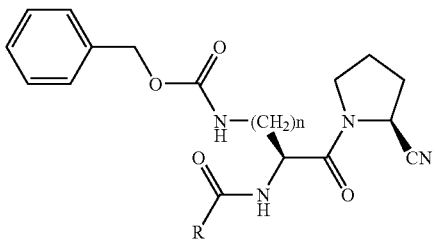
| Example No | R | n | Mol Wt | [M + H]+ |
|---|---|---|---|---|
| 1552 | 1-naphthyl-CH< | 2 | 484.556 | 485.34 |
| 1553 | | 1 | 470.529 | 471.2 |
| 1554 | | 3 | 498.583 | 499.41 |
| 1555 | | 4 | 512.61 | 513.43 |
| 1556 | 2-naphthyl-CH< | 2 | 484.556 | 485.35 |
| 1557 | | 1 | 470.529 | 471.2 |
| 1558 | | 3 | 498.583 | 499.41 |
| 1559 | | 4 | 512.61 | 513.45 |
| 1560 | 4-tBu-C6H4-CH< | 2 | 490.604 | 491.39 |
| 1561 | | 1 | 476.577 | 477.25 |
| 1562 | | 3 | 504.631 | 505.44 |
| 1563 | | 4 | 518.658 | 519.5 |
| 1564 | 2-F-C6H4-CH< | 2 | 452.486 | 453.33 |
| 1565 | | 1 | 438.459 | 439.18 |
| 1566 | | 3 | 466.513 | 467.33 |
| 1567 | | 4 | 480.54 | 481.4 |
| 1568 | 2,6-diCl-C6H3-CH< | 2 | 503.386 | 503.23 |
| 1569 | | 1 | 489.359 | 489.09 |
| 1570 | | 3 | 517.413 | 517.28 |
| 1571 | | 4 | 531.44 | 531.35 |
| 1572 | 4-CF3-C6H4-CH< | 2 | 502.493 | 503.35 |
| 1573 | | 1 | 488.466 | 489.16 |
| 1574 | | 3 | 516.52 | 517.4 |
| 1575 | | 4 | 530.547 | 531.4 |
| 1576 | 3-Br-C6H4-CH< | 2 | 513.397 | 513.22 |
| 1577 | | 1 | 499.37 | 499.1 |
| 1578 | | 3 | 527.424 | 527.27 |
| 1579 | | 4 | 541.451 | 541.32 |
| 1580 | 2-OMe-C6H4-CH< | 3 | 478.549 | 479.4 |
| 1581 | | 4 | 492.576 | 493.4 |

TABLE 8-continued
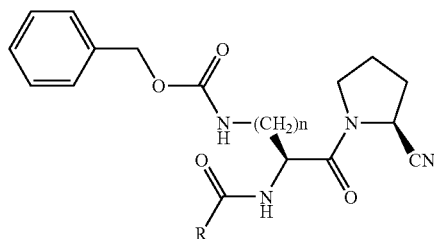
| Example No | R | n | Mol Wt | [M + H]+ |
|---|---|---|---|---|
| 1582 | | 2 | 506.603 | 507.34 |
| 1583 | | 1 | 492.576 | 493.25 |
| 1584 | | 3 | 520.63 | 521.46 |
| 1585 | | 4 | 534.657 | 535.49 |
| 1586 | | 2 | 508.575 | 509.36 |
| 1587 | | 1 | 494.548 | 495.23 |
| 1588 | | 3 | 522.602 | 523.44 |
| 1589 | | 4 | 536.629 | 537.44 |
| 1590 | | 2 | 518.658 | 519.42 |
| 1591 | | 1 | 504.631 | 505.31 |
| 1592 | | 3 | 532.685 | 533.43 |
| 1593 | | 4 | 546.712 | 547.49 |
| 1594 | | 2 | 448.523 | 449.29 |
| 1595 | | 1 | 434.496 | 435.21 |
| 1596 | | 3 | 462.55 | 463.4 |
| 1597 | | 4 | 476.577 | 477.43 |
| 1598 | | 2 | 462.55 | 463.36 |
| 1599 | | 1 | 448.523 | 449.24 |
| 1600 | | 3 | 476.577 | 477.4 |
| 1601 | | 4 | 490.604 | 491.45 |
| 1602 | | 2 | 440.522 | 441.28 |
| 1603 | | 1 | 426.495 | 427.16 |
| 1604 | | 3 | 454.549 | 455.33 |
| 1605 | | 4 | 468.576 | 469.39 |
| 1606 | | 2 | 424.457 | 425.24 |
| 1607 | | 1 | 410.43 | 411.19 |
| 1608 | | 3 | 438.484 | 439.32 |
| 1609 | | 4 | 452.511 | 453.41 |
| 1610 | | 3 | 483.956 | 484.34 |
| 1611 | | 4 | 497.983 | 498.4 |
| 1612 | | 2 | 478.549 | 479.35 |
| 1613 | | 1 | 464.522 | 465.2 |
| 1614 | | 3 | 492.576 | 493.41 |
| 1615 | | 4 | 506.603 | 507.45 |

TABLE 8-continued
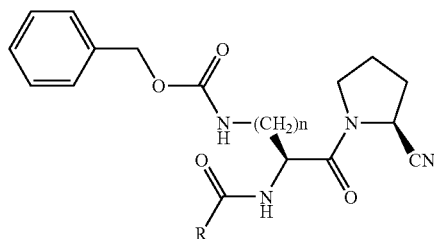
| Example No | R | n | Mol Wt | [M + H]+ |
|---|---|---|---|---|
| 1616 | cyclohexyl-CH< | 2 | 440.544 | 441.31 |
| 1617 | | 1 | 426.517 | 427.24 |
| 1618 | | 3 | 454.571 | 455.44 |
| 1619 | | 4 | 468.598 | 469.45 |
| 1620 | cyclopentyl-CH< | 2 | 426.517 | 427.29 |
| 1621 | | 1 | 412.49 | 413.24 |
| 1622 | | 3 | 440.544 | 441.43 |
| 1623 | | 4 | 454.571 | 455.45 |
| 1624 | cyclobutyl-CH< | 2 | 412.49 | 413.3 |
| 1625 | | 1 | 398.463 | 399.23 |
| 1626 | | 3 | 426.517 | 427.4 |
| 1627 | | 4 | 440.544 | 441.44 |
| 1628 | cyclopropyl-CH< | 2 | 398.463 | 399.29 |
| 1629 | | 1 | 384.436 | 385.23 |
| 1630 | | 3 | 412.49 | 413.34 |
| 1631 | | 4 | 426.517 | 427.39 |
| 1632 | cyclopentyl-CH2-CH< | 2 | 440.544 | 441.3 |
| 1633 | | 1 | 426.517 | 427.24 |
| 1634 | | 3 | 454.571 | 455.39 |
| 1635 | | 4 | 468.598 | 469.42 |
| 1636 | t-Bu-CH< | 2 | 414.506 | 415.29 |
| 1637 | | 1 | 400.479 | 401.25 |
| 1638 | | 3 | 428.533 | 429.39 |
| 1639 | | 4 | 442.56 | 443.46 |
| 1640 | t-Bu-CH2-CH< | 3 | 442.56 | 443.44 |
| 1641 | | 4 | 456.587 | 457.47 |
| 1642 | n-pentyl-CH< | 1 | 414.506 | 415.24 |
| 1643 | | 3 | 442.56 | 443.42 |
| 1644 | | 4 | 456.587 | 457.48 |
| 1645 | 2-ethylhexyl | 2 | 456.587 | 457.41 |
| 1646 | | 1 | 442.56 | 443.28 |
| 1647 | | 3 | 470.614 | 471.46 |
| 1648 | | 4 | 484.641 | 485.48 |
| 1649 | MeO-CO-CH2-CH2-CH< | 3 | 458.515 | 459.41 |
| 1650 | | 4 | 472.542 | 473.43 |

TABLE 8-continued
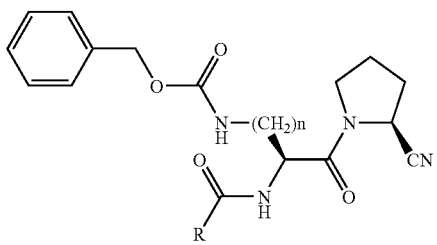
| Example No | R | n | Mol Wt | [M + H]+ |
|---|---|---|---|---|
| 1651 | (methyl ester long chain) | 1 | 486.569 | 487.24 |
| 1652 | | 3 | 514.623 | 515.41 |
| 1653 | | 4 | 528.65 | 529.5 |
| 1654 | (phenylcyclopropyl) | 2 | 474.561 | 475.38 |
| 1655 | | 1 | 460.534 | 461.24 |
| 1656 | | 3 | 488.588 | 489.4 |
| 1657 | | 4 | 502.615 | 503.45 |
| 1658 | (2-OCF3-phenyl) | 2 | 518.492 | 519.3 |
| 1659 | | 1 | 504.465 | 505.19 |
| 1660 | | 3 | 532.519 | 533.37 |
| 1661 | | 4 | 546.546 | 547.39 |
| 1662 | (2,6-difluorophenyl) | 2 | 470.476 | 471.31 |
| 1663 | | 1 | 456.449 | 457.18 |
| 1664 | | 3 | 484.503 | 485.35 |
| 1665 | | 4 | 498.53 | 499.42 |
| 1666 | (4-NMe2-phenyl) | 2 | 477.565 | 478.36 |
| 1667 | | 1 | 463.538 | 464.23 |
| 1668 | | 3 | 491.592 | 492.45 |
| 1669 | | 4 | 505.619 | 506.42 |
| 1670 | (3-pyridyl) | 3 | 449.511 | 450.4 |
| 1671 | | 4 | 463.538 | 464.42 |
| 1672 | (4-pyridyl) | 3 | 449.511 | 450.39 |
| 1673 | | 4 | 463.538 | 464.38 |
| 1674 | (adamantyl) | 2 | 492.62 | 493.41 |
| 1675 | | 1 | 478.593 | 479.27 |
| 1676 | | 4 | 520.674 | 521.51 |

TABLE 8-continued
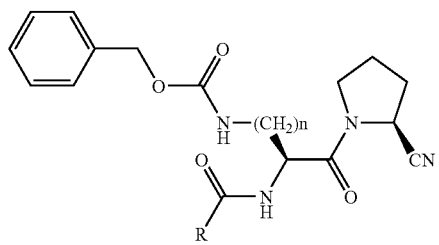
| Example No | R | n | Mol Wt | [M + H]+ |
|---|---|---|---|---|
| 1677 | 2,4,5-trifluorophenyl | 2 | 488.466 | 489.29 |
| 1678 | | 1 | 474.439 | 475.16 |
| 1679 | | 3 | 502.493 | 503.35 |
| 1680 | | 4 | 516.52 | 517.42 |
| 1681 | 2-thienyl | 2 | 454.549 | 455.3 |
| 1682 | | 1 | 440.522 | 441.14 |
| 1683 | | 3 | 468.576 | 469.37 |
| 1684 | | 4 | 482.603 | 483.37 |
| 1685 | phenoxy | 2 | 464.522 | 465.3 |
| 1686 | | 1 | 450.495 | 451.2 |
| 1687 | | 3 | 478.549 | 479.39 |
| 1688 | | 4 | 492.576 | 493.42 |
| 1689 | 3,4-difluorophenyl | 2 | 470.476 | 471.32 |
| 1690 | | 1 | 456.449 | 457.19 |
| 1691 | | 3 | 484.503 | 485.34 |
| 1692 | | 4 | 498.53 | 499.39 |
| 1693 | phenyl-t-butyl | 2 | 476.577 | 477.38 |
| 1694 | | 1 | 462.55 | 463.23 |
| 1695 | | 3 | 490.604 | 491.41 |
| 1696 | | 4 | 504.631 | 505.46 |
| 1697 | 3-thienyl | 2 | 440.522 | 441.27 |
| 1698 | | 1 | 426.495 | 427.15 |
| 1699 | | 3 | 454.549 | 455.32 |
| 1700 | | 4 | 468.576 | 469.36 |
| 1701 | 2,3-difluorophenyl | 2 | 470.476 | 471.25 |
| 1702 | | 1 | 456.449 | 457.18 |
| 1703 | | 3 | 484.503 | 485.37 |
| 1704 | | 4 | 498.53 | 499.39 |
| 1705 | benzothiophene-t-butyl | 3 | 504.609 | 505.37 |

TABLE 8-continued
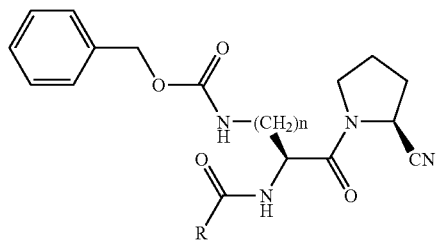
| Example No | R | n | Mol Wt | [M + H]+ |
|---|---|---|---|---|
| 1706 | F (3,5-difluorophenyl) | 2 | 470.476 | 471.3 |
| 1707 | | 1 | 456.449 | 457.18 |
| 1708 | | 3 | 484.503 | 485.38 |
| 1709 | | 4 | 498.53 | 499.39 |
TABLE 9
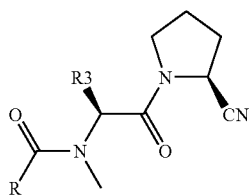
| Example No | R | R3 | Mol Wt | [M + H]+ |
|---|---|---|---|---|
| 1710 | CH₃ | H | 209.249 | 209.36 |
| 1711 | CH₃ | Me | 223.276 | 223.34 |
| 1712 | phenyl | H | 271.32 | 272.36 |
| 1713 | 3-Cl-phenyl | H | 305.765 | 306.25 |
| 1714 | 3-Cl-phenyl | CH₂Ph | 395.89 | 396.33 |
| 1715 | 4-Cl-phenyl | H | 305.765 | 306.27 |
| 1716 | 4-Cl-phenyl | CH₂Ph | 395.89 | 396.31 |
| 1717 | 2-Cl-phenyl | H | 305.765 | 306.29 |
| 1718 | 2-Cl-phenyl | CH₂Ph | 395.89 | 396.28 |

TABLE 9-continued

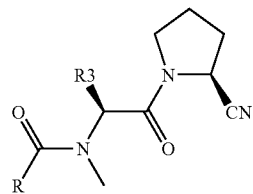

| Example No | R | R3 | Mol Wt | [M + H]+ |
|---|---|---|---|---|
| 1719 | 2,4-diCl-phenyl | H | 340.21 | 340.23 |
| 1720 | 2,4-diCl-phenyl | CH₂Ph | 430.335 | 430.21 |
| 1721 | 3,4-diCl-phenyl | H | 340.21 | 340.23 |
| 1722 | 3,4-diCl-phenyl | Me | 354.237 | 354.25 |
| 1723 | 3,4-diCl-phenyl | secBu | 396.318 | 396.15 |
| 1724 | 3,4-diCl-phenyl | CH₂Ph | 430.335 | 430.2 |
| 1725 | 3,5-diCl-phenyl | H | 340.21 | 340.24 |
| 1726 | 3,5-diCl-phenyl | Me | 354.237 | 354.24 |
| 1727 | 3,5-diCl-phenyl | CH₂Ph | 430.335 | 430.28 |
| 1728 | 3-F-phenyl | H | 289.31 | 290.32 |
| 1729 | 3-F-phenyl | CH₂Ph | 379.435 | 380.32 |
| 1730 | 4-F-phenyl | H | 289.31 | 290.28 |
| 1731 | 4-F-phenyl | CH₂Ph | 379.435 | 380.32 |
| 1732 | 4-OMe-phenyl | H | 301.346 | 302.37 |
| 1733 | 4-OMe-phenyl | Me | 315.373 | 316.34 |
| 1734 | 4-OMe-phenyl | secBu | 357.454 | 358.27 |
| 1735 | 4-OMe-phenyl | CH₂Ph | 391.471 | 392.36 |
| 1736 | 3-OMe-phenyl | H | 301.346 | 302.31 |
| 1737 | 3-OMe-phenyl | Me | 315.373 | 316.33 |
| 1738 | 3-OMe-phenyl | secBu | 357.454 | 358.25 |
| 1739 | 3-OMe-phenyl | CH₂Ph | 391.471 | 392.37 |
| 1740 | 2-Me-phenyl | H | 285.347 | 286.33 |
| 1741 | 2-Me-phenyl | CH₂Ph | 375.472 | 376.34 |

TABLE 9-continued
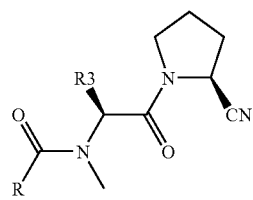
| Example No | R | R3 | Mol Wt | [M + H]+ |
|---|---|---|---|---|
| 1742 | 3-methylphenyl | H | 285.347 | 286.35 |
| 1743 | | Me | 299.374 | 300.33 |
| 1744 | | secBu | 341.455 | 342.24 |
| 1745 | | CH₂Ph | 375.472 | 376.36 |
| 1746 | 4-methylphenyl | H | 285.347 | 286.33 |
| 1747 | | Me | 299.374 | 300.32 |
| 1748 | | CH₂Ph | 375.472 | 376.36 |
| 1749 | 4-cyanophenyl | H | 296.33 | 297.29 |
| 1750 | | CH₂Ph | 386.455 | 387.27 |
| 1751 | 3-CF₃-phenyl | H | 339.317 | 340.32 |
| 1752 | | CH₂Ph | 429.442 | 430.29 |
| 1753 | 3-NO₂-phenyl | H | 316.317 | 317.31 |
| 1754 | | Me | 330.344 | 331.35 |
| 1755 | | CH₂Ph | 406.442 | 407.31 |
| 1756 | 1-naphthyl | H | 321.38 | 322.33 |
| 1757 | | Me | 335.407 | 336.35 |
| 1758 | | CH₂Ph | 411.505 | 412.32 |
| 1759 | 2-naphthyl | H | 321.38 | 322.33 |
| 1760 | | Me | 335.407 | 336.37 |
| 1761 | | secBu | 377.488 | 378.31 |
| 1762 | | CH₂Ph | 411.505 | 412.31 |

TABLE 9-continued
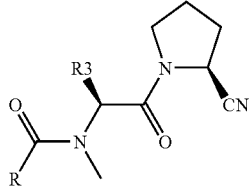
| Example No | R | R3 | Mol Wt | [M + H]+ |
|---|---|---|---|---|
| 1763 | 4-tert-butylphenyl-CH(CH3)- | H | 327.428 | 328.38 |
| 1764 | | Me | 341.455 | 342.37 |
| 1765 | | secBu | 383.536 | 384.31 |
| 1766 | | CH2Ph | 417.553 | 418.4 |
| 1767 | 2-fluorophenyl-CH(CH3)- | H | 289.31 | 290.32 |
| 1768 | | CH2Ph | 379.435 | 380.32 |
| 1769 | 2,6-dichlorophenyl-CH(CH3)- | H | 340.21 | 340.24 |
| 1770 | | CH2Ph | 430.335 | 430.25 |
| 1771 | 4-CF3-phenyl-CH(CH3)- | H | 339.317 | 340.29 |
| 1772 | | secBu | 395.425 | 396.3 |
| 1773 | | CH2Ph | 429.442 | 430.31 |
| 1774 | 3-bromophenyl-CH(CH3)- | H | 350.221 | 350.27 |
| 1775 | | Me | 364.248 | 364.22 |
| 1776 | | secBu | 406.329 | 406.2 |
| 1777 | | CH2Ph | 440.346 | 440.17 |
| 1778 | 2-methoxyphenyl-CH(CH3)- | H | 301.346 | 302.3 |
| 1779 | | Me | 315.373 | 316.4 |
| 1780 | | CH2Ph | 391.471 | 392.35 |
| 1781 | 4-butoxyphenyl-CH(CH3)- | H | 343.427 | 344.39 |
| 1782 | | Me | 357.454 | 358.38 |
| 1783 | | secBu | 399.535 | 400.32 |
| 1784 | | CH2Ph | 433.552 | 434.36 |
| 1785 | 2,5-dimethoxyphenyl-C(CH3)2-CH2- | H | 345.399 | 346.36 |
| 1786 | | Me | 359.426 | 360.33 |
| 1787 | | CH2Ph | 435.524 | 436.37 |

TABLE 9-continued
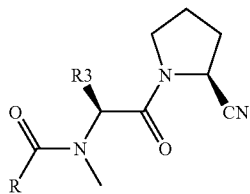
| Example No | R | R3 | Mol Wt | [M + H]+ |
|---|---|---|---|---|
| 1788 | (pentyl-phenyl-CH(CH₃)-) | H | 355.482 | 356.42 |
| 1789 | | Me | 369.509 | 370.4 |
| 1790 | | secBu | 411.59 | 412.34 |
| 1791 | | CH₂Ph | 445.607 | 446.42 |
| 1792 | (PhCH₂C(CH₃)₂-) | H | 285.347 | 286.32 |
| 1793 | | CH₂Ph | 375.472 | 376.34 |
| 1794 | (Ph-CH₂CH₂-CH(CH₃)-) | H | 299.374 | 300.34 |
| 1795 | | CH₂Ph | 389.499 | 390.36 |
| 1796 | (2-thienyl-CH(CH₃)-) | H | 277.346 | 278.28 |
| 1797 | | Me | 291.373 | 292.25 |
| 1798 | | CH₂Ph | 367.471 | 368.3 |
| 1799 | (2-furyl-CH(CH₃)-) | H | 261.281 | 262.34 |
| 1800 | | CH₂Ph | 351.406 | 352.32 |
| 1801 | (PhCH₂O-CH₂-C(CH₃)₂-) | H | 315.373 | 316.34 |
| 1802 | | Me | 329.4 | 330.38 |
| 1803 | | secBu | 371.481 | 372.3 |
| 1804 | | CH₂Ph | 405.498 | 406.31 |
| 1805 | (cyclohexyl-CH(CH₃)-) | H | 277.368 | 278.38 |
| 1806 | (cyclopentyl-CH(CH₃)-) | H | 263.341 | 264.38 |
| 1807 | | CH₂Ph | 353.466 | 354.34 |
| 1808 | (cyclobutyl-CH(CH₃)-) | H | 249.314 | 250.38 |
| 1809 | | CH₂Ph | 339.439 | 340.32 |
| 1810 | (cyclopropyl-CH(CH₃)-) | H | 235.287 | 236.33 |
| 1811 | | CH₂Ph | 325.412 | 326.34 |

TABLE 9-continued
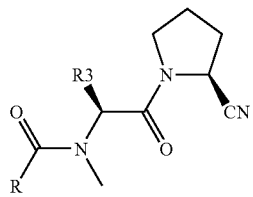
| Example No | R | R3 | Mol Wt | [M + H]+ |
|---|---|---|---|---|
| 1812 | cyclopentylethyl | H | 277.368 | 278.38 |
| 1813 | | CH₂Ph | 367.493 | 368.34 |
| 1814 | neopentyl | H | 251.33 | 252.36 |
| 1815 | | CH₂Ph | 341.455 | 342.31 |
| 1816 | 3,3-dimethylbutyl | H | 265.357 | 266.42 |
| 1817 | | CH₂Ph | 355.482 | 356.3 |
| 1818 | hexyl-branched | H | 265.357 | 266.38 |
| 1819 | | CH₂Ph | 355.482 | 356.34 |
| 1820 | 2-ethylhexyl | H | 293.411 | 294.42 |
| 1821 | | CH₂Ph | 383.536 | 384.42 |
| 1822 | methyl ester chain | H | 281.312 | 282.37 |
| 1823 | | Me | 295.339 | 296.37 |
| 1824 | | CH₂Ph | 371.437 | 372.34 |
| 1825 | methyl ester long chain | H | 337.42 | 338.37 |
| 1826 | | CH₂Ph | 427.545 | 428.39 |
| 1827 | phenylcyclopropyl | H | 311.385 | 312.34 |
| 1828 | | Me | 325.412 | 326.29 |
| 1829 | | secBu | 367.493 | 368.26 |
| 1830 | | CH₂Ph | 401.51 | 402.37 |
| 1831 | 2-(trifluoromethoxy)phenyl | H | 355.316 | 356.3 |
| 1832 | | secBu | 411.424 | 412.22 |
| 1833 | | CH₂Ph | 445.441 | 446.3 |
| 1834 | 2,6-difluorophenyl | H | 307.3 | 308.3 |
| 1835 | | CH₂Ph | 397.425 | 398.3 |

TABLE 9-continued
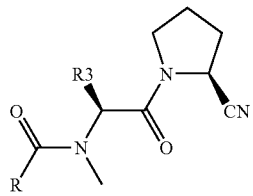
| Example No | R | R3 | Mol Wt | [M + H]+ |
|---|---|---|---|---|
| 1836 | 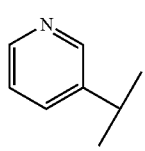 | Me | 286.335 | 287.32 |
| 1837 | | CH₂Ph | 362.433 | 363.33 |
| 1838 | 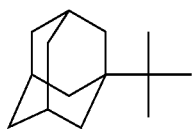 | H | 329.444 | 330.43 |
| 1839 | | Me | 343.471 | 344.37 |
| 1840 | | CH₂Ph | 419.569 | 420.41 |
| 1841 | 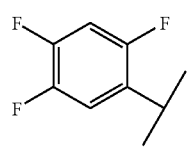 | H | 325.29 | 326.26 |
| 1842 | | CH₂Ph | 415.415 | 416.26 |
| 1843 | 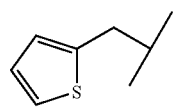 | H | 291.373 | 292.28 |
| 1844 | | CH₂Ph | 381.498 | 382.27 |
| 1845 | 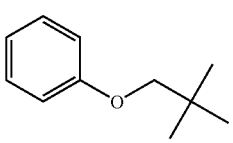 | H | 301.346 | 302.32 |
| 1846 | | CH₂Ph | 391.471 | 392.34 |
| 1847 | 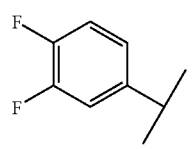 | H | 307.3 | 308.31 |
| 1848 | | CH₂Ph | 397.425 | 398.29 |
| 1849 | 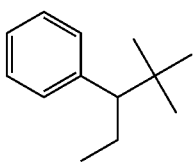 | H | 313.401 | 314.37 |
| 1850 | | CH₂Ph | 403.526 | 404.42 |
| 1851 | 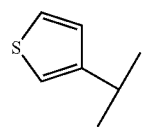 | H | 277.346 | 278.29 |
| 1852 | | Me | 291.373 | 292.29 |
| 1853 | | CH₂Ph | 367.471 | 368.26 |

TABLE 9-continued
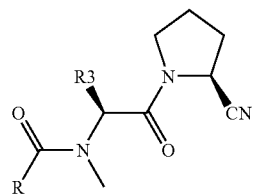
| Example No | R | R3 | Mol Wt | [M + H]+ |
|---|---|---|---|---|
| 1854 | | H | 307.3 | 308.3 |
| 1855 | (2,3-difluorophenyl)ethyl | CH₂Ph | 397.425 | 398.32 |
TABLE 10
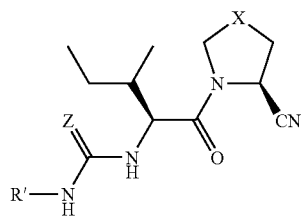
| Example No | R' | Z | X | Mol Wt | [M + H]+ |
|---|---|---|---|---|---|
| 1855 | Et | O | CH₂CH₂ | 294.399 | 295.14 |
| 1856 | | O | S | 298.409 | 299.16 |
| 1857 | iPr | O | CH₂ | 294.399 | 295.51 |
| 1858 | | O | CH₂CH₂ | 308.426 | 309.21 |
| 1859 | | O | CF₂ | 330.379 | 331.49 |
| 1860 | nHex | O | CH₂ | 336.48 | 337.56 |
| 1861 | | O | CH₂CH₂ | 350.507 | 351.29 |
| 1862 | | O | S | 354.517 | 355.2 |
| 1863 | | O | CF₂ | 372.46 | 373.53 |
| 1864 | cyclohexylmethyl | O | CH₂ | 334.464 | 335.55 |
| 1865 | | O | CH₂CH₂ | 348.491 | 349.27 |
| 1866 | | O | S | 352.501 | 353.2 |
| 1867 | | O | CF₂ | 370.444 | 371.54 |
| 1868 | benzyl-methyl | O | CH₂ | 342.443 | 343.52 |
| 1869 | | O | CH₂CH₂ | 356.47 | 357.22 |
| 1870 | | O | S | 360.48 | 361.16 |
| 1871 | | O | CF₂ | 378.423 | 379.5 |
| 1872 | ethyl ester chain | O | CH₂ | 352.435 | 353.5 |
| 1873 | | O | CH₂CH₂ | 366.462 | 367.26 |
| 1874 | | O | S | 370.472 | 371.16 |
| 1875 | | O | CF₂ | 388.415 | 389.49 |
| 1876 | phenacyl | O | CH₂CH₂ | 370.453 | 371.21 |
| 1877 | | O | S | 374.463 | 375.14 |

TABLE 10-continued
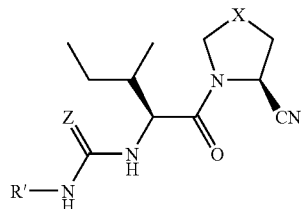
| Example No | R' | Z | X | Mol Wt | [M + H]+ |
|---|---|---|---|---|---|
| 1878 | phenyl | O | CH₂ | 328.416 | 329.5 |
| 1879 | | O | CH₂CH₂ | 342.443 | 343.24 |
| 1880 | | O | S | 346.453 | 347.15 |
| 1881 | | O | CF₂ | 364.396 | 365.46 |
| 1882 | 4-methoxyphenyl | O | CH₂ | 358.442 | 359.5 |
| 1883 | | O | CH₂CH₂ | 372.469 | 373.21 |
| 1884 | | O | S | 376.479 | 377.22 |
| 1885 | | O | CF₂ | 394.422 | 395.48 |
| 1886 | 4-methylphenyl | O | CH₂ | 342.443 | 343.51 |
| 1887 | | O | CH₂CH₂ | 356.47 | 357.23 |
| 1888 | | O | S | 360.48 | 361.17 |
| 1889 | | O | CF₂ | 378.423 | 379.52 |
| 1890 | 2,3-dichlorophenyl | O | CH₂ | 397.306 | 397.47 |
| 1891 | | O | CH₂CH₂ | 411.333 | 411.15 |
| 1892 | | O | S | 415.343 | 415.06 |
| 1893 | | O | CF₂ | 433.286 | 433.34 |
| 1894 | 4-fluorophenyl | O | CH₂ | 346.406 | 347.5 |
| 1895 | | O | CH₂CH₂ | 360.433 | 361.18 |
| 1896 | | O | S | 364.443 | 365.12 |
| 1897 | | O | CF₂ | 382.386 | 383.46 |
| 1898 | 3-fluorophenyl | O | CH₂CH₂ | 360.433 | 361.18 |
| 1899 | 2-fluorophenyl | O | CH₂ | 346.406 | 347.43 |
| 1900 | | O | CH₂CH₂ | 360.433 | 361.22 |
| 1901 | | O | S | 364.443 | 365.15 |
| 1902 | | O | CF₂ | 382.386 | 383.5 |
| 1903 | 1-naphthyl | O | CH₂ | 378.476 | 379.5 |
| 1904 | | O | CH₂CH₂ | 392.503 | 393.23 |
| 1905 | | O | S | 396.513 | 397.2 |
| 1906 | | O | CF₂ | 414.456 | 415.47 |

TABLE 10-continued
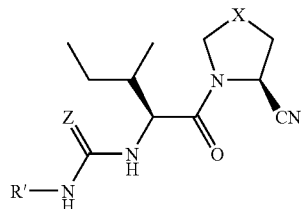
| Example No | R' | Z | X | Mol Wt | [M + H]+ |
|---|---|---|---|---|---|
| 1907 | CF₃-phenyl (3-CF₃) | O | CH₂ | 396.413 | 397.49 |
| 1908 | | O | CH₂CH₂ | 410.44 | 411.21 |
| 1909 | | O | S | 414.45 | 415.15 |
| 1910 | | O | CF₂ | 432.393 | 433.43 |
| 1911 | 4-Cl-phenyl | O | CH₂ | 362.861 | 363.45 |
| 1912 | | O | CH₂CH₂ | 376.888 | 377.18 |
| 1913 | | O | S | 380.898 | 381.12 |
| 1914 | | O | CF₂ | 398.841 | 399.43 |
| 1915 | 3-Cl-phenyl | O | CH₂ | 362.861 | 363.47 |
| 1916 | | O | CH₂CH₂ | 376.888 | 377.2 |
| 1917 | | O | S | 380.898 | 381.12 |
| 1918 | | O | CF₂ | 398.841 | 399.45 |
| 1919 | 2-Cl-phenyl | O | CH₂ | 362.861 | 363.46 |
| 1920 | | O | CH₂CH₂ | 376.888 | 377.19 |
| 1921 | | O | S | 380.898 | 381.11 |
| 1922 | | O | CF₂ | 398.841 | 399.45 |
| 1923 | 3-OMe-phenyl | O | CH₂ | 358.442 | 359.51 |
| 1924 | | O | CH₂CH₂ | 372.469 | 373.22 |
| 1925 | | O | S | 376.479 | 377.17 |
| 1926 | | O | CF₂ | 394.422 | 395.54 |
| 1927 | 2-OMe-phenyl | O | CH₂ | 358.442 | 359.54 |
| 1928 | | O | CH₂CH₂ | 372.469 | 373.25 |
| 1929 | | O | S | 376.479 | 377.18 |
| 1930 | | O | CF₂ | 394.422 | 395.51 |
| 1931 | 3-NO₂-phenyl | O | CH₂ | 373.413 | 374.44 |
| 1932 | | O | CH₂CH₂ | 387.44 | 388.23 |
| 1933 | | O | S | 391.45 | 392.15 |
| 1934 | | O | CF₂ | 409.393 | 410.45 |
| 1935 | 2,4-diCl-phenyl | O | CH₂ | 397.306 | 397.41 |
| 1936 | | O | CH₂CH₂ | 411.333 | 411.17 |
| 1937 | | O | S | 415.343 | 415.09 |
| 1938 | | O | CF₂ | 433.286 | 433.34 |

TABLE 10-continued

| Example No | R' | Z | X | Mol Wt | [M + H]+ |
|---|---|---|---|---|---|
| 1939 | (1-phenyl-2,2-dimethylpropyl) | O | CH₂ | 356.47 | 357.54 |
| 1940 | | O | CH₂CH₂ | 370.497 | 371.25 |
| 1941 | | O | S | 374.507 | 375.19 |
| 1942 | | O | CF₂ | 392.45 | 393.52 |
| 1943 | (3,5-dichlorophenyl)isopropyl | O | CH₂ | 397.306 | 397.42 |
| 1944 | | O | CH₂CH₂ | 411.333 | 411.15 |
| 1945 | | O | S | 415.343 | 415.05 |
| 1946 | | O | CF₂ | 433.286 | 433.38 |
| 1947 | (2,5-dimethoxyphenyl)isopropyl | O | CH₂ | 388.468 | 389.53 |
| 1948 | | O | CH₂CH₂ | 402.495 | 403.25 |
| 1949 | | O | S | 406.505 | 407.15 |
| 1950 | | O | CF₂ | 424.448 | 425.48 |
| 1951 | (2,6-difluorophenyl)isopropyl | O | CH₂ | 364.396 | 365.49 |
| 1952 | | O | CH₂CH₂ | 378.423 | 379.2 |
| 1953 | | O | S | 382.433 | 383.14 |
| 1954 | | O | CF₂ | 400.376 | 401.46 |
| 1955 | (biphenyl-2-yl)isopropyl | O | CH₂ | 404.514 | 405.51 |
| 1956 | | O | CH₂CH₂ | 418.541 | 419.23 |
| 1957 | | O | S | 422.551 | 423.19 |
| 1958 | | O | CF₂ | 440.494 | 441.49 |
| 1959 | nPr | S | CH₂ | 310.464 | 311.48 |
| 1960 | | S | CH₂ | 324.491 | 325.22 |
| 1961 | | S | S | 328.501 | 329.11 |
| 1962 | | S | CF₂ | 346.444 | 347.49 |
| 1963 | (neopentyl)phenyl | S | CH₂ | 358.508 | 359.5 |
| 1964 | | S | CH₂CH₂ | 372.535 | 373.19 |
| 1965 | | S | S | 376.545 | 377.16 |
| 1966 | | S | CF₂ | 394.488 | 395.46 |
| 1967 | (phenylpropyl-dimethyl) | S | CH₂CH₂ | 386.562 | 387.22 |
| 1968 | | S | S | 390.572 | 391.17 |
| 1969 | | S | CF₂ | 408.515 | 409.45 |

TABLE 10-continued

[Structure: isoleucine-derived guanidine/thiourea linked to cyanopyrrolidine-type ring with X and N-R' substituents]

| Example No | R' | Z | X | Mol Wt | [M + H]+ |
|---|---|---|---|---|---|
| 1970 | 4-methoxyphenyl-isopropyl | S | CH₂ | 374.507 | 375.49 |
| 1971 | | S | CH₂CH₂ | 388.534 | 389.25 |
| 1972 | | S | S | 392.544 | 393.15 |
| 1973 | | S | CF₂ | 410.487 | 411.43 |
| 1974 | phenyl-C(O)-C(CH₃)₂- | O | CH₂ | 372.491 | 373.47 |
| 1975 | | S | CH₂CH₂ | 386.518 | 387.2 |
| 1976 | | S | S | 390.528 | 391.1 |
| 1977 | | S | CF₂ | 408.471 | 409.42 |
| 1978 | cyclopentyl-isopropyl | S | CH₂ | 336.502 | 337.52 |
| 1979 | | S | CH₂CH₂ | 350.529 | 351.19 |
| 1980 | | S | S | 354.539 | 355.16 |
| 1981 | | S | CF₂ | 372.482 | 373.48 |
| 1982 | cyclohexyl-isobutyl | S | CH₂ | 364.556 | 365.59 |
| 1983 | | S | CH₂CH₂ | 378.583 | 379.24 |
| 1984 | | S | S | 382.593 | 383.19 |
| 1985 | | S | CF₂ | 400.536 | 401.52 |

TABLE 11

[Structure: isoleucine-derived acyl-amino with azetidine-cyano ring, X' and R' substituents]

| Example No | R' | Z | X' | Mol Wt | [M + H]+ |
|---|---|---|---|---|---|
| 1986 | Et | O | CH₂ | 266.345 | 267.53 |
| 1987 | | O | —CH=CH— | 278.356 | 279.46 |
| 1988 | iPr | O | CH₂ | 280.372 | 281.53 |
| 1989 | | O | —CH=CH— | 292.383 | 293.49 |
| 1990 | nHex | O | CH₂ | 322.453 | 323.53 |
| 1991 | | O | —CH=CH— | 334.464 | 335.52 |
| 1992 | cyclohexyl-isopropyl | O | CH₂ | 320.437 | 321.53 |
| 1993 | | O | —CH=CH— | 332.448 | 333.49 |
| 1994 | phenyl-isobutyl | O | CH₂ | 328.416 | 329.48 |
| 1995 | | O | —CH=CH— | 340.427 | 341.51 |

TABLE 11-continued
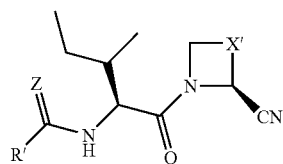
| Example No | R' | Z | X' | Mol Wt | [M + H]+ |
|---|---|---|---|---|---|
| 1996 | ethyl 5-methylhexanoate ester group | O | CH₂ | 338.408 | 339.57 |
| 1997 | | O | —CH=CH— | 350.419 | 351.5 |
| 1998 | phenacyl | O | CH₂ | 342.399 | 343.59 |
| 1999 | phenyl-CH(CH₃)- | O | CH₂ | 314.389 | 315.48 |
| 2000 | | O | —CH=CH— | 326.4 | 327.49 |
| 2001 | 4-methoxyphenyl-CH(CH₃)- | O | CH₂ | 344.415 | 345.49 |
| 2002 | | O | —CH=CH— | 356.426 | 357.49 |
| 2003 | 4-methylphenyl-CH(CH₃)- | O | CH₂ | 328.416 | 329.49 |
| 2004 | | O | —CH=CH— | 340.427 | 341.5 |
| 2005 | 2,3-dichlorophenyl-CH(CH₃)- | O | CH₂ | 383.279 | 383.45 |
| 2006 | | O | —CH=CH— | 395.29 | 395.4 |
| 2007 | 4-fluorophenyl-CH(CH₃)- | O | CH₂ | 332.379 | 333.48 |
| 2008 | | O | —CH=CH— | 344.39 | 345.48 |
| 2009 | 2-fluorophenyl-CH(CH₃)- | O | CH₂ | 332.379 | 333.48 |
| 2010 | | O | —CH=CH— | 344.39 | 345.47 |
| 2011 | 1-naphthyl-CH(CH₃)- | O | CH₂ | 364.449 | 365.51 |
| 2012 | | O | —CH=CH— | 376.46 | 377.52 |

TABLE 11-continued
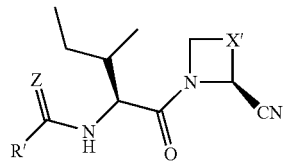
| Example No | R' | Z | X' | Mol Wt | [M + H]+ |
|---|---|---|---|---|---|
| 2013 | 3-CF₃-phenyl | O | CH₂ | 382.386 | 383.46 |
| 2014 | | O | —CH=CH— | 394.397 | 395.48 |
| 2015 | 4-Cl-phenyl | O | CH₂ | 348.834 | 349.45 |
| 2016 | | O | —CH=CH— | 360.845 | 361.43 |
| 2017 | 3-Cl-phenyl | O | CH₂ | 348.834 | 349.47 |
| 2018 | | O | —CH=CH— | 360.845 | 361.43 |
| 2019 | 2-Cl-phenyl | O | CH₂ | 348.834 | 349.46 |
| 2020 | | O | —CH=CH— | 360.845 | 361.45 |
| 2021 | 3-OMe-phenyl | O | CH₂ | 344.415 | 345.51 |
| 2022 | | O | —CH=CH— | 356.426 | 357.5 |
| 2023 | 2-OMe-phenyl | O | CH₂ | 344.415 | 345.51 |
| 2024 | | O | —CH=CH— | 356.426 | 357.49 |
| 2025 | 3-NO₂-phenyl | O | CH₂ | 359.386 | 360.47 |
| 2026 | | O | —CH=CH— | 371.397 | 372.47 |
| 2027 | 2,4-diCl-phenyl | O | CH₂ | 383.279 | 383.42 |
| 2028 | | O | —CH=CH— | 395.29 | 395.41 |
| 2029 | t-Bu-CH(Ph)- | O | CH₂ | 342.443 | 343.47 |
| 2030 | | O | —CH=CH— | 354.454 | 355.49 |

TABLE 11-continued

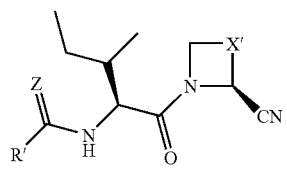

| Example No | R' | Z | X' | Mol Wt | [M + H]+ |
|---|---|---|---|---|---|
| 2031 | 3,5-dichlorophenyl-CH(CH₃)- | O | CH₂ | 383.279 | 383.43 |
| 2032 | 3,5-dichlorophenyl-CH(CH₃)- | O | —CH=CH— | 395.29 | 395.42 |
| 2033 | 2,5-dimethoxyphenyl-CH(CH₃)- | O | CH₂ | 374.441 | 375.54 |
| 2034 | 2,5-dimethoxyphenyl-CH(CH₃)- | O | —CH=CH— | 386.452 | 387.54 |
| 2035 | 2,6-difluorophenyl-CH(CH₃)- | O | CH₂ | 350.369 | 351.46 |
| 2036 | 2,6-difluorophenyl-CH(CH₃)- | O | —CH=CH— | 362.38 | 363.44 |
| 2037 | 2-biphenyl-CH(CH₃)- | O | CH₂ | 390.487 | 391.56 |
| 2038 | 2-biphenyl-CH(CH₃)- | O | —CH=CH— | 402.498 | 403.51 |
| 2039 | nPr | S | CH₂ | 296.437 | 297.49 |
| 2040 | nPr | S | —CH=CH— | 308.448 | 309.44 |
| 2041 | PhCH₂C(CH₃)₂- | S | CH₂ | 344.481 | 345.47 |
| 2042 | PhCH₂C(CH₃)₂- | S | —CH=CH— | 356.492 | 357.47 |
| 2043 | PhCH₂CH₂C(CH₃)₂- | S | CH₂ | 358.508 | 359.49 |
| 2044 | PhCH₂CH₂C(CH₃)₂- | S | —CH=CH— | 370.519 | 371.52 |
| 2045 | 4-methoxyphenyl-CH(CH₃)- | S | CH₂ | 360.48 | 361.45 |
| 2046 | 4-methoxyphenyl-CH(CH₃)- | S | —CH=CH— | 372.491 | 373.47 |
| 2047 | PhC(O)CH(CH₃)- | S | CH₂ | 358.464 | 359.49 |
| 2048 | PhC(O)CH(CH₃)- | S | —CH=CH— | 370.475 | 371.43 |

TABLE 11-continued
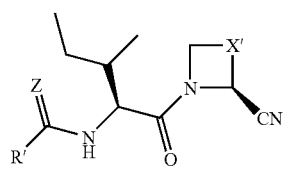
| Example No | R' | Z | X' | Mol Wt | [M + H]+ |
|---|---|---|---|---|---|
| 2049 | | S | CH$_2$ | 322.475 | 323.45 |
| 2050 | | S | —CH=CH— | 334.486 | 335.46 |
| 2051 | | S | CH$_2$ | 350.529 | 351.57 |
| 2052 | | S | —CH=CH— | 362.54 | 363.53 |
TABLE 12
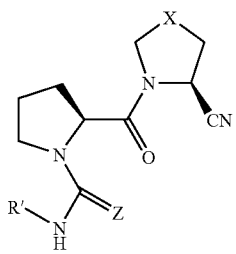
| Example No | R' | Z | X | Mol Wt | [M + H]+ |
|---|---|---|---|---|---|
| 2053 | Et | O | CH$_2$ | 264.329 | 265.11 |
| 2054 | | O | CF$_2$ | 300.309 | 301.42 |
| 2055 | | O | CH$_2$CH$_2$ | 278.356 | 279.25 |
| 2056 | | O | CF$_2$ | 314.336 | 315.44 |
| 2057 | | O | CH$_2$CH$_2$ | 292.383 | 293.26 |
| 2058 | nHex | O | CH$_2$ | 320.437 | 321.19 |
| 2059 | | O | CF$_2$ | 356.417 | 357.5 |
| 2060 | | O | CH$_2$CH$_2$ | 334.464 | 335.32 |
| 2061 | | O | CH$_2$ | 318.421 | 319.16 |
| 2062 | | O | CF$_2$ | 354.401 | 355.49 |
| 2063 | | O | CH$_2$CH$_2$ | 332.448 | 333.31 |
| 2064 | | O | CH$_2$ | 326.4 | 327.14 |
| 2065 | | O | CF$_2$ | 362.38 | 363.47 |
| 2066 | | O | CH$_2$CH$_2$ | 340.427 | 341.26 |
| 2067 | | O | CH$_2$ | 336.392 | 337.16 |
| 2068 | | O | CF$_2$ | 372.372 | 373.48 |
| 2069 | | O | CH$_2$CH$_2$ | 350.419 | 351.25 |
| 2070 | | O | CH$_2$ | 276.34 | 331.41 |

TABLE 12-continued
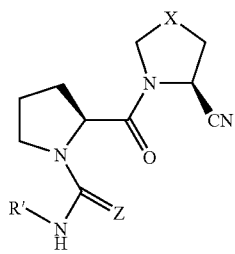
| Example No | R' | Z | X | Mol Wt | [M + H]+ |
|---|---|---|---|---|---|
| 2071 | (phenyl-C(O)-CH(CH3)-) | O | CH2 | 340.383 | 341.1 |
| 2072 | | O | CH2CH2 | 354.41 | 355.26 |
| 2073 | (phenyl-CH(CH3)-) | O | CH2 | 312.373 | 313.09 |
| 2074 | | O | CF2 | 348.353 | 349.44 |
| 2075 | | O | CH2CH2 | 326.4 | 327.28 |
| 2076 | (4-MeO-phenyl-CH(CH3)-) | O | CH2 | 342.399 | 343.24 |
| 2077 | | O | CF2 | 378.379 | 379.48 |
| 2078 | | O | CH2CH2 | 356.426 | 357.27 |
| 2079 | (4-Me-phenyl-CH(CH3)-) | O | CH2 | 326.4 | 327.14 |
| 2080 | | O | CF2 | 362.38 | 363.49 |
| 2081 | | O | CH2CH2 | 340.427 | 341.29 |
| 2082 | (2,3-diCl-phenyl-CH(CH3)-) | O | CH2 | 381.263 | 381.09 |
| 2083 | | O | CF2 | 417.243 | 417.24 |
| 2084 | | O | CH2CH2 | 395.29 | 395.17 |
| 2085 | (4-F-phenyl-CH(CH3)-) | O | CH2 | 330.363 | 331.14 |
| 2086 | | O | CF2 | 366.343 | 367.43 |
| 2087 | | O | CH2CH2 | 344.39 | 345.27 |
| 2088 | (3-F-phenyl-CH(CH3)-) | O | CH2 | 330.363 | 330.98 |
| 2089 | | O | CH2CH2 | 344.39 | 345.25 |
| 2090 | (2-F-phenyl-CH(CH3)-) | O | CH2 | 330.363 | 331.11 |
| 2091 | | O | CF2 | 366.343 | 367.43 |
| 2092 | | O | CH2CH2 | 344.39 | 345.29 |

TABLE 12-continued

| Example No | R' | Z | X | Mol Wt | [M + H]+ |
|---|---|---|---|---|---|
| 2093 | naphthyl | O | CH$_2$ | 362.433 | 363.26 |
| 2094 | | O | CF$_2$ | 398.413 | 399.46 |
| 2095 | | O | CH$_2$CH$_2$ | 376.46 | 377.28 |
| 2096 | 3-CF$_3$-phenyl | O | CH$_2$ | 380.37 | 381.04 |
| 2097 | | O | CF$_2$ | 416.35 | 417.43 |
| 2098 | | O | CH$_2$CH$_2$ | 394.397 | 396.28 |
| 2099 | 4-Cl-phenyl | O | CH$_2$ | 346.818 | 347.04 |
| 2100 | | O | CF$_2$ | 382.798 | 383.44 |
| 2101 | | O | CH$_2$CH$_2$ | 360.845 | 361.25 |
| 2102 | 3-Cl-phenyl | O | CH$_2$ | 346.818 | 347.1 |
| 2103 | | O | CF$_2$ | 382.798 | 383.42 |
| 2104 | | O | CH$_2$CH$_2$ | 360.845 | 361.23 |
| 2105 | 2-Cl-phenyl | O | CH$_2$ | 346.818 | 347.1 |
| 2106 | | O | CF$_2$ | 382.798 | 383.46 |
| 2107 | | O | CH$_2$CH$_2$ | 360.845 | 361.24 |
| 2108 | 3-OMe-phenyl | O | CH$_2$ | 342.399 | 343.18 |
| 2109 | | O | CF$_2$ | 378.379 | 419.17 |
| 2110 | | O | CH$_2$CH$_2$ | 356.426 | 357.28 |
| 2111 | 2-OMe-phenyl | O | CH$_2$ | 342.399 | 343.24 |
| 2112 | | O | CF$_2$ | 378.379 | 379.46 |
| 2113 | | O | CH$_2$CH$_2$ | 356.426 | 357.28 |
| 2114 | 3-O$_2$N-phenyl | O | CH$_2$ | 357.37 | 358.22 |
| 2115 | | O | CF$_2$ | 393.35 | 394.43 |
| 2116 | | O | CH$_2$CH$_2$ | 371.397 | 372.27 |

TABLE 12-continued
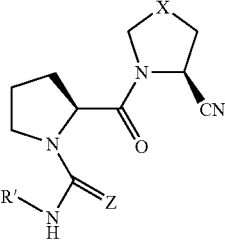
| Example No | R' | Z | X | Mol Wt | [M + H]+ |
|---|---|---|---|---|---|
| 2117 | | O | CH₂ | 381.263 | 381.1 |
| 2118 | 2,4-dichlorophenyl-CH(CH₃)- | O | CF₂ | 417.243 | 417.32 |
| 2119 | | O | CH₂CH₂ | 395.29 | 395.88 |
| 2120 | | O | CH₂ | 340.427 | 341.16 |
| 2121 | phenyl-CH(CH₃)-C(CH₃)₃ | O | CF₂ | 376.407 | 377.49 |
| 2122 | | O | CH₂CH₂ | 354.454 | 355.3 |
| 2123 | | O | CH₂ | 381.263 | 381.08 |
| 2124 | 3,5-dichlorophenyl-CH(CH₃)- | O | CF₂ | 417.243 | 417.33 |
| 2125 | | O | CH₂CH₂ | 395.29 | 395.22 |
| 2126 | | O | CH₂ | 372.425 | 373.19 |
| 2127 | 2,5-dimethoxyphenyl-CH(CH₃)- | O | CF₂ | 408.405 | 409.48 |
| 2128 | | O | CH₂CH₂ | 386.452 | 387.33 |
| 2129 | | O | CH₂ | 348.353 | 349.1 |
| 2130 | 2,6-difluorophenyl-CH(CH₃)- | O | CF₂ | 384.333 | 385.43 |
| 2131 | | O | CH₂CH₂ | 362.38 | 363.25 |
| 2132 | | O | CH₂ | 388.471 | 389.18 |
| 2133 | biphenyl-CH(CH₃)- | O | CF₂ | 424.451 | 425.44 |
| 2134 | | O | CH₂CH₂ | 402.498 | 403.28 |
| 2135 | nPr | S | CH₂ | 294.421 | 295.17 |
| 2136 | | S | CF₂ | 330.401 | 331.42 |
| 2137 | | S | CH₂ | 342.465 | 343.14 |
| 2138 | phenyl-CH₂-C(CH₃)₃ | S | CF₂ | 378.445 | 379.49 |
| 2139 | | S | CH₂CH₂ | 356.492 | 357.24 |

TABLE 12-continued
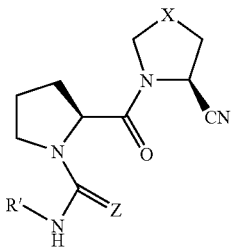
| Example No | R' | Z | X | Mol Wt | [M + H]+ |
|---|---|---|---|---|---|
| 2140 | (cyclohexylmethyl, branched) | S | CH₂ | 348.513 | 349.25 |
TABLE 13
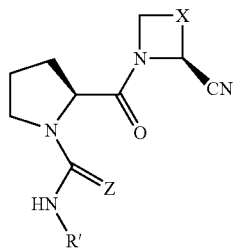
| Example No | R' | Z | X | Mol Wt | [M + H]+ |
|---|---|---|---|---|---|
| 2141 | Et | O | —CH=CH— | 262.313 | 263.49 |
| 2142 | iPr | O | CH₂ | 264.329 | 265.53 |
| 2143 |  | O | —CH=CH— | 276.34 | 277.49 |
| 2144 | nHex | O | CH₂ | 306.41 | 307.52 |
| 2145 |  | O | —CH=CH— | 318.421 | 319.49 |
| 2146 | (cyclohexyl-branched) | O | CH₂ | 304.394 | 305.48 |
| 2147 | | O | —CH=CH— | 316.405 | 317.48 |
| 2148 | (benzyl-branched) | O | CH₂ | 312.373 | 313.48 |
| 2149 | | O | —CH=CH— | 324.384 | 325.46 |
| 2150 | (ethyl ester chain) | O | CH₂ | 322.365 | 323.49 |
| 2151 | | O | —CH=CH— | 334.376 | 335.47 |
| 2152 | (phenyl-branched) | O | CH₂ | 298.346 | 299.45 |
| 2153 | | O | —CH=CH— | 310.357 | 311.44 |

TABLE 13-continued
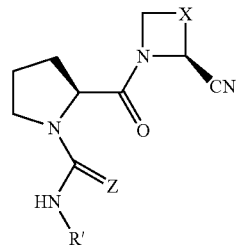
| Example No | R' | Z | X | Mol Wt | [M + H]+ |
|---|---|---|---|---|---|
| 2154 | 4-methoxyphenyl-CH(CH₃)- | O | CH₂ | 328.372 | 329.46 |
| 2155 | | O | —CH=CH— | 340.383 | 341.45 |
| 2156 | 4-methylphenyl-CH(CH₃)- | O | CH₂ | 312.373 | 313.45 |
| 2157 | | O | —CH=CH— | 324.384 | 325.45 |
| 2158 | 2,3-dichlorophenyl-CH(CH₃)- | O | CH₂ | 367.236 | 367.43 |
| 2159 | | O | —CH=CH— | 379.247 | 379.39 |
| 2160 | 4-fluorophenyl-CH(CH₃)- | O | CH₂ | 316.336 | 317.45 |
| 2161 | | O | —CH=CH— | 328.347 | 329.44 |
| 2162 | 3-fluorophenyl-CH(CH₃)- | O | —CH=CH— | 328.347 | 329.33 |
| 2163 | 2-fluorophenyl-CH(CH₃)- | O | CH₂ | 316.336 | 317.44 |
| 2164 | | O | —CH=CH— | 328.347 | 329.45 |
| 2165 | 1-naphthyl-CH(CH₃)- | O | CH₂ | 348.406 | 349.46 |
| 2166 | | O | —CH=CH— | 360.417 | 361.45 |
| 2167 | 3-trifluoromethylphenyl-CH(CH₃)- | O | CH₂ | 366.343 | 367.46 |
| 2168 | | O | —CH=CH— | 378.354 | 379.45 |

TABLE 13-continued
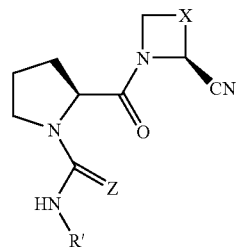
| Example No | R' | Z | X | Mol Wt | [M + H]+ |
|---|---|---|---|---|---|
| 2169 | 4-Cl-phenyl-CH(CH₃)- | O | CH₂ | 332.791 | 333.42 |
| 2170 | | O | —CH=CH— | 344.802 | 345.41 |
| 2171 | 3-Cl-phenyl-CH(CH₃)- | O | CH₂ | 332.791 | 333.42 |
| 2172 | | O | —CH=CH— | 344.802 | 345.39 |
| 2173 | 2-Cl-phenyl-CH(CH₃)- | O | CH₂ | 332.791 | 333.42 |
| 2174 | | O | —CH=CH— | 344.802 | 345.42 |
| 2175 | 3-MeO-phenyl-CH(CH₃)- | O | CH₂ | 328.372 | 329.48 |
| 2176 | | O | —CH=CH— | 340.383 | 341.46 |
| 2177 | 2-MeO-phenyl-CH(CH₃)- | O | CH₂ | 328.372 | 329.46 |
| 2178 | | O | —CH=CH— | 340.383 | 341.46 |
| 2179 | 3-O₂N-phenyl-CH(CH₃)- | O | CH₂ | 343.343 | 344.46 |
| 2180 | | O | —CH=CH— | 355.354 | 356.44 |
| 2181 | 2,4-diCl-phenyl-CH(CH₃)- | O | CH₂ | 367.236 | 367.36 |
| 2182 | | O | —CH=CH— | 379.247 | 379.37 |
| 2183 | phenyl-CH(CH₃)-C(CH₃)₃ | O | CH₂ | 326.4 | 327.52 |
| 2184 | | O | —CH=CH— | 338.411 | 339.5 |

TABLE 13-continued

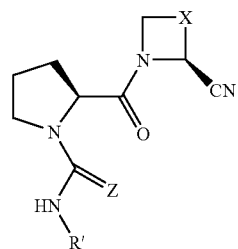

| Example No | R' | Z | X | Mol Wt | [M + H]+ |
|---|---|---|---|---|---|
| 2185 | 3,5-dichlorophenyl-CH(CH₃)- | O | CH₂ | 367.236 | 367.41 |
| 2186 | 3,5-dichlorophenyl-CH(CH₃)- | O | —CH=CH— | 379.247 | 379.39 |
| 2187 | 2,5-dimethoxyphenyl-CH(CH₃)- | O | CH₂ | 358.398 | 359.47 |
| 2188 | 2,5-dimethoxyphenyl-CH(CH₃)- | O | —CH=CH— | 370.409 | 371.5 |
| 2189 | 2,6-difluorophenyl-CH(CH₃)- | O | CH₂ | 334.326 | 335.42 |
| 2190 | 2,6-difluorophenyl-CH(CH₃)- | O | —CH=CH— | 346.337 | 347.44 |
| 2191 | biphenyl-CH(CH₃)- | O | CH₂ | 374.444 | 375.49 |
| 2192 | biphenyl-CH(CH₃)- | O | —CH=CH— | 386.455 | 387.51 |
| 2193 | nPr | S | CH₂ | 280.394 | 281.47 |
| 2194 | nPr | S | —CH=CH— | 292.405 | 293.46 |
| 2195 | PhCH₂C(CH₃)₂- | S | CH₂ | 328.438 | 329.49 |
| 2196 | PhCH₂C(CH₃)₂- | S | —CH=CH— | 340.449 | 341.45 |
| 2197 | PhCH₂CH₂CH(CH₃)- | S | CH₂ | 342.465 | 343.47 |
| 2198 | PhCH₂CH₂CH(CH₃)- | S | —CH=CH— | 354.476 | 355.46 |
| 2199 | 4-methoxyphenyl-CH(CH₃)- | S | CH₂ | 344.437 | 344.45 |
| 2200 | 4-methoxyphenyl-CH(CH₃)- | S | —CH=CH— | 356.448 | 357.48 |

TABLE 13-continued

| Example No | R' | Z | X | Mol Wt | [M + H]+ |
|---|---|---|---|---|---|
| 2201 | (phenyl C(O) C(CH3)3) | S | CH₂ | 342.421 | 343.45 |
| 2202 | | S | —CH=CH— | 354.432 | 355.44 |
| 2203 | (cyclopentyl-CH(CH3)) | S | CH₂ | 306.432 | 307.38 |
| 2204 | | S | —CH=CH— | 318.443 | 319.47 |
| 2205 | (cyclohexyl-CH2-CH(CH3)) | S | CH₂ | 334.486 | 335.52 |
| 2206 | | S | —CH=CH— | 346.497 | 347.49 |

TABLE 14

| Example No | R' | Z | R4 | Mol Wt | [M + H]+ |
|---|---|---|---|---|---|
| 2207 | Et | O | iBu | 280.372 | 281.62 |
| 2208 | | O | iPr | 266.32 | 267.53 |
| 2209 | | O | Ph | 300.362 | 301.07 |
| 2210 | | O | Me | 238.291 | 239.54 |
| 2211 | | O | tBu | 280.372 | 267.53 |
| 2212 | iPr | O | iBu | 294.399 | 295.55 |
| 2213 | | O | iPr | 280.372 | 281.45 |
| 2214 | | O | Ph | 314.389 | 315.03 |
| 2215 | | O | Me | 252.318 | 253.54 |
| 2216 | | O | tBu | 294.399 | 295.51 |
| 2217 | | O | Ch | 320.437 | 321.57 |
| 2218 | nHex | O | iBu | 336.48 | 337.6 |
| 2219 | | O | iPr | 322.453 | 323.56 |
| 2220 | | O | Ph | 356.47 | 357.12 |
| 2221 | | O | Me | 294.399 | 295.54 |
| 2222 | | O | nBu | 336.48 | 337.58 |
| 2223 | | O | tBu | 336.48 | 337.56 |
| 2224 | | O | Ch | 362.518 | 363.64 |

TABLE 14-continued
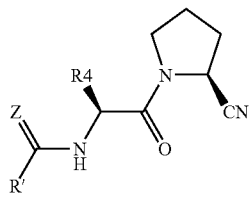
| Example No | R' | Z | R4 | Mol Wt | [M + H]+ |
|---|---|---|---|---|---|
| 2225 | cyclohexyl-CH(CH3)- | O | iBu | 334.464 | 335.58 |
| 2226 | | O | iPr | 320.437 | 321.55 |
| 2227 | | O | Ph | 354.454 | 354.87 |
| 2228 | | O | Me | 292.383 | 293.53 |
| 2229 | | O | Ch | 360.502 | 361.6 |
| 2230 | PhCH2CH(CH3)- | O | iBu | 342.443 | 343.55 |
| 2231 | | O | iPr | 328.416 | 329.53 |
| 2232 | | O | Ph | 362.433 | 363.16 |
| 2233 | | O | Me | 300.362 | 301.51 |
| 2234 | | O | nBu | 342.443 | 343.52 |
| 2235 | | O | tBu | 342.443 | 343.53 |
| 2236 | | O | Ch | 368.481 | 369.61 |
| 2237 | EtO2C-(CH2)3-CH(CH3)- | O | iBu | 352.435 | 353.57 |
| 2238 | | O | iPr | 338.408 | 339.51 |
| 2239 | | O | Ph | 372.425 | 373.12 |
| 2240 | | O | Me | 310.354 | 311.51 |
| 2241 | | O | nBu | 352.435 | 353.53 |
| 2242 | | O | tBu | 352.435 | 353.52 |
| 2243 | | O | Ch | 378.473 | 379.57 |
| 2244 | PhC(O)CH(CH3)- | O | tBu | 356.426 | 357.49 |
| 2245 | PhCH(CH3)- | O | iBu | 328.416 | 329.54 |
| 2246 | | O | iPr | 314.389 | 315.49 |
| 2247 | | O | Ph | 348.406 | 349.1 |
| 2248 | | O | Me | 286.335 | 287.52 |
| 2249 | | O | nBu | 328.416 | 329.5 |
| 2250 | | O | tBu | 328.416 | 329.5 |
| 2251 | | O | Ch | 354.454 | 354.87 |
| 2252 | 4-MeO-C6H4-CH(CH3)- | O | iBu | 358.442 | 359.58 |
| 2253 | | O | iPr | 344.415 | 345.48 |
| 2254 | | O | Ph | 378.432 | 379.1 |
| 2255 | | O | Me | 316.361 | 317.52 |
| 2256 | | O | nBu | 358.442 | 359.51 |
| 2257 | | O | tBu | 358.442 | 359.5 |
| 2258 | | O | Ch | 384.48 | 385.59 |
| 2259 | 4-Me-C6H4-CH(CH3)- | O | iBu | 342.443 | 343.56 |
| 2260 | | O | iPr | 328.416 | 329.51 |
| 2261 | | O | Ph | 362.433 | 363.1 |
| 2262 | | O | Me | 300.362 | 301.5 |
| 2263 | | O | nBu | 342.443 | 343.56 |
| 2264 | | O | tBu | 342.443 | 343.52 |
| 2265 | | O | Ch | 368.481 | 369.58 |
| 2266 | 2,3-Cl2-C6H3-CH(CH3)- | O | iBu | 397.306 | 397.51 |
| 2267 | | O | iPr | 383.279 | 383.46 |
| 2268 | | O | Ph | 417.296 | 417.06 |
| 2269 | | O | Me | 355.225 | 355.42 |
| 2270 | | O | nBu | 397.306 | 397.46 |
| 2271 | | O | tBu | 397.306 | 397.45 |
| 2272 | | O | Ch | 423.344 | 423.46 |

TABLE 14-continued

| Example No | R' | Z | R4 | Mol Wt | [M + H]+ |
|---|---|---|---|---|---|
| 2273 | | O | iBu | 346.406 | 347.55 |
| 2274 | | O | iPr | 332.379 | 333.47 |
| 2275 | | O | Ph | 366.396 | 367.11 |
| 2276 | 4-F-phenyl | O | Me | 304.325 | 305.5 |
| 2277 | | O | nBu | 346.406 | 347.53 |
| 2278 | | O | tBu | 346.406 | 347.5 |
| 2279 | | O | Ch | 372.444 | 373.56 |
| 2280 | | O | iBu | 346.406 | 347.54 |
| 2281 | | O | iPr | 332.379 | 333.47 |
| 2282 | | O | Ph | 366.396 | 367.15 |
| 2283 | 2-F-phenyl | O | Me | 304.325 | 305.49 |
| 2284 | | O | nBu | 346.406 | 347.5 |
| 2285 | | O | tBu | 346.406 | 347.46 |
| 2286 | | O | Ch | 372.444 | 373.56 |
| 2287 | | O | iBu | 378.476 | 379.59 |
| 2288 | | O | iPr | 364.449 | 365.52 |
| 2289 | | O | Ph | 398.466 | 399.13 |
| 2290 | naphthyl | O | Me | 336.395 | 337.49 |
| 2291 | | O | nBu | 378.476 | 379.55 |
| 2292 | | O | tBu | 378.476 | 379.5 |
| 2293 | | O | Ch | 404.514 | 405.54 |
| 2294 | | O | iBu | 396.413 | 397.55 |
| 2295 | | O | iPr | 382.386 | 383.52 |
| 2296 | | O | Ph | 416.403 | 417.13 |
| 2297 | 3-CF3-phenyl | O | Me | 354.332 | 355.47 |
| 2298 | | O | nBu | 396.413 | 397.5 |
| 2299 | | O | tBu | 396.413 | 397.48 |
| 2300 | | O | Ch | 422.451 | 423.5 |
| 2301 | | O | iBu | 362.861 | 363.49 |
| 2302 | | O | iPr | 348.834 | 349.46 |
| 2303 | | O | Ph | 382.851 | 383.13 |
| 2304 | 4-Cl-phenyl | O | Me | 320.78 | 321.46 |
| 2305 | | O | nBu | 362.861 | 363.47 |
| 2306 | | O | tBu | 362.861 | 363.45 |
| 2307 | | O | Ch | 388.899 | 389.53 |
| 2308 | | O | iBu | 362.861 | 363.52 |
| 2309 | | O | iPr | 348.834 | 349.44 |
| 2310 | | O | Ph | 382.851 | 383.16 |
| 2311 | 3-Cl-phenyl | O | Me | 320.78 | 321.46 |
| 2312 | | O | nBu | 362.861 | 363.47 |
| 2313 | | O | tBu | 362.861 | 363.48 |
| 2314 | | O | Ch | 388.899 | 389.56 |
| 2315 | | O | iBu | 362.861 | 363.5 |
| 2316 | | O | iPr | 348.834 | 349.48 |
| 2317 | | O | Ph | 382.851 | 383.11 |
| 2318 | 2-Cl-phenyl | O | Me | 320.78 | 321.43 |
| 2319 | | O | nBu | 362.861 | 363.46 |
| 2320 | | O | tBu | 362.861 | 363.46 |
| 2321 | | O | Ch | 388.899 | 389.55 |
| 2322 | | O | iBu | 358.442 | 359.59 |
| 2323 | | O | iPr | 344.415 | 345.55 |
| 2324 | | O | Ph | 378.432 | 379.11 |
| 2325 | 3-OMe-phenyl | O | Me | 316.361 | 317.5 |
| 2326 | | O | nBu | 358.442 | 359.52 |
| 2327 | | O | tBu | 358.442 | 359.52 |
| 2328 | | O | Ch | 384.48 | 385.6 |

TABLE 14-continued

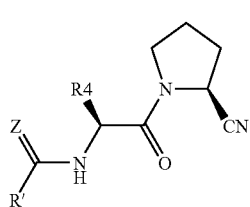

| Example No | R' | Z | R4 | Mol Wt | [M + H]+ |
|---|---|---|---|---|---|
| 2329 | 2-isopropyl-methoxyphenyl | O | iBu | 358.442 | 359.55 |
| 2330 | | O | iPr | 344.415 | 345.49 |
| 2331 | | O | Ph | 378.432 | 379.16 |
| 2332 | | O | Me | 316.361 | 317.5 |
| 2333 | | O | nBu | 358.442 | 359.52 |
| 2334 | | O | Ch | 384.48 | 385 |
| 2335 | 3-nitrophenyl | O | iBu | 373.413 | 374.57 |
| 2336 | | O | iPr | 359.386 | 360.5 |
| 2337 | | O | Ph | 393.403 | 394.21 |
| 2338 | | O | Me | 331.332 | 332.47 |
| 2339 | | O | nBu | 373.413 | 374.52 |
| 2340 | | O | tBu | 373.413 | 374.44 |
| 2341 | | O | Ch | 399.451 | 400.56 |
| 2342 | 2,4-dichlorophenyl | O | iBu | 397.306 | 397.47 |
| 2343 | | O | iPr | 383.279 | 383.44 |
| 2344 | | O | Ph | 417.296 | 417.1 |
| 2345 | | O | Me | 355.225 | 355.49 |
| 2346 | | O | nBu | 397.306 | 397.46 |
| 2347 | | O | tBu | 397.306 | 397.42 |
| 2348 | | O | Ch | 423.344 | 423.41 |
| 2349 | phenyl-tBu | O | iBu | 356.47 | 357.58 |
| 2350 | | O | iPr | 342.443 | 343.53 |
| 2351 | | O | Ph | 376.46 | 377.14 |
| 2352 | | O | Me | 314.389 | 315.55 |
| 2353 | | O | nBu | 356.47 | 357.54 |
| 2354 | | O | tBu | 356.47 | 357.52 |
| 2355 | | O | Ch | 382.508 | 383.58 |
| 2356 | 3,5-dichlorophenyl | O | iBu | 397.306 | 397.48 |
| 2357 | | O | iPr | 383.279 | 383.43 |
| 2358 | | O | Ph | 417.296 | 417.04 |
| 2359 | | O | Me | 355.225 | 355.43 |
| 2360 | | O | nBu | 397.306 | 397.43 |
| 2361 | | O | tBu | 397.306 | 397.44 |
| 2362 | | O | Ch | 423.344 | 423.44 |
| 2363 | 2,5-dimethoxyphenyl | O | iBu | 388.468 | 389.6 |
| 2364 | | O | iPr | 374.441 | 375.57 |
| 2365 | | O | Ph | 408.458 | 409.19 |
| 2366 | | O | Me | 346.387 | 347.52 |
| 2367 | | O | nBu | 388.468 | 388.95 |
| 2368 | | O | tBu | 388.468 | 389.55 |
| 2369 | | O | Ch | 414.506 | 415.58 |
| 2370 | 2,6-difluorophenyl | O | iBu | 364.396 | 365.54 |
| 2371 | | O | iPr | 350.369 | 351.48 |
| 2372 | | O | Ph | 384.386 | 385.09 |
| 2373 | | O | Me | 322.315 | 323.49 |
| 2374 | | O | nBu | 364.396 | 365.51 |
| 2375 | | O | tBu | 364.396 | 365.49 |
| 2376 | | O | Ch | 390.434 | 391.57 |

TABLE 14-continued

| Example No | R' | Z | R4 | Mol Wt | [M + H]+ |
|---|---|---|---|---|---|
| 2377 | 2-isopropylbiphenyl | O | iBu | 404.514 | 405.58 |
| 2378 | | O | iPr | 390.487 | 391.56 |
| 2379 | | O | Ph | 424.504 | 425.17 |
| 2380 | | O | Me | 362.433 | 363.53 |
| 2381 | | O | nBu | 404.514 | 405.56 |
| 2382 | | O | tBu | 404.514 | 405.55 |
| 2383 | | O | Ch | 430.552 | 431.57 |
| 2384 | nPr | S | secBu | 310.464 | 311.45 |
| 2385 | | S | iPr | 296.437 | 297.52 |
| 2386 | | S | Ph | 330.454 | 331.11 |
| 2387 | | S | tBu | 310.464 | 311.45 |
| 2388 | neopentylbenzyl | S | iBu | 358.508 | 359.55 |
| 2389 | | S | iPr | 344.481 | 345.47 |
| 2390 | | S | Ph | 378.498 | 379.13 |
| 2391 | | S | Me | 316.427 | 317.47 |
| 2392 | | S | nBu | 358.508 | 359.5 |
| 2393 | | S | tBu | 358.508 | 359.5 |
| 2394 | | S | Ch | 384.546 | 385.24 |
| 2395 | | S | iBu | 372.535 | 373.6 |
| 2396 | | S | iPr | 358.508 | 359.49 |
| 2397 | | S | Ph | 392.525 | 393.17 |
| 2398 | | S | Me | 330.454 | 331.5 |
| 2399 | | S | nBu | 372.535 | 373.59 |
| 2400 | | S | tBu | 372.535 | 373.51 |
| 2401 | | S | Ch | 398.573 | 399.61 |
| 2402 | | S | iBu | 374.507 | 375.57 |
| 2403 | | S | Ph | 394.497 | 395.13 |
| 2404 | | S | tBu | 374.507 | 375.51 |
| 2405 | | S | Ch | 400.545 | 401.53 |
| 2406 | | S | iBu | 372.491 | 373.5 |
| 2407 | | S | iPr | 358.464 | 359.49 |
| 2408 | | S | Ph | 392.481 | 393.14 |
| 2409 | | S | Me | 330.41 | 331.52 |
| 2410 | | S | nBu | 372.491 | 373.5 |
| 2411 | | S | tBu | 372.491 | 373.49 |
| 2412 | | S | Ch | 398.529 | 399.52 |
| 2413 | | S | iBu | 336.502 | 337.58 |
| 2414 | | S | iPr | 322.475 | 323.43 |
| 2415 | | S | Ph | 356.492 | 357.11 |
| 2416 | | S | Me | 294.421 | 295.51 |
| 2417 | | S | tBu | 336.502 | 337.52 |
| 2418 | | S | Ch | 362.54 | 363.6 |
| 2419 | | S | iBu | 364.556 | 365.6 |
| 2420 | | S | iPr | 350.529 | 351.46 |
| 2421 | | S | Ph | 384.546 | 385.24 |
| 2422 | | S | Me | 322.475 | 323.49 |
| 2423 | | S | tBu | 364.556 | 345.49 |

TABLE 15
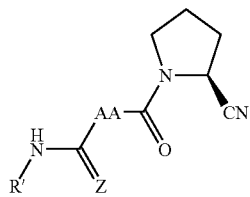
| Example No | R' | Z | AA | Mol Wt | [M + H]+ |
|---|---|---|---|---|---|
| 2424 | Et | O | Tic | 326.4 | 327.54 |
| 2425 | iPr | O | Tic | 340.427 | 341.57 |
| 2426 | | O | Pic | 292.383 | 293.58 |
| 2427 | | O | Oic | 332.448 | 333.17 |
| 2428 | nHex | O | Tic | 382.508 | 383.58 |
| 2429 | | O | Oic | 374.529 | 375.38 |
| 2430 | | O | Tic | 380.492 | 381.62 |
| 2431 | | O | Pic | 332.448 | 333.53 |
| 2432 | | O | Oic | 372.513 | 373.21 |
| 2433 | | O | Tic | 388.471 | 389.59 |
| 2434 | | O | Pic | 340.427 | 341.57 |
| 2435 | | O | Oic | 380.492 | 381.26 |
| 2436 | | O | Tic | 398.463 | 399.56 |
| 2437 | | O | Pic | 350.419 | 351.56 |
| 2438 | | O | Oic | 390.484 | 391.26 |
| 2439 | | O | Tic | 374.444 | 375.53 |
| 2440 | | O | Pic | 326.4 | 327.5 |
| 2441 | | O | Oic | 366.465 | 368.04 |
| 2442 | | O | Tic | 404.47 | 405.52 |
| 2443 | | O | Pic | 356.426 | 357.51 |
| 2444 | | O | Oic | 396.491 | 397.24 |
| 2445 | | O | Tic | 388.471 | 389.6 |
| 2446 | | O | Pic | 340.427 | 341.52 |
| 2447 | | O | Oic | 380.492 | 381.3 |
| 2448 | | O | Tic | 443.334 | 443.43 |
| 2449 | | O | Oic | 435.355 | 435.21 |
| 2450 | | O | Tic | 392.434 | 393.69 |
| 2451 | | O | Pic | 344.39 | 345.48 |
| 2452 | | O | Oic | 384.455 | 385.26 |

TABLE 15-continued
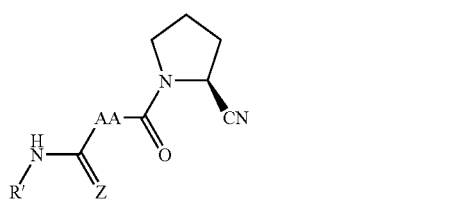
| Example No | R' | Z | AA | Mol Wt | [M + H]+ |
|---|---|---|---|---|---|
| 2453 | 2-F-α-methylbenzyl | O | Tic | 392.434 | 393.48 |
| 2454 |  | O | Pic | 344.39 | 345.46 |
| 2455 |  | O | Oic | 384.455 | 385.18 |
| 2456 | 1-naphthyl-ethyl | O | Tic | 424.504 | 425.49 |
| 2457 |  | O | Oic | 416.525 | 417.31 |
| 2458 | 3-CF3-α-methylbenzyl | O | Tic | 442.441 | 443.48 |
| 2459 |  | O | Pic | 394.397 | 395.52 |
| 2460 |  | O | Oic | 434.462 | 435.25 |
| 2461 | 4-Cl-α-methylbenzyl | O | Tic | 408.889 | 409.48 |
| 2462 |  | O | Pic | 360.845 | 361.4 |
| 2463 |  | O | Oic | 400.91 | 401.24 |
| 2464 | 3-Cl-α-methylbenzyl | O | Tic | 408.889 | 409.5 |
| 2465 |  | O | Pic | 360.845 | 361.43 |
| 2466 |  | O | Oic | 400.91 | 401.23 |
| 2467 | 2-Cl-α-methylbenzyl | O | Tic | 408.889 | 409.47 |
| 2468 |  | O | Pic | 360.845 | 361.4 |
| 2469 |  | O | Oic | 400.91 | 401.17 |
| 2470 | 3-OMe-α-methylbenzyl | O | Tic | 404.47 | 405.54 |
| 2471 |  | O | Pic | 356.426 | 357.52 |
| 2472 |  | O | Oic | 396.491 | 397.24 |
| 2473 | 2-OMe-α-methylbenzyl | O | Tic | 404.47 | 405.55 |
| 2474 |  | O | Pic | 356.426 | 357.52 |
| 2475 |  | O | Oic | 396.491 | 397.25 |

TABLE 15-continued

| Example No | R' | Z | AA | Mol Wt | [M + H]+ |
|---|---|---|---|---|---|
| 2476 | (3-O₂N-phenyl)-CH(CH₃)- | O | Tic | 419.441 | 420.48 |
| 2477 | | O | Pic | 371.397 | 372.44 |
| 2478 | | O | Oic | 411.462 | 412.26 |
| 2479 | (2,4-diCl-phenyl)-CH(CH₃)- | O | Tic | 443.334 | 443.41 |
| 2480 | phenyl-CH(C(CH₃)₃)- | O | Tic | 402.498 | 403.53 |
| 2481 | | O | Pic | 354.454 | 355.53 |
| 2482 | | O | Oic | 394.519 | 395.28 |
| 2483 | (3,5-diCl-phenyl)-CH(CH₃)- | O | Tic | 443.334 | 443.43 |
| 2484 | | O | Pic | 395.29 | 395.46 |
| 2485 | | O | Oic | 435.355 | 435.16 |
| 2486 | (2,5-diMeO-phenyl)-CH(CH₃)- | O | Tic | 434.496 | 435.51 |
| 2487 | | O | Pic | 386.452 | 387.55 |
| 2488 | | O | Oic | 426.517 | 427.25 |
| 2489 | (2,6-diF-phenyl)-CH(CH₃)- | O | Oic | 402.445 | 403.27 |
| 2490 | (2-phenyl-phenyl)-CH(CH₃)- | O | Tic | 450.542 | 451.59 |
| 2491 | | O | Pic | 402.498 | 403.57 |
| 2492 | | O | Oic | 442.563 | 443.22 |
| 2493 | nPr | S | Pic | 308.448 | 309.46 |
| 2494 | | S | Oic | 348.513 | 349.21 |

TABLE 15-continued

| Example No | R' | Z | AA | Mol Wt | [M + H]+ |
|---|---|---|---|---|---|
| 2495 | (phenyl-CH2-C(CH3)2-) | S | Pic | 356.492 | 357.47 |
| 2496 | | S | Oic | 396.557 | 397.24 |
| 2497 | (phenyl-CH2CH2-C(CH3)2-) | S | Pic | 370.519 | 371.5 |
| 2498 | | S | Oic | 410.584 | 411.27 |
| 2499 | (4-MeO-phenyl-CH(CH3)-) | S | Oic | 412.556 | 413.18 |
| 2500 | (PhC(O)CH(CH3)-) | S | Tic | 418.519 | 419.49 |
| 2501 | | S | Oic | 410.54 | 411.2 |
| 2502 | (cyclopentyl-CH(CH3)-) | S | Tic | 382.53 | 383.58 |
| 2503 | | S | Oic | 374.551 | 375.28 |
| 2504 | (cyclohexyl-CH2-CH(CH3)-) | S | Tic | 410.584 | 411.57 |
| 2505 | | S | Pic | 362.54 | 363.64 |
| 2506 | | S | Oic | 402.605 | 403.28 |

TABLE 16

| Example No | R' | Z | R5 | Mol Wt | [M + H]+ |
|---|---|---|---|---|---|
| 2507 | Et | O | Ph | 314.389 | 315.09 |
| 2508 | | O | Ch | 320.437 | 321.51 |
| 2509 | | O | OCH2Ph | 300.362 | 301.07 |
| 2510 | | O | CH2CO2CH2Ph | 386.452 | 387.18 |
| 2511 | iPr | O | OCH2Ph | 314.389 | 315.03 |
| 2512 | | O | CH2CO2CH2Ph | 400.479 | 401.27 |
| 2513 | nHex | O | Ph | 370.497 | 371.33 |
| 2514 | | O | Ch | 376.545 | 377.66 |
| 2515 | | O | OCH2Ph | 356.47 | 357.12 |

TABLE 16-continued

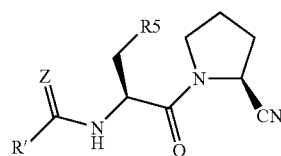

| Example No | R' | Z | R5 | Mol Wt | [M + H]+ |
|---|---|---|---|---|---|
| 2516 | | O | CH₂CO₂CH₂Ph | 442.56 | 443.23 |
| 2517 | | O | CO₂CH₃ | 352.435 | 353.56 |
| 2518 | cyclohexyl-CH(CH₃)- | O | Ph | 368.481 | 369.27 |
| 2519 | | O | Ch | 374.529 | 375.69 |
| 2520 | | O | OCH₂Ph | 354.454 | 354.87 |
| 2521 | | O | CH₂CO₂CH₂Ph | 440.544 | 441.23 |
| 2522 | | O | CO₂CH₃ | 350.419 | 351.51 |
| 2523 | PhCH₂CH(CH₃)- | O | Ph | 376.46 | 377.19 |
| 2524 | | O | Ch | 382.508 | 383.6 |
| 2525 | | O | OCH₂Ph | 362.433 | 363.16 |
| 2526 | | O | CH₂CO₂CH₂Ph | 448.523 | 449.26 |
| 2527 | | O | CO₂CH₃ | 358.398 | 359.51 |
| 2528 | EtO₂C-(CH₂)₃-CH(CH₃)- | O | Ph | 386.452 | 387.24 |
| 2529 | | O | Ch | 392.5 | 393.61 |
| 2530 | | O | OCH₂Ph | 372.425 | 373.12 |
| 2531 | | O | CH₂CO₂CH₂Ph | 458.515 | 459.26 |
| 2532 | | O | CO₂CH₃ | 368.39 | 369.48 |
| 2533 | CH₂=CH-CH₂-CH(CH₃)- | O | CH₂CO₂CH₂Ph | 398.463 | 399.19 |
| 2534 | Ph-CH(CH₃)- | O | Ph | 362.433 | 363.24 |
| 2535 | | O | Ch | 368.481 | 369.27 |
| 2536 | | O | OCH₂Ph | 348.406 | 349.1 |
| 2537 | | O | CH₂CO₂CH₂Ph | 434.496 | 435.23 |
| 2538 | | O | CO₂CH₃ | 344.371 | 345.48 |
| 2539 | 4-MeO-C₆H₄-CH(CH₃)- | O | Ph | 392.459 | 393.19 |
| 2540 | | O | Ch | 398.507 | 399.54 |
| 2541 | | O | OCH₂Ph | 378.432 | 379.1 |
| 2542 | | O | CH₂CO₂CH₂Ph | 464.522 | 465.23 |
| 2543 | | O | CO₂CH₃ | 374.397 | 375.51 |
| 2544 | 4-Me-C₆H₄-CH(CH₃)- | O | Ph | 376.46 | 377.25 |
| 2545 | | O | Ch | 382.508 | 383.6 |
| 2546 | | O | OCH₂Ph | 362.433 | 363.1 |
| 2547 | | O | CH₂CO₂CH₂Ph | 448.523 | 449.23 |
| 2548 | | O | CO₂CH₃ | 358.398 | 359.49 |
| 2549 | 2,3-Cl₂-C₆H₃-CH(CH₃)- | O | Ph | 431.323 | 431.02 |
| 2550 | | O | Ch | 437.371 | 437.45 |
| 2551 | | O | OCH₂Ph | 417.296 | 417.06 |
| 2552 | | O | CH₂CO₂CH₂Ph | 503.386 | 503.18 |
| 2553 | | O | CO₂CH₃ | 413.261 | 413.39 |
| 2554 | 4-F-C₆H₄-CH(CH₃)- | O | Ph | 380.423 | 381.13 |
| 2555 | | O | Ch | 386.471 | 387.59 |
| 2556 | | O | OCH₂Ph | 366.396 | 367.11 |
| 2557 | | O | CH₂CO₂CH₂Ph | 452.486 | 453.36 |
| 2558 | | O | CO₂CH₃ | 362.361 | 363.47 |

TABLE 16-continued

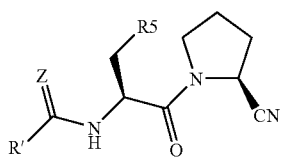

| Example No | R' | Z | R5 | Mol Wt | [M + H]+ |
|---|---|---|---|---|---|
| 2559 | 3-F-phenyl | O | CH₂CO₂CH₂Ph | 452.486 | 453.2 |
| 2560 | 2-F-phenyl | O | Ph | 380.423 | 381.15 |
| 2561 | 2-F-phenyl | O | Ch | 386.471 | 387.57 |
| 2562 | 2-F-phenyl | O | OCH₂Ph | 366.396 | 367.15 |
| 2563 | 2-F-phenyl | O | CH₂CO₂CH₂Ph | 452.486 | 453.17 |
| 2564 | 1-naphthyl | O | Ph | 412.493 | 413.21 |
| 2565 | 1-naphthyl | O | Ch | 418.541 | 419.55 |
| 2566 | 1-naphthyl | O | OCH₂Ph | 398.466 | 399.13 |
| 2567 | 1-naphthyl | O | CH₂CO₂CH₂Ph | 484.556 | 485.24 |
| 2568 | 1-naphthyl | O | CO₂CH₃ | 394.431 | 395.52 |
| 2569 | 3-CF₃-phenyl | O | Ph | 430.43 | 431.04 |
| 2570 | 3-CF₃-phenyl | O | Ch | 436.478 | 437.51 |
| 2571 | 3-CF₃-phenyl | O | OCH₂Ph | 416.403 | 417.13 |
| 2572 | 3-CF₃-phenyl | O | CH₂CO₂CH₂Ph | 502.493 | 503.23 |
| 2573 | 3-CF₃-phenyl | O | CO₂CH₃ | 412.368 | 413.46 |
| 2574 | 4-Cl-phenyl | O | Ph | 396.878 | 397.24 |
| 2575 | 4-Cl-phenyl | O | Ch | 402.926 | 403.53 |
| 2576 | 4-Cl-phenyl | O | OCH₂Ph | 382.851 | 383.13 |
| 2577 | 4-Cl-phenyl | O | CH₂CO₂CH₂Ph | 468.941 | 469.16 |
| 2578 | 4-Cl-phenyl | O | CO₂CH₃ | 378.816 | 378.84 |
| 2579 | 3-Cl-phenyl | O | Ph | 396.878 | 397.12 |
| 2580 | 3-Cl-phenyl | O | Ch | 402.926 | 403.46 |
| 2581 | 3-Cl-phenyl | O | OCH₂Ph | 382.851 | 383.16 |
| 2582 | 3-Cl-phenyl | O | CH₂CO₂CH₂Ph | 468.941 | 469.2 |
| 2583 | 3-Cl-phenyl | O | CO₂CH₃ | 378.816 | 379.47 |
| 2584 | 2-Cl-phenyl | O | Ph | 396.878 | 397.11 |
| 2585 | 2-Cl-phenyl | O | Ch | 402.926 | 403.51 |
| 2586 | 2-Cl-phenyl | O | OCH₂Ph | 382.851 | 383.11 |
| 2587 | 2-Cl-phenyl | O | CH₂CO₂CH₂Ph | 468.941 | 469.11 |
| 2588 | 2-Cl-phenyl | O | CO₂CH₃ | 378.816 | 379.48 |
| 2589 | 3-OMe-phenyl | O | Ph | 392.459 | 393.2 |
| 2590 | 3-OMe-phenyl | O | Ch | 398.507 | 399.58 |
| 2591 | 3-OMe-phenyl | O | OCH₂Ph | 378.432 | 379.11 |
| 2592 | 3-OMe-phenyl | O | CH₂CO₂CH₂Ph | 464.522 | 465.25 |
| 2593 | 3-OMe-phenyl | O | CO₂CH₃ | 374.397 | 375.49 |
| 2594 | 2-OMe-phenyl | O | Ph | 392.459 | 393.25 |
| 2595 | 2-OMe-phenyl | O | Ch | 398.507 | 399.54 |
| 2596 | 2-OMe-phenyl | O | OCH₂Ph | 378.432 | 379.16 |
| 2597 | 2-OMe-phenyl | O | CH₂CO₂CH₂Ph | 464.522 | 465.23 |
| 2598 | 2-OMe-phenyl | O | CO₂CH₃ | 374.397 | 375.51 |

TABLE 16-continued

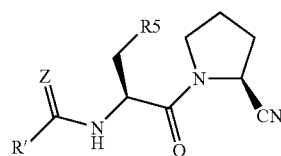

| Example No | R' | Z | R5 | Mol Wt | [M + H]+ |
|---|---|---|---|---|---|
| 2599 | O₂N-phenyl | O | Ph | 407.43 | 408.19 |
| 2600 | | O | Ch | 413.478 | 414.54 |
| 2601 | | O | OCH₂Ph | 393.403 | 394.21 |
| 2602 | | O | CH₂CO₂CH₂Ph | 479.493 | 480.25 |
| 2603 | | O | CO₂CH₃ | 389.368 | 390.48 |
| 2604 | 2,4-diClPh | O | Ph | 431.323 | 431.01 |
| 2605 | | O | Ch | 437.371 | 437.43 |
| 2606 | | O | OCH₂Ph | 417.296 | 417.1 |
| 2607 | | O | CH₂CO₂CH₂Ph | 503.386 | 503.15 |
| 2608 | | O | CO₂CH₃ | 413.261 | 413.37 |
| 2609 | PhC(CH₃)C(CH₃)₃ | O | Ph | 390.487 | 391.27 |
| 2610 | | O | Ch | 396.535 | 397.59 |
| 2611 | | O | OCH₂Ph | 376.46 | 377.14 |
| 2612 | | O | CH₂CO₂CH₂Ph | 462.55 | 463.31 |
| 2613 | | O | CO₂CH₃ | 372.425 | 373.51 |
| 2614 | 3,5-diClPh | O | Ch | 437.371 | 437.45 |
| 2615 | | O | OCH₂Ph | 417.296 | 417.04 |
| 2616 | | O | CH₂CO₂CH₂Ph | 503.386 | 503.14 |
| 2617 | | O | CO₂CH₃ | 413.261 | 413.38 |
| 2618 | 2,5-diOMePh | O | Ph | 422.485 | 423.28 |
| 2619 | | O | Ch | 428.533 | 429.58 |
| 2620 | | O | OCH₂Ph | 408.458 | 409.19 |
| 2621 | | O | CH₂CO₂CH₂Ph | 494.548 | 495.24 |
| 2622 | | O | CO₂CH₃ | 404.423 | 404.91 |
| 2623 | 2,6-diFPh | O | Ph | 398.413 | 399.19 |
| 2624 | | O | Ch | 404.461 | 405.53 |
| 2625 | | O | OCH₂Ph | 384.386 | 385.09 |
| 2626 | | O | CH₂CO₂CH₂Ph | 470.476 | 471.22 |
| 2627 | | O | CO₂CH₃ | 380.351 | 381.49 |
| 2628 | biphenyl | O | Ph | 438.531 | 439.24 |
| 2629 | | O | Ch | 444.579 | 445.57 |
| 2630 | | O | OCH₂Ph | 424.504 | 425.17 |
| 2631 | | O | CH₂CO₂CH₂Ph | 510.594 | 511.28 |
| 2632 | | O | CO₂CH₃ | 420.469 | 421.46 |
| 2633 | nPr | S | Ph | 344.481 | 345.27 |
| 2634 | | S | Ch | 350.529 | 351.15 |
| 2635 | | S | OCH₂Ph | 330.454 | 331.11 |
| 2636 | | S | CH₂CO₂CH₂Ph | 416.544 | 417.25 |
| 2637 | | S | CO₂CH₃ | 326.419 | 327.24 |

TABLE 16-continued

| Example No | R' | Z | R5 | Mol Wt | [M + H]+ |
|---|---|---|---|---|---|
| 2638 | benzyl-CH(CH3)- | S | Ph | 392.525 | 393.28 |
| 2639 | | S | Ch | 398.573 | 399.53 |
| 2640 | | S | OCH2Ph | 378.498 | 379.13 |
| 2641 | | S | CH2CO2CH2Ph | 464.588 | 465.18 |
| 2642 | | S | CO2CH3 | 374.463 | 375.44 |
| 2643 | phenylpropyl-CH(CH3)- | S | Ph | 406.552 | 407.3 |
| 2644 | | S | Ch | 412.6 | 413.53 |
| 2645 | | S | OCH2Ph | 392.525 | 393.17 |
| 2646 | | S | CH2CO2CH2Ph | 478.615 | 479.25 |
| 2647 | | S | CO2CH3 | 388.49 | 389.48 |
| 2648 | 4-methoxyphenyl-CH(CH3)- | S | Ph | 408.524 | 409.21 |
| 2649 | | S | Ch | 414.572 | 415.51 |
| 2650 | | S | OCH2Ph | 394.497 | 395.13 |
| 2651 | | S | CH2CO2CH2Ph | 480.587 | 481.18 |
| 2652 | PhC(O)-CH(CH3)- | S | Ph | 406.508 | 406.9 |
| 2653 | | S | Ch | 412.556 | 413.6 |
| 2654 | | S | OCH2Ph | 392.481 | 393.14 |
| 2655 | | S | CH2CO2CH2Ph | 478.571 | 479.14 |
| 2656 | | S | CO2CH3 | 388.446 | 389.45 |
| 2657 | cyclopentyl-CH(CH3)- | S | Ph | 370.519 | 371.04 |
| 2658 | | S | OCH2Ph | 356.492 | 357.11 |
| 2659 | | S | CH2CO2CH2Ph | 442.582 | 443.17 |
| 2660 | | S | CO2CH3 | 352.457 | 353.46 |
| 2661 | cyclohexyl-CH2-CH(CH3)- | S | Ph | 398.573 | 399.53 |
| 2662 | | S | OCH2Ph | 384.546 | 385.24 |
| 2663 | | S | CH2CO2CH2Ph | 470.636 | 471.2 |
| 2664 | | S | CO2CH3 | 380.511 | 381.54 |

TABLE 17

| Example No | R' | Z | n | Mol Wt | [M + H]+ |
|---|---|---|---|---|---|
| 2665 | Et | O | 1 | 387.44 | 388.27 |
| 2666 | | O | 3 | 415.494 | 416.24 |
| 2667 | | O | 2 | 401.467 | 402.28 |
| 2668 | | O | 4 | 429.521 | 430.25 |
| 2669 | iPr | O | 1 | 401.467 | 402.26 |
| 2670 | | O | 3 | 429.521 | 430.26 |

TABLE 17-continued
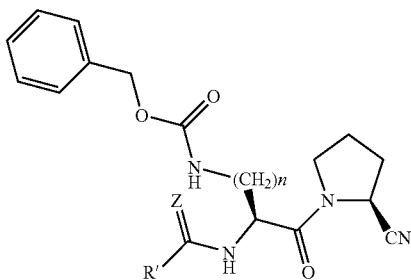
| Example No | R' | Z | n | Mol Wt | [M + H]+ |
|---|---|---|---|---|---|
| 2671 | | O | 2 | 415.494 | 416.27 |
| 2672 | | O | 4 | 443.548 | 444.23 |
| 2673 | nHex | O | 1 | 443.548 | 444.31 |
| 2674 | | O | 3 | 471.602 | 472.34 |
| 2675 | | O | 2 | 457.575 | 458.32 |
| 2676 | | O | 4 | 485.629 | 486.37 |
| 2677 | | O | 1 | 441.532 | 442.29 |
| 2678 | cyclohexyl-CH(CH3)- | O | 3 | 469.586 | 470.27 |
| 2679 | | O | 2 | 455.559 | 456.31 |
| 2680 | | O | 4 | 483.613 | 484.29 |
| 2681 | | O | 1 | 449.511 | 450.24 |
| 2682 | Ph-CH2-CH(CH3)- | O | 3 | 477.565 | 478.31 |
| 2683 | | O | 2 | 463.538 | 464.33 |
| 2684 | | O | 4 | 491.592 | 492.24 |
| 2685 | | O | 1 | 459.503 | 460.31 |
| 2686 | EtO2C-(CH2)3-CH(CH3)- | O | 3 | 487.557 | 488.24 |
| 2687 | | O | 2 | 473.53 | 474.33 |
| 2688 | | O | 4 | 501.584 | 502.26 |
| 2689 | | O | 1 | 463.494 | 464.22 |
| 2690 | PhC(O)-CH(CH3)- | O | 2 | 477.521 | 478.23 |
| 2691 | | O | 1 | 435.484 | 436.23 |
| 2692 | Ph-CH(CH3)- | O | 3 | 463.538 | 464.21 |
| 2693 | | O | 2 | 449.511 | 450.26 |
| 2694 | | O | 4 | 477.565 | 478.3 |
| 2695 | | O | 1 | 465.51 | 466.25 |
| 2696 | 4-MeO-C6H4-CH(CH3)- | O | 3 | 493.564 | 494.27 |
| 2697 | | O | 2 | 479.537 | 480.25 |
| 2698 | | O | 4 | 507.591 | 508.22 |
| 2699 | | O | 1 | 449.511 | 450.26 |
| 2700 | 4-Me-C6H4-CH(CH3)- | O | 3 | 477.565 | 478.27 |
| 2701 | | O | 2 | 463.538 | 464.31 |
| 2702 | | O | 4 | 491.592 | 492.23 |
| 2703 | | O | 1 | 504.374 | 504.22 |
| 2704 | 2,3-Cl2-C6H3-CH(CH3)- | O | 3 | 532.428 | 532.19 |
| 2705 | | O | 2 | 518.401 | 518.25 |
| 2706 | | O | 4 | 546.455 | 546.24 |

TABLE 17-continued
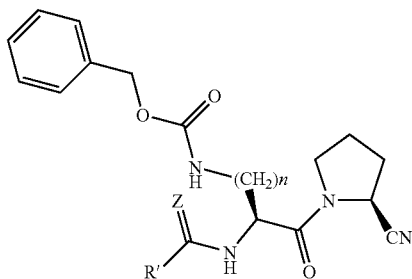
| Example No | R' | Z | n | Mol Wt | [M + H]+ |
|---|---|---|---|---|---|
| 2707 | 4-F-C6H4-CH(CH3)- | O | 1 | 453.474 | 454.23 |
| 2708 | | O | 3 | 481.528 | 482.2 |
| 2709 | | O | 2 | 467.501 | 468.28 |
| 2710 | | O | 4 | 495.555 | 496.21 |
| 2711 | 3-F-C6H4-CH(CH3)- | O | 1 | 453.474 | 454.3 |
| 2712 | | O | 2 | 467.501 | 468.25 |
| 2713 | | O | 4 | 495.555 | 496.25 |
| 2714 | 2-F-C6H4-CH(CH3)- | O | 1 | 453.474 | 454.23 |
| 2715 | | O | 3 | 481.528 | 482.23 |
| 2716 | | O | 2 | 467.501 | 468.24 |
| 2717 | | O | 4 | 495.555 | 496.28 |
| 2718 | 1-naphthyl-CH(CH3)- | O | 1 | 485.544 | 486.22 |
| 2719 | | O | 3 | 513.598 | 514.29 |
| 2720 | | O | 2 | 499.571 | 500.26 |
| 2721 | | O | 4 | 527.625 | 528.32 |
| 2722 | 3-CF3-C6H4-CH(CH3)- | O | 1 | 503.481 | 504.27 |
| 2723 | | O | 3 | 531.535 | 532.24 |
| 2724 | | O | 2 | 517.508 | 518.26 |
| 2725 | | O | 4 | 545.562 | 546.28 |
| 2726 | 4-Cl-C6H4-CH(CH3)- | O | 1 | 469.929 | 470.19 |
| 2727 | | O | 3 | 497.983 | 498.27 |
| 2728 | | O | 2 | 483.956 | 484.18 |
| 2729 | | O | 4 | 512.01 | 512.27 |
| 2730 | 3-Cl-C6H4-CH(CH3)- | O | 1 | 469.929 | 470.19 |
| 2731 | | O | 3 | 497.983 | 498.23 |
| 2732 | | O | 2 | 483.956 | 484.26 |
| 2733 | | O | 4 | 512.01 | 512.26 |
| 2734 | 2-Cl-C6H4-CH(CH3)- | O | 1 | 469.929 | 470.27 |
| 2735 | | O | 3 | 497.983 | 498.21 |
| 2736 | | O | 2 | 483.956 | 484.26 |
| 2737 | | O | 4 | 512.01 | 512.24 |

TABLE 17-continued
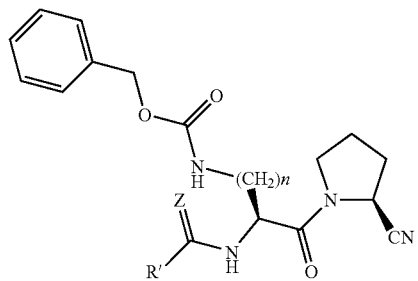
| Example No | R' | Z | n | Mol Wt | [M + H]+ |
|---|---|---|---|---|---|
| 2738 | 3-methoxyphenyl | O | 1 | 465.51 | 466.24 |
| 2739 | | O | 3 | 493.564 | 494.4 |
| 2740 | | O | 2 | 479.537 | 480.32 |
| 2741 | | O | 4 | 507.591 | 508.24 |
| 2742 | 2-methoxyphenyl | O | 1 | 465.51 | 466.26 |
| 2743 | | O | 3 | 493.564 | 494.23 |
| 2744 | | O | 2 | 479.537 | 480.26 |
| 2745 | | O | 4 | 507.591 | 508.23 |
| 2746 | 3-nitrophenyl | O | 1 | 480.481 | 481.22 |
| 2747 | | O | 3 | 508.535 | 509.3 |
| 2748 | | O | 2 | 494.508 | 495.28 |
| 2749 | | O | 4 | 522.562 | 523.25 |
| 2750 | 2,4-dichlorophenyl | O | 1 | 504.374 | 504.17 |
| 2751 | | O | 3 | 532.428 | 532.18 |
| 2752 | | O | 2 | 518.401 | 518.19 |
| 2753 | | O | 4 | 546.455 | 546.27 |
| 2754 | phenyl (sec-butyl) | O | 1 | 463.538 | 464.25 |
| 2755 | | O | 3 | 491.592 | 492.27 |
| 2756 | | O | 2 | 477.565 | 478.28 |
| 2757 | | O | 4 | 505.619 | 506.27 |
| 2758 | 3,5-dichlorophenyl | O | 1 | 504.374 | 504.23 |
| 2759 | | O | 3 | 532.428 | 532.13 |
| 2760 | | O | 2 | 518.401 | 518.2 |
| 2761 | | O | 4 | 546.455 | 546.24 |
| 2762 | 2,5-dimethoxyphenyl | O | 1 | 495.536 | 496.29 |
| 2763 | | O | 3 | 523.59 | 524.24 |
| 2764 | | O | 2 | 509.563 | 510.28 |
| 2765 | | O | 4 | 537.617 | 538.3 |

TABLE 17-continued
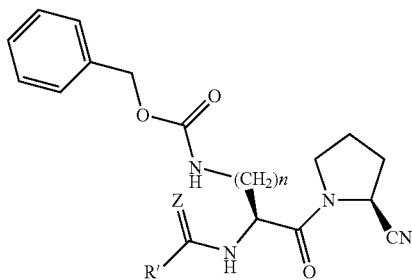
| Example No | R' | Z | n | Mol Wt | [M + H]+ |
|---|---|---|---|---|---|
| 2766 | 2,6-difluorophenyl-CH(CH3) | O | 1 | 471.464 | 472.21 |
| 2767 |  | O | 3 | 499.518 | 500.18 |
| 2768 |  | O | 2 | 485.491 | 486.29 |
| 2769 |  | O | 4 | 513.545 | 514.27 |
| 2770 | 2-biphenyl-CH(CH3) | O | 1 | 511.582 | 512.3 |
| 2771 |  | O | 3 | 539.636 | 540.28 |
| 2772 |  | O | 2 | 525.609 | 526.31 |
| 2773 |  | O | 4 | 553.663 | 554.35 |
| 2774 | nPr | S | 1 | 417.532 | 418.23 |
| 2775 |  | S | 3 | 445.586 | 446.31 |
| 2776 |  | S | 2 | 431.559 | 432.22 |
| 2777 |  | S | 4 | 459.613 | 460.25 |
| 2778 | phenyl-CH2-CH(CH3) | S | 1 | 465.576 | 466.21 |
| 2779 |  | S | 3 | 493.63 | 494.32 |
| 2780 |  | S | 2 | 479.603 | 480.25 |
| 2781 |  | S | 4 | 507.657 | 508.23 |
| 2782 | phenyl-(CH2)2-CH(CH3) | S | 1 | 479.603 | 480.23 |
| 2783 |  | S | 3 | 507.657 | 508.23 |
| 2784 |  | S | 2 | 493.63 | 494.3 |
| 2785 |  | S | 4 | 521.684 | 522.3 |
| 2786 | 4-methoxyphenyl-CH(CH3) | S | 1 | 481.575 | 482.21 |
| 2787 |  | S | 3 | 509.629 | 510.26 |
| 2788 |  | S | 2 | 495.602 | 496.22 |
| 2789 |  | S | 4 | 523.656 | 524.27 |
| 2790 | phenyl-C(O)-CH(CH3) | S | 1 | 479.559 | 480.23 |
| 2791 |  | S | 3 | 507.613 | 508.21 |
| 2792 |  | S | 2 | 493.586 | 494.25 |
| 2793 |  | S | 4 | 521.64 | 522.23 |

TABLE 18
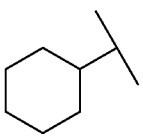
| Example No | R' | Z | R6 | Mol Wt | [M + H]+ |
|---|---|---|---|---|---|
| 2794 | Et | O | Me | 252.318 | 253.51 |
| 2795 |  | O | H | 238.291 | 239.54 |
| 2796 | iPr | O | Me | 266.345 | 267.56 |
| 2797 | nHex | O | Me | 308.426 | 309.55 |
| 2798 |  | O | H | 294.399 | 295.58 |
| 2799 |  | O | secBu | 350.507 | 351.41 |
| 2800 |  | O | CH$_2$Ph | 384.524 | 385.67 |
| 2801 | 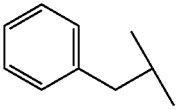 | O | Me | 306.41 | 307.53 |
| 2802 |  | O | H | 292.383 | 293.46 |
| 2803 |  | O | CH$_2$Ph | 382.508 | 383.59 |
| 2804 | 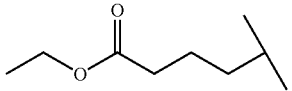 | O | H | 300.362 | 301.49 |
| 2805 |  | O | secBu | 356.47 | 357.3 |
| 2806 |  | O | CH$_2$Ph | 390.487 | 391.56 |
| 2807 | 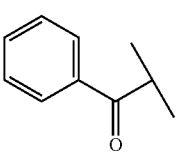 | O | Me | 324.381 | 325.54 |
| 2808 |  | O | H | 310.354 | 311.54 |
| 2809 |  | O | CH$_2$Ph | 400.479 | 401.58 |
| 2810 | 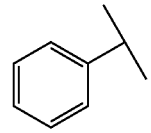 | O | secBu | 370.453 | 371.32 |
| 2811 |  | O | CH$_2$Ph | 404.47 | 405.46 |
| 2812 | 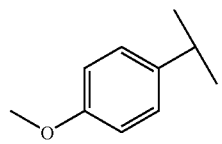 | O | Me | 300.362 | 301.55 |
| 2813 |  | O | H | 286.335 | 287.5 |
| 2814 |  | O | secBu | 342.443 | 343.32 |
| 2815 |  | O | CH$_2$Ph | 376.46 | 377.53 |
| 2816 | 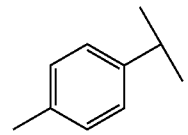 | O | Me | 330.388 | 331.55 |
| 2817 |  | O | H | 316.361 | 317.51 |
| 2818 |  | O | secBu | 372.469 | 373.33 |
| 2819 |  | O | CH$_2$Ph | 406.486 | 407.53 |
| 2820 | 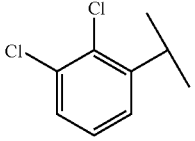 | O | Me | 314.389 | 315.54 |
| 2821 |  | O | H | 300.362 | 301.49 |
| 2822 |  | O | secBu | 356.47 | 357.31 |
| 2823 |  | O | CH$_2$Ph | 390.487 | 391.55 |
| 2824 |  | O | Me | 369.252 | 369.41 |
| 2825 |  | O | H | 355.225 | 355.42 |
| 2826 |  | O | secBu | 411.333 | 411.18 |
| 2827 |  | O | CH$_2$Ph | 445.35 | 445.36 |

TABLE 18-continued
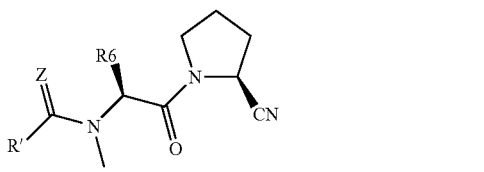
| Example No | R' | Z | R6 | Mol Wt | [M + H]+ |
|---|---|---|---|---|---|
| 2828 | 4-F-C6H4-CH(CH3)- | O | Me | 318.352 | 319.47 |
| 2829 | | O | H | 304.325 | 305.5 |
| 2830 | | O | secBu | 360.433 | 361.28 |
| 2831 | | O | CH2Ph | 394.45 | 395.52 |
| 2832 | 3-F-C6H4-CH(CH3)- | O | secBu | 360.433 | 361.28 |
| 2833 | 2-F-C6H4-CH(CH3)- | O | Me | 318.352 | 319.53 |
| 2834 | | O | H | 304.325 | 305.5 |
| 2835 | 1-naphthyl-CH(CH3)- | O | Me | 350.422 | 351.53 |
| 2836 | | O | H | 336.395 | 337.51 |
| 2837 | | O | secBu | 392.503 | 393.35 |
| 2738 | | O | CH2Ph | 426.52 | 427.5 |
| 2839 | 3-CF3-C6H4-CH(CH3)- | O | Me | 368.359 | 369.57 |
| 2840 | | O | H | 354.332 | 355.46 |
| 2841 | | O | secBu | 410.44 | 411.29 |
| 2842 | | O | CH2Ph | 444.457 | 445.51 |
| 2843 | 4-Cl-C6H4-CH(CH3)- | O | Me | 334.807 | 335.51 |
| 2844 | | O | H | 320.78 | 321.44 |
| 2845 | | O | secBu | 376.888 | 377.24 |
| 2846 | | O | CH2Ph | 410.905 | 411.51 |
| 2847 | 3-Cl-C6H4-CH(CH3)- | O | Me | 334.807 | 335.53 |
| 2848 | | O | H | 320.78 | 321.47 |
| 2849 | | O | secBu | 376.888 | 377.28 |
| 2850 | | O | CH2Ph | 410.905 | 411.47 |
| 2851 | 2-Cl-C6H4-CH(CH3)- | O | Me | 334.807 | 335.36 |
| 2852 | | O | H | 320.78 | 321.46 |
| 2853 | | O | secBu | 376.888 | 377.22 |
| 2854 | | O | CH2Ph | 410.905 | 411.46 |
| 2855 | 3-MeO-C6H4-CH(CH3)- | O | Me | 330.388 | 331.5 |
| 2856 | | O | H | 316.361 | 317.48 |
| 2857 | | O | secBu | 372.469 | 373.31 |
| 2858 | | O | CH2Ph | 406.486 | 407.52 |

TABLE 18-continued

| Example No | R' | Z | R6 | Mol Wt | [M + H]+ |
|---|---|---|---|---|---|
| 2859 | 2-isopropyl-methoxyphenyl | O | Me | 330.388 | 331.52 |
| 2860 | | O | H | 316.361 | 317.49 |
| 2861 | | O | secBu | 372.469 | 373.33 |
| 2862 | | O | CH₂Ph | 406.486 | 407.51 |
| 2863 | 3-nitro-isopropylphenyl | O | Me | 345.359 | 346.46 |
| 2864 | | O | H | 331.332 | 332.48 |
| 2865 | | O | secBu | 387.44 | 388.33 |
| 2866 | | O | CH₂Ph | 421.457 | 422.41 |
| 2867 | 2,4-dichloro-isopropylphenyl | O | Me | 369.252 | 369.38 |
| 2868 | | O | H | 355.225 | 355.42 |
| 2869 | | O | secBu | 411.333 | 411.12 |
| 2870 | | O | CH₂Ph | 445.35 | 445.33 |
| 2871 | sec-butylphenyl | O | Me | 328.416 | 329.53 |
| 2872 | | O | H | 314.389 | 315.51 |
| 2873 | | O | secBu | 370.497 | 371.34 |
| 2874 | | O | CH₂Ph | 404.514 | 405.52 |
| 2875 | 3,5-dichloro-isopropylphenyl | O | Me | 369.252 | 369.47 |
| 2876 | | O | H | 355.225 | 355.39 |
| 2877 | | O | secBu | 411.333 | 411.26 |
| 2878 | | O | CH₂Ph | 445.35 | 445.39 |
| 2879 | 2,5-dimethoxy-isopropylphenyl | O | Me | 360.414 | 361.38 |
| 2880 | | O | H | 346.387 | 347.54 |
| 2881 | | O | secBu | 402.495 | 403.35 |
| 2882 | | O | CH₂Ph | 436.512 | 437.41 |
| 2883 | 2,6-difluoro-isopropylphenyl | O | Me | 336.342 | 337.45 |
| 2884 | | O | H | 322.315 | 323.49 |
| 2885 | | O | secBu | 378.423 | 379.25 |
| 2886 | | O | CH₂Ph | 412.44 | 413.51 |
| 2887 | biphenyl-isopropyl | O | Me | 376.46 | 377.53 |
| 2888 | | O | H | 362.433 | 363.51 |
| 2889 | | O | secBu | 418.541 | 419.31 |
| 2890 | | O | CH₂Ph | 452.558 | 453.54 |

TABLE 18-continued

| Example No | R' | Z | R6 | Mol Wt | [M + H]+ |
|---|---|---|---|---|---|
| 2891 | nPr | S | Me | 282.41 | 283.56 |
| 2892 | | S | secBu | 324.491 | 325.23 |
| 2893 | PhCH2CH(CH3)- | S | H | 316.427 | 317.51 |
| 2894 | | S | secBu | 372.535 | 373.33 |
| 2895 | | S | CH2Ph | 406.552 | 407.55 |
| 2896 | Ph(CH2)2CH(CH3)- | S | H | 330.454 | 331.51 |
| 2897 | | S | secBu | 386.562 | 387.34 |
| 2898 | | S | CH2Ph | 420.579 | 421.53 |
| 2899 | PhC(O)CH(CH3)- | S | H | 330.41 | 331.46 |
| 2900 | | S | secBu | 386.518 | 387.3 |
| 2901 | cyclopentyl-CH(CH3)- | S | Me | 308.448 | 309.52 |
| 2902 | | S | H | 294.421 | 295.51 |
| 2903 | | S | secBu | 350.529 | 351.31 |
| 2904 | cyclohexyl-CH2CH(CH3)- | S | secBu | 378.583 | 379.36 |

TABLE 19

| Example No | R | R7 | Moll Wt | [M + H]+ |
|---|---|---|---|---|
| 2905 | CH3 | H | 195.222 | 196.17 |
| 2906 | | secBu | 251.33 | 252.27 |
| 2907 | | CH2Ph | 285.347 | 286.24 |
| 2908 | PhCH(CH3)- | H | 257.293 | 258.18 |
| 2909 | | iPr | 299.374 | 300.18 |
| 2910 | | secBu | 313.401 | 314.25 |
| 2911 | | CH2Ph | 347.418 | 348.22 |

TABLE 19-continued
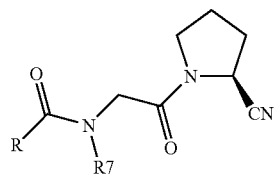
| Example No | R | R7 | Moll Wt | [M + H]+ |
|---|---|---|---|---|
| 2912 | 3-Cl-C6H4 | H | 291.738 | 292.12 |
| 2913 | | iPr | 333.819 | 334.16 |
| 2914 | | secBu | 347.846 | 348.23 |
| 2915 | | CH2Ph | 381.863 | 382.25 |
| 2916 | 4-Cl-C6H4 | H | 291.738 | 292.13 |
| 2917 | | iPr | 333.819 | 334.17 |
| 2918 | | secBu | 347.846 | 348.21 |
| 2919 | | CH2Ph | 381.863 | 382.21 |
| 2920 | 2-Cl-C6H4 | H | 291.738 | 292.11 |
| 2921 | | iPr | 333.819 | 334.15 |
| 2922 | | secBu | 347.846 | 348.19 |
| 2923 | | CH2Ph | 381.863 | 382.22 |
| 2924 | 2,4-diCl-C6H3 | H | 326.183 | 326.1 |
| 2925 | | iPr | 368.264 | 368.12 |
| 2926 | | secBu | 382.291 | 382.21 |
| 2927 | | CH2Ph | 416.308 | 416.15 |
| 2928 | 3,4-diCl-C6H3 | H | 326.183 | 326.07 |
| 2929 | | iPr | 368.264 | 368.13 |
| 2930 | | secBu | 382.291 | 382.2 |
| 2931 | | CH2Ph | 416.308 | 416.13 |
| 2932 | 3,5-diCl-C6H3 | iPr | 368.264 | 368.13 |
| 2933 | 3-F-C6H4 | H | 275.283 | 276.19 |
| 2934 | | iPr | 317.364 | 318.21 |
| 2935 | | secBu | 331.391 | 332.24 |
| 2936 | | CH2Ph | 365.408 | 366.24 |
| 2937 | 4-F-C6H4 | H | 275.283 | 276.19 |
| 2938 | | iPr | 317.364 | 318.18 |
| 2939 | | secBu | 331.391 | 332.23 |
| 2940 | | CH2Ph | 365.408 | 366.26 |

TABLE 19-continued
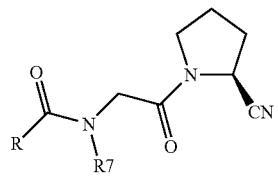
| Example No | R | R7 | Moll Wt | [M + H]+ |
|---|---|---|---|---|
| 2941 | 4-methoxyphenyl | H | 287.319 | 288.17 |
| 2942 | | iPr | 329.4 | 330.24 |
| 2943 | | secBu | 343.427 | 344.25 |
| 2944 | | CH₂Ph | 377.444 | 378.29 |
| 2945 | 3-methoxyphenyl | H | 287.319 | 288.2 |
| 2946 | | iPr | 329.4 | 330.23 |
| 2947 | | secBu | 343.427 | 344.25 |
| 2948 | | CH₂Ph | 377.444 | 378.26 |
| 2949 | benzo[1,3]dioxol-5-yl | CH₂Ph | 391.427 | 391.33 |
| 2950 | 2-methylphenyl | H | 271.32 | 272.19 |
| 2951 | | iPr | 313.401 | 314.2 |
| 2952 | | secBu | 327.428 | 328.24 |
| 2953 | | CH₂Ph | 361.445 | 362.26 |
| 2954 | 3-methylphenyl | H | 271.32 | 272.16 |
| 2955 | | iPr | 313.401 | 314.22 |
| 2956 | | secBu | 327.428 | 328.28 |
| 2957 | | CH₂Ph | 361.445 | 362.24 |
| 2958 | 4-methylphenyl | H | 271.32 | 272.21 |
| 2959 | | iPr | 313.401 | 314.22 |
| 2960 | | secBu | 327.428 | 328.26 |
| 2961 | | CH₂Ph | 361.445 | 362.28 |
| 2962 | 4-cyanophenyl | secBu | 338.411 | 339.07 |
| 2963 | 3-CF₃-phenyl | H | 325.29 | 326.15 |
| 2964 | | iPr | 367.371 | 368.2 |
| 2965 | | secBu | 381.398 | 382.26 |
| 2966 | | CH₂Ph | 415.415 | 416.21 |

TABLE 19-continued
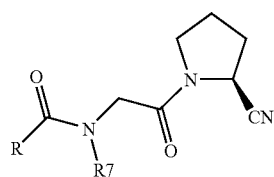
| Example No | R | R7 | Moll Wt | [M + H]+ |
|---|---|---|---|---|
| 2967 | 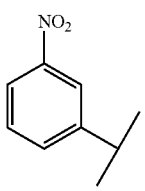 | H | 302.29 | 303.13 |
| 2968 | | CH$_2$Ph | 392.415 | 393.24 |
| 2969 | 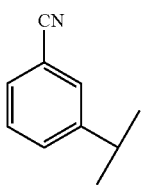 | H | 282.303 | 284.13 |
| 2970 | | iPr | 349.434 | 350.23 |
| 2971 | | SecBu | 363.461 | 364.29 |
| 2972 | | CH$_2$Ph | 397.478 | 398.27 |
| 2973 | 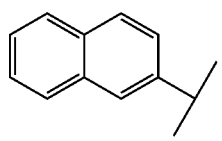 | H | 307.353 | 308.18 |
| 2974 | | iPr | 349.434 | 350.23 |
| 2975 | | secBu | 363.461 | 364.26 |
| 2976 | | CH$_2$Ph | 397.478 | 398.29 |
| 2977 | 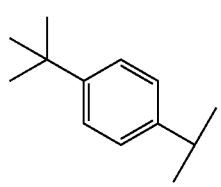 | H | 313.401 | 314.21 |
| 2978 | | iPr | 355.482 | 356.26 |
| 2979 | | secBu | 369.509 | 370.33 |
| 2980 | | CH$_2$Ph | 403.526 | 404.29 |
| 2981 | 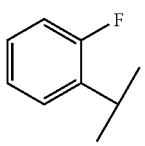 | H | 275.283 | 276.15 |
| 2982 | | iPr | 317.364 | 318.21 |
| 2983 | | secBu | 331.391 | 332.24 |
| 2984 | | CH$_2$Ph | 365.408 | 366.26 |
| 2985 | 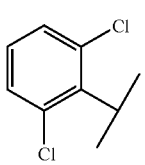 | H | 326.183 | 326.12 |
| 2986 | | iPr | 368.264 | 368.13 |
| 2987 | | secBu | 382.291 | 382.18 |
| 2988 | | CH$_2$Ph | 416.308 | 416.14 |
| 2989 | 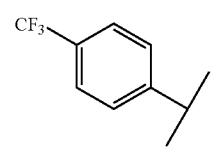 | H | 325.29 | 326.19 |
| 2990 | | iPr | 367.371 | 368.19 |
| 2991 | | secBu | 381.398 | 382.25 |
| 2992 | | CH$_2$Ph | 415.415 | 416.21 |

TABLE 19-continued
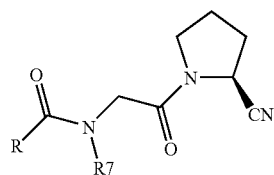
| Example No | R | R7 | Moll Wt | [M + H]+ |
|---|---|---|---|---|
| 2993 | 3-Br-C6H4-CH(CH3)- | H | 336.194 | 336.0 |
| 2994 | | iPr | 378.275 | 378.14 |
| 2995 | | secBu | 392.302 | 392.19 |
| 2996 | | CH2Ph | 426.319 | 426.15 |
| 2997 | 2-MeO-C6H4-CH(CH3)- | iPr | 329.4 | 330.25 |
| 2998 | 4-BuO-C6H4-CH(CH3)- | H | 329.4 | 330.24 |
| 2999 | | iPr | 371.481 | 372.24 |
| 3000 | | secBu | 385.508 | 386.34 |
| 3001 | | CH2Ph | 419.525 | 420.28 |
| 3002 | 2,5-(MeO)2-C6H3-CH2CH(CH3)- | H | 331.372 | 332.22 |
| 3003 | | iPr | 373.453 | 374.25 |
| 3004 | | secBu | 387.48 | 388.3 |
| 3005 | | CH2Ph | 421.497 | 422.25 |
| 3006 | 4-pentyl-C6H4-CH(CH3)- | H | 341.455 | 343.45 |
| 3007 | | iPr | 383.536 | 384.33 |
| 3008 | | secBu | 397.563 | 398.35 |
| 3009 | | CH2Ph | 431.58 | 432.3 |
| 3010 | PhCH(CH3)- | H | 271.32 | 272.18 |
| 3011 | | iPr | 313.401 | 314.2 |
| 3012 | | secBu | 327.428 | 328.29 |
| 3013 | | CH2Ph | 361.445 | 362.26 |
| 3014 | Ph(CH2)2CH(CH3)- | H | 285.347 | 286.21 |
| 3015 | | iPr | 327.428 | 328.25 |
| 3016 | | secBu | 341.455 | 342.32 |
| 3017 | | CH2Ph | 375.472 | 376.3 |
| 3018 | benzothiophen-2-yl-CH(CH3)- | iPr | 355.46 | 356.15 |
| 3019 | thiophen-2-yl-CH(CH3)- | H | 263.319 | 264.14 |
| 3020 | | iPr | 305.4 | 306.15 |
| 3021 | | secBu | 319.427 | 320.21 |
| 3022 | | CH2Ph | 353.444 | 354.22 |

TABLE 19-continued
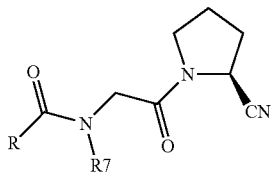
| Example No | R | R7 | Moll Wt | [M + H]+ |
|---|---|---|---|---|
| 3023 | 2-furyl-CH(CH3)- | H | 247.254 | 248.14 |
| 3024 | | iPr | 289.335 | 290.14 |
| 3025 | | secBu | 303.362 | 304.24 |
| 3026 | | CH2Ph | 337.379 | 338.21 |
| 3027 | PhCH2OCH2C(CH3)2- | H | 301.346 | 302.2 |
| 3028 | | iPr | 343.427 | 344.22 |
| 3029 | | secBu | 357.454 | 358.3 |
| 3030 | | CH2Ph | 391.471 | 392.31 |
| 3031 | cyclohexyl-CH(CH3)- | H | 263.341 | 264.19 |
| 3032 | | iPr | 305.422 | 306.2 |
| 3033 | | secBu | 319.449 | 320.32 |
| 3034 | | CH2Ph | 353.466 | 354.33 |
| 3035 | cyclopentyl-CH(CH3)- | H | 249.314 | 250.18 |
| 3036 | | iPr | 291.395 | 292.19 |
| 3037 | | CH2Ph | 339.439 | 340.25 |
| 3038 | cyclobutyl-CH(CH3)- | H | 235.287 | 236.13 |
| 3039 | | iPr | 277.368 | 278.17 |
| 3040 | | secBu | 291.395 | 292.29 |
| 3041 | | CH2Ph | 325.412 | 326.26 |
| 3042 | cyclopropyl-CH(CH3)- | H | 221.26 | 222.13 |
| 3043 | | iPr | 263.341 | 264.18 |
| 3044 | | secBu | 277.368 | 278.24 |
| 3045 | | CH2Ph | 311.385 | 312.23 |
| 3046 | cyclopentyl-CH2CH(CH3)- | H | 263.341 | 264.23 |
| 3047 | | iPr | 305.422 | 306.24 |
| 3048 | | secBu | 319.449 | 320.31 |
| 3049 | | CH2Ph | 353.466 | 354.3 |
| 3050 | tBu-CH(CH3)- | H | 237.303 | 238.2 |
| 3051 | | iPr | 279.384 | 280.21 |
| 3052 | | secBu | 293.411 | 294.28 |
| 3053 | | CH2Ph | 327.428 | 328.29 |
| 3054 | (CH3)3CCH2CH(CH3)- | iPr | 293.411 | 294.2 |
| 3055 | CH3(CH2)4CH(CH3)- | iPr | 293.411 | 294.2 |
| 3056 | (C4H9)(C2H5)CHCH(CH3)- | H | 279.384 | 280.25 |
| 3057 | | iPr | 321.465 | 322.27 |
| 3058 | | CH2Ph | 369.509 | 370.36 |

TABLE 19-continued
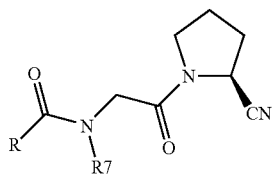
| Example No | R | R7 | Moll Wt | [M + H]+ |
|---|---|---|---|---|
| 3059 | (methyl ester, branched chain) | iPr | 309.366 | 310.2 |
| 3060 | (methyl ester, longer branched chain) | iPr | 365.474 | 366.29 |
| 3061 | phenyl-cyclopropyl | H | 297.358 | 298.18 |
| 3062 | | iPr | 339.439 | 340.23 |
| 3063 | | secBu | 353.466 | 354.3 |
| 3064 | | CH₂Ph | 387.483 | 388.28 |
| 3065 | 2-(OCF₃)phenyl | H | 341.289 | 342.15 |
| 3066 | | iPr | 383.37 | 384.2 |
| 3067 | | secBu | 397.397 | 398.25 |
| 3068 | | CH₂Ph | 431.414 | 432.16 |
| 3069 | 2,6-difluorophenyl | H | 293.273 | 294.16 |
| 3070 | | iPr | 335.354 | 336.21 |
| 3071 | | secBu | 349.381 | 350.19 |
| 3072 | | CH₂Ph | 383.398 | 384.22 |
| 3073 | 4-(NMe₂)phenyl | H | 300.362 | 301.18 |
| 3074 | | CH₂Ph | 390.487 | 391.34 |
| 3075 | adamantyl | H | 315.417 | 316.26 |
| 3076 | | iPr | 357.498 | 358.27 |
| 3077 | | secBu | 371.525 | 372.32 |
| 3078 | | CH₂Ph | 405.542 | 406.31 |
| 3079 | 2,4,5-trifluorophenyl | H | 311.263 | 312.13 |
| 3080 | | iPr | 353.344 | 354.17 |
| 3081 | | secBu | 367.371 | 368.24 |
| 3082 | | CH₂Ph | 401.388 | 402.22 |
| 3083 | thienyl | H | 277.346 | 278.15 |
| 3084 | | secBu | 333.454 | 334.24 |
| 3085 | | CH₂Ph | 367.471 | 368.23 |

TABLE 19-continued
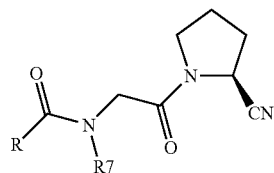
| Example No | R | R7 | Moll Wt | [M + H]+ |
|---|---|---|---|---|
| 3086 | phenoxyisobutyl | H | 287.319 | 288.18 |
| 3087 | | iPr | 329.4 | 330.22 |
| 3088 | | secBu | 343.427 | 344.28 |
| 3089 | | CH2Ph | 377.444 | 378.27 |
| 3090 | 3,4-difluorophenyl-CH(CH3)- | H | 293.273 | 294.13 |
| 3091 | | iPr | 335.354 | 336.2 |
| 3092 | | secBu | 349.381 | 350.24 |
| 3093 | | CH2Ph | 383.398 | 384.22 |
| 3094 | 1-phenylpropyl(CH3)- | H | 299.374 | 300.21 |
| 3095 | | iPr | 341.455 | 342.26 |
| 3096 | | secBu | 355.482 | 356.28 |
| 3097 | | CH2Ph | 389.499 | 390.3 |
| 3098 | thiophen-3-yl-CH(CH3)- | H | 263.319 | 264.12 |
| 3099 | | iPr | 305.4 | 306.14 |
| 3100 | | secBu | 319.427 | 320.21 |
| 3101 | | CH2Ph | 353.444 | 354.19 |
| 3102 | 2,3-difluorophenyl-CH(CH3)- | H | 293.273 | 294.15 |
| 3103 | | iPr | 335.354 | 336.19 |
| 3104 | | secBu | 349.381 | 350.21 |
| 3105 | | CH2Ph | 383.398 | 384.22 |
| 3106 | benzothiophen-3-yl-CH(CH3)- | iPr | 355.46 | 356.16 |
| 3107 | 3,5-difluorophenyl-CH(CH3)- | H | 293.273 | 294.16 |
| 3108 | | iPr | 335.354 | 336.17 |
| 3109 | | secBu | 349.381 | 350.27 |
| 3110 | | CH2Ph | 383.398 | 384.27 |

TABLE 20

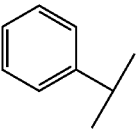

| Example No | R | R8 | X | Y | Mol Wt | [M + H]+ |
|---|---|---|---|---|---|---|
| 3111 | CH₃ | CH₂Ph | S | CH₂ | 303.384 | 304.27 |
| 3112 | | tBu | S | CH₂ | 269.367 | 270.24 |
| 3113 | | iPr | S | CH₂ | 255.34 | 256.26 |
| 3114 | | iPr | CF₂ | CH₂ | 273.283 | 274.17 |
| 3115 | | iPr | —CH=CH— | | 235.287 | 236.1 |
| 3116 | 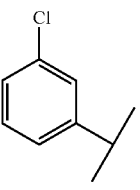 | CH₂Ph | S | CH₂ | 365.455 | 366.25 |
| 3117 | | tBu | S | CH₂ | 331.438 | 332.21 |
| 3118 | | iPr | S | CH₂ | 317.411 | 318.15 |
| 3119 | | iPr | CF₂ | CH₂ | 335.354 | 336.2 |
| 3120 | | iPr | —CH=CH— | | 297.358 | 298.14 |
| 3121 | 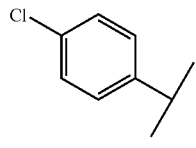 | CH₂Ph | S | CH₂ | 399.9 | 401.29 |
| 3122 | | iPr | S | CH₂ | 351.856 | 352.2 |
| 3123 | | iPr | CF₂ | CH₂ | 369.799 | 370.16 |
| 3124 | | iPr | —CH=CH— | | 331.803 | 332.16 |
| 3125 | 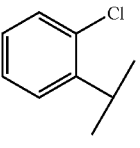 | CH₂Ph | S | CH₂ | 399.9 | 401.26 |
| 3126 | | tBu | S | CH₂ | 365.883 | 366.21 |
| 3127 | | iPr | S | CH₂ | 351.856 | 352.19 |
| 3128 | | iPr | CF₂ | CH₂ | 369.799 | 370.15 |
| 3129 | | iPr | —CH=CH— | | 331.803 | 332.13 |
| 3130 | 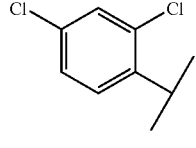 | CH₂Ph | S | CH₂ | 399.9 | 401.26 |
| 3131 | | tBu | S | CH₂ | 365.883 | 366.2 |
| 3132 | | iPr | S | CH₂ | 351.856 | 352.26 |
| 3133 | | iPr | CF₂ | CH₂ | 369.799 | 370.18 |
| 3134 | | iPr | —CH=CH— | | 331.803 | 332.16 |
| 3135 | 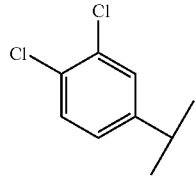 | CH₂Ph | S | CH₂ | 434.345 | 435.33 |
| 3136 | | iPr | S | CH₂ | 386.301 | 386.11 |
| 3137 | | iPr | CF₂ | CH₂ | 404.244 | 404.12 |
| 3138 | | iPr | —CH=CH— | | 366.248 | 366.1 |
| 3139 | 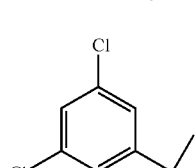 | CH₂Ph | S | CH₂ | 434.345 | 435.23 |
| 3140 | | tBu | S | CH₂ | 400.328 | 400.25 |
| 3141 | | iPr | S | CH₂ | 386.301 | 386.2 |
| 3142 | | iPr | CF₂ | CH₂ | 404.244 | 404.14 |
| 3143 | | iPr | —CH=CH— | | 366.248 | 366.12 |
| 3144 | | CH₂Ph | S | CH₂ | 434.345 | 435.13 |
| 3145 | | iPr | S | CH₂ | 386.301 | 386.2 |

TABLE 20-continued

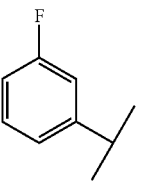

| Example No | R | R8 | X | Y | Mol Wt | [M + H]+ |
|---|---|---|---|---|---|---|
| 3146 | 3-F-C6H4- | CH2Ph | S | CH2 | 383.445 | 384.27 |
| 3147 | | tBu | S | CH2 | 349.428 | 350.18 |
| 3148 | | iPr | S | CH2 | 335.401 | 336.21 |
| 3149 | | iPr | CF2 | CH2 | 353.344 | 354.16 |
| 3150 | | iPr | —CH=CH— | | 315.348 | 316.16 |
| 3151 | 4-F-C6H4- | CH2Ph | S | CH2 | 383.445 | 384.25 |
| 3152 | | iPr | S | CH2 | 335.401 | 336.24 |
| 3153 | | iPr | CF2 | CH2 | 353.344 | 354.23 |
| 3154 | | iPr | —CH=CH— | | 315.348 | 316.17 |
| 3155 | 4-MeO-C6H4- | CH2Ph | S | CH2 | 395.481 | 396.26 |
| 3156 | | tBu | S | CH2 | 361.464 | 362.25 |
| 3157 | | iPr | S | CH2 | 347.437 | 348.25 |
| 3158 | | iPr | CF2 | CH2 | 365.38 | 366.21 |
| 3159 | | iPr | —CH=CH— | | 327.384 | 328.2 |
| 3160 | 3-MeO-C6H4- | CH2Ph | S | CH2 | 395.481 | 396.26 |
| 3161 | | tBu | S | CH2 | 361.464 | 362.21 |
| 3162 | | iPr | S | CH2 | 347.437 | 348.23 |
| 3163 | | iPr | CF2 | CH2 | 365.38 | 366.22 |
| 3164 | | iPr | —CH=CH— | | 327.384 | 328.19 |
| 3165 | benzodioxole | CH2Ph | S | CH2 | 409.464 | 410.34 |
| 3166 | 2-Me-C6H4- | CH2Ph | S | CH2 | 379.482 | 380.32 |
| 3167 | | tBu | S | CH2 | 345.465 | 0 |
| 3168 | | iPr | S | CH2 | 331.438 | 332.26 |
| 3169 | | iPr | CF2 | CH2 | 349.381 | 350.26 |
| 3170 | | iPr | —CH=CH— | | 311.385 | 312.21 |
| 3171 | 3-Me-C6H4- | CH2Ph | S | CH2 | 379.482 | 380.27 |
| 3172 | | tBu | S | CH2 | 345.465 | 346.26 |
| 3173 | | iPr | S | CH2 | 331.438 | 332.21 |
| 3174 | | iPr | CF2 | CH2 | 349.381 | 350.2 |
| 3175 | | iPr | —CH=CH— | | 311.385 | 312.17 |
| 3176 | 4-Me-C6H4- | CH2Ph | S | CH2 | 379.482 | 380.3 |
| 3177 | | tBu | S | CH2 | 345.465 | 346.24 |
| 3178 | | iPr | S | CH2 | 331.438 | 332.23 |
| 3179 | | iPr | CF2 | CH2 | 349.381 | 350.22 |
| 3180 | | iPr | —CH=CH— | | 311.385 | 312.2 |

TABLE 20-continued
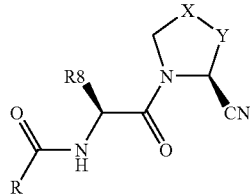
| Example No | R | R8 | X | Y | Mol Wt | [M + H]+ |
|---|---|---|---|---|---|---|
| 3181 | 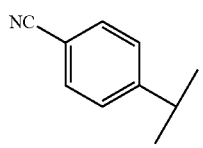 | CH₂Ph | S | CH₂ | 390.465 | 391.31 |
| 3182 | | iPr | —CH=CH— | | 322.368 | 322.26 |
| 3183 | 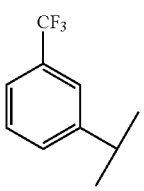 | CH₂Ph | S | CH₂ | 433.452 | 434.16 |
| 3184 | | iPr | S | CH₂ | 385.408 | 386.23 |
| 3185 | | iPr | CF₂ | CH₂ | 403.351 | 404.15 |
| 3186 | | iPr | —CH=CH— | | 365.355 | 366.18 |
| 3187 | 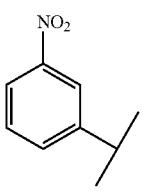 | CH₂Ph | S | CH₂ | 410.452 | 410.3 |
| 3188 | | iPr | S | CH₂ | 362.408 | 363.22 |
| 3189 | | iPr | CF₂ | CH₂ | 380.351 | 381.21 |
| 3190 | | iPr | —CH=CH— | | 342.355 | 343.21 |
| 3191 | 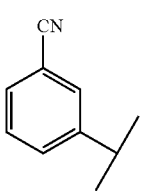 | CH₂Ph | S | CH₂ | 390.465 | 391.23 |
| 3192 | 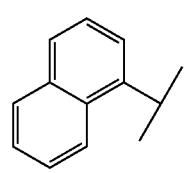 | CH₂Ph | S | CH₂ | 415.515 | 416.24 |
| 3193 | | iPr | S | CH₂ | 367.471 | 368.28 |
| 3194 | | iPr | CF₂ | CH₂ | 385.414 | 386.24 |
| 3195 | | iPr | —CH=CH— | | 347.418 | 348.19 |
| 3196 | 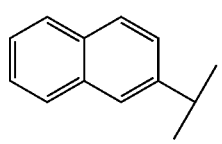 | CH₂Ph | S | CH₂ | 415.515 | 416.66 |
| 3197 | | tBu | S | CH₂ | 381.498 | 382.26 |
| 3198 | | iPr | S | CH₂ | 367.471 | 368.26 |
| 3199 | | iPr | CF₂ | CH₂ | 385.414 | 386.23 |
| 3200 | | iPr | —CH=CH— | | 347.418 | 348.21 |
| 3201 | 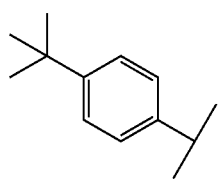 | CH₂Ph | S | CH₂ | 421.563 | 422.28 |
| 3202 | | tBu | S | CH₂ | 387.546 | 388.29 |
| 3203 | | iPr | S | CH₂ | 373.519 | 374.27 |
| 3204 | | iPr | CF₂ | CH₂ | 391.462 | 392.29 |
| 3205 | | iPr | —CH=CH— | | 353.466 | 354.23 |

TABLE 20-continued
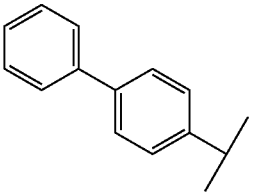
| Example No | R | R8 | X | Y | Mol Wt | [M + H]+ |
|---|---|---|---|---|---|---|
| 3206 | 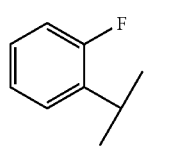 | CH₂Ph | S | CH₂ | 441.553 | 443.9 |
| 3207 | 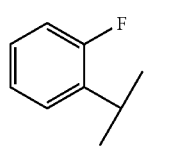 | CH₂Ph | S | CH₂ | 383.445 | 384.27 |
| 3208 | | iPr | CF₂ | CH₂ | 353.344 | 354.17 |
| 3209 | | iPr | —CH=CH— | | 315.348 | 316.19 |
| 3210 | 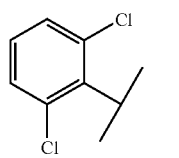 | CH₂Ph | S | CH₂ | 434.345 | 435.22 |
| 3211 | | tBu | S | CH₂ | 400.328 | 400.13 |
| 3212 | | iPr | S | CH₂ | 386.301 | 386.2 |
| 3213 | | iPr | CF₂ | CH₂ | 404.244 | 404.13 |
| 3214 | | iPr | —CH=CH— | | 366.248 | 366.06 |
| 3215 | 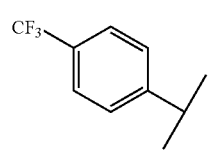 | CH₂Ph | S | CH₂ | 433.452 | 434.19 |
| 3216 | | tBu | S | CH₂ | 399.435 | 400.26 |
| 3217 | | iPr | S | CH₂ | 385.408 | 386.24 |
| 3218 | | iPr | CH₂ | CH₂ | 403.351 | 404.17 |
| 3219 | | iPr | —CH=CH— | | 365.355 | 366.15 |
| 3220 | 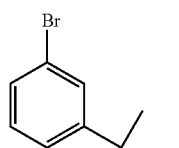 | CH₂Ph | S | CH₂ | 444.356 | 445.14 |
| 3221 | | tBu | S | CH₂ | 410.339 | 410.09 |
| 3222 | | iPr | S | CH₂ | 396.312 | 396.15 |
| 3223 | | iPr | CF₂ | CH₂ | 414.255 | 414.09 |
| 3224 | | iPr | —CH=CH— | | 376.259 | 376.12 |
| 3225 | 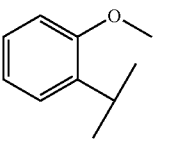 | CH₂Ph | S | CH₂ | 395.481 | 396.26 |
| 3226 | 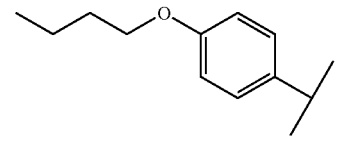 | CH₂Ph | S | CH₂ | 437.562 | 438.3 |
| 3227 | | iPr | S | CH₂ | 389.518 | 390.29 |
| 3228 | | iPr | CF₂ | CH₂ | 407.461 | 408.26 |
| 3229 | | iPr | —CH=CH— | | 369.465 | 370.25 |
| 3230 | 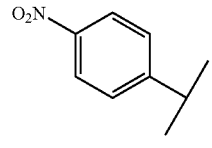 | CH₂Ph | S | CH₂ | 410.452 | 411.52 |

TABLE 20-continued

| Example No | R | R8 | X | Y | Mol Wt | [M + H]+ |
|---|---|---|---|---|---|---|
| 3231 | 2,5-dimethoxybenzyl-CH(CH3)- | CH2Ph | S | CH2 | 439.534 | 440.29 |
| 3232 | | tBu | S | CH2 | 405.517 | 406.26 |
| 3233 | | iPr | CF2 | CH2 | 409.433 | 410.23 |
| 3234 | 4-pentylbenzyl-CH(CH3)- | CH2Ph | S | CH2 | 449.617 | 450.34 |
| 3235 | | tBu | S | CH2 | 415.6 | 416.32 |
| 3236 | | iPr | S | CH2 | 401.573 | 402.3 |
| 3237 | | iPr | CF2 | CH2 | 419.516 | 420.25 |
| 3238 | | iPr | —CH=CH— | | 381.52 | 382.29 |
| 3239 | benzyl-CH(CH3)- | CH2Ph | S | CH2 | 379.482 | 380.28 |
| 3240 | | tBu | S | CH2 | 345.465 | 346.24 |
| 3241 | | iPr | S | CH2 | 331.438 | 332.23 |
| 3242 | | iPr | CF2 | CH2 | 349.381 | 350.2 |
| 3243 | | iPr | —CH=CH— | | 311.385 | 312.18 |
| 3244 | phenethyl-CH(CH3)- | CH2Ph | S | CH2 | 393.509 | 394.31 |
| 3245 | | tBu | S | CH2 | 359.492 | 360.23 |
| 3246 | | iPr | S | CH2 | 345.465 | 346.27 |
| 3247 | | iPr | CF2 | CH2 | 363.408 | 364.21 |
| 3248 | | iPr | —CH=CH— | | 325.412 | 326.23 |
| 3249 | benzothiophene-2-yl-CH(CH3)- | CH2Ph | S | CH2 | 421.541 | 422.18 |
| 3250 | thiophen-2-yl-CH(CH3)- | CH2Ph | S | CH2 | 371.481 | 372.24 |
| 3251 | | tBu | S | CH2 | 337.464 | 338.17 |
| 3252 | | iPr | S | CH2 | 323.437 | 324.19 |
| 3253 | | iPr | CF2 | CH2 | 341.38 | 342.14 |
| 3254 | | iPr | —CH=CH— | | 303.384 | 304.1 |
| 3255 | furan-2-yl-CH(CH3)- | CH2Ph | S | CH2 | 355.416 | 356.22 |
| 3256 | | tBu | S | CH2 | 321.399 | 322.19 |
| 3257 | | iPr | S | CH2 | 307.372 | 308.27 |
| 3258 | | iPr | CF2 | CH2 | 325.315 | 326.2 |
| 3259 | | iPr | —CH=CH— | | 287.319 | 288.13 |
| 3260 | 2-chloropyridin-3-yl-CH(CH3)- | CH2Ph | S | CH2 | 400.888 | 401.19 |
| 3261 | benzyloxy-CH(CH3)- | CH2Ph | S | CH2 | 409.508 | 410.23 |
| 3262 | | tBu | S | CH2 | 375.491 | 376.29 |
| 3263 | | iPr | S | CH2 | 361.464 | 362.26 |
| 3264 | | iPr | CF2 | CH2 | 379.407 | 380.25 |
| 3265 | | iPr | —CH=CH— | | 341.411 | 342.21 |
| 3266 | cyclohexyl-CH(CH3)- | CH2Ph | S | CH2 | 371.503 | 372.32 |
| 3267 | | tBu | S | CH2 | 337.486 | 338.16 |
| 3268 | | iPr | S | CH2 | 323.459 | 324.25 |
| 3269 | | iPr | CF2 | CH2 | 341.402 | 342.22 |
| 3270 | | iPr | —CH=CH— | | 303.406 | 304.21 |

TABLE 20-continued

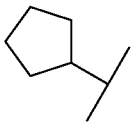

| Example No | R | R8 | X | Y | Mol Wt | [M + H]+ |
|---|---|---|---|---|---|---|
| 3271 |  | CH₂Ph | S | CH₂ | 357.476 | 358.27 |
| 3272 | cyclopentyl-CH< | iPr | —CH=CH— |  | 289.379 | 290.24 |
| 3273 |  | CH₂Ph | S | CH₂ | 343.449 | 344.27 |
| 3274 |  | tBu | S | CH₂ | 309.432 | 310.34 |
| 3275 | cyclobutyl-CH< | iPr | S | CH₂ | 295.405 |  |
| 3276 |  | iPr | CF₂ | CH₂ | 313.348 | 314.19 |
| 3277 |  | iPr | —CH=CH— |  | 275.352 | 276.2 |
| 3278 |  | CH₂Ph | S | CH₂ | 329.422 | 330.23 |
| 3279 |  | tBu | S | CH₂ | 295.405 | 296.24 |
| 3280 | cyclopropyl-CH< | iPr | S | CH₂ | 281.378 | 282.25 |
| 3281 |  | iPr | CF₂ | CH₂ | 299.321 | 300.18 |
| 3282 |  | iPr | —CH=CH— |  | 261.325 | 262.15 |
| 3283 |  | CH₂Ph | S | CH₂ | 371.503 | 372.32 |
| 3284 |  | tBu | S | CH₂ | 337.486 | 338.29 |
| 3285 | cyclopentyl-CH₂-CH< | iPr | S | CH₂ | 323.459 | 324.28 |
| 3286 |  | iPr | CF₂ | CH₂ | 341.402 | 342.25 |
| 3287 |  | iPr | —CH=CH— |  | 303.406 | 304.19 |
| 3288 |  | CH₂Ph | S | CH₂ | 345.465 | 346.29 |
| 3289 |  | tBu | S | CH₂ | 311.448 | 312.23 |
| 3290 | tBu-CH< | iPr | S | CH₂ | 297.421 | 298.23 |
| 3291 |  | iPr | CF₂ | CH₂ | 315.364 | 316.22 |
| 3292 |  | iPr | —CH=CH— |  | 277.368 | 278.22 |
| 3293 |  | CH₂Ph | S | CH₂ | 359.492 | 360.29 |
| 3294 |  | CH₂Ph | S | CH₂ | 359.492 | 360.3 |
| 3295 |  | CH₂Ph | S | CH₂ | 387.546 | 388.35 |
| 3296 |  | tBu | S | CH₂ | 353.529 | 354.32 |
| 3297 |  | iPr | S | CH₂ | 339.502 | 340.36 |
| 3298 |  | iPr | CF₂ | CH₂ | 357.445 | 358.29 |
| 3299 |  | iPr | —CH=CH— |  | 319.449 | 320.27 |
| 3300 |  | CH₂Ph | S | CH₂ | 375.447 | 376.25 |
| 3301 |  | CH₂Ph | S | CH₂ | 431.555 | 432.31 |
| 3302 |  | CH₂Ph | S | CH₂ | 405.52 | 406.26 |
| 3303 |  | tBu | S | CH₂ | 371.503 | 372.24 |
| 3304 |  | iPr | S | CH₂ | 357.476 | 358.25 |
| 3305 |  | iPr | CF₂ | CH₂ | 375.419 | 376.24 |
| 3306 |  | iPr | —CH=CH— |  | 337.423 | 338.21 |

TABLE 20-continued

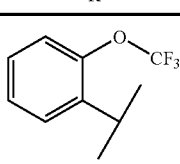

| Example No | R | R8 | X | Y | Mol Wt | [M + H]+ |
|---|---|---|---|---|---|---|
| 3307 | 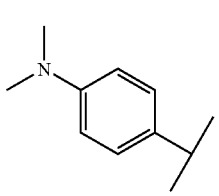 | CH₂Ph | S | CH₂ | 449.451 | 450.25 |
| 3308 | | tBu | S | CH₂ | 415.434 | 416.19 |
| 3309 | | iPr | S | CH₂ | 401.407 | 402.23 |
| 3310 | | iPr | CF₂ | CH₂ | 419.35 | 420.19 |
| 3311 | | iPr | —CH=CH— | | 381.354 | 382.17 |
| 3312 | 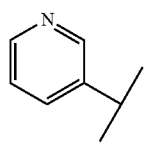 | CH₂Ph | S | CH₂ | 401.435 | 402.22 |
| 3313 | | tBu | S | CH₂ | 367.418 | 368.18 |
| 3314 | | iPr | S | CH₂ | 353.391 | 354.22 |
| 3315 | | iPr | CF₂ | CH₂ | 371.334 | 372.19 |
| 3316 | | iPr | —CH=CH— | | 333.338 | 334.14 |
| 3317 | 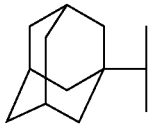 | CH₂Ph | S | CH₂ | 408.524 | 409.29 |
| 3318 | | tBu | S | CH₂ | 374.507 | 375.28 |
| 3319 | | iPr | S | CH₂ | 360.48 | 361.28 |
| 3320 | | iPr | CF₂ | CH₂ | 378.423 | 379.27 |
| 3321 | 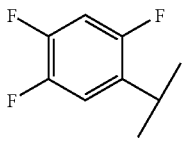 | CH₂Ph | S | CH₂ | 366.443 | 367.24 |
| 3322 | 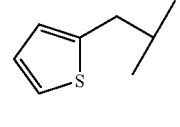 | CH₂Ph | S | CH₂ | 423.579 | 424.3 |
| 3323 | | tBu | S | CH₂ | 389.562 | 390.31 |
| 3324 | | iPr | CF₂ | CH₂ | 393.478 | 394.3 |
| 3325 | | iPr | —CH=CH— | | 355.482 | 356.25 |
| 3326 | 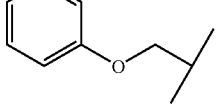 | CH₂Ph | S | CH₂ | 419.425 | 420.17 |
| 3327 | | tBu | S | CH₂ | 385.408 | 385.24 |
| 3328 | | iPr | S | CH₂ | 371.381 | 372.2 |
| 3329 | | iPr | CF₂ | CH₂ | 389.324 | 390.22 |
| 3330 | | iPr | —CH=CH— | | 351.328 | 352.15 |
| 3331 | 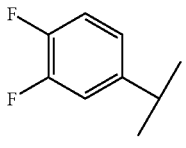 | CH₂Ph | S | CH₂ | 385.508 | 386.26 |
| 3332 | | tBu | S | CH₂ | 351.491 | 352.23 |
| 3333 | | iPr | S | CH₂ | 337.464 | 338.25 |
| 3334 | | iPr | CF₂ | CH₂ | 355.407 | 356.18 |
| 3335 | | iPr | —CH=CH— | | 317.411 | 318.15 |
| 3336 | | CH₂Ph | S | CH₂ | 395.481 | 396.28 |
| 3337 | | tBu | S | CH₂ | 361.464 | 362.29 |
| 3338 | | iPr | S | CH₂ | 347.437 | 348.24 |
| 3339 | | iPr | CF₂ | CH₂ | 365.38 | 366.19 |
| 3340 | | iPr | —CH=CH— | | 327.384 | 328.22 |
| 3341 | | CH₂Ph | S | CH₂ | 401.435 | 402.23 |
| 3342 | | tBu | S | CH₂ | 367.418 | 368.29 |
| 3343 | | iPr | S | CH₂ | 353.391 | 354.17 |
| 3344 | | iPr | CF₂ | CH₂ | 371.334 | 372.16 |
| 3345 | | iPr | —CH=CH— | | 333.338 | 334.21 |

TABLE 20-continued

| Example No | R | R8 | X | Y | Mol Wt | [M + H]+ |
|---|---|---|---|---|---|---|
| 3346 | (1-ethylpropyl)phenyl | CH₂Ph | S | CH₂ | 407.536 | 408.25 |
| 3347 | | tBu | S | CH₂ | 373.519 | 374.29 |
| 3348 | | iPr | S | CH₂ | 359.492 | 360.28 |
| 3349 | | iPr | CF₂ | CH₂ | 377.435 | 378.27 |
| 3350 | | iPr | —CH=CH— | | 339.439 | 340.23 |
| 3351 | thienyl-isopropyl | CH₂Ph | S | CH₂ | 371.481 | 372.2 |
| 3352 | | tBu | S | CH₂ | 337.464 | 338.16 |
| 3353 | | iPr | S | CH₂ | 323.437 | 324.13 |
| 3354 | | iPr | CF₂ | CH₂ | 341.38 | 342.16 |
| 3355 | | iPr | —CH=CH— | | 303.384 | 304.1 |
| 3356 | 2,3-difluorophenyl-isopropyl | CH₂Ph | S | CH₂ | 401.435 | 402.24 |
| 3357 | | tBu | S | CH₂ | 367.418 | 368.3 |
| 3358 | | iPr | S | CH₂ | 353.391 | 354.15 |
| 3359 | | iPr | CF₂ | CH₂ | 371.334 | 372.18 |
| 3360 | | iPr | —CH=CH— | | 333.338 | 334.16 |
| 3361 | tert-butyl-benzothienyl | CH₂Ph | S | CH₂ | 421.541 | 422.22 |
| 3362 | 3,5-difluorophenyl-isopropyl | tBu | S | CH₂ | 367.418 | 368.27 |
| 3363 | | iPr | S | CH₂ | 353.391 | 354.2 |
| 3364 | | iPr | CF₂ | CH₂ | 371.334 | 372.24 |
| 3365 | | iPr | —CH=CH— | | 333.338 | 334.23 |

TABLE 21

| Example No | R' | Z | R9 | Mol Wt | [M + H]+ |
|---|---|---|---|---|---|
| 3366 | Et | O | H | 224.264 | 225.13 |
| 3367 | | O | CH₂Ph | 314.389 | 315.25 |
| 3368 | iPr | O | H | 238.291 | 239.21 |
| 3369 | | O | CH₂Ph | 328.416 | 329.26 |
| 3370 | | O | secBu | 294.399 | 295.27 |
| 3371 | nHex | O | H | 280.372 | 281.3 |
| 3372 | | O | CH₂Ph | 370.497 | 371.31 |

TABLE 21-continued
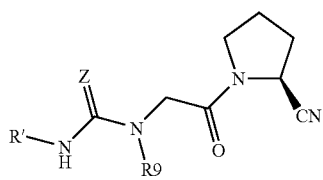
| Example No | R' | Z | R9 | Mol Wt | [M + H]+ |
|---|---|---|---|---|---|
| 3373 | cyclohexylmethyl | O | H | 278.356 | 279.28 |
| 3374 | | O | CH₂Ph | 368.481 | 369.32 |
| 3375 | | O | secBu | 334.464 | 335.31 |
| 3376 | phenethyl | O | H | 286.335 | 287.23 |
| 3377 | | O | CH₂Ph | 376.46 | 377.26 |
| 3378 | | O | secBu | 342.443 | 343.26 |
| 3379 | ethyl ester chain | O | H | 296.327 | 297.23 |
| 3380 | | O | CH₂Ph | 386.452 | 387.29 |
| 3381 | phenyl ketone | O | H | 300.318 | 301.19 |
| 3382 | | O | CH₂Ph | 390.443 | 391.26 |
| 3383 | 1-phenylethyl | O | H | 272.308 | 273.22 |
| 3384 | | O | CH₂Ph | 362.433 | 363.23 |
| 3385 | | O | secBu | 328.416 | 329.25 |
| 3386 | 4-methoxyphenyl-ethyl | O | H | 302.334 | 303.23 |
| 3387 | | O | CH₂Ph | 392.459 | 393.27 |
| 3388 | 4-methylphenyl-ethyl | O | H | 286.335 | 287.25 |
| 3389 | | O | CH₂Ph | 376.46 | 377.29 |
| 3390 | | O | secBu | 342.443 | 343.29 |
| 3391 | 2,3-dichlorophenyl-ethyl | O | H | 341.198 | 341.14 |
| 3392 | | O | CH₂Ph | 431.323 | 431.15 |
| 3393 | 4-fluorophenyl-ethyl | O | H | 290.298 | 291.22 |
| 3394 | | O | CH₂Ph | 380.423 | 381.25 |
| 3395 | | O | secBu | 346.406 | 347.22 |

TABLE 21-continued
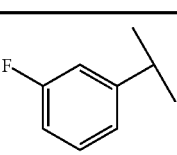
| Example No | R' | Z | R9 | Mol Wt | [M + H]+ |
|---|---|---|---|---|---|
| 3396 | | O | H | 290.298 | 291.21 |
| 3397 | 3-F-C6H4-CH(CH3)- | O | CH2Ph | 380.423 | 381.26 |
| 3398 | | O | H | 290.298 | 291.19 |
| 3399 | 2-F-C6H4-CH(CH3)- | O | CH2Ph | 380.423 | 381.26 |
| 3400 | | O | H | 322.368 | 323.22 |
| 3401 | 1-naphthyl-CH(CH3)- | O | CH2Ph | 412.493 | 413.24 |
| 3402 | | O | secBu | 378.476 | 379.33 |
| 3403 | | O | H | 340.305 | 341.23 |
| 3404 | 3-CF3-C6H4-CH(CH3)- | O | CH2Ph | 430.43 | 431.2 |
| 3405 | | O | secBu | 396.413 | 397.24 |
| 3406 | | O | H | 306.753 | 307.16 |
| 3407 | 4-Cl-C6H4-CH(CH3)- | O | CH2Ph | 396.878 | 397.23 |
| 3408 | | O | secBu | 362.861 | 363.26 |
| 3409 | | O | H | 306.753 | 307.16 |
| 3410 | 3-Cl-C6H4-CH(CH3)- | O | CH2Ph | 396.878 | 397.22 |
| 3411 | | O | secBu | 362.861 | 363.21 |
| 3412 | | O | H | 306.753 | 307.18 |
| 3413 | 2-Cl-C6H4-CH(CH3)- | O | CH2Ph | 396.878 | 397.21 |
| 3414 | | O | secBu | 362.861 | 363.21 |
| 3415 | | O | H | 302.334 | 303.2 |
| 3416 | 3-MeO-C6H4-CH(CH3)- | O | CH2Ph | 392.459 | 393.28 |
| 3417 | | O | secBu | 358.442 | 359.28 |
| 3418 | | O | H | 302.334 | 303.21 |
| 3419 | 2-MeO-C6H4-CH(CH3)- | O | CH2Ph | 392.459 | 393.31 |

TABLE 21-continued
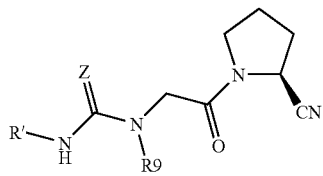
| Example No | R' | Z | R9 | Mol Wt | [M + H]+ |
|---|---|---|---|---|---|
| 3420 | 3-nitrophenyl-CH(CH3)- | O | H | 317.305 | 318.21 |
| 3421 |  | O | CH2Ph | 407.43 | 408.23 |
| 3422 |  | O | secBu | 373.413 | 374.26 |
| 3423 | 2,4-dichlorophenyl-CH(CH3)- | O | H | 341.198 | 341.14 |
| 3424 |  | O | CH2Ph | 431.323 | 431.15 |
| 3425 | phenyl-CH(CH3)C(CH3)3 | O | H | 300.362 | 301.24 |
| 3426 |  | O | CH2Ph | 390.487 | 391.3 |
| 3427 | 3,5-dichlorophenyl-CH(CH3)- | O | H | 341.198 | 341.17 |
| 3428 |  | O | CH2Ph | 431.323 | 431.15 |
| 3429 | 2,5-dimethoxyphenyl-CH(CH3)- | O | H | 332.36 | 333.25 |
| 3430 |  | O | CH2Ph | 422.485 | 423.23 |
| 3431 | 2,6-difluorophenyl-CH(CH3)- | O | H | 308.288 | 309.17 |
| 3432 |  | O | CH2Ph | 398.413 | 399.24 |
| 3433 | biphenyl-CH(CH3)- | O | H | 348.406 | 349.26 |
| 3434 |  | O | CH2Ph | 438.531 | 439.25 |
| 3435 |  | O | secBu | 404.514 | 405.29 |
| 3436 | nPr | S | H | 254.356 | 255.23 |
| 3437 | phenyl-CH2C(CH3)3 | S | H | 302.4 | 303.21 |

TABLE 21-continued
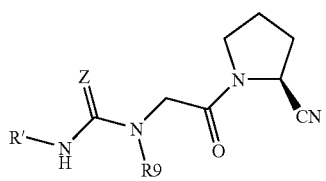
| Example No | R' | Z | R9 | Mol Wt | [M + H]+ |
|---|---|---|---|---|---|
| 3438 | (phenyl-CH2CH2-C(CH3)2-) | S | H | 316.427 | 317.21 |
| 3439 | (4-MeO-phenyl-CH(CH3)-) | S | H | 318.399 | 319.22 |
| 3440 | (phenyl-C(O)-CH(CH3)-) | S | H | 316.383 | 317.16 |
| 3441 | | S | CH2Ph | 406.508 | 407.19 |
| 3442 | (cyclopentyl-CH(CH3)-) | S | H | 280.394 | 281.23 |
| 3443 | | S | CH2Ph | 370.519 | 371.25 |
| 3444 | | S | secBu | 336.502 | 337.26 |
| 3445 | (cyclohexyl-CH2-CH(CH3)-) | S | H | 308.448 | 309.23 |
| 3446 | | S | CH2Ph | 398.573 | 399.31 |
TABLE 22
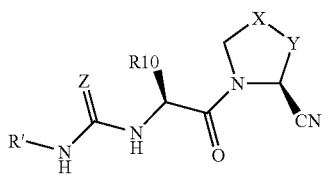
| Example No | R' | Z | R10 | X | Y | Mol Wt | [M + H]+ |
|---|---|---|---|---|---|---|---|
| 3447 | Et | O | iPr | S | CH2 | 284.382 | 285.24 |
| 3448 | | O | tBu | S | CH2 | 298.409 | 299.26 |
| 3449 | | O | iPr | CH=CH | | 264.329 | 265.25 |
| 3450 | iPr | O | iPr | S | CH2 | 298.409 | 299.25 |
| 3451 | | O | iPr | CF2 | CH2 | 316.352 | 317.22 |
| 3452 | | O | tBu | S | CH2 | 312.436 | 313.26 |
| 3453 | | O | iPr | CH=CH | | 278.356 | 279.25 |
| 3454 | nHex | O | iPr | S | CH2 | 340.49 | 341.31 |
| 3455 | | O | iPr | CF2 | CH2 | 358.433 | 359.28 |
| 3456 | | O | tBu | S | CH2 | 354.517 | 355.33 |
| 3457 | | O | iPr | CH=CH | | 320.437 | 321.28 |

TABLE 22-continued

| Example No | R' | Z | R10 | X | Y | Mol Wt | [M + H]+ |
|---|---|---|---|---|---|---|---|
| 3458 | cyclohexyl-CH(CH3)- | O | iPr | S | CH₂ | 338.474 | 339.27 |
| 3459 | | O | iPr | CF₂ | CH₂ | 356.417 | 357.28 |
| 3460 | | O | tBu | S | CH₂ | 352.501 | 353.31 |
| 3461 | | O | iPr | CH=CH | | 318.421 | 319.26 |
| 3462 | phenyl-CH2CH(CH3)- | O | iPr | S | CH₂ | 346.453 | 347.25 |
| 3463 | | O | iPr | CF₂ | CH₂ | 364.396 | 365.27 |
| 3464 | | O | tBu | S | CH₂ | 360.48 | 361.29 |
| 3465 | | O | iPr | CH=CH | | 326.4 | 327.26 |
| 3466 | EtO2C-CH2CH2CH2CH(CH3)- | O | iPr | S | CH₂ | 356.445 | 357.28 |
| 3467 | | O | iPr | CF₂ | CH₂ | 374.388 | 375.26 |
| 3468 | | O | tBu | S | CH₂ | 370.472 | 371.3 |
| 3469 | | O | iPr | CH=CH | | 336.392 | 337.25 |
| 3470 | PhC(O)CH(CH3)- | O | iPr | CF₂ | CH₂ | 378.379 | 379.23 |
| 3471 | | O | iPr | CH=CH | | 340.383 | 341.22 |
| 3472 | Ph-CH(CH3)- | O | iPr | S | CH₂ | 332.426 | 333.23 |
| 3473 | | O | iPr | CF₂ | CH₂ | 350.369 | 351.22 |
| 3474 | | O | tBu | S | CH₂ | 346.453 | 347.26 |
| 3475 | | O | iPr | CH=CH | | 312.373 | 313.21 |
| 3476 | 4-MeO-C6H4-CH(CH3)- | O | iPr | S | CH₂ | 362.452 | 363.25 |
| 3477 | | O | iPr | CF₂ | CH₂ | 380.395 | 381.23 |
| 3478 | | O | tBu | S | CH₂ | 376.479 | 377.28 |
| 3479 | | O | iPr | CH=CH | | 342.399 | 343.22 |
| 3480 | 4-Me-C6H4-CH(CH3)- | O | iPr | S | CH₂ | 346.453 | 347.24 |
| 3481 | | O | iPr | CF₂ | CH₂ | 364.396 | 365.23 |
| 3482 | | O | tBu | S | CH₂ | 360.48 | 361.29 |
| 3483 | | O | iPr | CH=CH | | 326.4 | 327.25 |
| 3484 | 2,3-diCl-C6H3-CH(CH3)- | O | iPr | S | CH₂ | 401.316 | 401.17 |
| 3485 | | O | iPr | CF₂ | CH₂ | 419.259 | 419.14 |
| 3486 | | O | tBu | S | CH₂ | 415.343 | 415.17 |
| 3487 | | O | iPr | CH=CH | | 381.263 | 381.17 |
| 3488 | 4-F-C6H4-CH(CH3)- | O | iPr | S | CH₂ | 350.416 | 351.23 |
| 3489 | | O | iPr | CF₂ | CH₂ | 368.359 | 369.24 |
| 3490 | | O | tBu | S | CH₂ | 364.443 | 365.25 |
| 3491 | | O | iPr | CH=CH | | 330.363 | 331.2 |

TABLE 22-continued

| Example No | R' | Z | R10 | X | Y | Mol Wt | [M + H]+ |
|---|---|---|---|---|---|---|---|
| 3492 | 3-F-C6H4-CH(CH3)- | O | iPr | S | CH2 | 350.416 | 351.23 |
| 3493 | | O | iPr | CF2 | CH2 | 368.359 | 369.2 |
| 3494 | | O | tBu | S | CH2 | 364.443 | 365.26 |
| 3495 | | O | iPr | CH=CH | | 330.363 | 331.25 |
| 3496 | 2-F-C6H4-CH(CH3)- | O | iPr | S | CH2 | 350.416 | 351.24 |
| 3497 | | O | iPr | CF2 | CH2 | 368.359 | 369.24 |
| 3498 | | O | tBu | S | CH2 | 364.443 | 365.25 |
| 3499 | | O | iPr | CH=CH | | 330.363 | 331.23 |
| 3500 | 1-naphthyl-CH(CH3)- | O | iPr | S | CH2 | 382.486 | 383.28 |
| 3501 | | O | iPr | CF2 | CH2 | 400.429 | 401.24 |
| 3502 | | O | tBu | S | CH2 | 396.513 | 397.29 |
| 3503 | | O | iPr | CH=CH | | 362.433 | 363.26 |
| 3504 | 3-CF3-C6H4-CH(CH3)- | O | iPr | S | CH2 | 400.423 | 401.24 |
| 3505 | | O | iPr | CF2 | CH2 | 418.366 | 419.19 |
| 3506 | | O | tBu | S | CH2 | 414.45 | 415.24 |
| 3507 | | O | iPr | CH=CH | | 380.37 | 381.23 |
| 3508 | 4-Cl-C6H4-CH(CH3)- | O | iPr | S | CH2 | 366.871 | 367.21 |
| 3509 | | O | iPr | CF2 | CH2 | 384.814 | 385.21 |
| 3510 | | O | tBu | S | CH2 | 380.898 | 381.24 |
| 3511 | | O | iPr | CH=CH | | 346.818 | 347.2 |
| 3512 | 3-Cl-C6H4-CH(CH3)- | O | iPr | S | CH2 | 366.871 | 367.21 |
| 3513 | | O | iPr | CF2 | CH2 | 384.814 | 385.2 |
| 3514 | | O | tBu | S | CH2 | 380.898 | 381.24 |
| 3515 | | O | iPr | CH=CH | | 346.818 | 347.19 |
| 3516 | 2-Cl-C6H4-CH(CH3)- | O | iPr | S | CH2 | 366.871 | 367.2 |
| 3517 | | O | iPr | CF2 | CH2 | 384.814 | 385.2 |
| 3518 | | O | tBu | S | CH2 | 380.898 | 381.23 |
| 3519 | | O | iPr | CH=CH | | 346.818 | 347.18 |
| 3520 | 3-MeO-C6H4-CH(CH3)- | O | iPr | S | CH2 | 362.452 | 363.26 |
| 3521 | | O | iPr | CF2 | CH2 | 380.395 | 381.25 |
| 3522 | | O | tBu | S | CH2 | 376.479 | 377.28 |
| 3523 | | O | iPr | CH=CH | | 342.399 | 343.25 |
| 3524 | 2-MeO-C6H4-CH(CH3)- | O | iPr | S | CH2 | 362.452 | 363.27 |
| 3525 | | O | tBu | S | CHs | 376.479 | 377.27 |
| 3526 | | O | iPr | CH=CH | | 342.399 | 343.27 |

TABLE 22-continued

| Example No | R' | Z | R10 | X | Y | Mol Wt | [M + H]+ |
|---|---|---|---|---|---|---|---|
| 3527 | 3-O₂N-C₆H₄-CH(CH₃)- | O | iPr | S | CH₂ | 377.423 | 378.25 |
| 3528 | | O | iPr | CF₂ | CH₂ | 395.366 | 396.23 |
| 3529 | | O | tBu | S | CH₂ | 391.45 | 392.26 |
| 3530 | | O | iPr | CH=CH | | 357.37 | 358.25 |
| 3531 | 2,4-Cl₂-C₆H₃-CH(CH₃)- | O | iPr | S | CH₂ | 401.316 | 401.15 |
| 3532 | | O | iPr | CF₂ | CH₂ | 419.259 | 419.12 |
| 3533 | | O | tBu | S | CH₂ | 415.343 | 415.16 |
| 3534 | | O | iPr | CH=CH | | 381.263 | 381.14 |
| 3535 | PhC(CH₃)₂CH(CH₃)- | O | iPr | S | CH₂ | 360.48 | 361.28 |
| 3536 | | O | iPr | CF₂ | CH₂ | 378.423 | 379.28 |
| 3537 | | O | tBu | S | CH₂ | 374.507 | 375.3 |
| 3538 | | O | iPr | CH=CH | | 340.427 | 341.25 |
| 3539 | 3,5-Cl₂-C₆H₃-CH(CH₃)- | O | iPr | S | CH₂ | 401.316 | 401.2 |
| 3540 | | O | iPr | CF₂ | CH₂ | 419.259 | 419.13 |
| 3541 | | O | tBu | S | CH₂ | 415.343 | 415.15 |
| 3542 | | O | iPr | CH=CH | | 381.263 | 381.18 |
| 3543 | 2,5-(MeO)₂-C₆H₃-CH(CH₃)- | O | iPr | S | CH₂ | 392.478 | 393.28 |
| 3544 | | O | iPr | CF₂ | CH₂ | 410.421 | 411.23 |
| 3545 | | O | tBu | S | CH₂ | 406.505 | 407.29 |
| 3546 | | O | iPr | CH=CH | | 372.425 | 373.26 |
| 3547 | 2,6-F₂-C₆H₃-CH(CH₃)- | O | iPr | S | CH₂ | 368.406 | 369.25 |
| 3548 | | O | iPr | CF₂ | CH₂ | 386.349 | 387.22 |
| 3549 | | O | tBu | S | CH₂ | 382.433 | 383.26 |
| 3550 | | O | iPr | CH=CH | | 348.353 | 349.19 |
| 3551 | 2-biphenyl-CH(CH₃)- | O | iPr | S | CH₂ | 408.524 | 409.27 |
| 3552 | | O | iPr | CF₂ | CH₂ | 426.467 | 427.22 |
| 3553 | | O | tBu | S | CH₂ | 422.551 | 423.27 |
| 3554 | | O | iPr | CH=CH | | 388.471 | 389.28 |
| 3555 | nPr | S | iPr | S | CH₂ | 314.474 | 315.22 |
| 3556 | | S | iPr | CF₂ | CH₂ | 332.417 | 333.2 |
| 3557 | | S | tBu | S | CH₂ | 328.501 | 329.27 |
| 3558 | | S | iPr | CH=CH | | 294.421 | 295.19 |

TABLE 22-continued

| Example No | R' | Z | R10 | X | Y | Mol Wt | [M + H]+ |
|---|---|---|---|---|---|---|---|
| 3559 | (phenyl-CH2-C(CH3)2-CH2-) | S | iPr | S | CH2 | 362.518 | 363.26 |
| 3560 | | S | iPr | CF2 | CH2 | 380.461 | 381.23 |
| 3561 | | S | tBu | S | CH2 | 376.545 | 377.26 |
| 3562 | | S | iPr | CH=CH | | 342.465 | 343.22 |
| 3563 | (phenyl-CH2CH2-C(CH3)2-CH2-) | S | iPr | S | CH2 | 376.545 | 377.27 |
| 3564 | | S | iPr | CF2 | CH2 | 394.488 | 395.25 |
| 3565 | | S | tBu | S | CH2 | 390.572 | 391.29 |
| 3566 | | S | iPr | CH=CH | | 356.492 | 357.23 |
| 3567 | (4-methoxyphenyl-CH(CH3)-) | S | iPr | S | CH2 | 378.517 | 379.28 |
| 3568 | | S | iPr | CF2 | CH2 | 396.46 | 397.22 |
| 3569 | | S | tBu | S | CH2 | 392.544 | 393.27 |
| 3570 | | S | iPr | CH=CH | | 358.464 | 359.22 |
| 3571 | (phenyl-C(O)-CH(CH3)-) | S | iPr | S | CH2 | 376.501 | 377.21 |
| 3572 | | S | iPr | CF2 | CH2 | 394.444 | 395.2 |
| 3573 | | S | tBu | S | CH2 | 390.528 | 391.26 |
| 3574 | | S | iPr | CH=CH | | 356.448 | 357.2 |
| 3575 | (cyclopentyl-CH(CH3)-) | S | iPr | S | CH2 | 340.512 | 341.25 |
| 3576 | | S | iPr | CF2 | CH2 | 358.455 | 359.24 |
| 3577 | | S | tBu | S | CH2 | 354.539 | 355.26 |
| 3578 | | S | iPr | CH=CH | | 320.459 | 321.22 |
| 3579 | (cyclohexyl-CH2-CH(CH3)-) | S | iPr | S | CH2 | 368.566 | 369.29 |
| 3580 | | S | iPr | CF2 | CH2 | 386.509 | 387.28 |
| 3581 | | S | tBu | S | CH2 | 382.593 | 383.32 |
| 3582 | | S | iPr | CH=CH | | 348.513 | 349.24 |

TABLE 23

| Example No | R | R11 | Mol Wt | [M + H]+ |
|---|---|---|---|---|
| 3583 | CH3 | (CH2)4NHCOCH3 | 308.382 | 309.22 |
| 3584 | | C(CH3)2SCH2NHCOCH3 | 340.446 | 341.22 |
| 3585 | (phenyl-CH(CH3)-) | (CH2)4NHCONH2 | 371.441 | 372.26 |
| 3586 | | (CH2)3NHCONH2 | 357.414 | 358.25 |
| 3587 | | (CH2)2CONH2 | 328.372 | 329.29 |
| 3588 | | C(CH3)2SCH2NHCOCH3 | 402.517 | 403.25 |

TABLE 23-continued

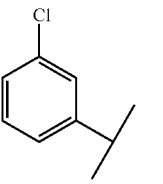

| Example No | R | R11 | Mol Wt | [M + H]+ |
|---|---|---|---|---|
| 3589 | 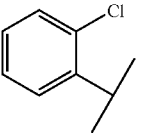 | (CH$_2$)$_4$NHCONH$_2$ | 405.886 | 406.2 |
| 3590 | | (CH$_2$)$_3$NHCONH$_2$ | 391.859 | 392.19 |
| 3591 | | (CH$_2$)$_2$CONH$_2$ | 362.817 | 363.21 |
| 3592 | | C(CH$_3$)$_2$SCH$_2$NHCOCH$_3$ | 436.962 | 437.2 |
| 3593 | 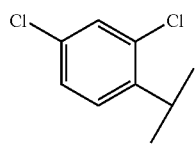 | (CH$_2$)$_4$NHCOCH$_3$ | 404.898 | 405.21 |
| 3594 | | (CH$_2$)$_4$NHCONH$_2$ | 405.886 | 406.23 |
| 3595 | | (CH$_2$)$_3$NHCONH$_2$ | 391.859 | 392.19 |
| 3596 | | C(CH$_3$)$_2$SCH$_2$NHCOCH$_3$ | 436.962 | 437.21 |
| 3597 | 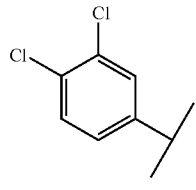 | (CH$_2$)$_4$NHCOCH$_3$ | 404.898 | 405.21 |
| 3598 | | (CH$_2$)$_4$NHCONH$_2$ | 405.886 | 406.22 |
| 3599 | | (CH$_2$)$_3$NHCONH$_2$ | 391.859 | 392.22 |
| 3600 | | (CH$_2$)$_2$CONH$_2$ | 362.817 | 363.18 |
| 3601 | | C(CH$_3$)$_2$SCH$_2$NHCOCH$_3$ | 436.962 | 437.18 |
| 3602 | 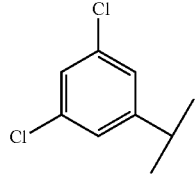 | (CH$_2$)$_4$NHCOCH$_3$ | 439.343 | 439.18 |
| 3603 | | (CH$_2$)$_4$NHCONH$_2$ | 440.331 | 440.21 |
| 3604 | | C(CH$_3$)$_2$SCH$_2$NHCOCH$_3$ | 471.407 | 471.17 |
| 3605 | 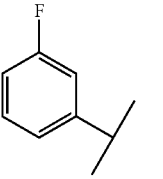 | (CH$_2$)$_4$NHCOCH$_3$ | 439.343 | 439.17 |
| 3606 | | (CH$_2$)$_4$NHCONH$_2$ | 440.331 | 440.18 |
| 3607 | | (CH$_2$)$_3$NHCONH$_2$ | 426.304 | 426.16 |
| 3608 | | (CH$_2$)$_2$CONH$_2$ | 397.262 | 397.16 |
| 3609 | | C(CH$_3$)$_2$SCH$_2$NHCOCH$_3$ | 471.407 | 471.16 |
| 3610 | 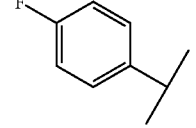 | (CH$_2$)$_4$NHCOCH$_3$ | 439.343 | 439.18 |
| 3611 | | (CH$_2$)$_3$NHCONH$_2$ | 426.304 | 426.14 |
| 3612 | | (CH$_2$)$_2$CONH$_2$ | 397.262 | 397.19 |
| 3613 | | C(CH$_3$)$_2$SCH$_2$NHCOCH$_3$ | 471.407 | 471.18 |
| 3614 | F-phenyl (m) | (CH$_2$)$_4$NHCOCH$_3$ | 388.443 | 389.25 |
| 3615 | | (CH$_2$)$_4$NHCONH$_2$ | 389.431 | 390.26 |
| 3616 | | (CH$_2$)$_3$NHCONH$_2$ | 375.404 | 376.22 |
| 3617 | | C(CH$_3$)$_2$SCH$_2$NHCOCH$_3$ | 420.507 | 421.24 |
| 3618 | F-phenyl (p) | (CH$_2$)$_4$NHCOCH$_3$ | 388.443 | 389.25 |
| 3619 | | (CH$_2$)$_4$NHCONH$_2$ | 389.431 | 390.24 |
| 3620 | | (CH$_2$)$_3$NHCONH$_2$ | 375.404 | 376.23 |
| 3621 | | C(CH$_3$)$_2$SCH$_2$NHCOCH$_3$ | 420.507 | 421.21 |

TABLE 23-continued

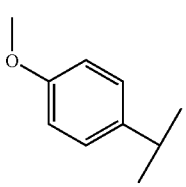

| Example No | R | R11 | Mol Wt | [M + H]+ |
|---|---|---|---|---|
| 3622 | 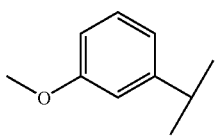 | (CH$_2$)$_4$NHCOCH$_3$ | 400.479 | 401.26 |
| 3623 | | (CH$_2$)$_4$NHCONH$_2$ | 401.467 | 402.27 |
| 3624 | | (CH$_2$)$_3$NHCONH$_2$ | 387.44 | 388.25 |
| 3625 | | (CH$_2$)$_2$CONH$_2$ | 358.398 | 359.23 |
| 3626 | | C(CH$_3$)$_2$SCH$_2$NHCOCH$_3$ | 432.543 | 433.24 |
| 3627 | 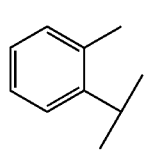 | (CH$_2$)$_4$NHCOCH$_3$ | 400.479 | 401.26 |
| 3628 | | (CH$_2$)$_4$NHCONH$_2$ | 401.467 | 402.29 |
| 3629 | | (CH$_2$)$_3$NHCONH$_2$ | 387.44 | 388.27 |
| 3630 | | (CH$_2$)$_2$CONH$_2$ | 358.398 | 359.25 |
| 3631 | | C(CH$_3$)$_2$SCH$_2$NHCOCH$_3$ | 432.543 | 433.24 |
| 3632 | 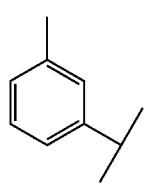 | (CH$_2$)$_4$NHCOCH$_3$ | 384.48 | 385.28 |
| 3633 | | C(CH$_3$)$_2$SCH$_2$NHCOCH$_3$ | 416.544 | 417.22 |
| 3634 | 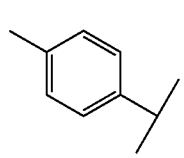 | (CH$_2$)$_4$NHCOCH$_3$ | 384.48 | 385.28 |
| 3635 | | (CH$_2$)$_4$NHCONH$_2$ | 385.468 | 386.26 |
| 3636 | | (CH$_2$)$_3$NHCONH$_2$ | 371.441 | 372.29 |
| 3637 | | (CH$_2$)$_2$CONH$_2$ | 342.399 | 343.26 |
| 3638 | | C(CH$_3$)$_2$SCH$_2$NHCOCH$_3$ | 416.544 | 417.24 |
| 3639 | 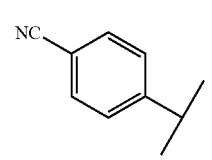 | (CH$_2$)$_4$NHCOCH$_3$ | 384.48 | 385.27 |
| 3640 | | (CH$_2$)$_4$NHCONH$_2$ | 385.468 | 386.28 |
| 3641 | | (CH$_2$)$_3$NHCONH$_2$ | 371.441 | 372.24 |
| 3642 | | (CH$_2$)$_2$CONH$_2$ | 342.399 | 343.26 |
| 3643 | | C(CH$_3$)$_2$SCH$_2$NHCOCH$_3$ | 416.544 | 417.25 |
| 3644 | 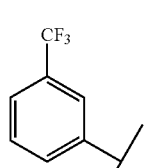 | C(CH$_3$)$_2$SCH$_2$NHCOCH$_3$ | 427.527 | 428.23 |
| 3645 | 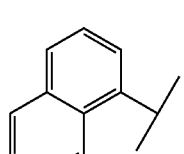 | (CH$_2$)$_4$NHCOCH$_3$ | 438.45 | 439.25 |
| 3646 | | (CH$_2$)$_4$NHCONH$_2$ | 439.438 | 440.25 |
| 3647 | | (CH$_2$)$_3$NHCONH$_2$ | 425.411 | 426.21 |
| 3648 | | C(CH$_3$)$_2$SCH$_2$NHCOCH$_3$ | 470.514 | 471.24 |
| 3649 |  | (CH$_2$)$_4$NHCOCH$_3$ | 420.513 | 421.25 |
| 3650 | | (CH$_2$)$_4$NHCONH$_2$ | 421.501 | 422.27 |
| 3651 | | (CH$_2$)$_3$NHCONH$_2$ | 407.474 | 408.25 |
| 3652 | | (CH$_2$)$_2$CONH$_2$ | 378.432 | 379.23 |
| 3653 | | C(CH$_3$)$_2$SCH$_2$NHCOCH$_3$ | 452.577 | 453.29 |

TABLE 23-continued

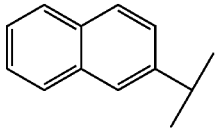

| Example No | R | R11 | Mol Wt | [M + H]+ |
|---|---|---|---|---|
| 3654 | 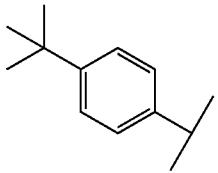 | (CH$_2$)$_4$NHCOCH$_3$ | 420.513 | 421.25 |
| 3655 | | (CH$_2$)$_4$NHCONH$_2$ | 421.501 | 422.3 |
| 3656 | | (CH$_2$)$_3$NHCONH$_2$ | 407.474 | 408.24 |
| 3657 | | (CH$_2$)$_2$CONH$_2$ | 378.432 | 379.25 |
| 3658 | | C(CH$_3$)$_2$SCH$_2$NHCOCH$_3$ | 452.577 | 453.26 |
| 3659 | 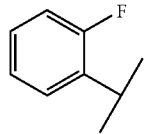 | (CH$_2$)$_4$NHCOCH$_3$ | 426.561 | 427.33 |
| 3660 | | (CH$_2$)$_4$NHCONH$_2$ | 427.549 | 428.31 |
| 3661 | | (CH$_2$)$_3$NHCONH$_2$ | 413.522 | 414.3 |
| 3662 | | (CH$_2$)$_2$CONH$_2$ | 384.48 | 385.31 |
| 3663 | | C(CH$_3$)$_2$SCH$_2$NHCOCH$_3$ | 458.625 | 459.34 |
| 3664 | 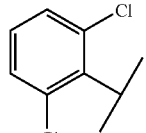 | (CH$_2$)$_4$NHCOCH$_3$ | 388.443 | 389.27 |
| 3665 | | (CH$_2$)$_4$NHCONH$_2$ | 389.431 | 390.26 |
| 3666 | | (CH$_2$)$_3$NHCONH$_2$ | 375.404 | 376.22 |
| 3667 | | (CH$_2$)$_2$CONH$_2$ | 346.362 | 347.24 |
| 3668 | | C(CH$_3$)$_2$SCH$_2$NHCOCH$_3$ | 420.507 | 421.21 |
| 3669 | 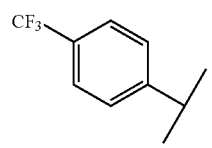 | (CH$_2$)$_4$NHCOCH$_3$ | 439.343 | 439.18 |
| 3670 | | (CH$_2$)$_4$NHCONH$_2$ | 440.331 | 440.19 |
| 3671 | | (CH$_2$)$_3$NHCONH$_2$ | 426.304 | 426.15 |
| 3672 | | (CH$_2$)$_2$CONH$_2$ | 397.262 | 397.14 |
| 3673 | | C(CH$_3$)$_2$SCH$_2$NHCOCH$_3$ | 471.407 | 471.16 |
| 3674 | 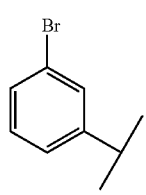 | (CH$_2$)$_4$NHCOCH$_3$ | 438.45 | 439.24 |
| 3675 | | (CH$_2$)$_4$NHCONH$_2$ | 439.438 | 440.25 |
| 3676 | | (CH$_2$)$_3$NHCONH$_2$ | 425.411 | 426.21 |
| 3677 | | (CH$_2$)$_2$CONH$_2$ | 396.369 | 397.21 |
| 3678 | | C(CH$_3$)$_2$SCH$_2$NHCOCH$_3$ | 470.514 | 471.23 |
| 3679 | 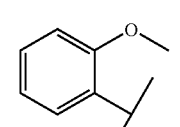 | (CH$_2$)$_4$NHCOCH$_3$ | 449.354 | 449.17 |
| 3680 | | (CH$_2$)$_4$NHCONH$_2$ | 450.342 | 450.21 |
| 3681 | | (CH$_2$)$_3$NHCONH$_2$ | 436.315 | 436.14 |
| 3682 | | (CH$_2$)$_2$CONH$_2$ | 407.273 | 407.15 |
| 3683 | | C(CH$_3$)$_2$SCH$_2$NHCOCH$_3$ | 481.418 | 481.13 |
| 3684 | 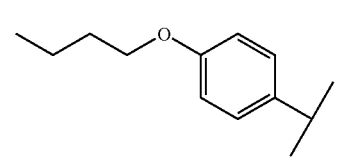 | (CH$_2$)$_4$NHCOCH$_3$ | 400.479 | 401.26 |
| 3685 | | (CH$_2$)$_4$NHCONH$_2$ | 401.467 | 402.29 |
| 3686 | | (CH$_2$)$_3$NHCONH$_2$ | 387.44 | 388.23 |
| 3687 | | (CH$_2$)$_2$CONH$_2$ | 358.398 | 359.22 |
| 3688 | | C(CH$_3$)$_2$SCH$_2$NHCOCH$_3$ | 432.543 | 433.23 |
| 3689 |  | (CH$_2$)$_4$NHCOCH$_3$ | 442.56 | 443.32 |
| 3690 | | (CH$_2$)$_4$NHCONH$_2$ | 443.548 | 444.36 |
| 3691 | | (CH$_2$)$_3$NHCONH$_2$ | 429.521 | 430.27 |
| 3692 | | (CH$_2$)$_2$CONH$_2$ | 400.479 | 401.27 |
| 3693 | | C(CH$_3$)$_2$SCH$_2$NHCOCH$_3$ | 474.624 | 475.28 |

TABLE 23-continued

| Example No | R | R11 | Mol Wt | [M + H]+ |
|---|---|---|---|---|
| 3694 | 2,5-dimethoxybenzyl-neopentyl | (CH₂)₄NHCOCH₃ | 444.532 | 445.29 |
| 3695 | | (CH₂)₄NHCONH₂ | 445.52 | 446.3 |
| 3696 | | (CH₂)₃NHCONH₂ | 431.493 | 432.27 |
| 3697 | | (CH₂)₂CONH₂ | 402.451 | 404.24 |
| 3698 | | C(CH₃)₂SCH₂NHCOCH₃ | 476.596 | 477.28 |
| 3699 | 4-pentylphenyl | (CH₂)₄NHCOCH₃ | 454.615 | 455.37 |
| 3700 | | (CH₂)₄NHCONH₂ | 455.603 | 456.38 |
| 3701 | | (CH₂)₃NHCONH₂ | 441.576 | 442.33 |
| 3702 | | (CH₂)₂CONH₂ | 412.534 | 413.34 |
| 3703 | | C(CH₃)₂SCH₂NHCOCH₃ | 486.679 | 487.33 |
| 3704 | benzyl | (CH₂)₄NHCOCH₃ | 384.48 | 385.26 |
| 3705 | | (CH₂)₄NHCONH₂ | 385.468 | 386.29 |
| 3706 | | (CH₂)₃NHCONH₂ | 371.441 | 372.23 |
| 3707 | | (CH₂)₂CONH₂ | 342.399 | 343.25 |
| 3708 | | C(CH₃)₂SCH₂NHCOCH₃ | 416.544 | 417.24 |
| 3709 | phenethyl | (CH₂)₄NHCOCH₃ | 398.507 | 399.29 |
| 3710 | | (CH₂)₄NHCONH₂ | 399.495 | 400.31 |
| 3711 | | (CH₂)₃NHCONH₂ | 385.468 | 386.28 |
| 3712 | | (CH₂)₂CONH₂ | 356.426 | 357.24 |
| 3713 | | C(CH₃)₂SCH₂NHCOCH₃ | 430.571 | 431.26 |
| 3714 | benzothiophen-2-yl | (CH₂)₄NHCONH₂ | 427.527 | 428.21 |
| 3715 | | C(CH₃)₂SCH₂NHCOCH₃ | 458.603 | 459.25 |
| 3716 | thiophen-2-yl | (CH₂)₄NHCOCH₃ | 376.479 | 377.23 |
| 3717 | | (CH₂)₄NHCONH₂ | 377.467 | 378.21 |
| 3718 | | (CH₂)₃NHCONH₂ | 363.44 | 364.2 |
| 3719 | | (CH₂)₂CONH₂ | 334.398 | 335.26 |
| 3720 | | C(CH₃)₂SCH₂NHCOCH₃ | 408.543 | 409.2 |
| 3721 | furan-2-yl | (CH₂)₄NHCOCH₃ | 360.414 | 361.24 |
| 3722 | | (CH₂)₄NHCONH₂ | 361.402 | 362.21 |
| 3723 | | (CH₂)₃NHCONH₂ | 347.375 | 348.24 |
| 3724 | | (CH₂)₂CONH₂ | 318.333 | 319.25 |
| 3725 | | C(CH₃)₂SCH₂NHCOCH₃ | 392.478 | 393.21 |
| 3726 | 2-chloropyridin-3-yl | (CH₂)₂CONH₂ | 363.805 | 364.16 |
| 3727 | benzyloxy-neopentyl | (CH₂)₄NHCOCH₃ | 414.506 | 415.27 |
| 3728 | | (CH₂)₄NHCONH₂ | 415.494 | 416.3 |
| 3729 | | (CH₂)₃NHCONH₂ | 401.467 | 402.25 |
| 3730 | | (CH₂)₂CONH₂ | 372.425 | 373.24 |
| 3731 | | C(CH₃)₂SCH₂NHCOCH₃ | 446.57 | 447.28 |
| 3732 | cyclohexyl | (CH₂)₄NHCOCH₃ | 376.501 | 377.3 |
| 3733 | | (CH₂)₄NHCONH₂ | 377.489 | 378.34 |
| 3734 | | (CH₂)₃NHCONH₂ | 363.462 | 364.29 |
| 3735 | | (CH₂)₂CONH₂ | 334.42 | 335.26 |
| 3736 | | C(CH₃)₂SCH₂NHCOCH₃ | 408.565 | 409.26 |

TABLE 23-continued

| Example No | R | R11 | Mol Wt | [M + H]+ |
|---|---|---|---|---|
| 3737 | cyclopentylmethyl | (CH₂)₄NHCOCH₃ | 362.474 | 363.28 |
| 3738 | | (CH₂)₄NHCONH₂ | 363.462 | 364.29 |
| 3739 | | (CH₂)₃NHCONH₂ | 349.435 | 350.25 |
| 3740 | | (CH₂)₂CONH₂ | 320.393 | 321.25 |
| 3741 | | C(CH₃)₂SCH₂NHCOCH₃ | 394.538 | 395.28 |
| 3742 | cyclobutylmethyl | (CH₂)₄NHCOCH₃ | 348.447 | 349.26 |
| 3743 | | (CH₂)₄NHCONH₂ | 349.435 | 350.29 |
| 3744 | | (CH₂)₃NHCONH₂ | 335.408 | 336.25 |
| 3745 | | (CH₂)₂CONH₂ | 306.366 | 307.23 |
| 3746 | | C(CH₃)₂SCH₂NHCOCH₃ | 380.511 | 381.23 |
| 3747 | cyclopropylmethyl | (CH₂)₄NHCOCH₃ | 334.42 | 335.27 |
| 3748 | | (CH₂)₄NHCONH₂ | 335.408 | 336.27 |
| 3749 | | (CH₂)₃NHCONH₂ | 321.381 | 322.24 |
| 3750 | | (CH₂)₂CONH₂ | 292.339 | 293.21 |
| 3751 | | C(CH₃)₂SCH₂NHCOCH₃ | 366.484 | 367.21 |
| 3752 | cyclopentylethyl | (CH₂)₄NHCOCH₃ | 376.501 | 377.3 |
| 3753 | | (CH₂)₄NHCONH₂ | 377.489 | 378.3 |
| 3754 | | (CH₂)₂CONH₂ | 334.42 | 335.29 |
| 3755 | | C(CH₃)₂SCH₂NHCOCH₃ | 408.565 | 409.26 |
| 3756 | tert-butyl-methyl | (CH₂)₄NHCOCH₃ | 350.463 | 351.28 |
| 3757 | | (CH₂)₄NHCONH₂ | 351.451 | 352.29 |
| 3758 | | (CH₂)₃NHCONH₂ | 337.424 | 338.26 |
| 3759 | | (CH₂)₂CONH₂ | 308.382 | 309.24 |
| 3760 | | C(CH₃)₂SCH₂NHCOCH₃ | 382.527 | 383.27 |
| 3761 | neopentyl-ethyl | (CH₂)₄NHCOCH₃ | 364.49 | 365.3 |
| 3762 | | (CH₂)₄NHCONH₂ | 365.478 | 366.34 |
| 3763 | | C(CH₃)₂SCH₂NHCOCH₃ | 396.554 | 397.28 |
| 3764 | branched alkyl | (CH₂)₄NHCOCH₃ | 364.49 | 365.31 |
| 3765 | | (CH₂)₄NHCONH₂ | 365.478 | 366.32 |
| 3766 | | (CH₂)₃NHCONH₂ | 351.451 | 352.29 |
| 3767 | | (CH₂)₂CONH₂ | 322.409 | 323.32 |
| 3768 | | C(CH₃)₂SCH₂NHCOCH₃ | 396.554 | 397.28 |
| 3769 | 2-ethylhexyl | (CH₂)₄NHCOCH₃ | 392.544 | 393.33 |
| 3770 | | (CH₂)₄NHCONH₂ | 393.532 | 394.37 |
| 3771 | | (CH₂)₃NHCONH₂ | 379.505 | 380.31 |
| 3772 | | (CH₂)₂CONH₂ | 350.463 | 351.3 |
| 3773 | | C(CH₃)₂SCH₂NHCOCH₃ | 424.608 | 425.3 |
| 3774 | methyl ester short | (CH₂)₄NHCOCH₃ | 380.445 | 381.28 |
| 3775 | | (CH₂)₄NHCONH₂ | 381.433 | 382.26 |
| 3776 | | (CH₂)₃NHCONH₂ | 367.406 | 368.26 |
| 3777 | | C(CH₃)₂SCH₂NHCOCH₃ | 412.509 | 413.23 |
| 3778 | methyl ester long | (CH₂)₄NHCOCH₃ | 436.553 | 437.34 |
| 3779 | | (CH₂)₄NHCONH₂ | 437.541 | 438.33 |
| 3780 | | (CH₂)₃NHCONH₂ | 423.514 | 424.28 |
| 3781 | | (CH₂)₂CONH₂ | 394.472 | 395.32 |
| 3782 | | C(CH₃)₂SCH₂NHCOCH₃ | 468.617 | 469.33 |
| 3783 | phenylcyclopropyl | (CH₂)₄NHCOCH₃ | 410.518 | 411.27 |
| 3784 | | (CH₂)₄NHCONH₂ | 411.506 | 412.29 |
| 3785 | | (CH₂)₃NHCONH₂ | 397.479 | 398.26 |
| 3786 | | (CH₂)₂CONH₂ | 368.437 | 369.28 |
| 3787 | | C(CH₃)₂SCH₂NHCOCH₃ | 442.582 | 443.28 |

TABLE 23-continued

| Example No | R | R11 | Mol Wt | [M + H]+ |
|---|---|---|---|---|
| 3788 | 2-(OCF3)-phenyl | (CH2)4NHCOCH3 | 454.449 | 455.25 |
| 3789 |  | (CH2)4NHCONH2 | 455.437 | 456.28 |
| 3790 |  | (CH2)3NHCONH2 | 441.41 | 442.23 |
| 3791 |  | (CH2)2CONH2 | 412.368 | 413.2 |
| 3792 |  | C(CH3)2SCH2NHCOCH3 | 486.513 | 487.21 |
| 3793 | 2,6-difluorophenyl | (CH2)4NHCOCH3 | 406.433 | 407.22 |
| 3794 |  | (CH2)4NHCONH2 | 407.421 | 408.27 |
| 3795 |  | (CH2)3NHCONH2 | 393.394 | 394.2 |
| 3796 |  | (CH2)2CONH2 | 364.352 | 365.2 |
| 3797 |  | C(CH3)2SCH2NHCOCH3 | 438.497 | 439.23 |
| 3798 | 4-(N,N-dimethylamino)phenyl | (CH2)4NHCOCH3 | 413.522 | 414.3 |
| 3799 |  | (CH2)4NHCONH2 | 414.51 | 415.31 |
| 3800 |  | (CH2)3NHCONH2 | 400.483 | 401.27 |
| 3801 |  | (CH2)2CONH2 | 371.441 | 372.28 |
| 3802 |  | C(CH3)2SCH2NHCOCH3 | 445.586 | 446.29 |
| 3803 | pyridin-3-yl | (CH2)4NHCOCH3 | 371.441 | 372.27 |
| 3804 |  | C(CH3)2SCH2NHCOCH3 | 403.505 | 404.22 |
| 3805 | 3-tert-butyl-adamantyl | (CH2)4NHCOCH3 | 428.577 | 429.33 |
| 3806 |  | (CH2)4NHCONH2 | 429.565 | 430.32 |
| 3807 |  | (CH2)3NHCONH2 | 415.538 | 416.32 |
| 3808 |  | (CH2)2CONH2 | 386.496 | 387.33 |
| 3809 |  | C(CH3)2SCH2NHCOCH3 | 460.641 | 461.33 |
| 3810 | 2,4,5-trifluorophenyl | (CH2)4NHCOCH3 | 424.423 | 425.23 |
| 3811 |  | (CH2)4NHCONH2 | 425.411 | 426.23 |
| 3812 |  | (CH2)3NHCONH2 | 411.384 | 412.21 |
| 3813 |  | (CH2)2CONH2 | 382.342 | 383.23 |
| 3814 |  | C(CH3)2SCH2NHCOCH3 | 456.487 | 457.22 |
| 3815 | phenoxymethyl | (CH2)4NHCOCH3 | 400.479 | 401.26 |
| 3816 |  | (CH2)4NHCONH2 | 401.467 | 402.29 |
| 3817 |  | (CH2)3NHCONH2 | 387.44 | 388.25 |
| 3818 |  | C(CH3)2SCH2NHCOCH3 | 432.543 | 433.25 |
| 3819 | 3,4-difluorophenyl | (CH2)4NHCOCH3 | 406.433 | 407.24 |
| 3820 |  | (CH2)4NHCONH2 | 407.421 | 408.23 |
| 3821 |  | (CH2)3NHCONH2 | 393.394 | 394.21 |
| 3822 |  | C(CH3)2SCH2NHCOCH3 | 438.497 | 439.24 |
| 3823 | 2-methyl-2-phenylbutyl | (CH2)4NHCOCH3 | 412.534 | 413.3 |
| 3824 |  | (CH2)4NHCONH2 | 413.522 | 414.27 |
| 3825 |  | (CH2)3NHCONH2 | 399.495 | 400.27 |
| 3826 |  | (CH2)2CONH2 | 370.453 | 371.31 |
| 3827 |  | C(CH3)2SCH2NHCOCH3 | 444.598 | 445.31 |

TABLE 23-continued

| Example No | R | R11 | Mol Wt | [M + H]+ |
|---|---|---|---|---|
| 3828 | thiophene | (CH$_2$)$_4$NHCOCH$_3$ | 376.479 | 377.21 |
| 3829 | | (CH$_2$)$_4$NHCONH$_2$ | 377.467 | 378.25 |
| 3830 | | (CH$_2$)$_3$NHCONH$_2$ | 363.44 | 364.19 |
| 3831 | | C(CH$_3$)$_2$SCH$_2$NHCOCH$_3$ | 408.543 | 409.18 |
| 3832 | 2,3-difluorophenyl | (CH$_2$)$_4$NHCOCH$_3$ | 406.433 | 407.23 |
| 3833 | | (CH$_2$)$_4$NHCONH$_2$ | 407.421 | 408.23 |
| 3834 | | (CH$_2$)$_3$NHCONH$_2$ | 393.394 | 394.22 |
| 3835 | | (CH$_2$)$_2$CONH$_2$ | 364.352 | 365.18 |
| 3836 | | C(CH$_3$)$_2$SCH$_2$NHCOCH$_3$ | 438.497 | 439.21 |
| 3837 | 3-tert-butylbenzothiophene | (CH$_2$)$_4$NHCONH$_2$ | 427.527 | 428.25 |
| 3838 | | (CH$_2$)$_3$NHCONH$_2$ | 413.5 | 414.17 |
| 3839 | | (CH$_2$)$_2$CONH$_2$ | 384.458 | 385.22 |
| 3840 | | C(CH$_3$)$_2$SCH$_2$NHCOCH$_3$ | 458.603 | 459.24 |
| 3841 | 3,5-difluorophenyl | (CH$_2$)$_4$NHCOCH$_3$ | 406.433 | 407.22 |
| 3842 | | (CH$_2$)$_4$NHCONH$_2$ | 407.421 | 408.27 |

TABLE 24

| Example No | R | X | Mol Wt | [M + H]+ |
|---|---|---|---|---|
| 3843 | CH$_3$ | CH$_2$ | 226.32 | 227.23 |
| 3844 | | CF$_2$ | 262.3 | 263.27 |
| 3845 | phenyl | CH$_2$ | 288.391 | 289.29 |
| 3846 | | S | 306.428 | 307.25 |
| 3847 | | CF$_2$ | 324.371 | 325.28 |
| 3848 | 3-chlorophenyl | CH$_2$ | 322.836 | 323.25 |
| 3849 | | S | 340.873 | 341.22 |
| 3850 | | CF$_2$ | 358.816 | 359.22 |

TABLE 24-continued
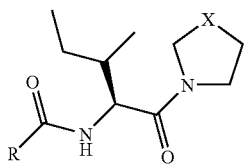
| Example No | R | X | Mol Wt | [M + H]+ |
|---|---|---|---|---|
| 3851 | 4-Cl-C6H4 | CH2 | 322.836 | 323.24 |
| 3852 | | S | 340.873 | 341.21 |
| 3853 | | CF2 | 358.816 | 359.23 |
| 3854 | 2-Cl-C6H4 | CH2 | 322.836 | 323.24 |
| 3855 | | S | 340.873 | 341.21 |
| 3856 | | CF2 | 358.816 | 359.24 |
| 3857 | 2,4-diCl-C6H3 | CH2 | 357.281 | 357.21 |
| 3858 | | S | 375.318 | 375.22 |
| 3859 | | CF2 | 393.261 | 393.18 |
| 3860 | 3,4-diCl-C6H3 | CH2 | 357.281 | 357.21 |
| 3861 | | S | 375.318 | 375.17 |
| 3862 | | CF2 | 393.261 | 393.23 |
| 3863 | 3,5-diCl-C6H3 | CH2 | 357.281 | 357.23 |
| 3864 | | S | 375.318 | 375.17 |
| 3865 | | CF2 | 393.261 | 393.22 |
| 3866 | 3-F-C6H4 | CH2 | 306.381 | 307.27 |
| 3867 | | S | 324.418 | 325.24 |
| 3868 | | CF2 | 342.361 | 343.27 |
| 3869 | 4-F-C6H4 | CH2 | 306.381 | 307.28 |
| 3870 | | S | 324.418 | 325.26 |
| 3871 | | CF2 | 342.361 | 343.28 |
| 3872 | 4-MeO-C6H4 | CH2 | 318.417 | 319.29 |
| 3873 | | S | 336.454 | 337.28 |
| 3874 | | CF2 | 354.397 | 355.3 |

TABLE 24-continued
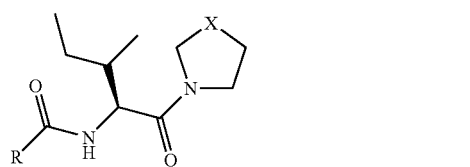
| Example No | R | X | Mol Wt | [M + H]+ |
|---|---|---|---|---|
| 3875 | 3-methoxyphenyl-CH(CH3)- | CH$_2$ | 318.417 | 319.3 |
| 3876 |  | S | 336.454 | 337.25 |
| 3877 |  | CF$_2$ | 354.397 | 355.29 |
| 3878 | 2-methylphenyl-CH(CH3)- | CH$_2$ | 302.418 | 303.29 |
| 3879 |  | S | 320.455 | 321.28 |
| 3880 |  | CF$_2$ | 338.398 | 339.3 |
| 3881 | 3-methylphenyl-CH(CH3)- | CH$_2$ | 302.418 | 303.3 |
| 3882 |  | S | 320.455 | 321.26 |
| 3883 |  | CF$_2$ | 338.398 | 339.29 |
| 3884 | 4-methylphenyl-CH(CH3)- | CH$_2$ | 302.418 | 303.31 |
| 3885 |  | S | 320.455 | 321.27 |
| 3886 |  | CF$_2$ | 338.398 | 339.28 |
| 3887 | 4-cyanophenyl-CH(CH3)- | CH$_2$ | 313.401 | 314.28 |
| 3888 | 3-trifluoromethylphenyl-CH(CH3)- | CH$_2$ | 356.388 | 357.3 |
| 3889 |  | S | 374.425 | 375.26 |
| 3890 |  | CF$_2$ | 392.368 | 393.27 |
| 3891 | 3-nitrophenyl-CH(CH3)- | S | 351.425 | 353.45 |
| 3892 | 1-naphthyl-CH(CH3)- | CH$_2$ | 338.451 | 339.31 |
| 3893 |  | S | 356.488 | 357.25 |
| 3894 |  | CF$_2$ | 374.431 | 375.33 |

TABLE 24-continued
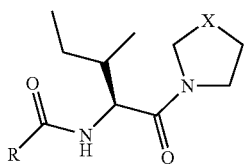
| Example No | R | X | Mol Wt | [M + H]+ |
|---|---|---|---|---|
| 3895 | naphthalen-2-yl | CH₂ | 338.451 | 339.31 |
| 3896 | | S | 356.488 | 357.25 |
| 3897 | | CF₂ | 374.431 | 375.3 |
| 3898 | 4-tert-butylphenyl | CH₂ | 344.499 | 345.36 |
| 3899 | | S | 362.536 | 363.32 |
| 3900 | | CF₂ | 380.479 | 381.36 |
| 3901 | biphenyl-4-yl | S | 382.526 | 384.3 |
| 3902 | 2-fluorophenyl | CH₂ | 306.381 | 307.29 |
| 3903 | | S | 324.418 | 325.25 |
| 3904 | | CF₂ | 342.361 | 343.29 |
| 3905 | 2,6-dichlorophenyl | CH₂ | 357.281 | 357.23 |
| 3906 | | S | 375.318 | 375.18 |
| 3907 | | CF₂ | 393.261 | 393.22 |
| 3908 | 4-trifluoromethylphenyl | CH₂ | 356.388 | 357.28 |
| 3909 | | S | 374.425 | 375.29 |
| 3910 | | CF₂ | 392.368 | 393.3 |
| 3911 | 3-bromophenyl | CH₂ | 367.292 | 367.22 |
| 3912 | | S | 385.329 | 385.19 |
| 3913 | | CF₂ | 403.272 | 403.17 |
| 3914 | 2-methoxyphenyl | S | 336.454 | 337.26 |

TABLE 24-continued

| Example No | R | X | Mol Wt | [M + H]+ |
|---|---|---|---|---|
| 3915 | butoxy-phenyl | CH$_2$ | 360.498 | 361.36 |
| 3916 | | S | 378.535 | 379.34 |
| 3917 | | CF$_2$ | 396.478 | 397.37 |
| 3918 | 4-nitrophenyl | CH$_2$ | 333.388 | 334.3 |
| 3919 | | S | 351.425 | 352.17 |
| 3920 | | CF$_2$ | 369.368 | 370.25 |
| 3921 | 2,5-dimethoxyphenyl | CH$_2$ | 362.47 | 363.33 |
| 3922 | | S | 380.507 | 381.31 |
| 3923 | | CF$_2$ | 398.45 | 399.32 |
| 3924 | 4-pentylphenyl | CH$_2$ | 372.553 | 373.38 |
| 3925 | | S | 390.59 | 391.4 |
| 3926 | | CF$_2$ | 408.533 | 409.38 |
| 3927 | phenyl | CH$_2$ | 302.418 | 303.32 |
| 3928 | | S | 320.455 | 321.25 |
| 3929 | | CF$_2$ | 338.398 | 339.28 |
| 3930 | phenyl-propyl | CH$_2$ | 316.445 | 317.33 |
| 3931 | | S | 334.482 | 335.25 |
| 3932 | | CF$_2$ | 352.425 | 353.32 |
| 3933 | benzothiophene | S | 362.514 | 363.22 |
| 3934 | | CF$_2$ | 380.457 | 381.28 |
| 3935 | thiophene | CH$_2$ | 294.417 | 295.26 |
| 3936 | | S | 312.454 | 313.21 |
| 3937 | | CF$_2$ | 330.397 | 331.24 |
| 3938 | furan | CH$_2$ | 278.352 | 279.28 |
| 3939 | | S | 296.389 | 297.27 |
| 3940 | | CF$_2$ | 314.332 | 315.21 |
| 3941 | 2-chloropyridine | CH$_2$ | 323.824 | 324.25 |
| 3942 | | S | 341.861 | 342.17 |
| 3943 | | CF$_2$ | 359.804 | 360.29 |

TABLE 24-continued
| Example No | R | X | Mol Wt | [M + H]+ |
| --- | --- | --- | --- | --- |
| 3944 | | CH₂ | 332.444 | 333.32 |
| 3945 | | S | 350.481 | 351.29 |
| 3946 | | CF₂ | 368.424 | 369.32 |
| 3947 | | CH₂ | 294.439 | 295.33 |
| 3948 | | S | 312.476 | 313.27 |
| 3949 | | CF₂ | 330.419 | 331.33 |
| 3950 | | CH₂ | 280.412 | 281.34 |
| 3951 | | S | 298.449 | 299.3 |
| 3952 | | CF₂ | 316.392 | 317.32 |
| 3953 | | CH₂ | 266.385 | 267.32 |
| 3954 | | S | 284.422 | 285.26 |
| 3955 | | CF₂ | 302.365 | 303.26 |
| 3956 | | CH₂ | 252.358 | 253.31 |
| 3957 | | CF₂ | 288.338 | 289.3 |
| 3958 | | CH₂ | 294.439 | 295.33 |
| 3959 | | S | 312.476 | 313.28 |
| 3960 | | CF₂ | 330.419 | 331.32 |
| 3961 | | CH₂ | 268.401 | 269.33 |
| 3962 | | CF₂ | 304.381 | 305.27 |
| 3963 | | CH₂ | 282.428 | 283.35 |
| 3964 | | S | 300.465 | 301.27 |
| 3965 | | CF₂ | 318.408 | 319.32 |
| 3966 | | CH₂ | 282.428 | 283.35 |
| 3967 | | S | 300.465 | 301.3 |
| 3968 | | CF₂ | 318.408 | 319.32 |
| 3969 | | CH₂ | 310.482 | 311.35 |
| 3970 | | S | 328.519 | 329.33 |
| 3971 | | CF₂ | 346.462 | 347.35 |
| 3972 | | CH₂ | 298.383 | 299.3 |
| 3973 | | S | 316.42 | 317.26 |
| 3974 | | CF₂ | 334.363 | 335.27 |

TABLE 24-continued
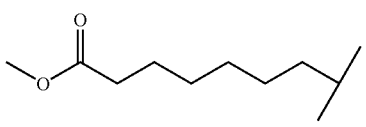
| Example No | R | X | Mol Wt | [M + H]+ |
|---|---|---|---|---|
| 3975 | 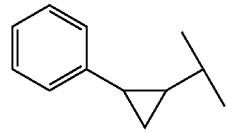 | CH$_2$ | 354.491 | 355.36 |
| 3976 | | S | 372.528 | 373.33 |
| 3977 | | CF$_2$ | 390.471 | 391.37 |
| 3978 | 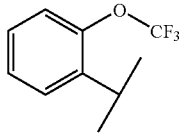 | CH$_2$ | 328.456 | 329.33 |
| 3979 | | S | 346.493 | 347.28 |
| 3980 | | CF$_2$ | 364.436 | 365.33 |
| 3981 | 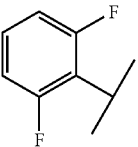 | CH$_2$ | 372.387 | 373.3 |
| 3982 | | S | 390.424 | 391.26 |
| 3983 | | CF$_2$ | 408.367 | 409.25 |
| 3984 | 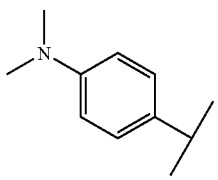 | CH$_2$ | 324.371 | 325.28 |
| 3985 | | S | 342.408 | 343.25 |
| 3986 | | CF$_2$ | 360.351 | 361.25 |
| 3987 | 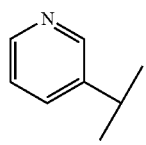 | CH$_2$ | 331.46 | 332.34 |
| 3988 | | S | 349.497 | 350.32 |
| 3989 | | CF$_2$ | 367.44 | 368.34 |
| 3990 | 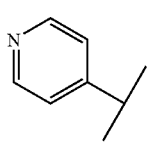 | CH$_2$ | 289.379 | 290.29 |
| 3991 | | S | 307.416 | 308.23 |
| 3992 | | CF$_2$ | 325.359 | 326.27 |
| 3993 | 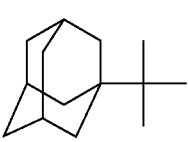 | CH$_2$ | 289.379 | 331.32 |
| 3994 | | CF$_2$ | 325.359 | 326.29 |
| 3995 | 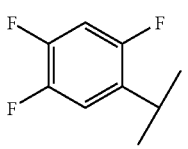 | CH$_2$ | 346.515 | 347.38 |
| 3996 | | S | 364.552 | 365.33 |
| 3997 | | CF$_2$ | 382.495 | 383.37 |
| 3998 |  | CH$_2$ | 342.361 | 343.25 |
| 3999 | | S | 360.398 | 361.21 |
| 4000 | | CF$_2$ | 378.341 | 379.3 |

TABLE 24-continued
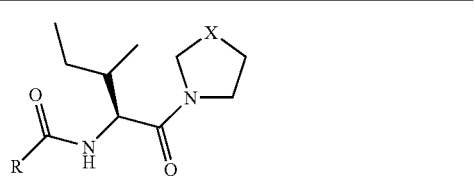
| Example No | R | X | Mol Wt | [M + H]+ |
|---|---|---|---|---|
| 4001 | 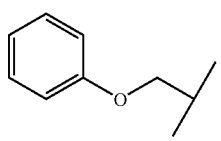 | CH₂ | 318.417 | 319.31 |
| 4002 | | S | 336.454 | 337.28 |
| 4003 | | CF₂ | 354.397 | 355.3 |
| 4004 | 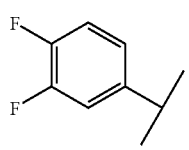 | CH₂ | 324.371 | 325.28 |
| 4005 | | S | 342.408 | 343.21 |
| 4006 | | CF₂ | 360.351 | 361.27 |
| 4007 | 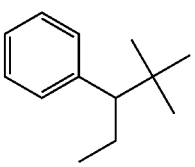 | CH₂ | 330.472 | 331.35 |
| 4008 | | S | 348.509 | 349.31 |
| 4009 | | CF₂ | 366.452 | 367.36 |
| 4010 | 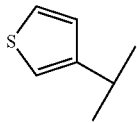 | CH₂ | 294.417 | 295.26 |
| 4011 | | S | 312.454 | 313.24 |
| 4012 | | CF₂ | 330.397 | 331.24 |
| 4013 | 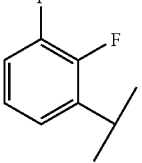 | CH₂ | 324.371 | 325.28 |
| 4014 | | S | 342.408 | 343.24 |
| 4015 | | CF₂ | 360.351 | 361.26 |
| 4016 | 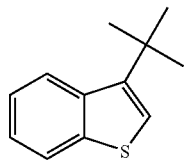 | CH₂ | 344.477 | 345.26 |
| 4017 | | S | 362.514 | 363.23 |
| 4018 | | CF₂ | 380.457 | 381.27 |
| 4019 | 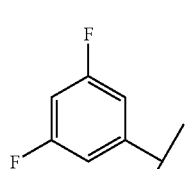 | CH₂ | 324.371 | 325.27 |
| 4020 | | S | 342.408 | 343.25 |
| 4021 | | CF₂ | 360.351 | 361.3 |

TABLE 25

| Example No | R' | Z | X | Mol Wt | [M + H]+ |
|---|---|---|---|---|---|
| 4022 | Et | O | CH₂ | 255.362 | 256.31 |
| 4023 |  | O | S | 273.399 | 274.29 |
| 4024 |  | O | CF₂ | 291.342 | 292.19 |
| 4025 | iPr | O | CH₂ | 269.389 | 270.36 |
| 4026 |  | O | S | 287.426 | 288.29 |
| 4027 |  | O | CF₂ | 305.369 | 306.23 |
| 4028 | nHex | O | CH₂ | 311.47 | 312.37 |
| 4029 |  | O | S | 329.507 | 330.34 |
| 4030 |  | O | CF₂ | 347.45 | 348.31 |
| 4031 | cyclohexyl-CH(CH₃)- | O | CH₂ | 309.454 | 310.37 |
| 4032 |  | O | S | 327.491 | 328.31 |
| 4033 |  | O | CF₂ | 345.434 | 346.3 |
| 4034 | PhCH₂CH(CH₃)- | O | CH₂ | 317.433 | 318.3 |
| 4035 |  | O | CF₂ | 353.413 | 354.25 |
| 4036 | EtO(O)C-(CH₂)₃-CH(CH₃)- | O | CH₂ | 327.425 | 328.34 |
| 4037 |  | O | S | 345.462 | 346.29 |
| 4038 |  | O | CF₂ | 363.405 | 364.26 |
| 4039 | PhC(O)CH(CH₃)- | O | CH₂ | 331.416 | 332.24 |
| 4040 | Ph-CH(CH₃)- | O | CH₂ | 303.406 | 304.31 |
| 4041 |  | O | S | 321.443 | 322.26 |
| 4042 |  | O | CF₂ | 339.386 | 340.25 |
| 4043 | 4-MeO-C₆H₄-CH(CH₃)- | O | CH₂ | 333.432 | 334.31 |
| 4044 |  | O | S | 351.469 | 352.29 |
| 4045 |  | O | CF₂ | 369.412 | 370.26 |
| 4046 | 4-Me-C₆H₄-CH(CH₃)- | O | CH₂ | 317.433 | 318.32 |
| 4047 |  | O | S | 335.47 | 336.28 |
| 4048 |  | O | CF₂ | 353.413 | 354.28 |
| 4049 | 2,3-Cl₂-C₆H₃-CH(CH₃)- | O | CH₂ | 372.296 | 372.25 |
| 4050 |  | O | S | 390.333 | 390.21 |
| 4051 |  | O | CF₂ | 408.276 | 408.19 |

TABLE 25-continued
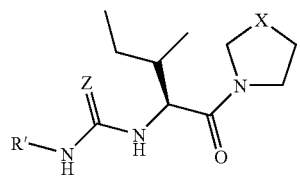
| Example No | R' | Z | X | Mol Wt | [M + H]+ |
|---|---|---|---|---|---|
| 4052 | 4-F-phenyl | O | CH₂ | 321.396 | 322.31 |
| 4053 | | O | S | 339.433 | 340.26 |
| 4054 | | O | CF₂ | 357.376 | 358.22 |
| 4055 | 3-F-phenyl | O | CH₂ | 321.396 | 322.3 |
| 4056 | | O | S | 339.433 | 340.26 |
| 4057 | | O | CF₂ | 357.376 | 358.22 |
| 4058 | 2-F-phenyl | O | CH₂ | 321.396 | 322.3 |
| 4059 | | O | S | 339.433 | 340.27 |
| 4060 | | O | CF₂ | 357.376 | 358.22 |
| 4061 | 1-naphthyl | O | CH₂ | 353.466 | 354.32 |
| 4062 | | O | S | 371.503 | 372.3 |
| 4063 | | O | CF₂ | 389.446 | 390.3 |
| 4064 | 3-CF₃-phenyl | O | CH₂ | 371.403 | 372.32 |
| 4065 | | O | S | 389.44 | 390.26 |
| 4066 | | O | CF₂ | 407.383 | 408.26 |
| 4067 | 4-Cl-phenyl | O | CH₂ | 337.851 | 338.27 |
| 4068 | | O | S | 355.888 | 356.24 |
| 4069 | | O | CF₂ | 373.831 | 374.23 |
| 4070 | 3-Cl-phenyl | O | CH₂ | 337.851 | 338.28 |
| 4071 | | O | S | 355.888 | 356.24 |
| 4072 | | O | CF₂ | 373.831 | 374.22 |
| 4073 | 2-Cl-phenyl | O | CH₂ | 337.851 | 338.27 |
| 4074 | | O | S | 355.888 | 356.23 |
| 4075 | | O | CF₂ | 373.831 | 374.2 |
| 4076 | 3-OMe-phenyl | O | CH₂ | 333.432 | 334.32 |
| 4077 | | O | S | 351.469 | 352.29 |
| 4078 | | O | CF₂ | 369.412 | 370.27 |

TABLE 25-continued
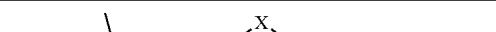
| Example No | R' | Z | X | Mol Wt | [M + H]+ |
|---|---|---|---|---|---|
| 4079 | 2-isopropoxyphenyl (iPr, OMe on phenyl) | O | CH₂ | 333.432 | 334.33 |
| 4080 | | O | S | 351.469 | 352.3 |
| 4081 | | O | CF₂ | 369.412 | 370.26 |
| 4082 | 3-nitrophenyl iPr | O | CH₂ | 348.403 | 349.3 |
| 4083 | | O | S | 366.44 | 367.27 |
| 4084 | | O | CF₂ | 384.383 | 385.25 |
| 4085 | 2,4-dichlorophenyl iPr | O | CH₂ | 372.296 | 372.25 |
| 4086 | | O | S | 390.333 | 390.23 |
| 4087 | | O | CF₂ | 408.276 | 408.21 |
| 4088 | | O | CH₂ | 331.46 | 332.35 |
| 4089 | | O | S | 349.497 | 350.3 |
| 4090 | | O | CF₂ | 367.44 | 368.29 |
| 4091 | 3,5-dichlorophenyl iPr | O | CH₂ | 372.296 | 372.26 |
| 4092 | | O | S | 390.333 | 390.22 |
| 4093 | | O | CF₂ | 408.276 | 408.2 |
| 4094 | 2,4-dimethoxyphenyl iPr | O | CH₂ | 363.458 | 364.34 |
| 4095 | | O | S | 381.495 | 382.32 |
| 4096 | | O | CF₂ | 399.438 | 400.3 |
| 4097 | 2,6-difluorophenyl iPr | O | CH₂ | 339.386 | 340.3 |
| 4098 | | O | S | 357.423 | 358.26 |
| 4099 | | O | CF₂ | 375.366 | 376.23 |
| 4100 | biphenyl iPr | O | CH₂ | 379.504 | 380.38 |
| 4101 | | O | S | 397.541 | 398.32 |
| 4102 | | O | CF₂ | 415.484 | 416.3 |

TABLE 25-continued

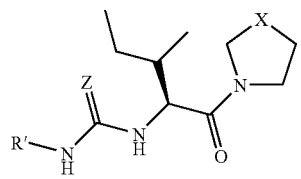

| Example No | R' | Z | X | Mol Wt | [M + H]+ |
|---|---|---|---|---|---|
| 4103 | nPr | S | CH₂ | 285.454 | 286.29 |
| 4104 | | S | S | 303.491 | 304.31 |
| 4105 | neopentylbenzyl | S | CH₂ | 333.498 | 334.3 |
| 4106 | | S | CF₂ | 369.478 | 370.24 |
| 4107 | phenylpropyl | S | CH₂ | 347.525 | 348.3 |
| 4108 | | S | CF₂ | 383.505 | 384.25 |
| 4109 | 4-methoxybenzyl | S | CH₂ | 349.497 | 350.27 |
| 4110 | | S | S | 367.534 | 368.2 |
| 4111 | | S | CF₂ | 385.477 | 386.27 |
| 4112 | benzoyl | S | CH₂ | 347.481 | 348.3 |
| 4113 | | S | S | 365.518 | 366.23 |
| 4114 | | S | CF₂ | 383.461 | 384.2 |
| 4115 | cyclopentyl | S | S | 329.529 | 330.27 |
| 4116 | | S | CF₂ | 347.472 | 348.27 |
| 4117 | cyclohexylmethyl | S | CH₂ | 339.546 | 340.35 |
| 4118 | | S | S | 357.583 | 358.29 |
| 4119 | | S | CF₂ | 375.526 | 376.3 |

The invention claimed is:

1. (2S)-1-(2-(1-Napthoylamino)acetyl)pyrrolidine-2-carbonitrile, or a pharmaceutically acceptable salt form thereof.

2. A pharmaceutical composition comprising a compound according to claim 1 and a pharmaceutically acceptable excipient.

3. The pharmaceutical composition according to claim 2, formulated for oral administration.

4. The pharmaceutical composition of claim 3, formulated as a tablet, capsule, or satchet.

* * * * *